US006246471B1

(12) United States Patent
Jung et al.

(10) Patent No.: US 6,246,471 B1
(45) Date of Patent: Jun. 12, 2001

(54) APPARATUS AND METHOD FOR MEASURING OPTICAL CHARACTERISTICS OF AN OBJECT

(75) Inventors: Wayne D. Jung; Russell W. Jung, both of Morton Grove; Alan R. Loudermilk, Chicago, all of IL (US)

(73) Assignee: LJ Laboratories, LLC, Chicago, IL (US)

( * ) Notice: Subject to any disclaimer, the term of this patent is extended or adjusted under 35 U.S.C. 154(b) by 0 days.

(21) Appl. No.: 09/480,312

(22) Filed: Jan. 10, 2000

Related U.S. Application Data

(63) Continuation-in-part of application No. 09/091,208, filed on Jun. 8, 1998, and a continuation-in-part of application No. 09/198,591, filed on Nov. 23, 1998.

(51) Int. Cl.[7] ........................................................ G01J 3/18
(52) U.S. Cl. ................................ 356/73; 356/71; 356/328
(58) Field of Search .................................... 356/326, 328, 356/71, 73

(56) References Cited

U.S. PATENT DOCUMENTS

| 3,327,584 | 6/1967 | Kissinger ........................... 356/375 |
| 3,436,157 | 4/1969 | Adler et al. . | |
| 3,507,042 | 4/1970 | Hana . | |
| 3,555,262 | 1/1971 | Shimada ............................ 235/193 |

(List continued on next page.)

FOREIGN PATENT DOCUMENTS

| 2256355 | 12/1973 | (DE) ................................. 356/402 |
| 0681256 | 11/1995 | (EP) . | |
| 2669526 | 5/1992 | (FR) ................................ 433/203.1 |
| 54-103055 | 8/1979 | (JP) ................................. 356/416 |
| 8603292 | 6/1986 | (WO) .............................. 433/203.1 |
| WO 95/17663 | * 6/1995 | (WO) . | |

OTHER PUBLICATIONS

Aswell, Cecil J. et al., "A Monolithic Light–to–Frequency Converter with a Scalable Sensor Array", IEEE, 1994, pp. 122–123 and 158–159.

Bangtson et al.; "The conversion of Chromascan designations to CIE tristimilus values"; Nov. 1982; pp 610–617 vol. 48 No. 5, Journal of Prosthetic Dentistry.

Barghi et al.; "Effects of batch variation on shade of dental porcelain"; Nov. 1985; pp 625–627, vol. 54 No. 5, Journal of Prosthetic Dentistry.

(List continued on next page.)

*Primary Examiner*—F. L. Evans
(74) *Attorney, Agent, or Firm*—Loudermilk & Associates

(57) ABSTRACT

Optical characteristic measuring systems and methods such as for determining the color or other optical characteristics of teeth are disclosed. Perimeter receiver fiber optics preferably are spaced apart from a source fiber optic and receive light from the surface of the object/tooth being measured. Light from the perimeter fiber optics pass to a variety of filters. The system utilizes the perimeter receiver fiber optics to determine information regarding the height and angle of the probe with respect to the object/tooth being measured. Under processor control, the optical characteristics measurement may be made at a predetermined height and angle. Various color spectral photometer arrangements are disclosed. Translucency, fluorescence, gloss and/or surface texture data also may be obtained. Audio feedback may be provided to guide operator use of the system. The probe may have a removable or shielded tip for contamination prevention. A method of producing dental prostheses based on measured data also is disclosed. Measured data also may be stored and/or organized as part of a patient data base. Such methods and implements may be desirably utilized for purposes of detecting and preventing counterfeiting or the like. Preferably, a two stage spectral separation is utilized, preferably utilizing a diffraction grating and interference filters.

58 Claims, 67 Drawing Sheets

U.S. PATENT DOCUMENTS

| | | | |
|---|---|---|---|
| 3,743,429 | 7/1973 | Kawai . | |
| 3,748,741 | 7/1973 | Yerkes, Jr. | 32/71 |
| 3,778,541 | 12/1973 | Bowker . | |
| 3,986,777 | 10/1976 | Roll . | |
| 4,054,389 | 10/1977 | Owen | 356/419 |
| 4,115,922 | 9/1978 | Alderman | 32/71 |
| 4,125,329 | 11/1978 | French et al. | 356/405 |
| 4,184,175 | 1/1980 | Mullane, Jr. | 356/237 |
| 4,207,678 | 6/1980 | Jeannette | 433/203 |
| 4,241,738 | 12/1980 | Lübbers | 128/666 |
| 4,278,353 | 7/1981 | Ostermayer et al. | 356/416 |
| 4,290,433 | 9/1981 | Alfano | 128/665 |
| 4,324,546 | 4/1982 | Heitlinger et al. | 433/25 |
| 4,382,784 | 5/1983 | Freller | 433/26 |
| 4,411,626 | 10/1983 | Becker et al. | 433/223 |
| 4,464,054 | 8/1984 | Karass et al. | 356/406 |
| 4,487,206 | 12/1984 | Aagard | 128/667 |
| 4,505,589 | 3/1985 | Oh et al. | 356/402 |
| 4,568,191 | 2/1986 | Barry | 356/446 |
| 4,575,805 | 3/1986 | Moermann et al. . | |
| 4,616,933 | 10/1986 | Leveque et al. | 356/416 |
| 4,654,794 | 3/1987 | O'Brien | 364/413 |
| 4,666,309 | 5/1987 | Barry et al. | 356/446 |
| 4,687,329 * | 8/1987 | Schultz | 356/328 |
| 4,773,063 | 9/1988 | Hunsperger et al. | 370/3 |
| 4,798,951 | 1/1989 | Walker | 250/227 |
| 4,823,169 | 4/1989 | Ogura | 356/446 |
| 4,836,674 | 6/1989 | Lequime et al. | 356/319 |
| 4,878,485 | 11/1989 | Adair | 600/125 |
| 4,881,811 | 11/1989 | O'Brien | 356/73 |
| 4,917,500 | 4/1990 | Lugos | 356/406 |
| 4,957,371 | 9/1990 | Pellicori et al. | 356/419 |
| 4,986,671 | 1/1991 | Sun et al. | 374/131 |
| 4,988,206 | 1/1991 | Melleney et al. | 356/446 |
| 5,028,139 | 7/1991 | Kramer et al. . | |
| 5,040,940 | 8/1991 | Kolodziej et al. | 414/764 |
| 5,095,210 | 3/1992 | Wheatley et al. | 356/71 |
| 5,142,383 | 8/1992 | Mallik | 356/71 |
| 5,159,199 * | 10/1992 | LaBaw | 356/328 |
| 5,164,597 | 11/1992 | Lodder | 356/338 |
| 5,166,755 | 11/1992 | Gat | 356/419 |
| 5,229,841 | 7/1993 | Taranowski et al. | 356/406 |
| 5,245,404 * | 9/1993 | Jannson et al. | 356/301 |
| 5,306,144 | 4/1994 | Hibst et al. | 433/29 |
| 5,308,771 | 5/1994 | Zhou et al. | 436/39 |
| 5,329,935 | 7/1994 | Takahashi . | |
| 5,377,669 | 1/1995 | Schultz . | |
| 5,383,020 | 1/1995 | Vieillefosse | 356/326 |
| 5,386,292 | 1/1995 | Massen et al. | 356/376 |
| 5,392,110 | 2/1995 | Yojima et al. | 356/376 |
| 5,401,967 | 3/1995 | Stedman et al. | 250/338.5 |
| 5,404,218 | 4/1995 | Nave et al. | 356/301 |
| 5,410,410 | 4/1995 | Yamazaki et al. | 356/376 |
| 5,410,413 | 4/1995 | Sela | 356/446 |
| 5,428,450 | 6/1995 | Vielleifosse et al. | 356/405 |
| 5,450,193 | 9/1995 | Carlsen et al. | 356/301 |
| 5,450,511 | 9/1995 | Dragone | 385/37 |
| 5,453,838 | 9/1995 | Danielian et al. | 356/371 |
| 5,457,525 | 10/1995 | Ohtsuka et al. | 356/3.06 |
| 5,461,476 | 10/1995 | Fournier | 356/343 |
| 5,467,289 | 11/1995 | Abe et al. | 364/560 |
| 5,469,249 | 11/1995 | Magyar, Jr. et al. | 356/4.07 |
| 5,474,449 | 12/1995 | Loge et al. | 433/29 |
| 5,477,332 | 12/1995 | Stone et al. | 356/371 |
| 5,483,335 | 1/1996 | Tobias | 356/310 |
| 5,497,227 | 3/1996 | Takeuchi et al. | 356/71 |
| 5,498,157 | 3/1996 | Hall | 433/26 |
| 5,560,355 | 10/1996 | Merchant et al. | 356/41 |
| 5,565,976 | 10/1996 | Fleggen et al. | 250/227.16 |
| 5,575,284 | 11/1996 | Athan et al. | 356/41 |
| 5,583,631 | 12/1996 | Lazzerini | 356/71 |
| 5,590,251 | 12/1996 | Takagi | 395/131 |
| 5,604,594 | 2/1997 | Juffinger | 356/405 |
| 5,625,459 | 4/1997 | Driver | 356/446 |
| 5,668,633 | 9/1997 | Cheetam et al. | 356/402 |
| 5,671,735 | 9/1997 | MacFarlane et al. | 128/633 |
| 5,690,486 | 11/1997 | Zigelbaum | 433/29 |
| 5,695,949 | 12/1997 | Galen et al. | 435/14 |
| 5,696,751 | 12/1997 | Juffinger | 369/119 |
| 5,745,229 | 4/1998 | Jung et al. | 356/73 |
| 5,757,496 | 5/1998 | Yamazaki | 356/373 |
| 5,759,030 | 6/1998 | Jung et al. | 433/29 |
| 5,766,006 | 6/1998 | Murljacic | 433/26 |
| 5,774,610 | 6/1998 | O'Rourke et al. | 385/52 |
| 5,784,507 | 7/1998 | Holm-Kennedy et al. | 385/31 |
| 5,798,839 | 8/1998 | Berner et al. | 356/402 |
| 5,822,474 | 10/1998 | Hara | 385/24 |
| 5,850,195 | 12/1998 | Berlien, Jr. et al. | 341/137 |
| 5,850,301 | 12/1998 | Mizuochi et al. | 359/124 |
| 5,880,826 | 3/1999 | Jung et al. | 433/29 |
| 5,883,708 | 3/1999 | Jung et al. | 356/371 |
| 5,924,981 | 7/1999 | Rothfritz et al. | 600/306 |
| 5,961,324 | 10/1999 | Lehmann | 433/26 |
| 5,995,235 | 11/1999 | Sui et al. | 356/419 |
| 6,040,902 | 3/2000 | Jung et al. | 356/73 |
| 6,100,988 | 8/2000 | Jung et al. . | |

OTHER PUBLICATIONS

Council on Dental Materials, Instruments, and Equipment; "How to improve shade matching in the dental operatory"; Feb. 1981; pp 209–210, vol. 102; JADA.

Davison et al.; "Shade selection by color vision–defective dental personnel"; Jan. 1990; pp 97–101 vol. 63 No. 1, Journal of Prosthetic Dentistry.

Demro, James C., R. Hartshome, P.A. Levine, L.M. Woody, "Design of Multispectral, Wedge Filter, Remote–Sensing Instrument incorporating a mulit–point, thinned, CCD area array" SPIE vol. 2480 p. 280.

Dickerson; "Trilogy of Creating an Esthetic Smile"; Jul. 1996; pp 1–7, vol. 1, Issue 3; Technical Update–A Publication of Micro Dental Laboratories.

Elerding, George T. John G. Thunen, Loren M. Woody "Wedge Imaging Spectrometer: Application to drug and pollution law enforcement" SPIE vol. 1479 *Surveillance Technologies*, p. 380 (1991).

Goldstein et al.; "Repeatability of a specially designed intraoral colorimeter"; Jun. 1993; pp 616–619, vol. 69 No. 6, Journal of Prosthetic Dentistry.

Goodkind et al.; "A comparison of Chromascan and spectrophotometric color measurement of 100 natural teeth"; Jan. 1985; pp 105–109, vol. 53 No. 1, Journal of Prosthetic Dentistry.

Ishikawa et al.; "Trial Manufacture of Photoelectric Colorimeter Using Optical Fibers"; Nov. 1969; pp 191–197, vol. 10, No. 4, Bull. Tokyo dent. Coll.

Johnston et al.; "The Color Accuracy of the Kubelka–Munk Theory for Various Colorants in Maxillofacial Prosthetic Material"; Sep. 1987; pp 1438–1444, vol. 66, No. 9; J. Dent. Res.

Johnston et al.; "Assessment of Appearance Match by Visual Observation and Clinical Colorimetry"; May 1989; pp 819–822, vol. 68, No. 5. J. Dent. Res.

Kato et al; "The Current State of Porcelain Shades: A Discussion"; Oct. 1984; pp 559–571, vol. 8, No. 9; Quintessence of Dental Technology.

Mika, Aram M., "Linear–Wedge Spectrometer" SPIE vol. 1298 *Imaging Spectroscopy of the Terrestrial Environment*, p. 127 (1990).

Miller; "Organizing color in dentistry"; Dec. 1987; pp 26E–40E, Special Issue; JADA.

Miller et al; "Shade selection and laboratory communication"; May 1993; pp 305–309, vol. 24, No. 5; Quintessence International.

O'Brien et al.; "Coverage Errors of Two Shade Guides"; Jan./Feb. 1991; pp 45–50, vol. 4, No. 1; The International Journal of Prosthodontics.

O'Brien et al.; "A New, Small–color–difference Equation for Dental Shades"; Nov. 1990; pp 1762–1764, vol. 69, No. 11; J. Dent. Res.

O'Keefe et al.; "Color Shade and Matching: The Weak Link in Esthetic Dentistry"; Feb. 1990; pp 116–120, vol. XI, No. 2, Compend Contin Educ Dent.

Pensler; "A New Approach to Shade Selection"; Sep. 1991; pp 668–675, vol. XII, No. 9, Compend Educ Dent.

Preston et al.; "Light and Lighting in the Dental Office"; Jul. 1978; pp 431–451, vol. 22, No. 3; Dental Clinics of North America.

Preston; "Current status of shade selection and color matching"; Jan. 1985; pp 47–58, vol. 16, No. 1, Quintessence International.

Rosenstiel et al.; "The effects of manipulative variables on the color of ceramic metal restorations"; Sep. 1987; pp 297–303, vol. 60 No. 3, Journal of Prosthetic Dentistry.

Rugh et al.; "The Relationship Between Elastomer Opacity, Colorimeter Beam Size, and Measured Colorimetric Response"; Nov./Dec. 1991; pp 569–576, vol. 4, No. 6; The International Journal of Prosthodontics.

Ryther et al.; "Colormetric Evaluation of Shade Guide Variability"; 1993; p. 215; J. Dent. Res. 72 (IADR Abstracts) Special Issue.

Schwabacher et al.; "Three–dimensional color coordiantes of natural teeth compared with three shade guides"; Oct. 1990; pp 425–431, vol. 64 No. 4, Journal of Prosthetic Dentistry.

Seghi et al.; "Spectrophotometric analysis of color differences between porcelain systems"; Jul. 1986; pp 35–40, vol. 56 No. 1, Journal of Prosthetic Dentistry.

Seghi et al.; "Visual and Instrumental Colorimetric Assessments of Small Color Differences on Translucent Dental Porcelain"; Dec. 1989; pp 1760–1764, vol. 68, No. 12; J. Dent. Res.

Seghi et al.; "Performance Assessment of Colorimetric Devices on Dental Porcelains"; Dec. 1989; pp 1755–1759, vol. 69, No. 11; J. Dent. Res.

Seghi; "Effects of Instrument–measuring Geometry on Colorimetric Assessments of Dental Porcelains"; May 1990; pp 1180–1183, vol. 69, No. 5; J. Dent. Res.

Sorensen et al.; "Improved color matching of metal–ceramic restorations. Part I: A systematic method for shade determination"; Aug. 1987; pp 133–139, vol. 58, No. 2, Journal of Prosthetic Dentistry.

Sorenson et al.; "Improved color matching of metal–ceramic restorations. Part II: Procedures for visual communication"; Dec. 1987; pp 669–677, vol. 58, No. 6, Journal of Prosthetic Dentistry.

Sproul, "Color matching in dentistry. Part 1. The three–dimensional nature of color"; Apr. 1973; pp 416–424, vol. 29, No. 4; Prosthet. Dent.

Sproul; "Color matching in dentistry. Part 1. Color control"; Feb. 1974; pp 146–154, vol. 31, No. 2; J. Prosthet. Dent.

Sproul; "Color matching in dentistry. Part 2. Practical applications of the organization of color"; May 1973; pp 556–566, vol. 29, No. 5; J. Prosthet. Dent.

Swift et al.; "Colormetric Evaluation of Vita Shade Resin Composites"; 1994; pp 356–361, vol. 7, No. 4; The International Journal of Prosthodontics.

van der Burgt et al.; "A comparison of new and conventional methods for quantification of tooth color"; Feb. 1990; pp 155–162, vol. 63 No. 2, Journal of Prosthetic Dentistry.

\* cited by examiner

R - LIGHT RECEIVER FIBER OPTICS
S - LIGHT SOURCE FIBER OPTIC

S - LIGHT SOURCE FIBER
R - RED RECEIVER
G - GREEN RECEIVER
B - BLUE RECEIVER
P - NEUTRAL (FULL BAND) RECEIVERS

S - LIGHT SOURCE FIBER
P - NEUTRAL (FULL BAND) RECEIVER
C - COLOR RECEIVER

S - LIGHT SOURCE FIBER
$R_{1X}$ - INNER RING RECEIVER FIBER
$R_{2X}$ - 2nd RING RECEIVER FIBER
$R_{3X}$ - 3rd RING RECEIVER FIBER

INTRAORAL POSITIONING DEVICE

Enamel - Dentin Layers

LIGHT REFLECTION AND SCATTERING

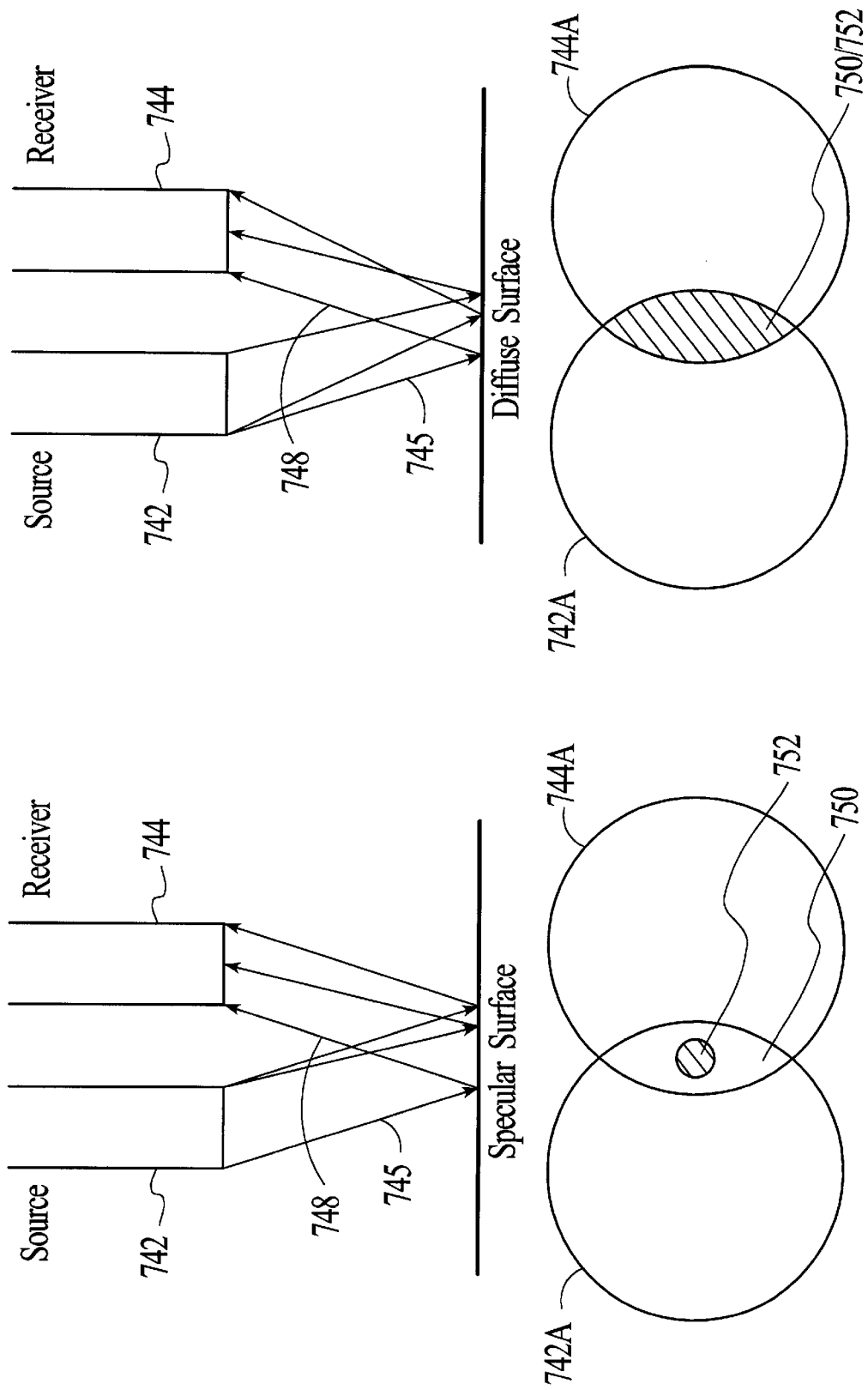

APPARATUS AND METHOD FOR MEASURING OPTICAL CHARACTERISTICS OF AN OBJECT

This is a Continuation-in-part (CIP) of Ser. No. 09/091,208 filed Jun. 8, 1998 and 09/198,591 filed Nov. 23, 1998.

FIELD OF THE INVENTION

The present invention relates to devices and methods for measuring optical characteristics such as color spectrums, translucence, gloss, and other characteristics of objects such as teeth, and more particularly to devices and methods for measuring the color and other optical characteristics of teeth, fabric or numerous other objects, materials or surfaces with a hand-held probe that presents minimal problems with height or angular dependencies and that may be applied to detecting and preventing counterfeiting, and in particular devices and methods employing two stages of spectral separation.

BACKGROUND OF THE INVENTION

A need has been recognized for devices and methods of measuring the color or other optical characteristics of teeth and other objects in the field of dentistry. There is also a need for devices and methods for detecting and preventing counterfeiting and the like based on measurements of various optical characteristics or properties of objects and materials. Various color measuring devices such as spectrophotometers and colorimeters are known in the art. To understand the limitations of such conventional devices, it is helpful to understand certain principles relating to color. Without being bound by theory, Applicants provide the following discussion. In the discussion herein, reference is made to an "object," "material," "surface," etc., and it should be understood that in general such discussion may include teeth as well as other objects or materials as the "object," "material," "surface," etc.

The color of an object determines the manner in which light is reflected from the object. When light is incident upon an object, the reflected light will vary in intensity and wavelength dependent upon the color of the object. Thus, a red object will reflect red light with a greater intensity than a blue or a green object, and correspondingly a green object will reflect green light with a greater intensity than a red or blue object.

The optical properties of an object are also affected by the manner in which light is reflected from the surface. Glossy objects, those that reflect light specularly such as mirrors or other highly polished surfaces, reflect light differently than diffuse objects or those that reflect light in all directions, such as the reflection from a rough or otherwise non-polished surface. Although both objects may have the same color and exhibit the same reflectance or absorption optical spectral responses, their appearances differ because of the manner in which they reflect light.

Additionally, many objects may be translucent or have semi-translucent surfaces or thin layers covering their surfaces. Examples of such materials are teeth, which have a complicated structure consisting of an outer enamel layer and an inner dentin layer. The outer enamel layer is semi-translucent. The inner layers are also translucent to a greater or lesser degree. Such materials and objects also appear different from objects that are opaque, even though they may be the same color because of the manner in which they can propagate light in the translucent layer and emit the light ray displaced from its point of entry.

One method of quantifying the color of an object is to illuminate it with broad band spectrum or "white" light, and measure the spectral properties of the reflected light over the entire visible spectrum and compare the reflected spectrum with the incident light spectrum. Such instruments typically require a broad band spectrophotometer, which generally are expensive, bulky and relatively cumbersome to operate, thereby limiting the practical application to of such instruments.

For certain applications, the broad band data provided by a spectrophotometer is unnecessary. For such applications, devices have been produced or proposed that quantify color in terms of a numerical value or relatively small set of values representative of the color of the object.

It is known that the color of an object can be represented by three values. For example, the color of an object can be represented by red, green and blue values, an intensity value and color difference values, by a CIE value, or by what are known as "tristimulus values" or numerous other orthogonal combinations. For most tristimulus systems, the three values are orthogonal; i.e., any combination of two elements in the set cannot be included in the third element.

One such method of quantifying the color of an object is to illuminate an object with broad band "white" light and measure the intensity of the reflected light after it has been passed through narrow band filters. Typically three filters (such as red, green and blue) are used to provide tristimulus light values representative of the color of the surface. Yet another method is to illuminate an object with three monochromatic light sources or narrow band light sources (such as red, green and blue) one at a time and then measure the intensity of the reflected light with a single light sensor. The three measurements are then converted to a tristimulus value representative of the color of the surface. Such color measurement techniques can be utilized to produce equivalent tristimulus values representative of the color of the surface. Generally, it does not matter if a "white" light source is used with a plurality of color sensors (or a continuum in the case of a spectrophotometer), or if a plurality of colored light sources are utilized with a single light sensor.

There are, however, difficulties with the conventional techniques. When light is incident upon a surface and reflected to a light receiver, the height of the light sensor and the angle of the sensor relative to the surface and to the light source also affect the intensity of the received light. Since the color determination is being made by measuring and quantifying the intensity of the received light for different colors, it is important that the height and angular dependency of the light receiver be eliminated or accounted for in some manner.

One method for eliminating the height and angular dependency of the light source and receiver is to provide a fixed mounting arrangement where the light source and receiver are stationary and the object is always positioned and measured at a preset height and angle. The fixed mounting arrangement greatly limits the applicability of such a method. Another method is to add mounting feet to the light source and receiver probe and to touch the object with the probe to maintain a constant height and angle. The feet in such an apparatus must be wide enough apart to insure that a constant angle (usually perpendicular) is maintained relative to the object. Such an apparatus tends to be very difficult to utilize on small objects or on objects that are hard to reach, and in general does not work satisfactorily in measuring objects with curved surfaces.

Such devices are particularly difficult to implement in the field of dentistry.

The use of color measuring devices in the field of dentistry has been proposed. In modem dentistry, the color of teeth typically are quantified by manually comparing a patient's teeth with a set of "shade guides." There are numerous shade guides available for dentists in order to properly select the desired color of dental prosthesis. Such shade guides have been utilized for decades and the color determination is made subjectively by the dentist by holding a set of shade guides next to a patient's teeth and attempting to find the best match. Unfortunately, however, the best match often is affected by the ambient light color in the dental operatory and the surrounding color of the patient's makeup or clothing and by the fatigue level of the dentist. In addition, such pseudo trial and error methods based on subjective matching with existing industry shade guides for forming dental prostheses, fillings and the like often result in unacceptable color matching, with the result that the prosthesis needs to be remade, leading to increased costs and inconvenience to the patient, dental professional and/or prosthesis manufacturer.

Similar subjective color quantification also is made in the paint industry by comparing the color of an object with a paint reference guide. There are numerous paint guides available in the industry and the color determination also often is affected by ambient light color, user fatigue and the color sensitivity of the user. Many individuals are color insensitive (color blind) to certain colors, further complicating color determination.

In general, color quantification is needed in many industries. Several, but certainly not all, applications include: dentistry (color of teeth); dermatology (color of skin lesions); interior decorating (color of paint, fabrics); the textile industry; automotive repair (matching paint colors); photography (color of reproductions, color reference of photographs to the object being photographed); printing and lithography; cosmetics (hair and skin color, makeup matching); and other applications in which it useful to measure color in an expedient and reliable manner.

While a need has been recognized in the field of dentistry, however, the limitations of conventional color/optical measuring techniques typically restrict the utility of such techniques. For example, the high cost and bulkiness of typical broad band spectrometers, and the fixed mounting arrangements or feet required to address the height and angular dependency, often limit the applicability of such conventional techniques.

Moreover, another limitation of such conventional methods and devices are that the resolution of the height and angular dependency problems typically require contact with the object being measured. In certain applications, it may be desirable to measure and quantify the color of an object with a small probe that does not require contact with the surface of the object. In certain applications, for example, hygienic considerations make such contact undesirable. In the other applications such as interior decorating, contact with the object can mar the surface (such as if the object is coated in some manner) or otherwise cause undesirable effects.

In summary, there is a need for a low cost, hand-held probe of small size that can reliably measure and quantify the color and other optical characteristics of an object without requiring physical contact with the object, and also a need for methods based on such a device in the field of dentistry and other applications.

SUMMARY OF THE INVENTION

In accordance with the present invention, devices and methods are provided for measuring the color and other optical characteristics of objects such as teeth, reliably and with minimal problems of height and angular dependence and which may be applied to detecting or preventing counterfeiting or the like. A handheld probe is utilized in the present invention, with the handheld probe containing a number of fiber optics in certain preferred embodiments. Light is directed from one (or more) light source(s) towards the object/tooth to be measured, which in certain preferred embodiments is a central light source fiber optic (other light sources and light source arrangements also may be utilized). Light reflected from the object is detected by a number of light receivers. Included in the light receivers (which may be light receiver fiber optics) are a plurality of perimeter and/or broadband or other receivers (which may be light receiver fiber optics, etc.). In certain preferred embodiments, a number of groups of perimeter fiber optics are utilized in order to take measurements at a desired, and predetermined height and angle, thereby minimizing height and angular dependency problems found in conventional methods, and to quantify other optical characteristics such as gloss. In certain embodiments, the present invention also may measure gloss, translucence and fluorescence characteristics of the object/tooth being measured, as well as surface texture and/or other optical or surface characteristics. In certain embodiments, the present invention may distinguish the surface spectral reflectance response and also a bulk spectral response.

The present invention may include constituent elements of a broad band spectrophotometer, or, alternatively, may include constituent elements of a tristimulus type calorimeter. The present invention may employ a variety of color measuring devices in order to measure color and other optical characteristics in a practical, reliable and efficient manner, and in certain preferred embodiments includes a color filter array and a plurality of color sensors. A microprocessor is included for control and calculation purposes. A temperature sensor is included to measure temperature in order to detect abnormal conditions and/or to compensate for temperature effects of the filters or other components of the system. In addition, the present invention may include audio feedback to guide the operator in making color/optical measurements, as well as one or more display devices for displaying control, status or other information.

With the present invention, color/optical measurements of teeth or the like may be made with a handheld probe in a practical and reliable manner, essentially free of height and angular dependency problems, without resorting to fixtures, feet or other undesirable mechanical arrangements for fixing the height and angle of the probe with respect to the object/tooth. In addition, the present invention includes methods of using such color measurement data to implement processes for forming dental prostheses and the like, as well as methods for keeping such color and/or other data as part of a patient record database.

In accordance with one preferred embodiment, a two stage spectral separation is utilized, preferably consisting of a curved/spherical-type diffraction grating and (preferably) interference filters and optical sensors.

Accordingly, it is an object of the present invention to address limitations of conventional color/optical measuring techniques.

It is another object of the present invention to provide a method and device useful in measuring the color or other optical characteristics of teeth, fabric or other objects or surfaces with a hand-held probe of practical size that may advantageously utilize, but does not necessarily require, contact with the object or surface.

It is a further object of the present invention to provide a color/optical measurement probe and method that does not require fixed position mechanical mounting, feet or other mechanical impediments.

It is yet another object of the present invention to provide a probe and method useful for measuring color and/or other optical characteristics that may be utilized with a probe simply placed near the surface to be measured.

It is a still further object of the present invention to provide a probe and method that are capable of determining translucency characteristics of the object being measured.

It is a still further object of the present invention to provide a probe and method that are capable of determining translucency characteristics of the object being measured by making measurements from one side of the object.

It is a further object of the present invention to provide a probe and method that are capable of determining surface texture characteristics of the object/tooth being measured.

It is a still further object of the present invention to provide a probe and method that are capable of determining fluorescence characteristics of the object/tooth being measured.

It is yet a further object of the present invention to provide a probe and method that are capable of determining gloss (or degree of specular reflectance) characteristics of the object/tooth being measured.

It is another object of the present invention to provide a probe and method that can measure the area of a small spot singularly, or that also can measure the color of irregular shapes by moving the probe over an area and integrating the color of the entire area.

It is a further object of the present invention to provide a method of measuring the color of teeth and preparing dental prostheses, dentures, intraoral tooth-colored fillings or other materials.

It is yet another object of the present invention to provide a method and apparatus that minimizes contamination problems, while providing a reliable and expedient manner in which to measure teeth and prepare dental prostheses, dentures, intraoral tooth-colored fillings or other materials.

It is an object of the present invention to provide methods of using measured data to implement processes for forming dental prostheses and the like, as well as methods for keeping such measurement and/or other data as part of a patient record database.

It also is an object of the present invention to provide probes and methods for measuring optical characteristics with a probe that is held substantially stationary with respect to the object or tooth being measured.

It is another object the present invention to provide probes, equipment and methods for detecting and preventing counterfeiting or the like by way of measuring or assessing surface or subsurface optical characteristics or features.

Finally, it is an object of the present invention to provide probes and methods for measuring optical characteristics with a probe that may have a removable tip or shield that may be removed for cleaning, disposed after use or the like.

BRIEF DESCRIPTION OF THE DRAWINGS

The present invention may be more fully understood by a description of certain preferred embodiments in conjunction with the attached drawings in which:

FIGS. 38 to 50 illustrate other embodiments (systems, sources, receivers, etc.), aspects and features within the scope of the present invention;

FIGS. 51A to 51C illustrate materials or object portions for purposes of explaining preferred embodiments of methods and devices for detecting or preventing counterfeiting or the like;

DETAILED DESCRIPTION OF THE PREFERRED EMBODIMENTS

The present invention will be described in greater detail with reference to certain preferred embodiments and certain other embodiments, which may serve to further the understanding of preferred embodiments of the present invention. At various places herein, reference is made to an "object," "material," "surface," etc., for example. It should be understood that an exemplary use of the present invention is in the field of dentistry, and thus the object typically should be understood to include teeth, dentures or other prosthesis or restorations, dental-type cements or the like or other dental objects, although for discussion purposes in certain instances reference is only made to the "object." As described elsewhere herein, various refinements and substitutions of the various embodiments are possible based on the principles and teachings herein.

Figure 1:
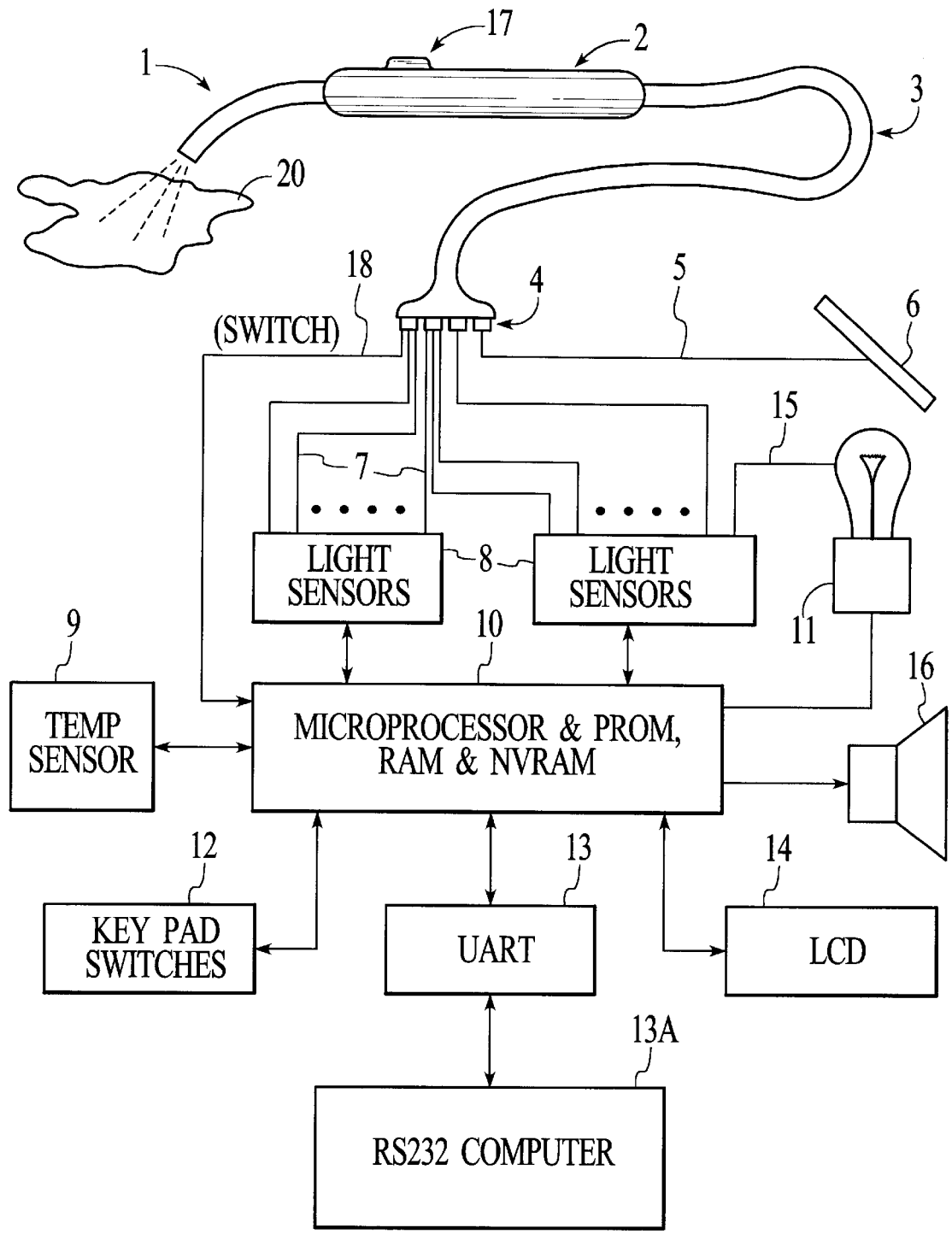
FIG. 1 is a diagram illustrating a preferred embodiment of the present invention.

With reference to FIG. 1, an exemplary preferred embodiment of a color/optical characteristic measuring system and method in accordance with the present invention will be described. It should be noted that, at various places herein, such a color measuring system is sometimes referred to as an intraoral reflectometer, etc.

Probe tip 1 encloses a plurality of fiber optics, each of which may constitute one or more fiber optic fibers. In a preferred embodiment, the fiber optics contained within probe tip 1 includes a single light source fiber optic and a number of groups of light receiver fiber optics. The use of such fiber optics to measure the color or other optical characteristics of an object will be described later herein. Probe tip 1 is attached to probe body 2, on which is fixed switch 17.

Switch 17 communicates with microprocessor through wire 18 and provides, for example, a mechanism by which an operator may activate the device in order to make a color/optical measurement. Fiber optics within probe tip 1 terminate at the forward end thereof (i.e., the end away from probe body 2). The forward end of probe tip 1 is directed towards the surface of the object to be measured as described more fully below. The fiber optics within probe tip 1 optically extend through probe body 2 and through fiber optic cable 3 to light sensors 8, which are coupled to microprocessor 10.

It should be noted that microprocessor includes conventional associated components, such as memory (programmable memory, such as PROM, EPROM or EEPROM; working memory such as DRAMs or SRAMs; and/or other types of memory such as non-volatile memory, such as FLASH), peripheral circuits, clocks and power supplies, although for clarity such components are not explicitly shown. Other types of computing devices (such as other microprocessor systems, programmable logic arrays or the like) are used in other embodiments of the present invention.

In the embodiment of FIG. 1, the fiber optics from fiber optic cable 3 end at splicing connector 4. From splicing connector 4, each or some of the receiver fiber optics used in this embodiment is/are spliced into a number of smaller fiber optics (generally denoted as fibers 7), which in this embodiment are fibers of equal diameter, but which in other preferred embodiments may be of unequal diameter and/or numeric aperture (NA) (including, for example, larger or smaller "height/angle" or perimeter fibers, as more fully described herein). One of the fibers of each group of fibers may pass to light sensors 8 through a neutral density filter (as more fully described with reference to FIG. 3), and collectively such neutrally filtered fibers may be utilized for purposes of height/angle determination, translucency determination and gloss determination (and also may be utilized to measure other surface characteristics, as more fully described herein). Remaining fibers of each group of fibers may pass to light sensors 8 through color filters and may be used to make color/optical measurements. In still other embodiments, splicing connector 4 is not used, and fiber bundles of, for example, five or more fibers each extend from light sensors 8 to the forward end of probe tip 1. In certain embodiments, unused fibers or other materials may be included as part of a bundle of fibers for purposes of, for example, easing the manufacturing process for the fiber bundle. What should be noted is that, for purposes of the present invention, a plurality of light receiver fiber optics or elements (such as fibers 7) are presented to light sensors 8, with the light from the light receiver fiber optics/elements representing light reflected from object 20. While the various embodiments described herein present tradeoffs and benefits that may not have been apparent prior to the present invention (and thus may be independently novel), what is important for the present discussion is that light from fiber optics/elements at the forward end of probe tip 1 is presented to sensors 8 for color/optical measurements and angle/height determination, etc. In particular, fiber optic configurations of certain preferred embodiments will be explained in more detail hereinafter.

Light source 11 in the preferred embodiment is a halogen light source (of, for example, 5–100 watts, with the particular wattage chosen for the particular application), which may be under the control of microprocessor 10. The light from light source 11 reflects from cold mirror 6 and into source fiber optic 5. Source fiber optic passes through to the forward end of probe tip 1 and provides the light stimulus used for purposes of making the measurements described herein. Cold mirror 6 reflects visible light and passes infra-red light, and is used to reduce the amount of infra-red light produced by light source 11 before the light is introduced into source fiber optic 5. Such infra-red light reduction of the light from a halogen source such as light source 11 can help prevent saturation of the receiving light sensors, which can reduce overall system sensitivity. Fiber receives light directly from light source 11 and passes through to light sensors 8 (which may be through a neutral density filter). Microprocessor monitors the light output of light source 11 through fiber 15, and thus may monitor and, if necessary compensate for, drift of the output of light source 11. In certain embodiments, microprocessor also may sound an alarm (such as through speaker 16) or otherwise provide some indication if abnormal or other undesired performance of light source 11 is detected.

The data output from light sensors 8 pass to microprocessor 10. Microprocessor processes the data from light sensors 8 to produce a measurement of color and/or other characteristics. Microprocessor also is coupled to key pad switches 12, which serve as an input device. Through key pad switches 12, the operator may input control information or commands, or information relating to the object being measured or the like. In general, key pad a switches 12, or other suitable data input devices (such as push button, toggle, membrane or other switches or the like), serve as a mechanism to input desired information to microprocessor 10.

Microprocessor also communicates with UART 13, which enables microprocessor to be coupled to an external device such as computer 13A. In such embodiments, data provided by microprocessor may be processed as desired for the particular application, such as for averaging, format conversion or for various display or print options, etc. In the preferred embodiment, UART 13 is configured so as to provide what is known as a RS232 interface, such as is commonly found in personal computers.

Microprocessor also communicates with LCD 14 for purposes of displaying status, control or other information as desired for the particular application. For example, color bars, charts or other graphic representations of the color or other collected data and/or the measured object or tooth may be displayed. In other embodiments, other display devices are used, such as CRTs, matrix-type LEDs, lights or other mechanisms for producing a visible indicia of system status or the like. Upon system initialization, for example, LCD 14 may provide an indication that the system is stable, ready and available for taking color measurements.

Also coupled to microprocessor is speaker 16. Speaker 16, in a preferred embodiment as discussed more fully below, serves to provide audio feedback to the operator, which may serve to guide the operator in the use of the device. Speaker 16 also may serve to provide status or other information alerting the operator of the condition of the system, including an audio tone, beeps or other audible indication (i.e., voice) that the system is initialized and available for taking measurements. Speaker 16 also may present audio information indicative of the measured data, shade guide or reference values corresponding to the measured data, or an indication of the status of the color/optical measurements.

Microprocessor also receives an input from temperature sensor 9. Given that many types of filters (and perhaps light sources or other components) may operate reliably only in a given temperature range, temperature sensor 9 serves to provide temperature information to microprocessor 10. In particular, color filters, such as may be included in light sensors 8, may be sensitive to temperature, and may operate reliably only over a certain temperature range. In certain embodiments, if the temperature is within a usable range, microprocessor may compensate for temperature variations of the color filters. In such embodiments, the color filters are characterized as to filtering characteristics as a function of temperature, either by data provided by the filter manufacturer, or through measurement as a function of temperature. Such filter temperature compensation data may be stored in the form of a look-up table in memory, or may be stored as a set of polynomial coefficients from which the temperature characteristics of the filters may be computed by microprocessor 10.

In general, under control of microprocessor 10, which may be in response to operator activation (through, for example, key pad switches 12 or switch 17), light is directed from light source 11, and reflected from cold mirror 6 through source fiber optic (and through fiber optic cable 3, probe body 2 and probe tip 1) or through some other suitable light source element and is directed onto object 20. Light reflected from object passes through the receiver fiber optics/elements in probe tip 1 to light sensors 8 (through probe body 2, fiber optic cable 3 and fibers 7). Based on the information produced by light sensors 8, microprocessor produces a color/optical measurement result or other information to the operator. Color measurement or other data produced by microprocessor may be displayed on display 14, passed through UART 13 to computer 13A, or used to generate audio information that is presented to speaker 16. Other operational aspects of the preferred embodiment illustrated in FIG. 1 will be explained hereinafter.

Figure 2:
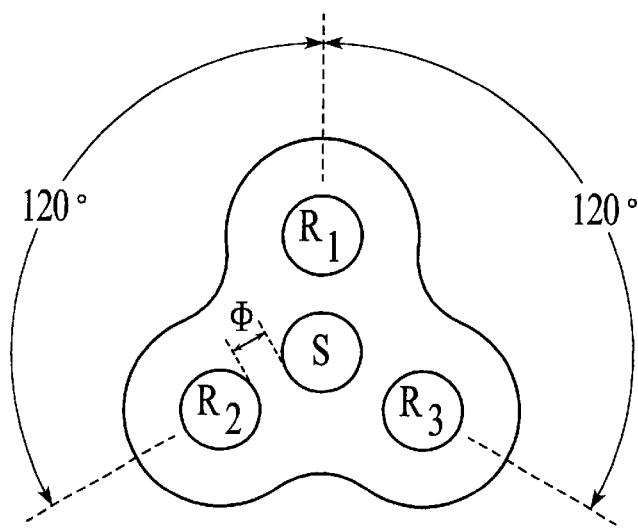
FIG. 2 is a diagram illustrating a cross section of a probe that may be used in accordance with certain embodiments of the present invention.

With reference to FIG. 2, an embodiment of a fiber optic arrangement presented at the forward end of probe tip 1 will now be described, which may serve to further the understanding of preferred embodiments of the present invention. As illustrated in FIG. 2, this embodiment utilizes a single central light source fiber optic, denoted as light source fiber optic S, and a plurality of perimeter light receiver fiber optics, denoted as light receivers R1, R2 and R3. As is illustrated, this embodiment utilizes three perimeter fiber optics, although in other embodiments two, four or some other number of receiver fiber optics are utilized. As more fully described herein, the perimeter light receiver fiber optics serve not only to provide reflected light for purposes of making the color/optical measurement, but such perimeter fibers also serve to provide information regarding the angle and height of probe tip 1 with respect to the surface of the object that is being measured, and also may provide information regarding the surface characteristics of the object that is being measured.

In the illustrated embodiment, receiver fiber optics R1 to R3 are positioned symmetrically around source fiber optic S, with a spacing of about 120 degrees from each other. It should be noted that spacing t is provided between receiver fiber optics R1 to R3 and source fiber optic S. While the precise angular placement of the receiver fiber optics around the perimeter of the fiber bundle in general is not critical, it has been determined that three receiver fiber optics positioned 120 degrees apart generally may give acceptable results. As discussed above, in certain embodiments light receiver fiber optics R1 to R3 each constitute a single fiber, which is divided at splicing connector 4 (refer again to FIG. 1), or, in alternate embodiments, light receiver fiber optics R1 to R3 each constitute a bundle of fibers, numbering, for example, at least five fibers per bundle. It has been determined that, with available fibers of uniform size, a bundle of, for example, seven fibers may be readily produced (although as will be apparent to one of skill in the art, the precise number of fibers may be determined in view of the desired number of receiver fiber optics, manufacturing considerations, etc.). The use of light receiver fiber optics R1 to R3 to produce color/optical measurements is further described elsewhere herein, although it may be noted here that receiver fiber optics R1 to R3 may serve to detect whether, for example, the angle of probe tip 1 with respect to the surface of the object being measured is at 90 degrees, or if the surface of the object being measured contains surface texture and/or spectral irregularities. In the case where probe tip 1 is perpendicular to the surface of the object being measured and the surface of the object being measured is a diffuse reflector (i.e., a matte-type reflector, as compared to a glossy or spectral or shiny-type reflector which may have "hot spots"), then the light intensity input into the perimeter fibers should be approximately equal. It also should be noted that spacing t serves to adjust the optimal height at which color/optical measurements should be made (as more fully described below). Preferred embodiments, as described hereinafter, may enable the quantification of the gloss or degree of spectral reflection of the object being measured.

In one particular aspect useful with embodiments of the present invention, area between the fiber optics on probe tip 1 may be wholly or partially filled with a non-reflective material and/or surface (which may be a black mat, contoured or other non-reflective surface). Having such exposed area of probe tip 1 non-reflective helps to reduce undesired reflections, thereby helping to increase the accuracy and reliability.

Figure 3:
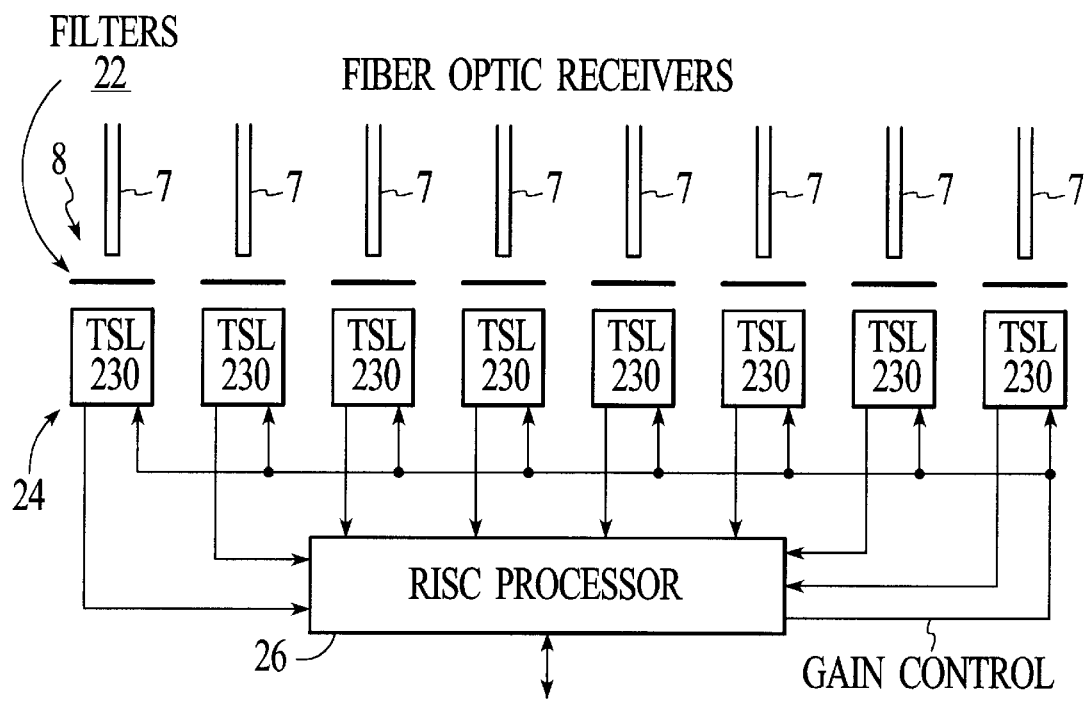
FIG. 3 is a diagram illustrating an illustrative arrangement of fiber optic receivers and sensors utilized with certain embodiments.

With reference to FIG. 3, a partial arrangement of light receiver fiber optics and sensors that may be used in a preferred embodiment of the present invention will now be described. Fibers 7 represent light receiving fiber optics, which transmit light reflected from the object being measured to light sensors 8. In an exemplary embodiment, sixteen sensors (two sets of eight) are utilized, although for ease of discussion only 8 are illustrated in FIG. 3 (in this preferred embodiment, the circuitry of FIG. 3 is duplicated, for example, in order to result in sixteen sensors). In other embodiments, other numbers of sensors are utilized in accordance with the present invention.

Light from fibers 7 is presented to sensors 8, which in a preferred embodiment pass through filters 22 to sensing elements 24. In this preferred embodiment, sensing elements 24 include light-to-frequency converters, manufactured by Texas Instruments and sold under the part number TSL230. Such converters constitute, in general, photo diode arrays that integrate the light received from fibers 7 and output an AC signal with a frequency proportional to the intensity (not frequency) of the incident light. Without being bound by theory, the basic principle of such devices is that, as the intensity increases, the integrator output voltage rises more quickly, and the shorter the integrator rise time, the greater the output frequency. The outputs of the TSL 230 sensors are TTL compatible digital signals, which may be coupled to various digital logic devices.

The outputs of sensing elements 24 are, in this embodiment, asynchronous signals of frequencies depending upon the light intensity presented to the particular sensing elements, which are presented to processor 26. In a preferred embodiment, processor 26 is a Microchip PIC16C55 or PIC16C57 microprocessor, which as described more fully herein implements an algorithm to measure the frequencies of the signals output by sensing elements 24. In other embodiments, a more integrated microprocessor/microcontroller, such as Hitachi's SH RISC microcontrollers, is utilized to provide further system integration or the like.

As previously described, processor 26 measures the frequencies of the signals output from sensing elements 24. In a preferred embodiment, processor 26 implements a software timing loop, and at periodic intervals processor 26 reads the states of the outputs of sensing elements 24. An internal counter is incremented each pass through the software timing loop. The accuracy of the timing loop generally is determined by the crystal oscillator time base (not shown in FIG. 3) coupled to processor 26 (such oscillators typically are quite stable). After reading the outputs of sensing elements 24, processor 26 performs an exclusive OR ("XOR") operation with the last data read (in a preferred embodiment such data is read in byte length). If any bit has changed, the XOR operation will produce a 1, and, if no bits have changed, the XOR operation will produce a 0. If the result is non-zero, the input byte is saved along with the value of the internal counter (that is incremented each pass through the software timing loop). If the result is zero, the systems waits (e.g., executes no operation instructions) the same amount of time as if the data had to be saved, and the looping operation continues. The process continues until all eight inputs have changed at least twice, which enables measurement of a full ½ period of each input. Upon conclusion of the looping process, processor 26 analyzes the stored input bytes and internal counter states. There should be 2 to 16 saved inputs (for the 8 total sensors of FIG. 3) and counter states (if two or more inputs change at the same time, they are saved simultaneously). As will be understood by one of skill in the art, the stored values of the internal counter contains information determinative of the period of the signals received from sensing elements 24. By proper subtraction of internal counter values at times when an input bit has changed, the period may be calculated. Such periods calculated for each of the outputs of sensing elements is provided by processor 26 to microprocessor (see, e.g., FIG. 1). From such calculated periods, a measure of the received light intensities may be calculated. In alternate embodiments, the frequency of the outputs of the TSL 230 sensors is measured directly by a similar software loop as the one described above. The outputs are monitored by the RISC processor in a software timing loop and are XORed with the previous input as described above. If a transition occurs for a particular TSL230 input, a counter register for the particular TSL230 input is incremented. The software loop is executed for a pre-determined period of time and the frequency of the input is calculated by dividing the number of transitions by the pre-determined time and scaling the result. It will also be apparent to one skilled in the art that more sophisticated measurement schemes can also be implemented whereby both the frequency and period are simultaneously measured by high speed RISC processors such as those of the Hitachi SH family.

It should be noted that the sensing circuitry and methodology illustrated in FIG. 3 have been determined to provide a practical and expedient manner in which to measure the light intensities received by sensing elements 24. In other embodiments, other circuits and methodologies are employed (such other exemplary sensing schemes are described elsewhere herein).

As discussed above with reference to FIG. 1, one or more of fibers 7 measures light source 11, which may be through a neutral density filter, which serves to reduce the intensity of the received light in order to maintain the intensity roughly in the range of the other received light intensities. A number of fibers 7 also are from perimeter receiver fiber optics R1 to R3 (see, e.g., FIG. 2) and also may pass through neutral density filters. Such receiving fibers 7 serve to provide data from which angle/height information and/or surface characteristics may be determined.

The remaining twelve fibers (of the illustrated embodiment's total of 16 fibers) of fibers 7 pass through color filters and are used to produce the color measurement. In an embodiment, the color filters are Kodak Sharp Cutting Wratten Gelatin Filters, which pass light with wavelengths greater than the cut-off value of the filter (i.e., redish values), and absorb light with wavelengths less than the cut-off value of the filter (i.e., bluish values). "Sharp Cutting" filters are available in a wide variety of cut-off frequencies/wavelengths, and the cut-off values generally may be selected by proper selection of the desired cut-off filter. In an embodiment, the filter cut-off values are chosen to cover the entire visible spectrum and, in general, to have band spacings of approximately the visible band range (or other desired range) divided by the number of receivers/filters. As an example, 700 nanometers minus 400 nanometers, divided by 11 bands (produced by twelve color receivers/sensors), is roughly nanometer band spacing.

With an array of cut-off filters as described above, and without being bound by theory or the specific embodiments described herein, the received optical spectrum may be measured/calculated by subtracting the light intensities of "adjacent" color receivers. For example, band 1 (400 nm to 430 nm)=(intensity of receiver 12) minus (intensity of receiver 11), and so on for the remaining bands. Such an array of cut-off filters, and the intensity values that may result from filtering with such an array, are more fully described in connection with FIGS. 3A to 14B.

It should be noted here that in alternate embodiments other color filter arrangements are utilized. For example, "notch" or bandpass filters may be utilized, such as may be developed using Schott glass-type filters (whether constructed from separate longpass/shortpass filters or otherwise) or notch interference filters such as those manufactured by Corion, etc.

In a preferred embodiment of the present invention, the specific characteristics of the light source, filters, sensors and fiber optics, etc., are normalized/calibrated by directing the probe towards, and measuring, a known color standard. Such normalization/calibration may be performed by placing the probe in a suitable fixture, with the probe directed from a predetermined position (i.e., height and angle) from the known color standard. Such measured normalization/calibration data may be stored, for example, in a look-up table, and used by microprocessor to normalize or correct measured color or other data. Such procedures may be conducted at start-up, at regular periodic intervals, or by operator command, etc. In particular embodiments, a large number of measurements may be taken on materials of particular characteristics and processed and/or statistically analyzed or the like, with data representing or derived from such measurements stored in memory (such as a look-up table or polynomial or other coefficients, etc.). Thereafter, based upon measurements of an object taken in accordance with the present invention, comparisons may be made with the stored data and assessments of the measured object made or predicted. In one illustrative example, an assessment or prediction may be made of whether the object is wet or dry (having water or other liquid on its surface, wet paint, etc.) based on measurements in accordance with the present invention. In yet another illustrative example, an assessment or prediction of the characteristics of an underlying material, such as the pulpal tissue within a tooth may be made. Such capabilities may be further enhanced by comparisons with measurements taken of the object at an earlier time, such as data taken of the tooth or other object at one or more earlier points in time. Such comparisons based on such historical data and/or stored data may allow highly useful assessments or predictions of the current or projected condition or status of the tooth, tissue or other object, etc. Many other industrial uses of such surface and subsurface assessment/prediction capabilities are possible.

What should be noted from the above description is that the receiving and sensing fiber optics and circuitry illustrated in FIG. 3 provide a practical and expedient way to determine the color and other optical or other characteristics by measuring the intensity of the light reflected from the surface of the object being measured.

It also should be noted that such a system measures the spectral band of the reflected light from the object, and once measured such spectral data may be utilized in a variety of ways. For example, such spectral data may be displayed directly as intensity-wavelength band values. In addition, tristimulus type values may be readily computed (through, for example, conventional matrix math), as may any other desired color values. In one particular embodiment useful in dental applications (such as for dental prostheses), the color data is output in the form of a closest match or matches of dental shade guide value(s). In a preferred embodiment, various existing shade guides (such as the shade guides produced by Vita Zahnfabrik) are characterized and stored in a look-up table, or in the graphics art industry Pantone color references, and the color measurement data are used to select the closest shade guide value or values, which may be accompanied by a confidence level or other suitable factor indicating the degree of closeness of the match or matches, including, for example, what are known as AEvalues or ranges of AE values, or criteria based on standard deviations, such as standard deviation minimization. In still other embodiments, the color measurement data are used (such as with look-up tables) to select materials for the composition of paint or ceramics such as for prosthetic teeth. There are many other uses of such spectral data measured in accordance with the present invention.

It is known that certain objects such as human teeth may fluoresce, and such optical characteristics also may be measured in accordance with the present invention. A light source with an ultraviolet component may be used to produce more accurate color/optical data with respect to such objects. Such data may be utilized to adjust the amounts and or proportions or types of dental fluorescing materials in dental restorations or prosthesis. In certain embodiments, a tungsten/halogen source (such as used in a preferred embodiment) may be combined with a UV light source (such as a mercury vapor, xenon or other fluorescent light source, etc.) to produce a light output capable of causing the object to fluoresce. Alternately, a separate UV light source, combined with a visible-light-blocking filter, may be used to illuminate the object. Such a UV light source may be combined with light from a red LED (for example) in order to provide a visual indication of when the UV light is on and also to serve as an aid for the directional positioning of the probe operating with such a light source. A second measurement may be taken using the UV light source in a manner analogous to that described earlier, with the band of the red LED or other supplemental light source being ignored. The second measurement may thus be used to produce an indication of the fluorescence of the tooth or other object being measured. With such a UV light source, a silica fiber optic (or other suitable material) typically would be required to transmit the light to the object (standard fiber optic materials such as glass and plastic in general do not propagate UV light in a desired manner, etc.).

As described earlier, in certain preferred embodiments the present invention utilizes a plurality of perimeter receiver fiber optics spaced apart from and around a central source fiber optic to measure color and determine information regarding the height and angle of the probe with respect to the surface of the object being measured, which may include other surface characteristic information, etc. Without being bound by theory, certain principles underlying certain aspects of the present invention will now be described with reference to FIGS. 4A to 4C.

Figure 4A:
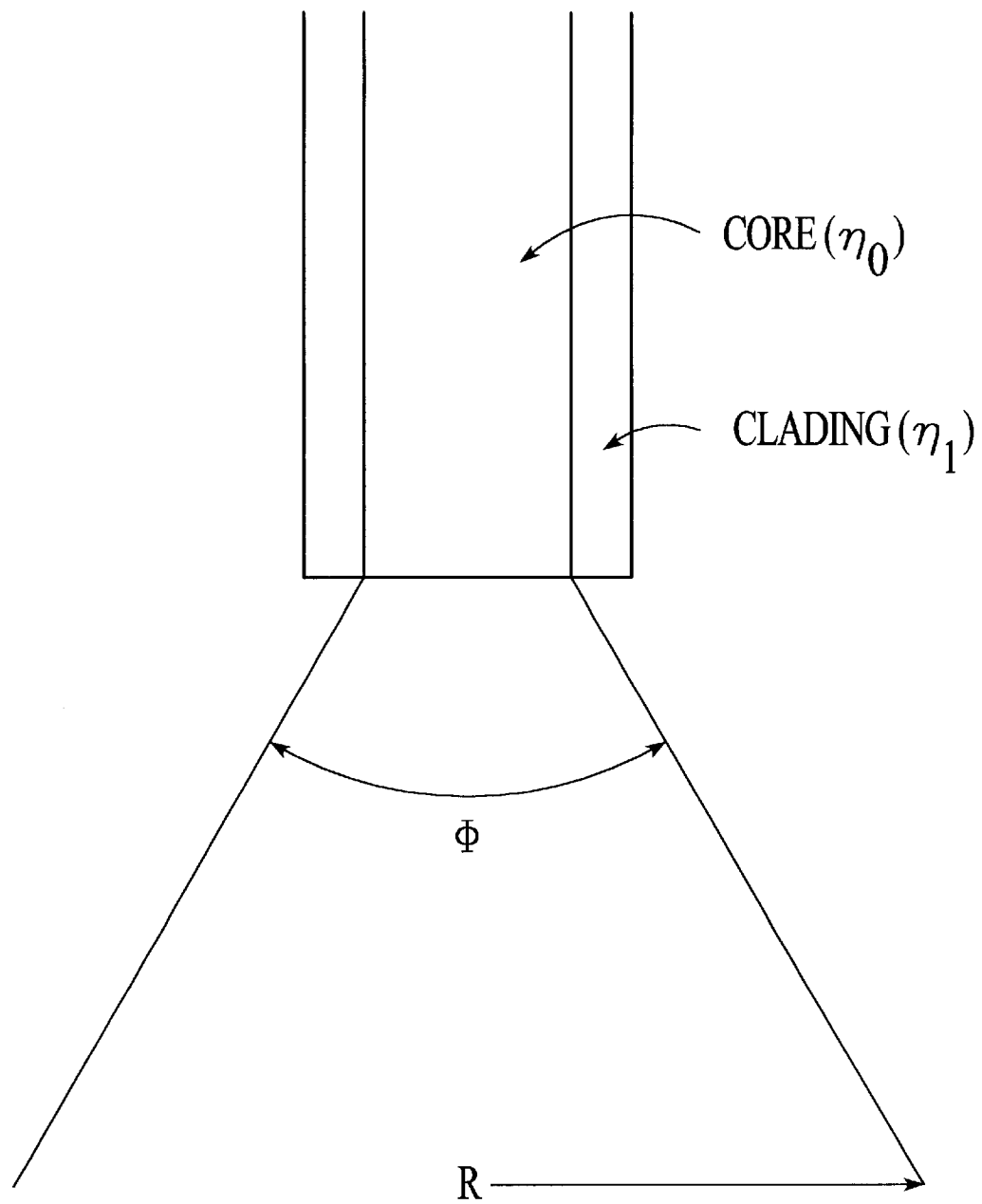
FIGS. 4A to 4C illustrate certain geometric considerations of fiber optics.

FIG. 4A illustrates a typical step index fiber optic consisting of a core and a cladding. For this discussion, it is assumed that the core has an index of refraction of $n_0$ and the cladding has an index of refraction of $n_1$. Although the following discussion is directed to "step index" fibers, it will be appreciated by those of skill in the art that such discussion generally is applicable for gradient index fibers as well.

In order to propagate light without loss, the light must be incident within the core of the fiber optic at an angle greater than the critical angle, which may be represented as $Sin^{-1}\{n_1/n_0\}$, where $n_0$ is the index of refraction of the core and $n_0$ is the index of refraction of the cladding. Thus, all light must enter the fiber at an acceptance angle equal to or less than phi, with phi=$2 \times Sin^{-1}\{\sqrt{(n_0^2-n_1^2)}\}$, or it will not be propagated in a desired manner.

For light entering a fiber optic, it must enter within the acceptance angle phi. Similarly, when the light exits a fiber optic, it will exit the fiber optic within a cone of angle phi as illustrated in FIG. 4A. The value $\sqrt{(n_0^2-n_1^2)}$ is referred to as the aperture of the fiber optic. For example, a typical fiber optic may have an aperture of 0.5, and an acceptance angle of 60°.

Consider using a fiber optic as a light source. One end is illuminated by a light source (such as light source 11 of FIG. 1), and the other is held near a surface. The fiber optic will emit a cone of light as illustrated in FIG. 4A. If the fiber optic is held perpendicular to a surface it will create a circular light pattern on the surface. As the fiber optic is raised, the radius r of the circle will increase. As the fiber optic is lowered, the radius of the light pattern will decrease. Thus, the intensity of the light (light energy per unit area) in the illuminated circular area will increase as the fiber optic is lowered and will decrease as the fiber optic is raised.

The same principle generally is true for a fiber optic being utilized as a receiver. Consider mounting a light sensor on one end of a fiber optic and holding the other end near an illuminated surface. The fiber optic can only propagate light without loss when the light entering the fiber optic is incident on the end of the fiber optic near the surface if the light enters the fiber optic within its acceptance angle phi. A fiber optic utilized as a light receiver near a surface will only accept and propagate light from the circular area of radius r on the surface. As the fiber optic is raised from the surface, the area increases. As the fiber optic is lowered to the surface, the area decreases.

Figure 4B:
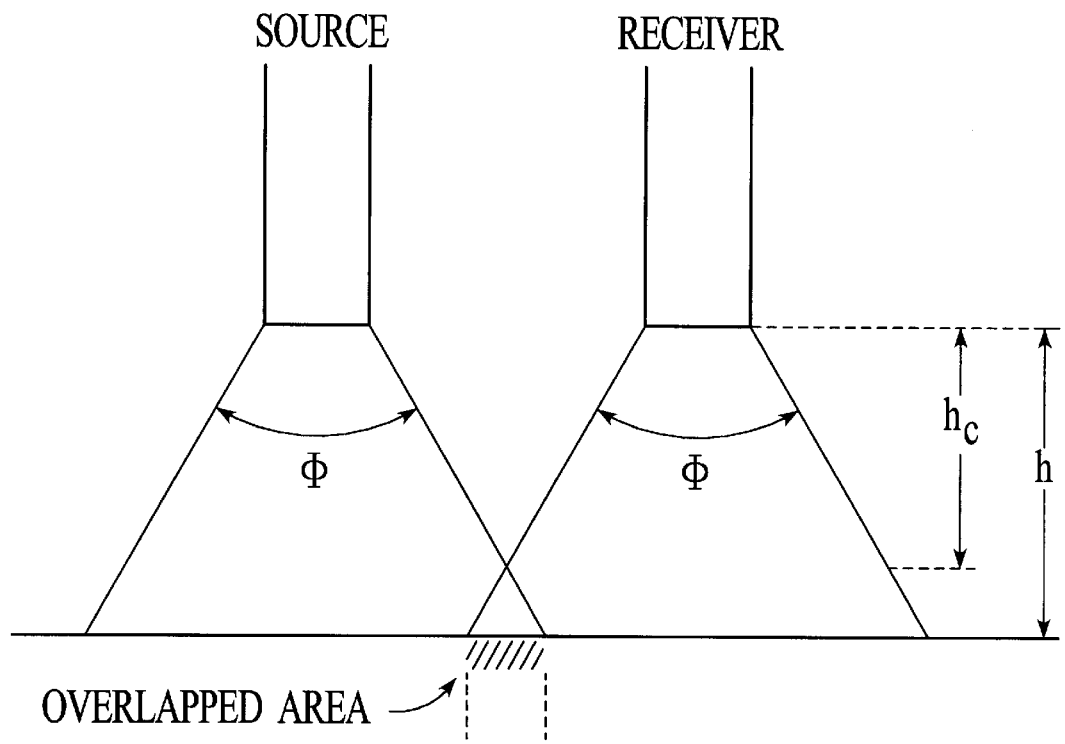
Figure 4C:
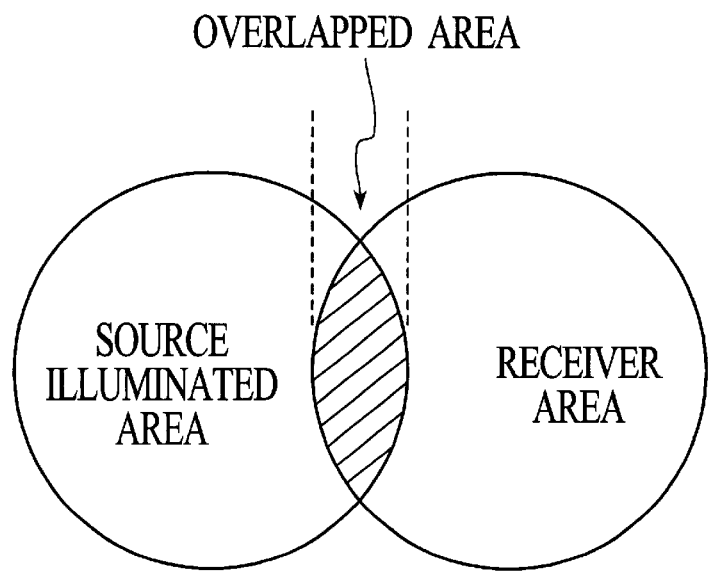

Consider two fiber optics parallel to each other as illustrated in FIG. 4B. For simplicity of discussion, the two fiber optics illustrated are identical in size and aperture. The following discussion, however, generally would be applicable for fiber optics that differ in size and aperture. One fiber optic is a source fiber optic, the other fiber optic is a receiver fiber optic. As the two fiber optics are held perpendicular to a surface, the source fiber optic emits a cone of light that illuminates a circular area of radius r. The receiver fiber optic can only accept light that is within its acceptance angle phi, or only light that is received within a cone of angle phi. If the only light available is that emitted by the source fiber optic, then the only light that can be accepted by the receiver fiber optic is the light that strikes the surface at the intersection of the two circles as illustrated in FIG. 4C. As the two fiber optics are lifted from the surface, the proportion of the intersection of the two circular areas relative to the circular area of the source fiber optic increases. As they near the surface, the proportion of the intersection of the two circular areas to the circular area of the source fiber optic decreases. If the fiber optics are held too close to the surface (i.e., at or below a "critical height" $h_c$), the circular areas will no longer intersect and no light emitted from the source fiber optic will be received by the receiver fiber optic.

As discussed earlier, the intensity of the light in the circular area illuminated by the source fiber increases as the fiber is lowered to the surface. The intersection of the two cones, however, decreases as the fiber optic pair is lowered. Thus, as the fiber optic pair is lowered to a surface, the total intensity of light received by the receiver fiber optic increases to a maximal value, and then decreases sharply as the fiber optic pair is lowered still further to the surface. Eventually, the intensity will decrease essentially to zero at or below the critical height $h_c$ (assuming the object being measured is not translucent, as described more fully herein), and will remain essentially zero until the fiber optic pair is in contact with the surface. Thus, as a source-receiver pair of fiber optics as described above are positioned near a surface and as their height is varied, the intensity of light received by the receiver fiber optic reaches a maximal value at a peaking or "peaking height" $h_p$.

Again without being bound by theory, an interesting property of the peaking height $h_p$ has been observed. The peaking height $h_p$ is a function primarily of the geometry of fixed parameters, such as fiber apertures, fiber diameters and fiber spacing. Since the receiver fiber optic in the illustrated arrangement is only detecting a maximum value and not attempting to quantify the value, its maximum in general is independent of the surface color. It is only necessary that the surface reflect sufficient light from the intersecting area of the source and receiver fiber optics to be within the detection range of the receiver fiber optic light sensor. Thus, in general red or green or blue or any color surface will all exhibit a maximum at the same peaking height $h_p$.

Although the above discussion has focused on two fiber optics perpendicular to a surface, similar analysis is applicable for fiber optic pairs at other angles. When a fiber optic is not perpendicular to a surface, it generally illuminates an elliptical area. Similarly, the acceptance area of a receiver fiber optic generally becomes elliptical. As the fiber optic pair is moved closer to the surface, the receiver fiber optic also will detect a maximal value at a peaking height independent of the surface color or characteristics. The maximal intensity value measured when the fiber optic pair is not perpendicular to the surface, however, will be less than the maximal intensity value measured when the fiber optic pair is perpendicular to the surface.

Figure 5A:
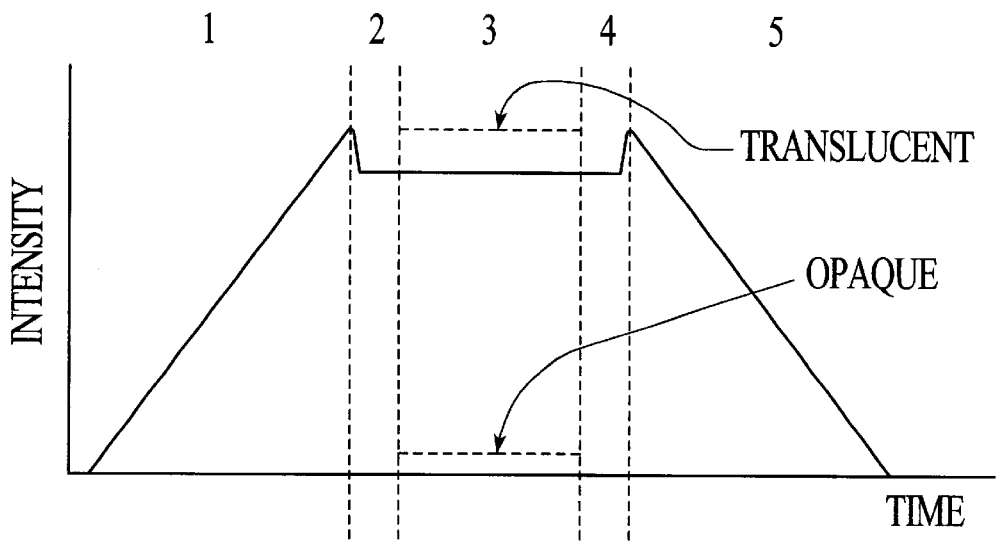
FIGS. 5A and 5B illustrate the light amplitude received by fiber optic light receivers as the receivers are moved towards and away from an object.
Figure 5B:
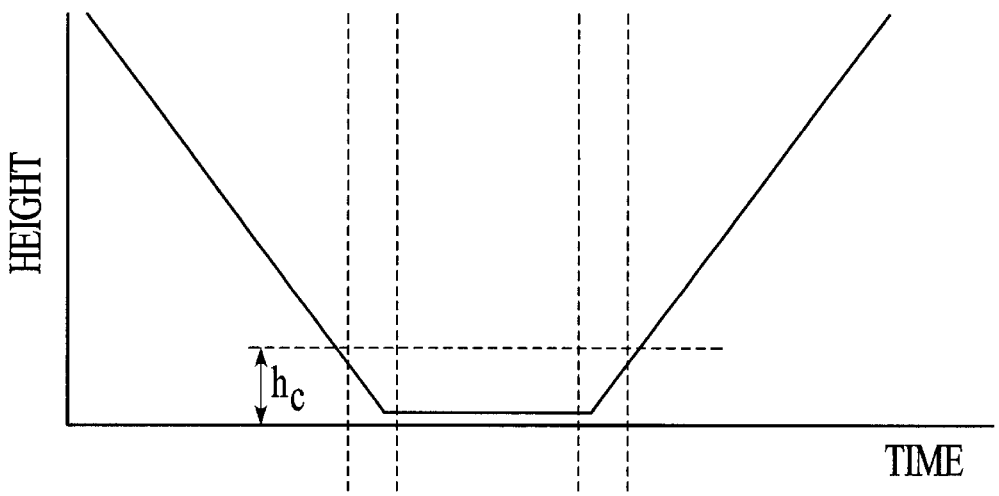

Referring now to FIGS. 5A and 5B, the intensity of light received as a fiber optic source-receiver pair is moved to and from a surface will now be described. FIG. 5A illustrates the intensity of the received light as a function of time. Corresponding FIG. 5B illustrates the height of the fiber optic pair from the surface of the object being measured. FIGS. 5A and 5B illustrate (for ease of discussion) a relatively uniform rate of motion of the fiber optic pair to and from the surface of the object being measured (although similar illustrations/analysis would be applicable for non-uniform rates as well).

FIG. 5A illustrates the intensity of received light as the fiber optic pair is moved to and then from a surface. While FIG. 5A illustrates the intensity relationship for a single receiver fiber optic, similar intensity relationships would be expected to be observed for other receiver fiber optics, such as, for example, the multiple receiver fiber optics of FIGS. 1 and 2. In general with the preferred embodiment described above, all fifteen fiber optic receivers (of fibers 7) will exhibit curves similar to that illustrated in FIG. 5A.

FIG. 5A illustrates five regions. In region 1, the probe is moved towards the surface of the object being measured, which causes the received light intensity to increase. In region 2, the probe is moved past the peaking height, and the received light intensity peaks and then falls off sharply. In region 3, the probe essentially is in contact with the surface of the object being measured. As illustrated, the received intensity in region 3 will vary depending upon the translucence of the object being measured. If the object is opaque, the received light intensity will be very low, or almost zero (perhaps out of range of the sensing circuitry). If the object is translucent, however, the light intensity will be quite high, but in general should be less than the peak value. In region 4, the probe is lifted and the light intensity rises sharply to a maximum value. In region 5, the probe is lifted further away from the object, and the light intensity decreases again.

As illustrated, two peak intensity values (discussed as P1 and P2 below) should be detected as the fiber optic pair moves to and from the object at the peaking height $h_p$. If peaks P1 and P2 produced by a receiver fiber optic are the same value, this generally is an indication that the probe has been moved to and from the surface of the object to be measured in a consistent manner. If peaks P1 and P2 are of different values, then these may be an indication that the probe was not moved to and from the surface of the object in a desired manner, or that the surface is curved or textured, as described more fully herein. In such a case, the data may be considered suspect and rejected. In addition, peaks P1 and P2 for each of the perimeter fiber optics (see, e.g., FIG. 2) should occur at the same height (assuming the geometric attributes of the perimeter fiber optics, such as aperture, diameter and spacing from the source fiber optic, etc.). Thus, the perimeter fiber optics of a probe moved in a consistent, perpendicular manner to and from the surface of the object being measured should have peaks P1 and P2 that occur at the same height. Monitoring receiver fibers from the perimeter receiver fiber optics and looking for simultaneous (or near simultaneous, e.g., within a predetermined range) peaks P1 and P2 provides a mechanism for determining if the probe is held at a desired perpendicular angle with respect to the object being measured.

In addition, the relative intensity level in region 3 serves as an indication of the level of translucency of the object being measured. Again, such principles generally are applicable to the totality of receiver fiber optics in the probe (see, e.g., fibers 7 of FIGS. 1 and 3). Based on such principles, measurement techniques that may be applicable with respect to embodiments disclosed herein will now be described.

Figure 6:
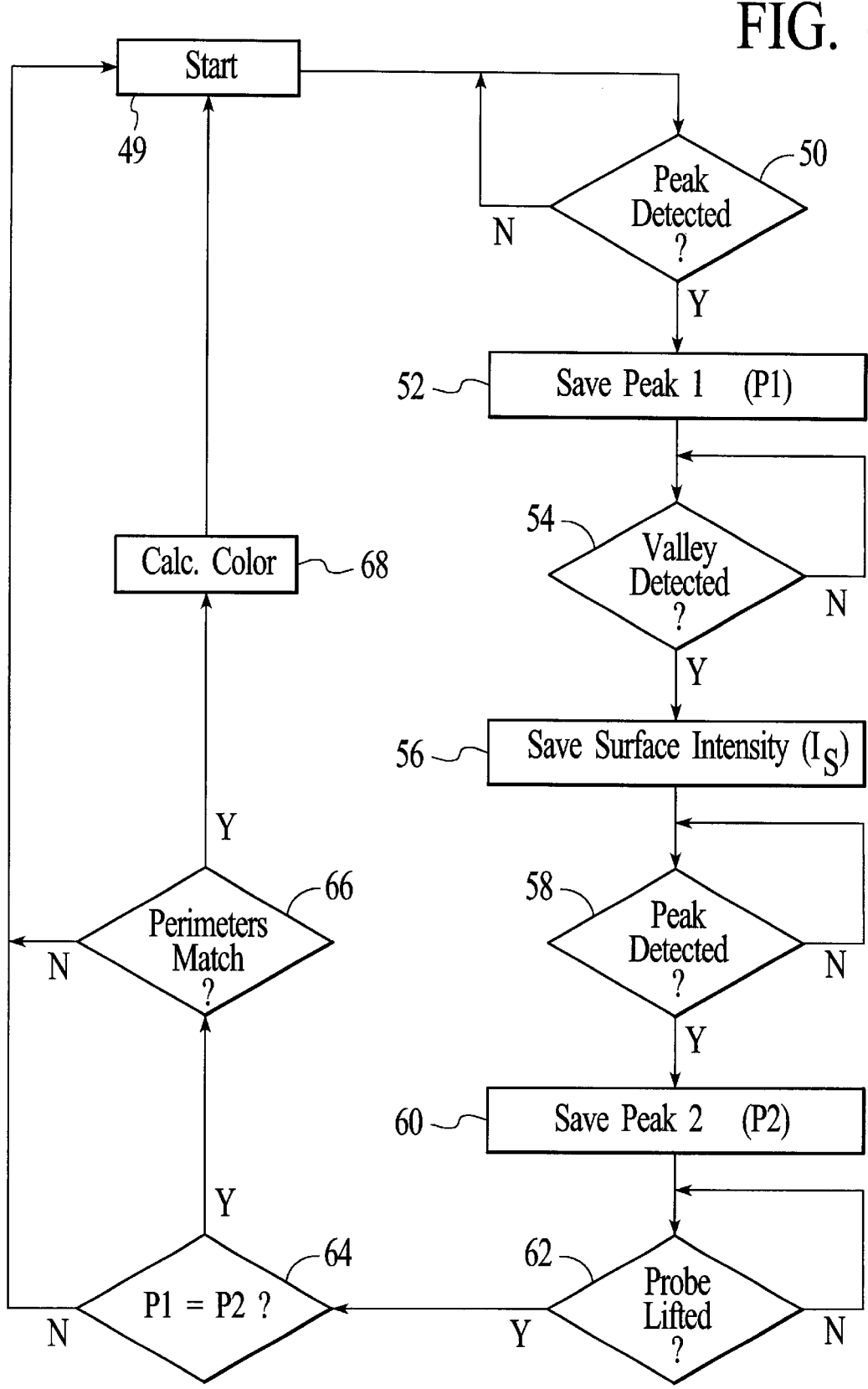
FIG. 6 is a flow chart illustrating a color measuring method in accordance with an embodiment of the present invention.

FIG. 6 is a flow chart illustrating a general measuring technique that may be used in accordance with certain embodiments of the present invention. Step 49 indicates the start or beginning of a color/optical measurement. During step 49, any equipment initialization, diagnostic or setup procedures may be performed. Audio or visual information or other indicia may be given to the operator to inform the operator that the system is available and ready to take a measurement. Initiation of the color/optical measurement commences by the operator moving the probe towards the object to be measured, and may be accompanied by, for example, activation of switch 17 (see FIG. 1).

In step 50, the system on a continuing basis monitors the intensity levels for the receiver fiber optics (see, e.g., fibers 7 of FIG. 1). If the intensity is rising, step 50 is repeated until a peak is detected. If a peak is detected, the process proceeds to step 52. In step 52, measured peak intensity P1, and the time at which such peak occurred, are stored in memory (such as in memory included as a part of microprocessor 10), and the process proceeds to step 54. In step 54, the system continues to monitor the intensity levels of the receiver fiber optics. If the intensity is falling, step 54 is repeated. If a "valley" or plateau is detected (i.e., the intensity is no longer falling, which generally indicates contact or near contact with the object), then the process proceeds to step 56. In step 56, the measured surface intensity (IS) is stored in memory, and the process proceeds to step 58. In step 58, the system continues to monitor the intensity levels of the receiver fibers. If the intensity is rising, step 58 is repeated until a peak is detected. If a peak is detected, the process proceeds to step 60. In step 60, measured peak intensity P 2, and the time at which such peak occurred, are stored in memory, and the process proceeds to step 62. In step 62, the system continues to monitor the intensity levels of the receiver fiber optics. Once the received intensity levels begin to fall from peak P2, the system perceives that region has been entered (see, e.g., FIG. 5A), and the process proceeds to step 64.

In step 64, the system, under control of microprocessor 10, may analyze the collected data taken by the sensing circuitry for the various receiver fiber optics. In step 64, peaks P1 and P2 of one or more of the various fiber optics may be compared. If any of peaks P1 and P2 for any of the various receiver fiber optics have unequal peak values, then the data may be rejected, and the entire color measuring process repeated. Again, unequal values of peaks P1 and P2 may be indicative, for example, that the probe was moved in a non-perpendicular or otherwise unstable manner (i.e., angular or lateral movement), and, for example, peak P1 may be representative of a first point on the object, while peak P2 may be representative of a second point on the object. As the data is suspect, in a preferred embodiment of the present invention, data taken in such circumstances are rejected in step 64.

If the data are not rejected in step 64, the process proceeds to step 66. In step 66, the system analyzes the data taken from the neutral-density-filtered receivers from each of the perimeter fiber optics (e.g., R1 to R3 of FIG. 2). If the peaks of the perimeter fiber optics did not occur at or about the same point in time, this may be indicative, for example, that the probe was not held perpendicular to the surface of the object being measured. As non-perpendicular alignment of the probe with the surface of the object being measured may cause suspect results, in a preferred embodiment of the present invention, data taken in such circumstances are rejected in step 66. In one preferred embodiment, detection of simultaneous or near simultaneous peaking (peaking within a predetermined range of time) serves as an acceptance criterion for the data, as perpendicular alignment generally is indicated by simultaneous or near simultaneous peaking of the perimeter fiber optics. In other embodiments, step 66 includes an analysis of peak values P1 and P2 of the perimeter fiber optics. In such embodiments, the system seeks to determine if the peak values of the perimeter fiber optics (perhaps normalized with any initial calibration data) are equal within a defined range. If the peak values of the perimeter fiber optics are within the defined range, the data may be accepted, and if not, the data may be rejected. In still other embodiments, a combination of simultaneous peaking and equal value detection are used as acceptance/rejection criteria for the data, and/or the operator may have the ability (such as through key pad switches 12) to control one or more of the acceptance criteria ranges. With such capability, the sensitivity of the system may be controllably altered by the operator depending upon the particular application and operative environment, etc.

If the data are not rejected in step 66, the process proceeds to step 68. In step 68, the color data may be processed in a desired manner to produce output color/optical measurement data. For example, such data may be normalized in some manner, or adjusted based on temperature compensation, or translucency data, or gloss data or surface texture data or non- perpendicular angle data other data detected by the system. The data also may be converted to different display or other formats, depending on the intended use of the data. In addition, the data indicative of the translucence of the object and/or glossiness of the object also may be quantified and/or displayed in step 68. After step 68, the process may proceed to starting step 49, or the process may be terminated, etc. As indicated previously, such data also may be compared with previously-stored data for purposes of making assessments or predictions, etc., of a current or future condition or status.

In accordance with the process illustrated in FIG. 6, three light intensity values (P1, P2 and IS) are stored per receiver fiber optic to make color and translucency, etc., measurements. If stored peak values P1 and P2 are not equal (for some or all of the receivers), this is an indication that the probe was not held steady over one area, and the data may be rejected (in other embodiments, the data may not be rejected, although the resulting data may be used to produce an average of the measured data). In addition, peak values P1 and P2 for the three neutral density perimeter fiber optics should be equal or approximately equal; if this is not the case, then this is an indication that the probe was not held perpendicular or a curved surface is being measured. In other embodiments, the system attempts to compensate for curved surfaces and/or non-perpendicular angles. In any event, if the system cannot make a color/optical measurement, or if the data is rejected because peak values P1 and P2 are unequal to an unacceptable degree or for some other reason, then the operator is notified so that another measurement or other action may be taken (such as adjust the sensitivity).

With a system constructed and operating as described above, color/optical measurements may be taken of an object, with accepted data having height and angular dependencies removed. Data not taken at the peaking height, or data not taken with the probe perpendicular to the surface of the object being measured, etc., are rejected in certain embodiments. In other embodiments, data received from the perimeter fiber optics may be used to calculate the angle of the probe with respect to the surface of the object being measured, and in such embodiments non-perpendicular or curved surface data may be compensated instead of rejected. It also should be noted that peak values P1 and P2 for the neutral density perimeter fiber optics provide a measurement of the luminance (gray value) of the surface of the object being measured, and also may serve to quantify the color value.

The translucency of the object being measured may be quantified as a ratio or percentage, such as, for example, (IS/P1)×100%. In other embodiments, other methods of quantifying translucency data provided in accordance with the present invention are utilized, such as some other arithmetic function utilizing IS and P1 or P2, etc. Translucence information, as would be known to those in the art, could be used to quantify and/or adjust the output color data, etc.

In another particular aspect of the present invention, data generated in accordance with the present invention may be used to implement an automated material mixing/generation machine and/or method. Certain objects/materials, such as dental prostheses or fillings, are made from porcelain or other powders/resins/materials or tissue substitutes that may be combined in the correct ratios or modified with additives to form the desired color of the object/prosthesis.

Certain powders often contain pigments that generally obey Beer's law and/or act in accordance with Kubelka-Munk equations and/or Saunderson equations (if needed) when mixed in a recipe.

Color and other data taken from a measurement in accordance with the present invention may be used to determine or predict desired quantities of pigment or other materials for the recipe. Porcelain powders and other materials are available in different colors, opacities, etc. Certain objects, such as dental prostheses, may be layered to simulate the degree of translucency of the desired object (such as to simulate a human tooth). Data generated in accordance with the present invention also may be used to determine the thickness and position of the porcelain or other material layers to more closely produce the desired color, translucency, surface characteristics, etc. In addition, based on fluorescence data for the desired object, the material recipe may be adjusted to include a desired quantity of fluorescing-type material. In yet other embodiments, surface characteristics (such as texture) information (as more fully described herein) may be used to add a texturing material to the recipe, all of which may be carried out in accordance with the present invention. In yet other embodiments, the degree of surface polish to the prosthesis may be monitored or adjusted, based on gloss data derived in accordance with the present invention.

For more information regarding such pigment-material recipe type technology, reference may be made to: "The Measurement of Appearance," Second Edition, edited by Hunter and Harold, copyright 1987; "Principles of Color Technology," by Billmeyer and Saltzman, copyright 1981; and "Pigment Handbook," edited by Lewis, copyright 1988. All of the foregoing are believed to have been published by John Wiley & Sons, Inc., New York, N.Y., and all of which are hereby incorporated by reference.

In certain operative environments, such as dental applications, contamination of the probe is of concern. In certain embodiments of the present invention, implements to reduce such contamination are provided.

Figure 7A:
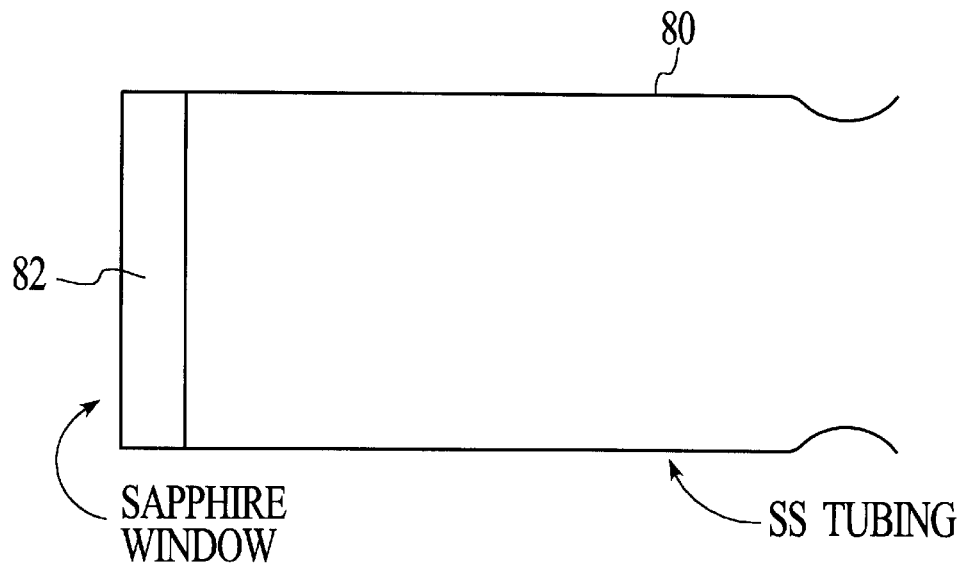
FIGS. 7A and 7B illustrate a protective cap that may be used with certain embodiments of the present invention.
Figure 7B:
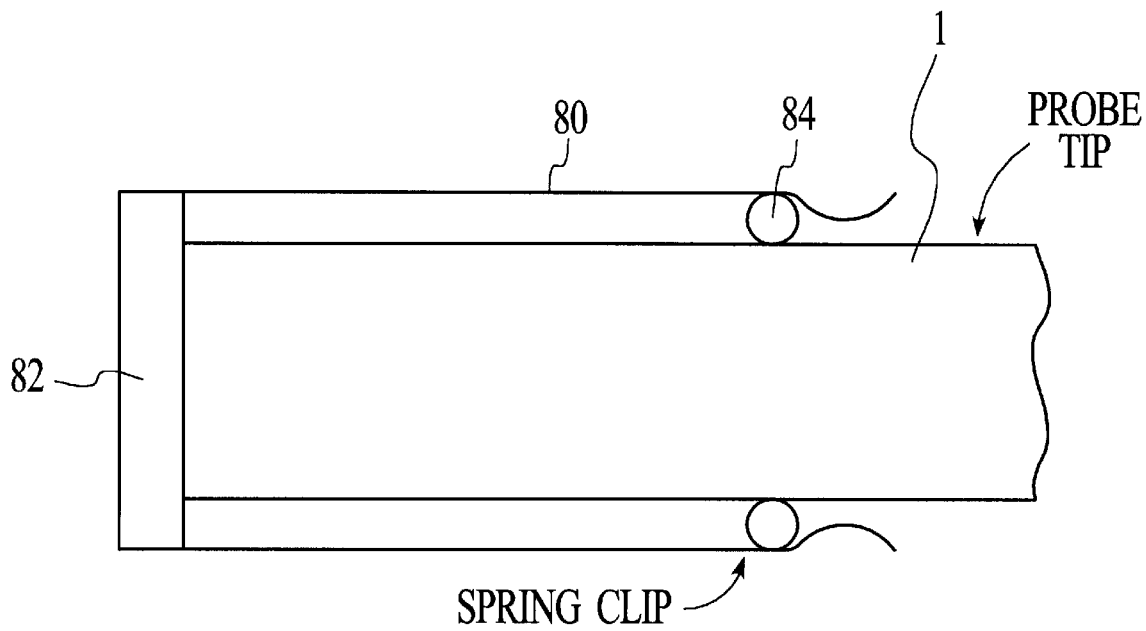

FIGS. 7A and 7B illustrate a protective cap that may be used to fit over the end of probe tip 1. Such a protective cap consists of body 80, the end of which is covered by optical window 82, which in a preferred embodiment consists of a structure having a thin sapphire window. In a preferred embodiment, body 80 consists of stainless steel. Body 80 fits over the end of probe tip 1 and may be held into place by, for example, indentations formed in body 80, which fit with ribs 84 (which may be a spring clip or other retainer) formed on probe tip 1. In other embodiments, other methods of affixing such a protective cap to probe tip 1 are utilized. The protective cap may be removed from probe tip 1 and sterilized in a typical autoclave, hot steam, chemiclave or other sterilizing system.

The thickness of the sapphire window should be less than the peaking height of the probe in order to preserve the ability to detect peaking in accordance with the present invention, and preferably has a thickness less than the critical height at which the source/receiver cones overlap (see FIGS. 4B and 4C). It also is believed that sapphire windows may be manufactured in a reproducible manner, and thus any light attenuation from one cap to another may be reproducible. In addition, any distortion of the color/optical measurements produced by the sapphire window may be calibrated out by microprocessor 10.

Similarly, in other embodiments body 80 has a cap with a hole in the center (as opposed to a sapphire window), with the hole positioned over the fiber optic source/receivers The cap with the hole serves to prevent the probe from coming into contact with the surface, thereby reducing the risk of contamination. It should be noted that, with such embodiments, the hole is positioned so that the light from/to the light source/receiver elements of the probe tip is not adversely affected by the cap.

Figure 8A:
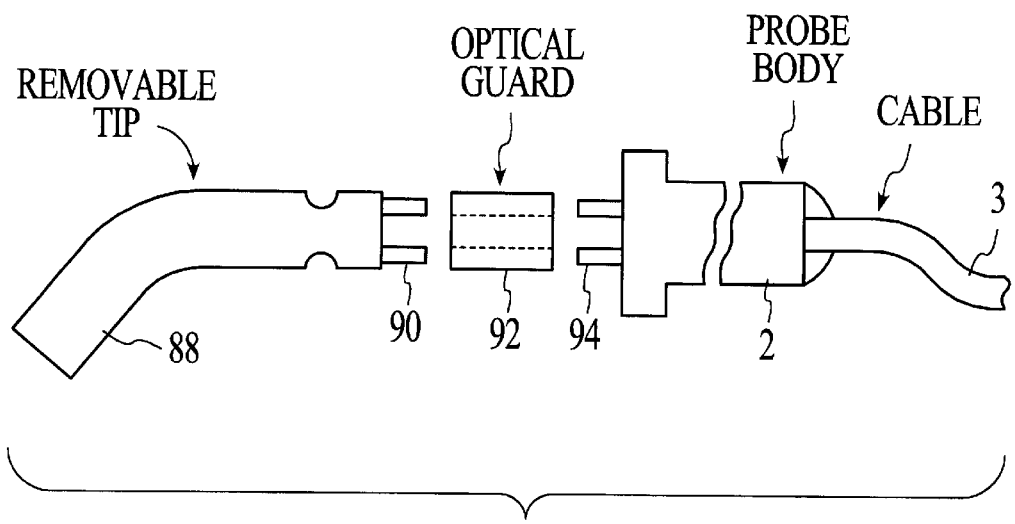
FIGS. 8A and 8B illustrate removable probe tips that may be used with certain embodiments of the present invention.
Figure 8B:
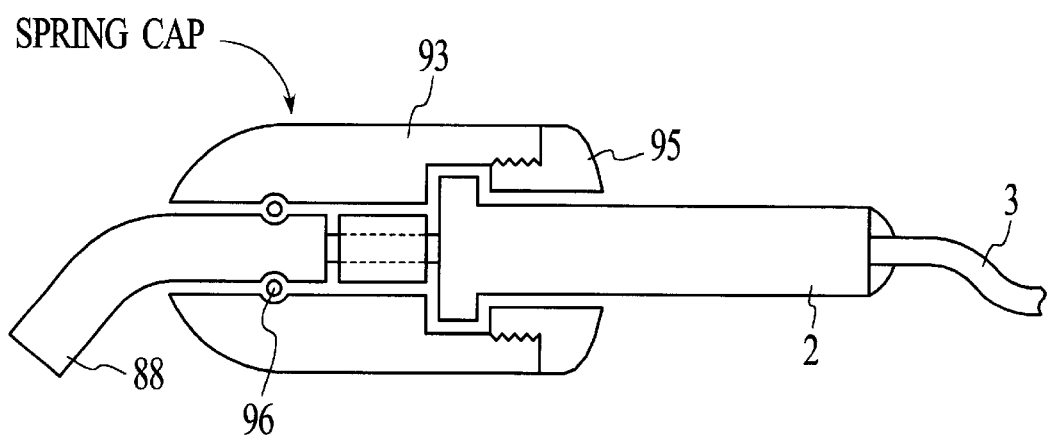

FIGS. 8A and 8B illustrate another embodiment of a removable probe tip that may be used to reduce contamination in accordance with the present invention. As illustrated in FIG. 8A, probe tip 88 is removable, and includes four (or a different number, depending upon the application) fiber optic connectors 90, which are positioned within optical guard 92 coupled to connector 94. Optical guard 92 serves to prevent "cross talk" between adjacent fiber optics. As illustrated in FIG. 8B, in this embodiment removable tip 88 is secured in probe tip housing 93 by way of spring clip 96 (other removable retaining implements are utilized in other embodiments). Probe tip housing 93 may be secured to base connector 95 by a screw or other conventional fitting. It should be noted that, with this embodiment, different size tips may be provided for different applications, and that an initial step of the process may be to install the properly-sized (or fitted tip) for the particular application. Removable tip 88 also may be sterilized in a typical autoclave, hot steam, chemiclave or other sterilizing system, or disposed of. In addition, the entire probe tip assembly is constructed so that it may be readily disassembled for cleaning or repair. In certain embodiments the light source/receiver elements of the removable tip are constructed of glass, silica or similar materials, thereby making them particularly suitable for autoclave or similar high temperature/pressure cleaning methods, which in certain other embodiments the light source/receiver elements of the removable tip are constructed of plastic or other similar materials, which may be of lower cost, thereby making them particularly suitable for disposable-type removable tips, etc.

In still other embodiments, a plastic, paper or other type shield (which may be disposable, cleanable/reusable or the like) may be used in order to address any contamination concerns that may exist in the particular application. In such embodiments, the methodology may include positioning such a shield over the probe tip prior to taking color/optical measurements, and may include removing and disposing/cleaning the shield after taking color/optical measurements, etc.

Figure 23A:
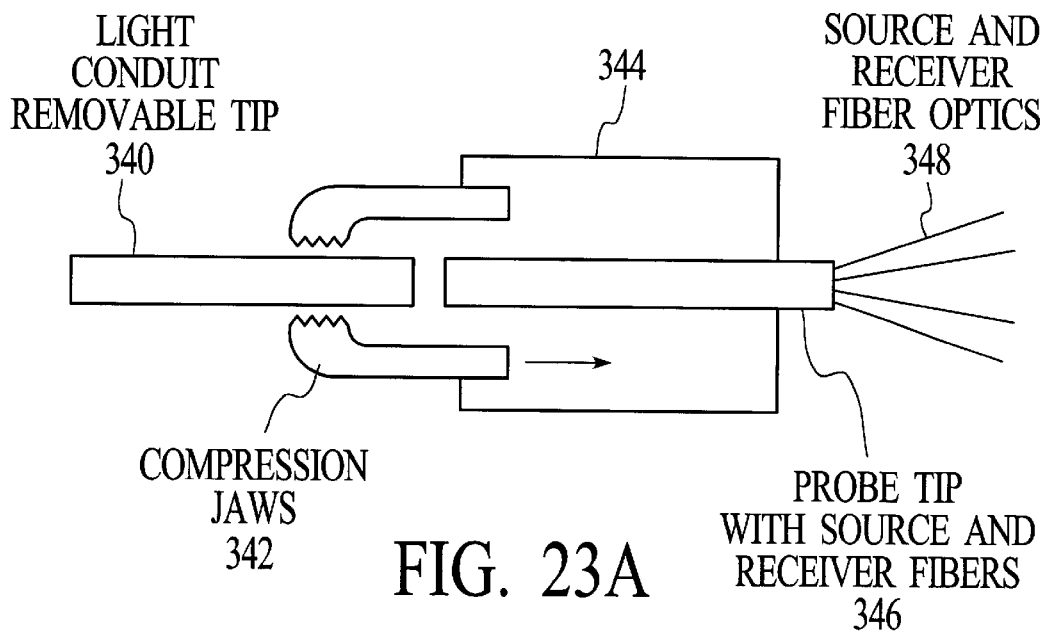
FIGS. 23A to 23C illustrate embodiments of the present invention in which coherent light conduits may serve as removable probe tips.
Figure 23B:
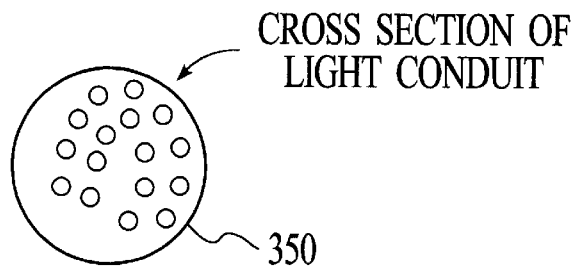

A further embodiment of the present invention utilizing an alternate removable probe tip will now be described with reference to FIGS. 23A–23C. As illustrated in FIG. 23A, this embodiment utilizes removable, coherent light conduit 340 as a removable tip. Light conduit 340 is a short segment of a light conduit that preferably may be a fused bundle of small fiber optics, in which the fibers are held essentially parallel to each other, and the ends of which are highly polished. Cross-section 350 of light conduit 340 is illustrated in FIG. 23B. Light conduits similar to light conduit 340 have been utilized in what are known as borescopes, and also have been utilized in medical applications such as endoscopes.

Light conduit 340 in this embodiment serves to conduct light from the light source to the surface of the object being measured, and also to receive reflected light from the surface and conduct it to light receiver fiber optics 346 in probe handle 344. Light conduit 340 is held in position with respect to fiber optics 346 by way or compression jaws 342 or other suitable fitting or coupled that reliably positions light conduit 340 so as to couple light effectively to/from fiber optics 346. Fiber optics 346 may be separated into separate fibers/light conduits 348, which may be coupled to appropriate light sensors, etc., as with previously described embodiments.

In general, the aperture of the fiber optics used in light conduit 340 may be chosen to match the aperture of the fiber optics f or the light source and the light receivers or alternately the light conduit aperture could be greater than or equal to the largest source or receiver aperture. Thus, the central part of the light conduit may conduct light from the light source and illuminate the surface as if it constituted a single fiber within a bundle of fibers. Similarly, the outer portion of the light conduit may receive reflected light and conduct it to light receiver fiber optics as if it constituted single fibers. Light conduit 340 has ends that preferably are highly polished and cut perpendicular, particularly the end coupling light to fiber optics 346. Similarly, the end of fiber optics 346 abutting light conduit 340 also is highly polished and cut perpendicular to a high degree of accuracy in order to minimize light reflection and cross talk between the light source fiber optic and the light receiver fiber optics and between adjacent receiver fiber optics. Light conduit 340 offers significant advantages including in the manufacture and installation of such a removable tip. For example, the probe tip need not be particularly aligned with the probe tip holder; rather, it only needs to be held against the probe tip holder such as with a compression mechanism (such as with compression jaws 342) so as to couple light effectively to/from fiber optics 346. Thus, such a removable tip mechanism may be implemented without alignment tabs or the like, thereby facilitating easy installation of the removable probe tip. Such an easy installable probe tip may thus be removed and cleaned prior to installation, thereby facilitating use of the color/optical measuring apparatus by dentists, medical professions or others working in an environment in which contamination may be a concern. Light conduit 340 also may be implemented, for example, as a small section of light conduit, which may facilitate easy and low cost mass production and the like.

Figure 23C:
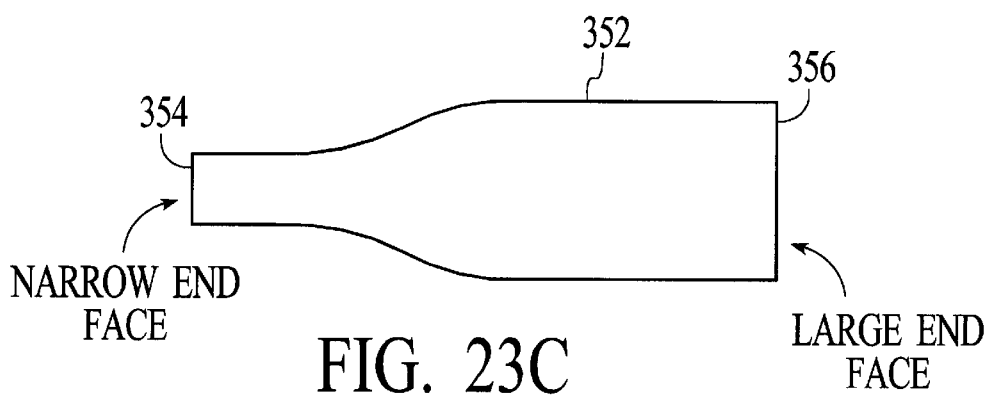

A further embodiment of such a light conduit probe tip is illustrated as light conduit 352 in FIG. 23C. Light conduit 352 is a light conduit that is narrower on one end (end 354) than the other end (end 356). Contoured/tapered light conduits such as light conduit 352 may be fabricated by heating and stretching a bundle of small fiber optics as part of the fusing process. Such light conduits have an additional interesting property of magnification or reduction. Such phenomena result because there are the same number of fibers in both ends. Thus, light entering narrow end 354 is conducted to wider end 356, and since wider end 356 covers a larger area, it has a magnifying affect.

Light conduit 352 of FIG. 23C may be utilized in a manner similar to light conduit 340 (which in general may be cylindrical) of FIG. 23A. Light conduit 352, however, measures smaller areas because of its reduced size at end 354. Thus, a relatively larger probe body may be manufactured where the source fiber optic is spaced widely from the receiver fiber optics, which may provide an advantage in reduced light reflection and cross talk at the junction, while still maintaining a small probe measuring area. Additionally, the relative sizes of narrow end 354 of light conduit 352 may be varied. This enables the operator to select the size/characteristic of the removable probe tip according to the conditions in the particular application. Such ability to select sizes of probe tips provides a further advantage in making optical characteristics measurements in a variety of applications and operative environments.

As should be apparent to those skilled in the art in view of the disclosures herein, light conduits 340 and 356 of FIGS. 23A and 23C need not necessarily be cylindrical/tapered as illustrated, but may be curved such as for specialty applications, in which a curved probe tip may be advantageously employed (such as in a confined or hard-to-reach place). It also should be apparent that light conduit 352 of FIG. 23C may be reversed (with narrow end 354 coupling light into fiber optics 346, etc., and wide end 356 positioned in order to take measurements) in order to cover larger areas.

Figure 9:
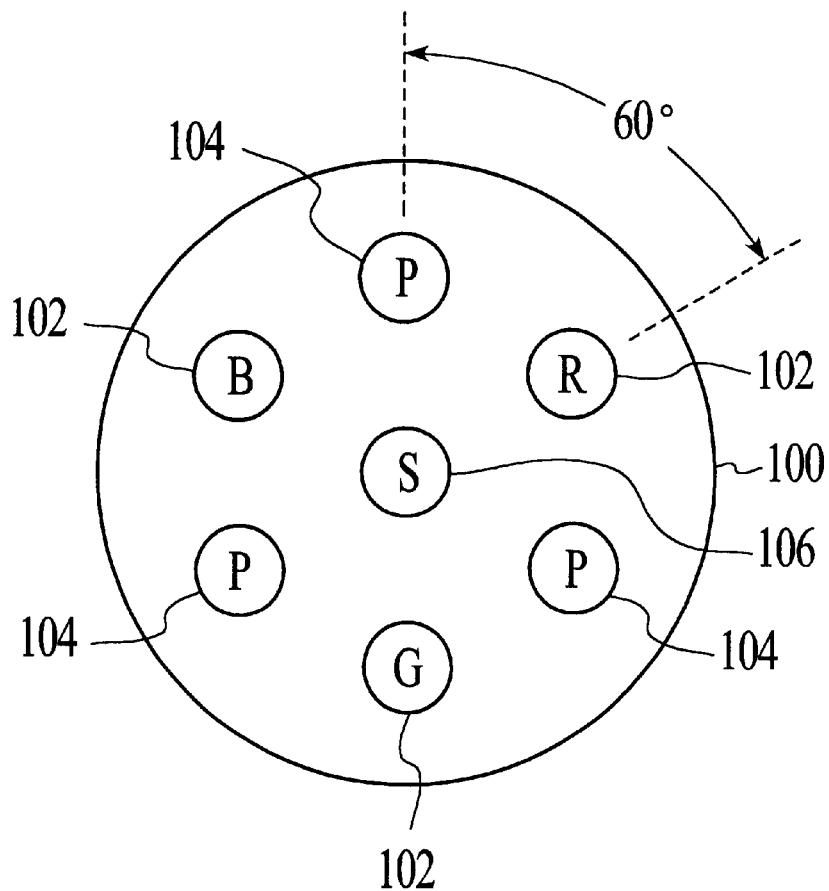
FIG. 9 illustrates a fiber optic bundle in accordance with another embodiment, which may serve to further the understanding of preferred embodiments of the present invention.

With reference to FIG. 9, a tristimulus embodiment will now be described, which may aid in the understanding of, or may be used in conjunction with, certain embodiments disclosed herein. In general, the overall system depicted in FIG. 1 and discussed in detail elsewhere herein may be used with this embodiment. FIG. 9 illustrates a cross section of the probe tip fiber optics used in this embodiment.

Probe tip 100 includes central source fiber optic 106, surrounded by (and spaced apart from) three perimeter receiver fiber optics 104 and three color receiver fiber optics 102. Three perimeter receiver fiber optics 104 are optically coupled to neutral density filters and serve as height/angle sensors in a manner analogous to the embodiment describe above. Three color receiver fiber optics are optically coupled to suitable tristimulus filters, such as red, green and blue filters. With this embodiment, a measurement may be made of tristimulus color values of the object, and the process described with reference to FIG. 6 generally is applicable to this embodiment. In particular, perimeter fiber optics 104 may be used to detect simultaneous peaking or otherwise whether the probe is perpendicular to the object being measured.

Figure 10A:
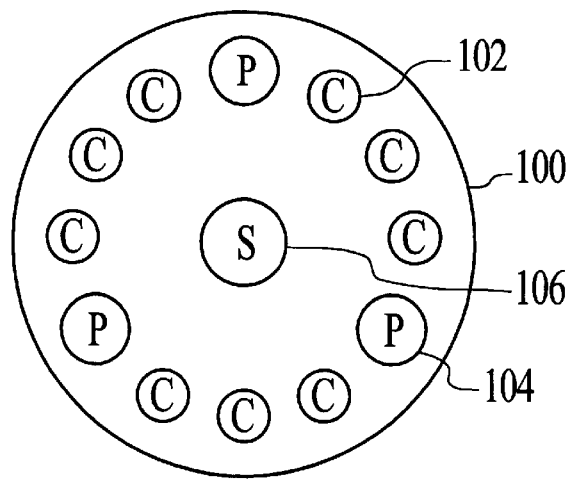
FIGS. 10A, 10B, 10C and 10D illustrate and describe other fiber optic bundle configurations and principles, which may serve to further the understanding of preferred embodiments of the present invention.

FIG. 10A illustrates another such embodiment, similar to the embodiment discussed with reference to FIG. 9. Probe tip 100 includes central source fiber optic 106, surrounded by (and spaced apart from) three perimeter receiver fiber optics 104 and a plurality of color receiver fiber optics 102. The number of color receiver fiber optics 102, and the filters associated with such receiver fiber optics 102, may be chosen based upon the particular application. As with the embodiment of FIG. 9, the process described with reference to FIG. 6 generally is applicable to this embodiment.

Figure 10B:
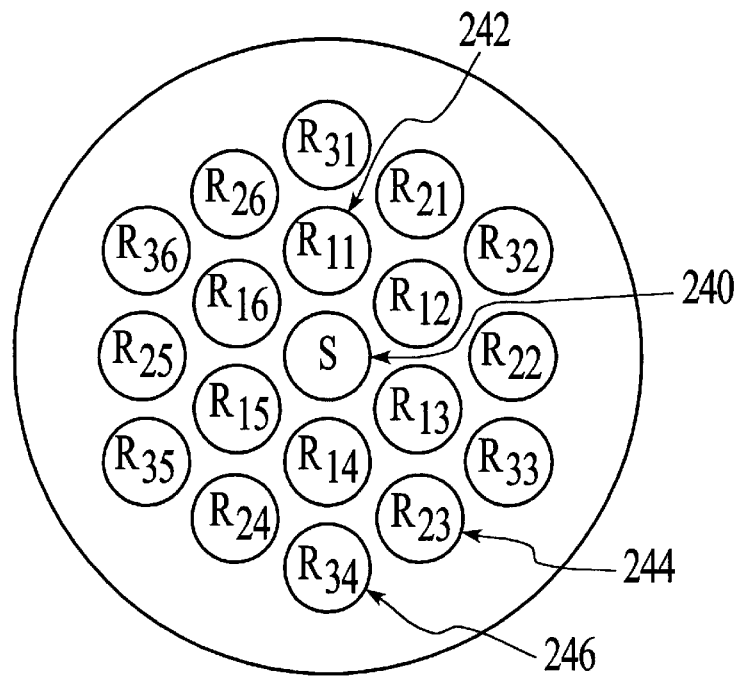

FIG. 10B illustrates another such embodiment in which there are a plurality of receiver fiber optics that surround central source fiber optic 240. The receiver fiber optics are arranged in rings surrounding the central source fiber optic. FIG. 10B illustrates three rings of receiver fiber optics (consisting of fiber optics 242, 244 and 246, respectively), in which there are six receiver fiber optics per ring. The rings may be arranged in successive larger circles as illustrated to cover the entire area of the end of the probe, with the distance from each receiver fiber optic within a given ring to the central fiber optic being equal (or approximately so). Central fiber optic 240 is utilized as the light source fiber optic and is connected to the light source in a manner similar to light source fiber optic illustrated in FIG. 1.

The plurality of receiver fiber optics are each coupled to two or more fiber optics in a manner similar to the arrangement illustrated in FIG. 1 for splicing connector 4. One fiber optic from such a splicing connector for each receiver fiber optic passes through a neutral density filter and then to light sensor circuitry similar to the light sensor circuitry illustrated in FIG. 3. A second fiber optic from the splicing connector per receiver fiber optic passes through a Sharp Cutting Wrattan Gelatin Filter (or notch filter as previously described) and then to light sensor circuitry as discussed elsewhere herein. Thus, each of the receiver fiber optics in the probe tip includes both color measuring elements and neutral light measuring or "perimeter" elements.

Figure 10C:
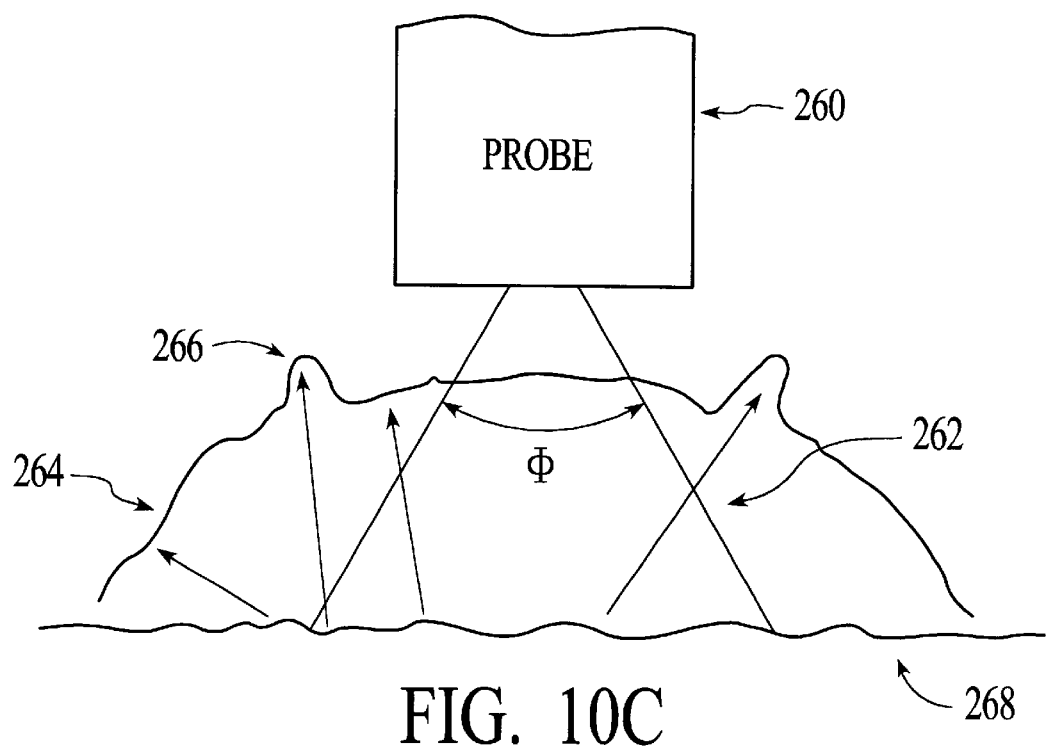
Figure 10D:
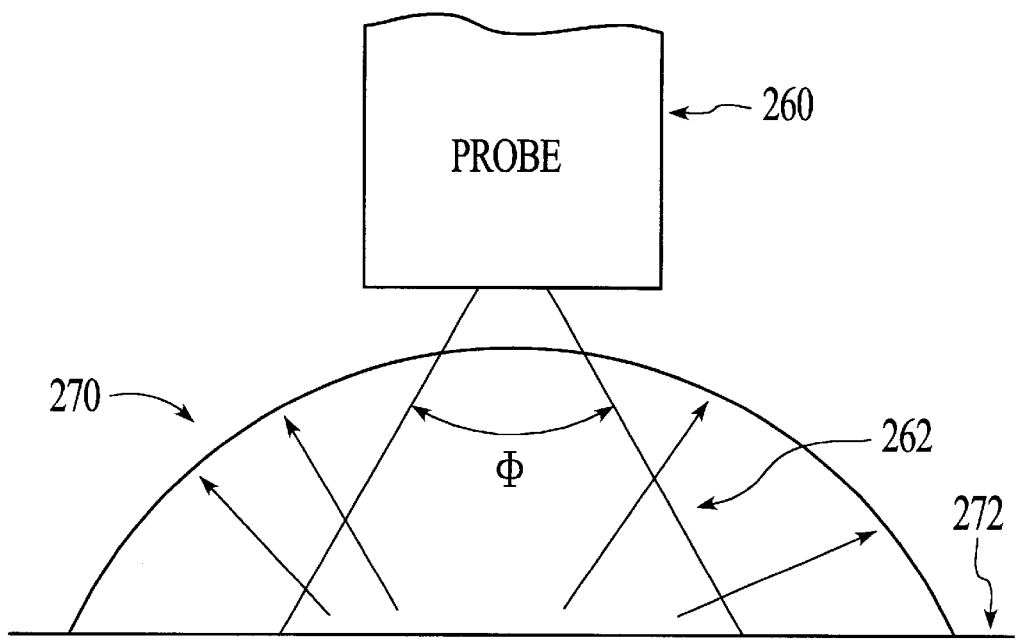

FIG. 10D illustrates the geometry of probe 260 (such as described above) illuminating an area on flat diffuse surface 272. Probe 260 creates light pattern 262 that is reflected diffusely from surface 272 in uniform hemispherical pattern 270. With such a reflection pattern, the reflected light that is incident upon the receiving elements in the probe will be equal (or nearly equal) for all elements if the probe is perpendicular to the surface as described above herein.

FIG. 10C illustrates a probe illuminating rough surface 268 or a surface that reflects light unevenly. The reflected light will exhibit hot spots or regions 266 where the reflected light intensity is considerably greater than it is on other areas 264. The reflected light pattern will be uneven when compared to a smooth surface as illustrate in FIG. 10D.

Since a probe as illustrated in FIG. 10B has a plurality of receiver fiber optics arranged over a large surface area, the probe may be utilized to determine the surface texture of the surface as well as being able to measure the color and translucency, etc., of the surface as described earlier herein. If the light intensity received by the receiver fiber optics is equal for all fiber optics within a given ring of receiver fiber optics, then generally the surface is smooth. If, however, the light intensity of receiver fibers in a ring varies with respect to each other, then generally the surface is rough. By comparing the light intensities measured within receiver fiber optics in a given ring and from ring to ring, the texture and other characteristics of the surface may be quantified.

Figure 11:
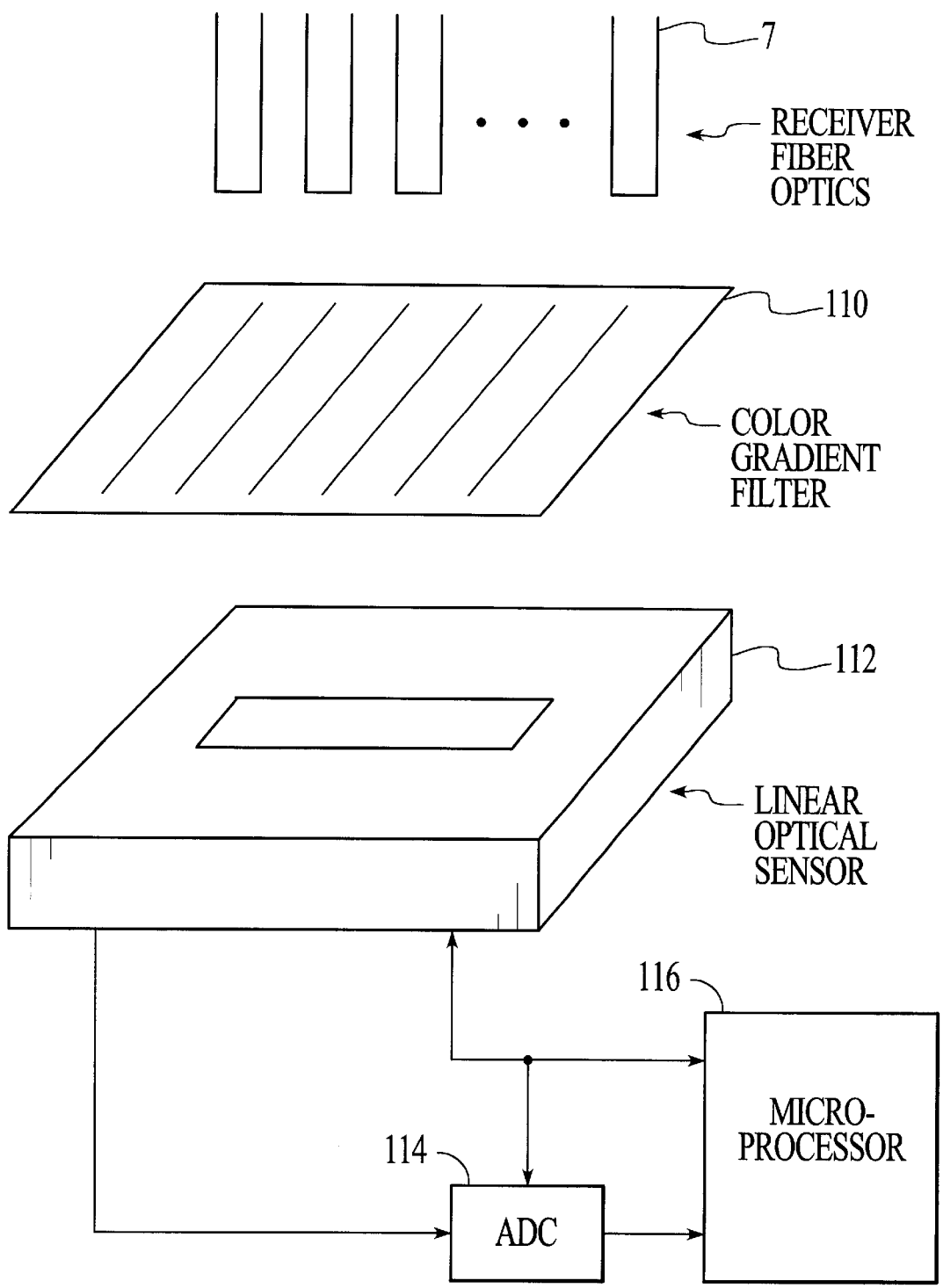
FIG. 11 illustrates a linear optical sensor array that may be used in certain embodiments of the present invention.

FIG. 11 illustrates an embodiment of the present invention in which linear optical sensors and a color gradient filter are utilized instead of light sensors 8 (and filters 22, etc.). Receiver fiber optics 7, which may be optically coupled to probe tip 1 as with the embodiment of FIG. 1, are optically coupled to linear optical sensor 112 through color gradient filter 110. In this embodiment, color gradient filter 110 may consist of series of narrow strips of cut-off type filters on a transparent or open substrate, which are constructed so as to positionally correspond to the sensor areas of linear optical sensor 112. An example of a commercially available linear optical sensor 112 is Texas Instruments part number TSL213, which has 61 photo diodes in a linear array. Light receiver fiber optics 7 are arranged correspondingly in a line over linear optical sensor 112. The number of receiver fiber optics may be chosen for the particular application, so long as enough are included to more or less evenly cover the full length of color gradient filter 110. With this embodiment, the light is received and output from receiver fiber optics 7, and the light received by linear optical sensor 112 is integrated for a short period of time (determined by the light intensity, filter characteristics and desired accuracy). The output of linear array sensor 112 is digitized by ADC 114 and output to microprocessor 116 (which may be the same processor as microprocessor or another processor).

In general, with the embodiment of FIG. 11, perimeter receiver fiber optics may be used as with the embodiment of FIG. 1, and in general the process described with reference to FIG. 6 is applicable to this embodiment.

Figure 12:
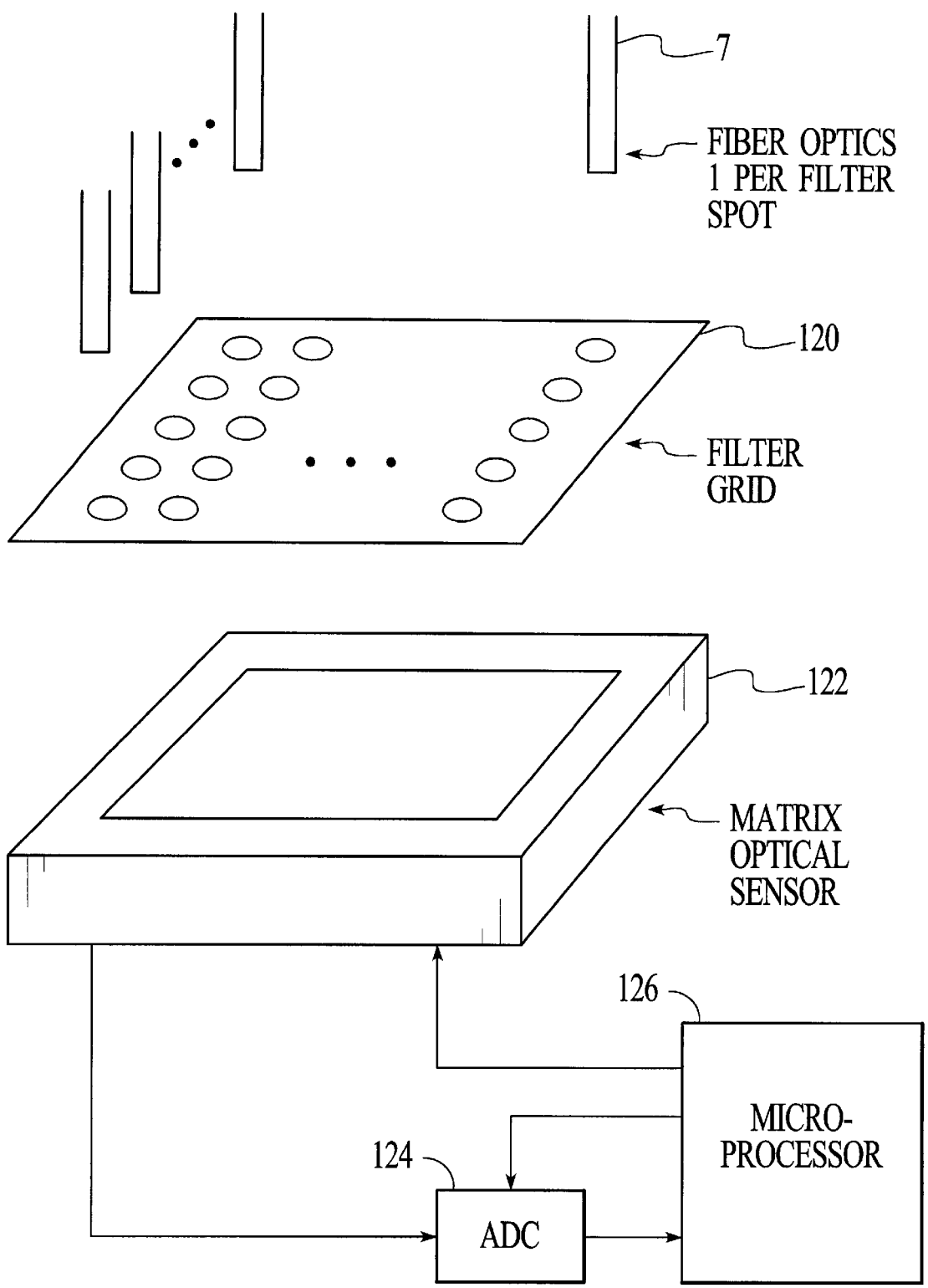
FIG. 12 illustrates a matrix optical sensor array that may be used in certain embodiments of the present invention.

FIG. 12 illustrates an embodiment of the present invention in which a matrix optical sensor and a color filter grid are utilized instead of light sensors 8 (and filters 22, etc.). Receiver fiber optics 7, which may be optically coupled to probe tip 1 as with the embodiment of FIG. 1, are optically coupled to matrix optical sensor 122 through filter grid 120. Filter grid 120 is a filter array consisting of a number of small colored spot filters that pass narrow bands of visible light. Light from receiver fiber optics 7 pass through corresponding filter spots to corresponding points on matrix optical sensor 122. In this embodiment, matrix optical sensor 122 may be a monochrome optical sensor array, such as CCD-type or other type of light sensor element such as may be used in a video camera. The output of matrix optical sensor 122 is digitized by ADC 124 and output to microprocessor 126 (which may the same processor as microprocessor or another processor). Under control of microprocessor 126, matrix optical sensor 126 collects data from receiver fiber optics 7 through color filter grid 120.

In general, with the embodiment of FIG. 12, perimeter receiver fiber optics may be used as with the embodiment of FIG. 1, and in general the process described with reference to FIG. 6 also is applicable to this embodiment.

In general with the embodiments of FIGS. 11 and 12, the color filter grid may consist of sharp cut off filters as described earlier or it may consist of notch filters. As will be apparent to one skilled in the art, they may also be constructed of a diffraction grating and focusing mirrors such as those utilized in conventional monochromators.

As will be clear from the foregoing description, with the present invention a variety of types of spectral color/optical photometers (or tristimulus-type colorimeters) may be constructed, with perimeter receiver fiber optics used to collect color/optical data essentially free from height and angular deviations. In addition, in certain embodiments, the present invention enables color/optical measurements to be taken at a peaking height from the surface of the object being measured, and thus color/optical data may be taken without physical contact with the object being measured (in such embodiments, the color/optical data is taken only by passing the probe through region 1 and into region 2, but without necessarily going into region 3 of FIGS. 5A and 5B). Such embodiments may be utilized if contact with the surface is undesirable in a particular application. In the embodiments described earlier, however, physical contact (or near physical contact) of the probe with the object may allow all five regions of FIGS. 5A and 5B to be utilized, thereby enabling measurements to be taken such that translucency information also may be obtained. Both types of embodiments generally are within the scope of the invention described herein.

Figure 13A:
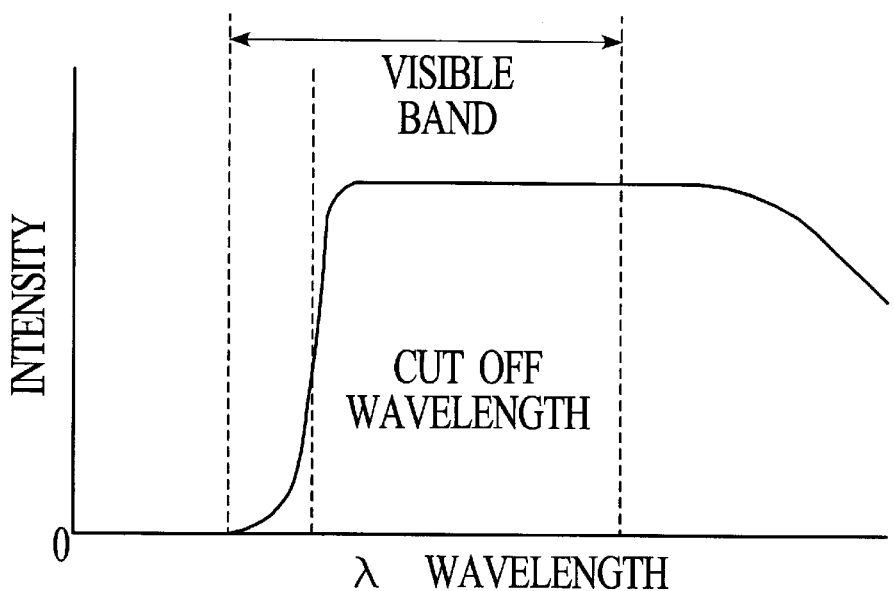
FIGS. 13A and 13B illustrate certain optical properties of a filter array that may be used in certain embodiments of the present invention.
Figure 13B:
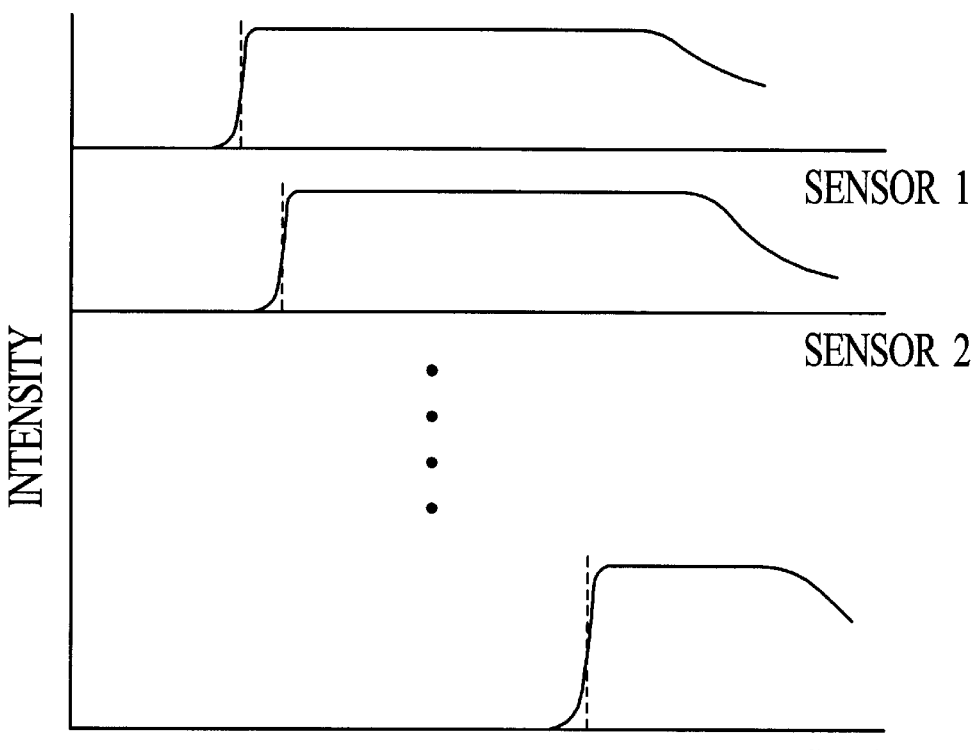

Additional description will now be provided with respect to cut-off filters of the type described in connection with the preferred embodiment(s) of FIGS. 1 and 3 (such as filters 22 of FIG. 3). FIG. 13A illustrates the properties of a single Kodak Sharp Cutting Wratten Gelatin Filter discussed in connection with FIG. 3. Such a cut-off filter passes light below a cut-off frequency (i.e., above a cut-off wavelength). Such filters may be manufactured to have a wide range of cut-off frequencies/wavelengths. FIG. 13B illustrates a number of such filters, twelve in a preferred embodiment, with cut-off frequencies/wavelengths chosen so that essentially the entire visible band is covered by the collection of cut-off filters.

Figure 14A:
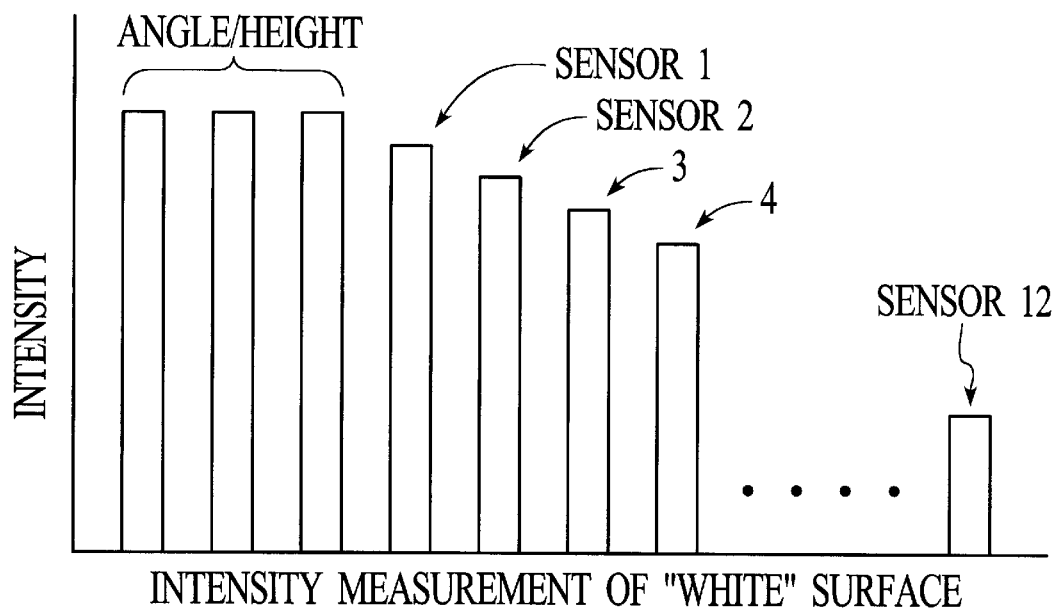
FIGS. 14A and 14B illustrate examples of received light intensities of receivers used in certain embodiments of the present invention.
Figure 14B:
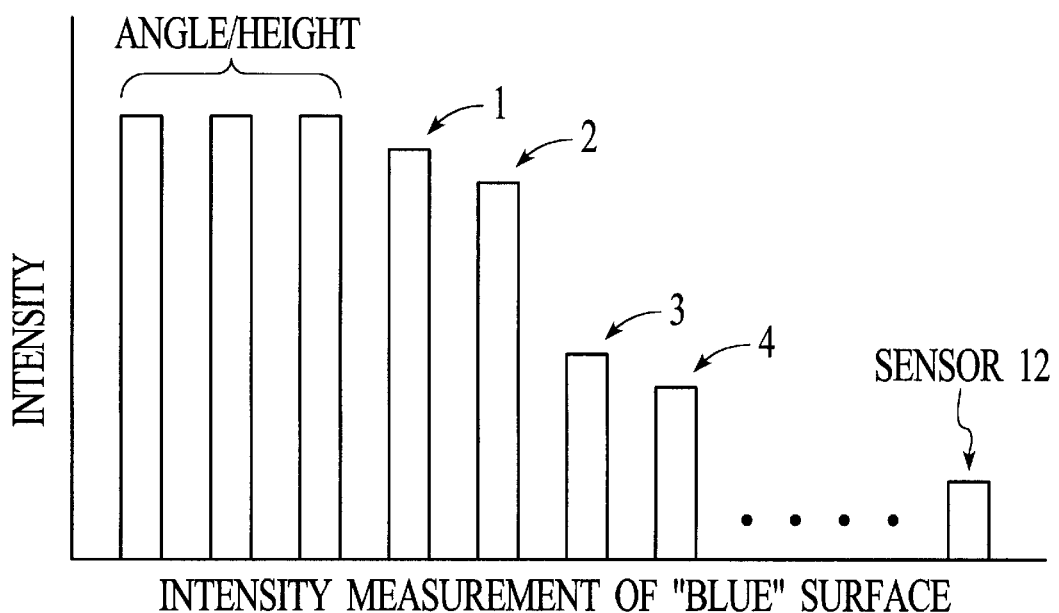

FIGS. 14A and 14B illustrate exemplary intensity measurements using a cut-off filter arrangement such as illustrated in FIG. 13B, first in the case of a white surface being measured (FIG. 14A), and also in the case of a blue surface being measured (FIG. 14B). As illustrated in FIG. 14A, in the case of a white surface, the neutrally filtered perimeter fiber optics, which are used to detect height and angle, etc., generally will produce the highest intensity (although this depends at least in part upon the characteristics of the neutral density filters). As a result of the stepped cut-off filtering provided by filters having the characteristics illustrated in FIG. 13B, the remaining intensities will gradually decrease in value as illustrated in FIG. 14A. In the case of a blue surface, the intensities will decrease in value generally as illustrated in FIG. 14B. Regardless of the surface, however, the intensities out of the filters will always decrease in value as illustrated, with the greatest intensity value being the output of the filter having the lowest wavelength cut-off value (i.e., passes all visible light up to blue), and the lowest intensity value being the output of the filter having the highest wavelength cut-off (i.e., passes only red visible light). As will be understood from the foregoing description, any color data detected that does not fit the decreasing intensity profiles of FIGS. 14A and 14B may be detected as an abnormality, and in certain embodiments detection of such a condition results in data rejection, generation of an error message or initiation of a diagnostic routine, etc.

Reference should be made to the FIGS. 1 and 3 and the related description for a detailed discussion of how such a cut-off filter arrangement may be utilized in accordance with the present invention.

Figure 15:
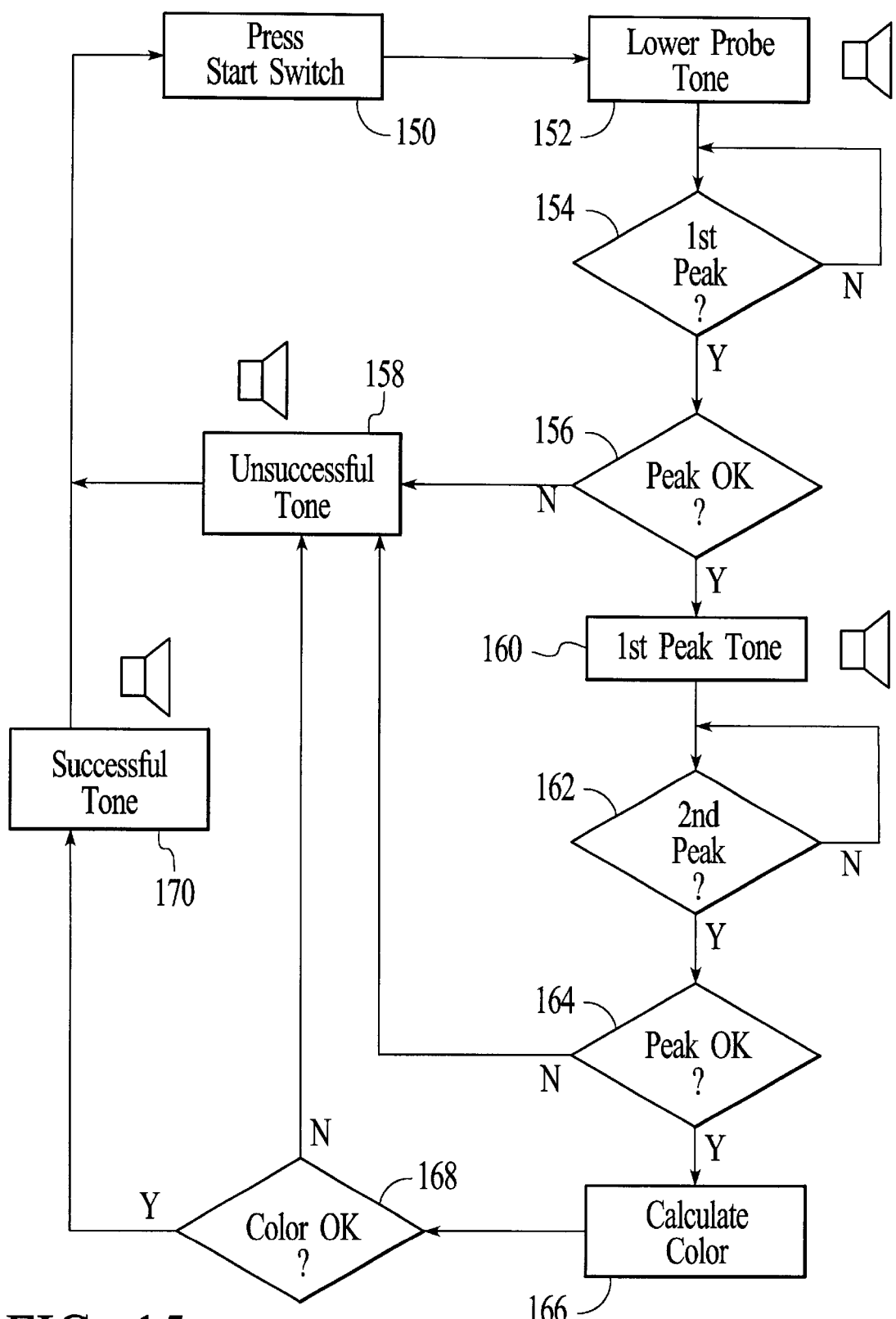
FIG. 15 is a flow chart illustrating audio tones that may be used in certain preferred embodiments of the present invention.

FIG. 15 is a flow chart illustrating audio tones that may be used in certain preferred embodiments of the present invention. It has been discovered that audio tones (such as tones, beeps, voice or the like such as will be described) present a particularly useful and instructive means to guide an operator in the proper use of a color measuring system of the type described herein.

The operator may initiate a color/optical measurement by activation of a switch (such as switch 17 of FIG. 1) at step 150. Thereafter, if the system is ready (set-up, initialized, calibrated, etc.), a lower-the-probe tone is emitted (such as through speaker 16 of FIG. 1) at step 152. The system attempts to detect peak intensity P1 at step 154. If a peak is detected, at step 156 a determination is made whether the measured peak PI meets the applicable criteria (such as discussed above in connection with FIGS. 5A, 5B and 6). If the measured peak P1 is accepted, a first peak acceptance tone is generated at step 160. If the measured peak P1 is not accepted, an unsuccessful tone is generated at step 158, and the system may await the operator to initiate a further color/optical measurement. Assuming that the first peak was accepted, the system attempts to detect peak intensity P2 at step 162. If a second peak is detected, at step 164 a determination is made whether the measured peak P2 meets the applicable criteria. If the measured peak P2 is accepted the process proceeds to color calculation step 166 (in other embodiments, a second peak acceptance tone also is generated at step 166). If the measured peak P2 is not accepted, an unsuccessful tone is generated at step 158, and the system may await the operator to initiate a further color/optical measurement. Assuming that the second peak was accepted, a color/optical calculation is made at step 166 (such as, for example, microprocessor of FIG. 1 processing the data output from light sensors 8, etc.). At step 168, a determination is made whether the color calculation meets the applicable criteria. If the color calculation is accepted, a successful tone is generated at step 170. If the color calculation is not accepted, an unsuccessful tone is generated at step 158, and the system may await the operator to initiate a further color/optical measurement.

With unique audio tones presented to an operator in accordance with the particular operating state of the system, the operator's use of the system may be greatly facilitated. Such audio information also tends to increase operator satisfaction and skill level, as, for example, acceptance tones provide positive and encouraging feedback when the system is operated in a desired manner.

The color/optical measuring systems and methods in accordance with the present invention may be applied to particular advantage in the field of dentistry, as will be more fully explained hereinafter. In particular the present invention includes the use of such systems and methods to measure the color and other attributes of a tooth in order to prepare a dental prosthesis or intraoral tooth-colored fillings, or to select denture teeth or to determine a suitable cement color for porcelain/resin prostheses. The present invention also provides methods for storing and organizing measured data such as in the form of a patient database.

Figure 16A:
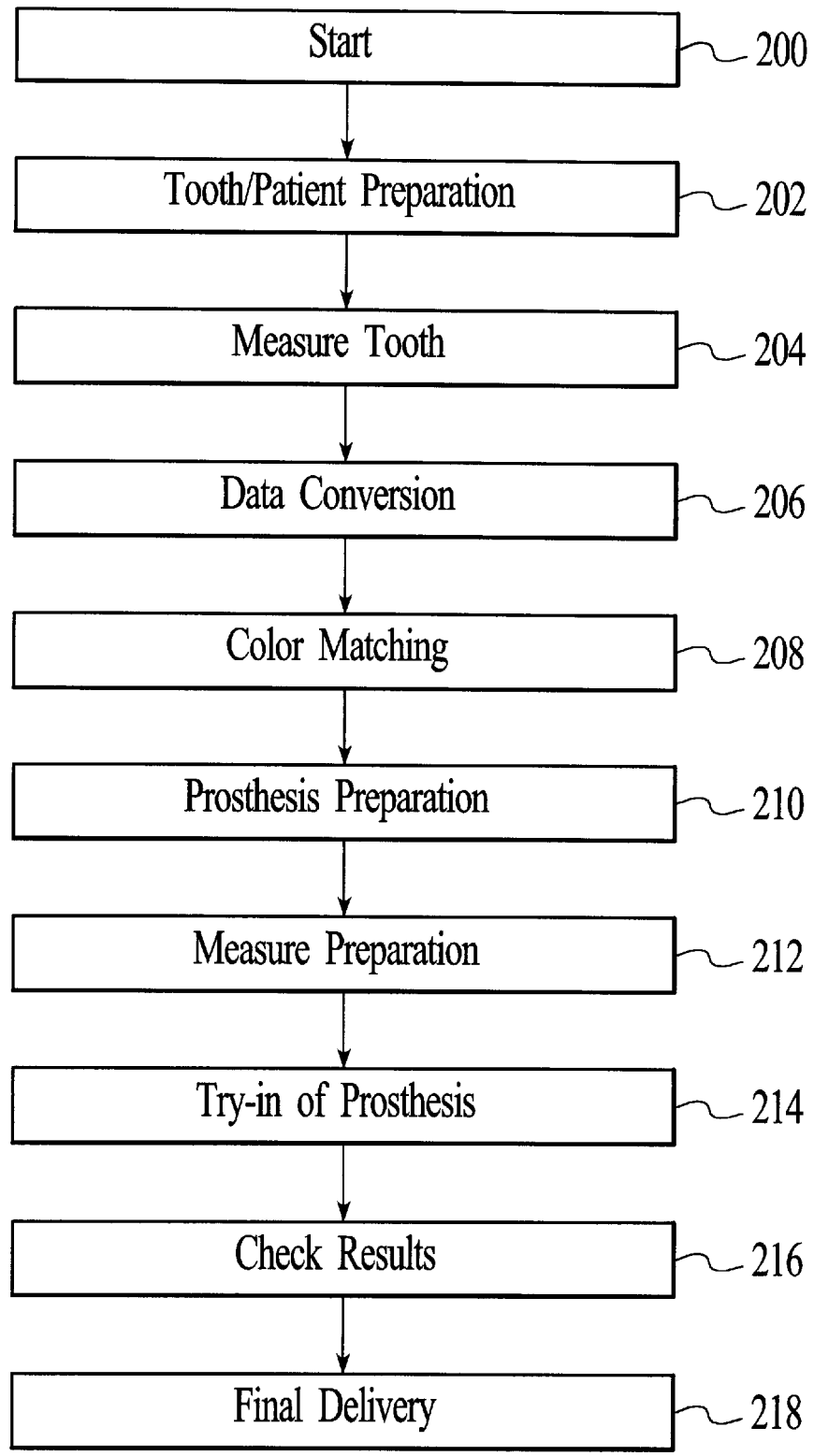
FIGS. 16A and 16B are flow charts illustrating dental prosthesis manufacturing methods in accordance with certain preferred embodiments of the present invention.

FIG. 16A is a flow chart illustrating a general dental application process flow for use of the color/optical measuring systems and methods in accordance with the present invention. At step 200, the color/optical measuring system may be powered-up and stabilized, with any required initialization or other setup routines performed. At step 200, an indication of the system status may be provided to the operator, such as through LCD 14 or speaker 16 of FIG. 1. Also at step 200, the probe tip may be shielded or a clean probe tip may be inserted in order to reduce the likelihood of contamination (see, e.g., FIGS. 7A to 8B and related description). In other embodiments, a plastic or other shield may also be used (which may be disposable, cleanable/reusable, etc., as previously described), so long as it is constructed and/or positioned so as to not adversely affect the measurement process.

Figure 17A:
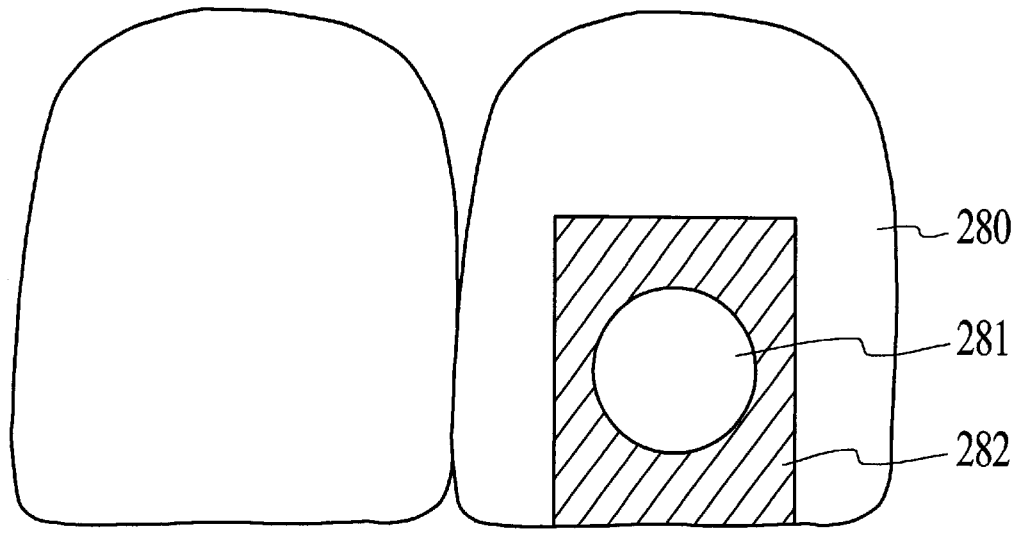
FIGS. 17A and 17B illustrate a positioning implement used in certain embodiments of the present invention.
Figure 17B:
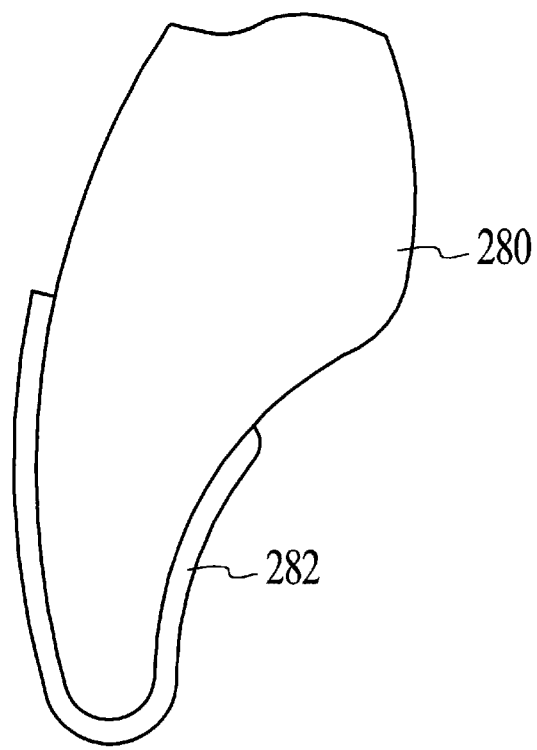

At step 202, the patient and the tooth to be measured are prepared. Any required cleaning or other tooth preparation would be performed at step 202. Any required patient consultation about the type of prosthesis or area of a tooth to be matched would be performed at (or before) step 202. In certain embodiments, a positioning device is prepared at step 202, such as is illustrated in FIGS. 17A and 17B. In such embodiments, for example, a black or other suitably-colored material 282, which may adhere to tooth 280 (such as with a suitable adhesive), is formed to have opening 281 larger than the diameter of the measuring probe, with opening 281 centered on the area of tooth 280 to be measured. The material of positioning device 282 is formed in a manner to fit on/over tooth 280 (such as over the incisal edge of tooth 280 and/or over one or more adjacent teeth) so that it may be placed on/over tooth 280 in a repeatable manner. Such a positioning device may serve to ensure that the desired area of tooth 280 is measured, and also allows for repeat measurements of the same area for purposes of confirmation, fluorescence measurement, or other optical measurement, or the like. Any other pre-measurement activities may be performed at (or before) step 202.

At step 204, the operator (typically a dentist or other dental professional) moves the probe towards the area of the tooth to be measured. This process preferably is conducted in accordance with the methodology described with reference to FIGS. 5A, 5B and 6, and preferably is accompanied by audio tones such as described with reference to FIG. 15. With the present invention, the operator may obtain color and translucency data, etc., for example, from a desired area of the tooth to be measured. During step 204, an accepted color/optical measurement is made, or some indication is given to the operator that the measurement step needs to be repeated or some other action taken. After an accepted color/optical measurement is made at step 204, for example, the dentist may operate on the desired tooth or teeth or take other action. Before or after such action, additional measurements may be taken as needed (see, e.g., FIG. 18 and related description).

Upon successful completion of one or more measurements taken at step 204, the process proceeds to step 206. At step 206, any data conversion or processing of data collected at step 204 may be performed. For example, in the embodiment of FIG. 1, detailed color spectrum and translucency information may be generated. In a particular dental application, however, it may be that a dental lab, for example, requires that the color be presented in Munsell format (i.e., chroma, hue and value), RGB values, XYZ coordinates, CIELAB values, Hunter values, or some other color data format. With the spectra color information produced by the present invention, data may be converted to such formats through conventional math, for example. Such math may be performed by microprocessor or computer 13A of FIG. 1, or in some other manner. It also should be noted that, in certain embodiments, the data produced at step 204 in accordance with the present invention may be used directly without data conversion. In such embodiments, step 206 may be omitted. In other embodiments, step 206 consists of data formatting, such as preparing the data for reproduction in hard copy, pictorial or other form, or for transmission as facsimile or modem data. Finally, in certain embodiments a translucency factor is computed in a format suitable for the particular application. In yet other embodiments, a surface texture or detail factor is computed in a format suitable for the particular application. In yet other embodiments, a surface gloss factor is computed in a format suitable for the particular application.

At step 208, a matching is optionally attempted between the data produced at steps 204 and 206 (if performed) and a desired color (in other embodiments, the process may proceed from 204 directly to 210, or alternatively steps 206 and 208 may be combined). For example, a number of "shade guides" are available in the market, some of which are known in the industry as Vita shade guides, Bioform shade guides or other color matching standards, guides or references or custom shade guides. In certain preferred embodiments, a lookup table is prepared and loaded into memory (such as memory associated with microprocessor or computer 13 A of FIG. 1), and an attempt is made to the closest match or matches of the collected data with the known shade guides, custom shade guides or reference values. In certain embodiments, a translucency factor and/or gloss factor and/or a surface texture or detail factor also is used in an effort to select the best possible match.

In a particular aspect of certain embodiments of the present invention, at step 208 a material correlation lookup table is accessed. Based on the color and translucency data obtained at step 204, a proposed recipe of materials, pigments or other instruction information is prepared for a prosthesis or filling, etc., of the desired color and translucency, etc. With the detailed color and other information made available in accordance with the present invention, a direct correlation with the relevant constituent materials may be made. In still other embodiments, such information is made available to an automated mixing or manufacturing machine for preparation of prosthesis or material of the desired color and translucency, etc., as more fully described elsewhere herein.

At step 210, based on the results of the preceding steps, the prosthesis, denture, intraoral tooth-colored filling material or other items are prepared. This step may be performed at a dental lab, or, in certain embodiments, at or near the dental operatory. For remote preparation, relevant data produced at steps 204, 206 and/or 208 may be sent to the remote lab or facility by hardcopy, facsimile or modem or other transmission. What should be understood from the foregoing is that, based on data collected at step 204, a prosthesis may be prepared of a desirable color and/or other optical characteristic at step 210.

At step 212, the prosthesis or other material prepared at step 210 may be measured for confirmation purposes, again preferably conducted in accordance with the methodology described with reference to FIGS. 5A, 5B and 6, and preferably accompanied by audio tones such as described with reference to FIG. 15. A re-measure of the tooth in the patient's mouth, etc. also may be made at this step for confirmation purposes. If the confirmation process gives satisfactory results, the prosthesis, denture, composite filling or other material may be preliminarily installed or applied in the patient at step 214. At step 216, a re-measure of the prosthesis, denture, composite filling or other materials optionally may be made. If the results of step 216 are acceptable, then the prosthesis may be more permanently installed or applied in the patient at step 218. If the results of step 216 are not acceptable, the prosthesis may be modified and/or other of the steps repeated as necessary in the particular situation.

Figure 16B:
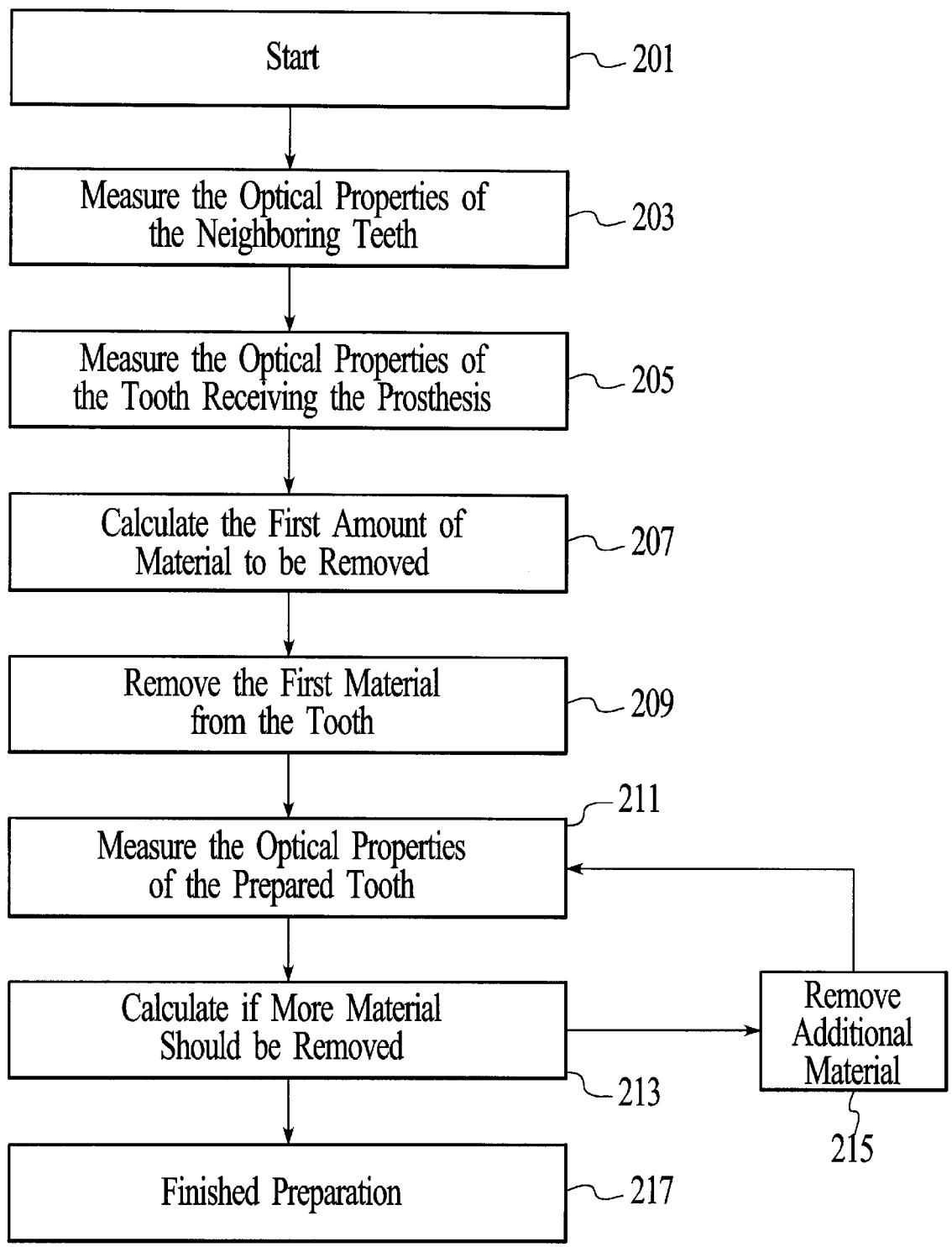

With reference to FIG. 16B, a further embodiment of the present invention will be explained. With this embodiment, an instrument and method such as previously described may be advantageously utilized to prepare a tooth to receive a prosthesis.

A dental prosthesis such as a crown or a laminate has optical properties that are determined by a number of factors. Determining factors include the material of the prosthesis, along with the cement utilized to bond the prosthesis to the tooth and the underlying optical properties of the tooth itself For example, in the preparation of a tooth for a laminate, the thickness of the laminate combined with the bonding cement and the color of the underlying prepared tooth all contribute to the final optical properties of the prosthesis. In order to prepare an optimum prosthesis such as from an esthetic standpoint, the dentist may need to prepare the tooth for the laminate by removing material from the tooth. The final desired esthetic color, shape and contours of the tooth determines the amount of material needed to be removed from the tooth, which determines the final thickness of the laminate, and in significant part may determine whether or not the final restoration will have a desired and esthetically pleasing result as compared to neighboring teeth. By measuring the color of the neighboring teeth, and by measuring the color of the underlying tooth being prepared for the laminate, the amount of tooth material to be removed, or the range of material that should be removed, may be determined and reported to the dentist as the tooth is being prepared.

At step 201, the process is commenced. Any initial calibration or other preparatory steps may be undertaken. At step 203, the dentist may measure the optical properties including color of one or more neighboring teeth. At step 205, the dentist may measure the optical properties including color of the tooth receiving the prosthesis. At step 207, a first amount of material to be removed is calculated or estimated (such as by microprocessor 10, computer 13A or other suitable computing device). The first amount is determined based on known color properties of the available laminates, the estimated thickness of the laminate, and the color of the tooth to receive the laminate. If, for example, the tooth to receive the laminate is dark to the degree that an esthetically pleasing laminate likely cannot be produced (based on the range of color/optical characteristics of the known available laminates), then an estimate is made of how much material should be removed such that a thicker laminate will result in a desired and esthetically pleasing result. At step 209 the dentist removes the first amount of material (or approximately such amount) from the tooth (using known removal techniques, etc.). At step 211, the dentist may again measure the optical properties including color of the tooth receiving the prosthesis. At step 213, a calculation or estimation is made (in a manner analogous to step 207) of whether additional material should be removed, and, if so, how much. At step 215, if needed, additional material is removed, with steps 211, 213 and 215 repeated as necessary. In preferred embodiments, based on known/measured/ empirical data analysis of color/optical properties of teeth, at steps such as steps 205 and 21 1, a comparison or assessment may be made of whether the tooth being prepared is getting too near the pulp (such as by detection of a pink color, for example). Based on such threshold or other type criteria, the dentist may be alerted that further material should not be removed in order to minimize exposure of the pulp and damage of the tooth. At step 217, if it is determined at step 213 that a desirable and esthetically pleasing laminate may be produced, such laminate preparation steps are conducted.

Similar steps could be taken in other industrial endeavors, such as painting or other finishes, etc.

Figure 18:
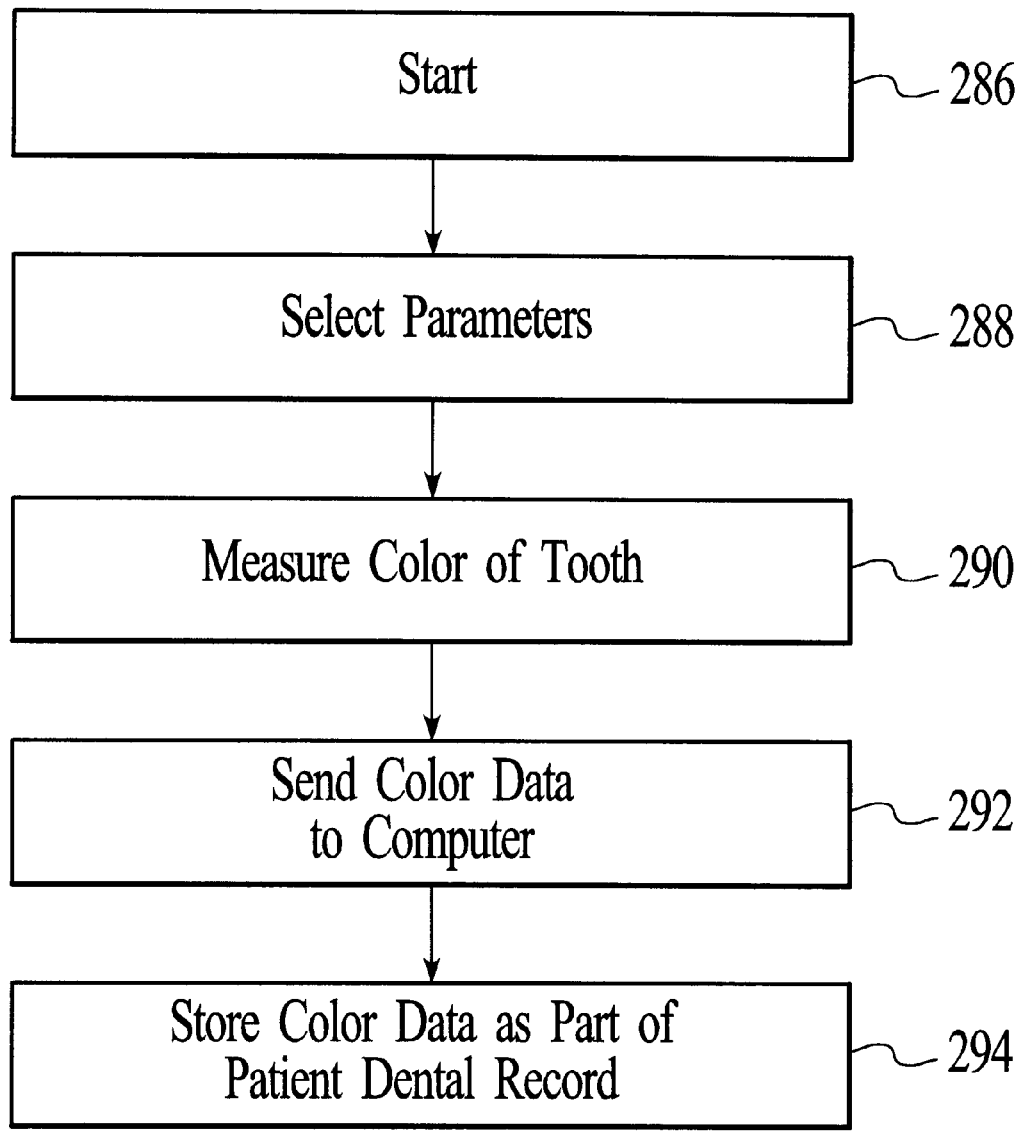
FIG. 18 is a flow chart illustrating a patient database method in accordance with certain embodiments of the present invention.

In another particular aspect of the present invention, for example, data processing such as illustrated in FIG. 18 may be taken in conjunction with the processes of FIGS. 16A and/or 16 B. At step 286, client database software is run on a computing device, such as computer 13A of FIG. 1. Such software may include data records for each patient, including fields storing the history of dental services performed on the patient, information regarding the status or condition of the patient's teeth, billing, address and other information. Such software may enter a mode by which it is in condition to accept color or other data taken in accordance with the present invention.

At step 288, for example, the dentist or other dental professional may select parameters for a particular tooth of the patient to be measured. Depending on the size and condition of the tooth (such as color gradient or the like), the dentist may sector the tooth into one or more regions, such as a grid. Thus, for example, in the case of tooth for which it is decided to take four measurements, the tooth may be sectored into four regions. Such parameters, which may include a pictorial representation on the computer of the tooth sectored into four regions (such as by grid lines), along with tooth identification and patient information may be entered into the computer at this time.

At step 290, one or more measurements of the tooth may be taken, such as with a system and method as described in connection with FIGS. 1, 5A, 5B and/or 6. The number of such measurements preferably is associated with the parameters entered at step 288. Thereafter, at step 292, the data collected from the measurement(s) may be sent to the computer for subsequent processing. As an illustrative example, four color/optical measurements may be taken (for the four regions of the tooth in the above example) and sent to the computer, with the data for the four color/optical measurements (such as RGB or other values) associated with the four regions in accordance with the entered parameters. Also, as an example, the displayed pictorial representation of the tooth may have overlaid thereof data indicative of the color/optical measurement(s). At step 294, such as after completion of color/optical measurements on the particular patient, the data collected during the process may be associatively stored as a part of the patient's dental records in the data base. In embodiments accompanied by use of an intraoral camera, for example (see, e.g., FIG. 19 and related description), captured images of one or more of the patient's teeth also may be associatively stored as part of the patient's dental records. In certain embodiments, a picture captured by the intraoral camera is overlaid with grid or sector lines (such as may be defined in step 288), with color or other data measured as described herein also overlaid over the captured image. In such a manner, the color or other data may be electronically and visually associated with a picture of the particular measured tooth, thereby facilitating the use of the system and the understanding of the collected data. In still other embodiments, all such captured image and color measurement records include a time and/or date, so that a record of the particular history of a particular tooth of a particular patient may be maintained. See FIGS. 24 to 26 and 32 to 34 and related description for additional embodiments utilizing an intraoral camera, etc., in accordance with the present invention.

Figure 19:
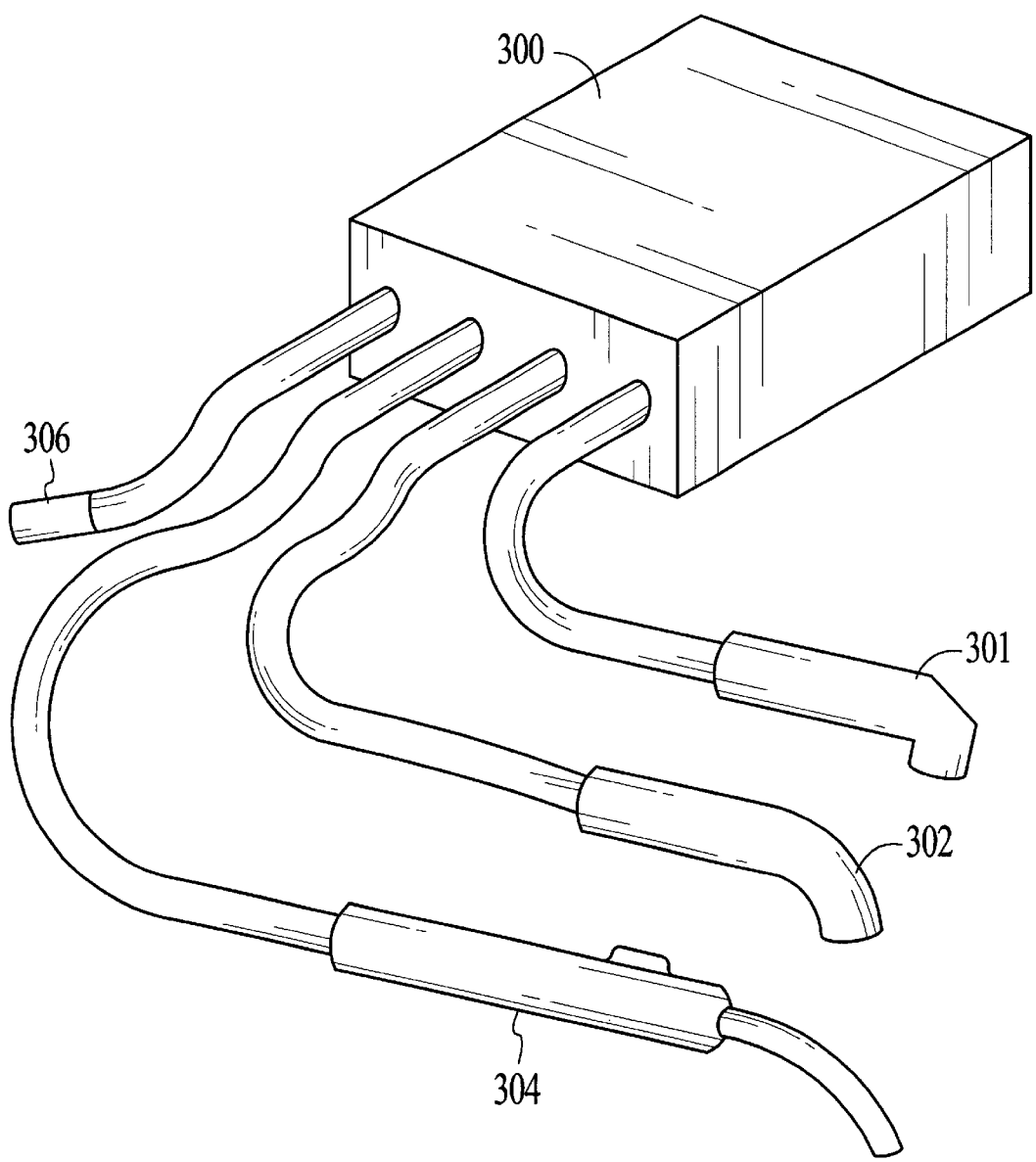
FIG. 19 illustrates an integrated unit in accordance with the present invention that includes a measuring device and other implements.

In yet another particular aspect of the present invention, a measuring device and method (such as described elsewhere herein) may be combined with an intraoral camera and other implements. As illustrated in FIG. 19, control unit 300 contains conventional electronics and circuitry, such as power supplies, control electronics, light sources and the like. Coupled to control unit 300 is intraoral camera 301 (for viewing, and capturing images of, a patient's tooth or mouth, etc.), curing light 302 (such as for curing light-cured intraoral filling material), measuring device 304 (such as described elsewhere herein), and visible light 306 (which may be an auxiliary light for intraoral examinations and the like). With such embodiments, color, translucency, fluorescence, gloss, surface texture and/or other data collected for a particular tooth from measuring device 304 may be combined with images captured by intraoral camera 301, with the overall examination and processing of the patient facilitated by having measuring device 304, intraoral camera 301, curing light 302 and visible light 306 integrated into a single unit. Such integration serves to provide synergistic benefits in the use of the instruments, while also reducing costs and saving physical space. In another particular aspect of such embodiments, the light source for measuring device 304 and intraoral camera 301 are shared, thereby resulting in additional benefits.

Further embodiments of the present invention will now be described with reference to FIGS. 20 to 23. The previously described embodiments generally rely on movement of the probe with respect to the object/tooth being measured. While such embodiments provide great utility in many applications, in certain applications, such as robotics, industrial control, automated manufacturing, etc. (such as positioning the object and/or the probe to be in proximity to each other, detecting color/optical properties of the object, and then directing the object, e.g., sorting, based on the detected color/optical properties, for further industrial processing, packaging, etc.) it may be desired to have the measurement made with the probe held or positioned substantially stationary above the surface of the object to be measured (in such embodiments, the positioned probe may not be hand-held as with certain other embodiments). Such embodiments also may have applicability in the field of dentistry (in such applications, "object" generally refers to a tooth, etc.).

Figure 20:
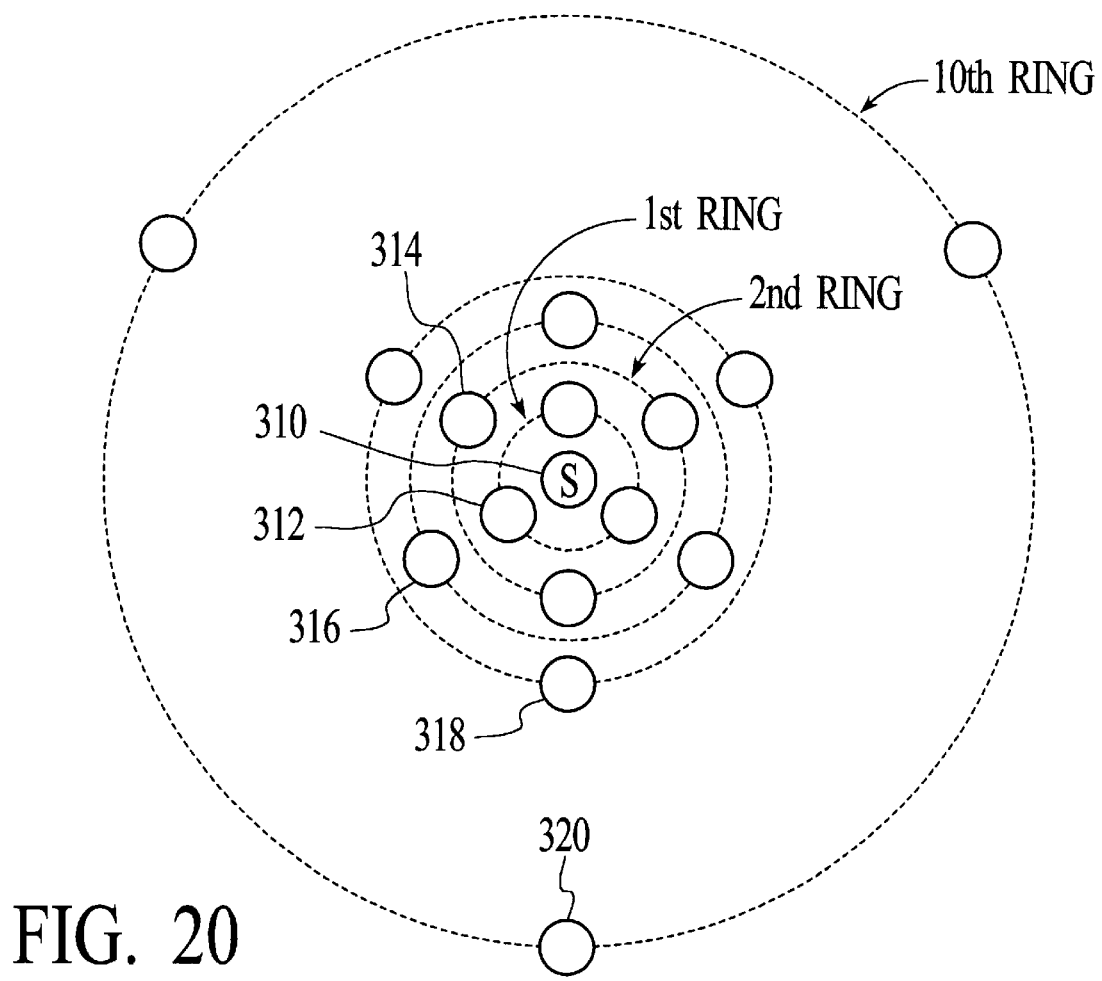
FIG. 20 illustrates an embodiment, which utilizes a plurality of rings of light receivers that may be utilized to take measurements with the probe held substantially stationary with respect to the object being measured, which may serve to further the understanding of preferred embodiments of the present invention.

FIG. 20 illustrates such a further embodiment. The probe of this embodiment includes a plurality of perimeter sensors and a plurality of color sensors coupled to receivers 312–320. The color sensors and related components, etc., may be constructed to operate in a manner analogous to previously described embodiments. For example, fiber optic cables or the like may couple light from source 310 that is received by receivers 312–320 to sharp cut-off filters or to notch filters, with the received light measured over precisely defined wavelengths (see, e.g., FIGS. 1, 3 and 11–14 and related description). Color/optical characteristics of the object may be determined from the plurality of color sensor measurements, which may include three such sensors in the case of a tristimulus instrument, or 8, 12, 15 or more color sensors for a more full bandwidth system (the precise number may be determined by the desired color resolution, etc.).

With this embodiment, a relatively greater number of perimeter sensors are utilized (as opposed, for example, to the three perimeter sensors used in certain preferred embodiments of the present invention). As illustrated in FIG. 20, a plurality of triads of receivers 312–320 coupled to perimeter sensors are utilized, where each triad in the preferred implementation consists of three fiber optics positioned equal distance from light source 310, which in the preferred embodiment is a central light source fiber optic. The triads of perimeter receivers/sensors may be configured as concentric rings of sensors around the central light source fiber optic. In FIG. 20, ten such triad rings are illustrated, although in other embodiments a lesser or greater number of triad rings may be utilized, depending upon the desired accuracy and range of operation, as well as cost considerations and the like.

The probe illustrated in FIG. 20 may operate within a range of heights (i.e., distances from the object being measured). As with earlier embodiments, such height characteristics are determined primarily by the geometry and constituent materials of the probe, with the spacing of the minimal ring of perimeter sensors determining the minimal height, and the spacing of the maximal ring of perimeter sensors determining the maximum height, etc. It therefore is possible to construct probes of various height ranges and accuracy, etc., by varying the number of perimeter sensor rings and the range of ring distances from the central source fiber optic. It should be noted that such embodiments may be particularly suitable when measuring similar types of materials, etc.

As described earlier, the light receiver elements for the plurality of receivers/perimeter sensors may be individual elements such as Texas Instruments TSL230 light-to-frequency converters, or may be constructed with rectangular array elements or the like such as may be found in a CCD camera. Other broadband-type of light measuring elements are utilized in other embodiments. Given the large number of perimeter sensors used in such embodiments (such as 30 for the embodiment of FIG. 16), an array such as CCD camera-type sensing elements may be desirable. It should be noted that the absolute intensity levels of light measured by the perimeter sensors is not as critical to such embodiments of the present invention; in such embodiments differences between the triads of perimeter light sensors are advantageously utilized in order to obtain optical measurements.

Optical measurements may be made with such a probe by holding/positioning the probe near the surface of the object being measured (i.e., within the range of acceptable heights of the particular probe). The light source providing light to light source 310 is turned on and the reflected light received by receivers 312–320 (coupled to the perimeter sensors) is measured. The light intensity of the rings of triad sensors is compared. Generally, if the probe is perpendicular to the surface and if the surface is flat, the light intensity of the three sensors of each triad should be approximately will be equal. If the probe is not perpendicular to the surface or if the surface is not flat, the light intensity of the three sensors within a triad will not be equal. It is thus possible to determine if the probe is perpendicular to the surface being measured, etc. It also is possible to compensate for non-perpendicular surfaces by mathematically adjusting the light intensity measurements of the color sensors with the variance in measurements of the triads of perimeters sensors.

Since the three sensors forming triads of sensors are at different distances (radii) from central light source 310, it is expected that the light intensities measured by light receivers 312 - 320 and the perimeter sensors will vary. For any given triad of sensors, as the probe is moved closer to the surface, the received light intensity will increase to a maximum and then sharply decrease as the probe is moved closer to the surface. As with previously-described embodiments, the intensity decreases rapidly as the probe is moved less than the peaking height and decreases rapidly to zero or almost zero for opaque objects. The value of the peaking height depends principally upon the distance of the particular receiver from light source 310. Thus, the triads of sensors will peak at different peaking heights. By analyzing the variation in light values received by the triads of sensors, the height of the probe can be determined. Again, this is particularly true when measuring similar types of materials. As discussed earlier, comparisons with previously-stored data also may be utilized to made such determinations or assessments, etc.

The system initially is calibrated against a neutral background (e.g., a gray background), and the calibration values are stored in non-volatile memory (see, e.g., processor of FIG. 1). For any given color or intensity, the intensity for the receivers/perimeter sensors (independent of distance from the central source fiber optic) in general should vary equally. Hence, a white surface should produce the highest intensities for the perimeter sensors, and a black surface will produce the lowest intensities. Although the color of the surface will affect the measured light intensities of the perimeter sensors, it should affect them substantially equally. The height of the probe from the surface of the object, however, will affect the triads of sensors differently. At the minimal height range of the probe, the triad of sensors in the smallest ring (those closest to the source fiber optic) will be at or about their maximal value. The rest of the rings of triads will be measuring light at intensities lower than their maximal values. As the probe is raised/positioned from the minimal height, the intensity of the smallest ring of sensors will decrease and the intensity of the next ring of sensors will increase to a maximal value and will then decrease in intensity as the probe is raised/positioned still further. Similarly for the third ring, fourth ring and so on. Thus, the pattern of intensities measured by the rings of triads will be height dependent. In such embodiments, characteristics of this pattern may be measured and stored in non-volatile RAM look-up tables (or the like) for the probe by calibrating it in a fixture using a neutral color surface. Again, the actual intensity of light is not as important in such embodiments, but the degree of variance from one ring of perimeter sensors to another is.

To determine a measure of the height of the probe from the surface being measured, the intensities of the perimeter sensors (coupled to receivers 312–320) is measured. The variance in light intensity from the inner ring of perimeter sensors to the next ring and so on is analyzed and compared to the values in the look-up table to determine the height of the probe. The determined height of the probe with respect to the surface thus may be utilized by the system processor to compensate for the light intensities measured by the color sensors in order to obtain reflectivity readings that are in general independent of height. As with previously described embodiments, the reflectivity measurements may then be used to determine optical characteristics of the object being measured, etc.

It should be noted that audio tones, such as previously described, may be advantageously employed when such an embodiment is used in a handheld configuration. For example, audio tones of varying pulses, frequencies and/or intensities may be employed to indicate the operational status of the instrument, when the instrument is positioned within an acceptable range for color measurements, when valid or invalid color measurements have been taken, etc. In general, audio tones as previously described may be adapted for advantageous use with such further embodiments.

Figure 21:
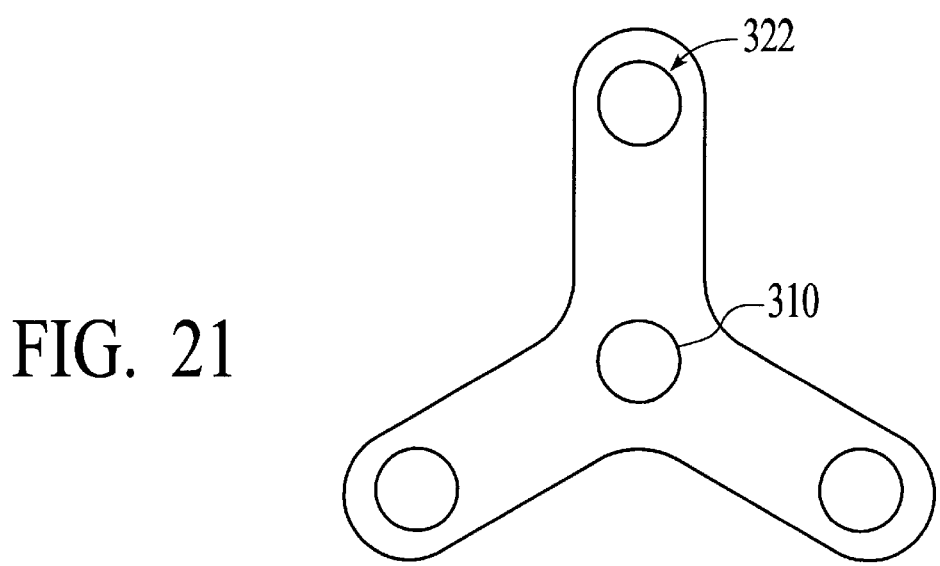
FIGS. 21 and 22 illustrate an embodiment, which utilizes a mechanical movement and also may be utilized to take measurements with the probe held substantially stationary with respect to the object being measured, which may serve to further the understanding of preferred embodiments of the present invention.

FIG. 21 illustrates a further such embodiment of the present invention. The preferred implementation of this embodiment consists of a central light source 310 (which in the preferred implementation is a central light source fiber optic), surrounded by a plurality of light receivers 322 (which in the preferred implementation consists of three perimeter light receiver fiber optics). The three perimeter light receiver fiber optics, as with earlier described embodiments, may be each spliced into additional fiber optics that pass to light intensity receivers/sensors, which may be implemented with Texas Instruments TSL 230 light to frequency converters as described previously. One fiber of each perimeter receiver is coupled to a sensor and measured full band width (or over substantially the same bandwidth)

such as via a neutral density filter, and other of the fibers of the perimeter receivers are coupled to sensors so that the light passes through sharp cut off or notch filters to measure the light intensity over distinct frequency ranges of light (again, as with earlier described embodiments). Thus, there are color light sensors and neutral "perimeter" sensors as with previously described embodiments. The color sensors are utilized to determine the color or other optical characteristics of the object, and the perimeter sensors are utilized to determine if the probe is perpendicular to the surface and/or are utilized to compensate for non-perpendicular angles within certain angular ranges.

In the embodiment of FIG. 21, the angle of the perimeter sensor fiber optics is mechanically varied with respect to the central source fiber optic. The angle of the perimeter receivers/sensors with respect to the central source fiber optic is measured and utilized as described hereinafter. An exemplary mechanical mechanism, the details of which are not critical so long as desired, control movement of the perimeter receivers with respect to the light source is obtained, is described with reference to FIG. 22.

The probe is held within the useful range of the instrument (determined by the particular configuration and construction, etc.), and a color measurement is initiated. The angle of the perimeter receivers/sensors with respect to the central light source is varied from parallel to pointing towards the central source fiber optic. While the angle is being varied, the intensities of the light sensors for the perimeter sensors (e.g., neutral sensors) and the color sensors is measured and saved along with the angle of the sensors at the time of the light measurement. The light intensities are measured over a range of angles. As the angle is increased the light intensity will increase to a maximum value and will then decrease as the angle is further increased. The angle where the light values is a maximum is utilized to determine the height of the probe from the surface. As will be apparent to those skilled in the art based on the teachings provided herein, with suitable calibration data, simple geometry or other math, etc., may be utilized to calculate the height based on the data measured during variation of the angle. The height measurement may then be utilized to compensate for the intensity of the color/optical measurements and/or utilized to normalize color values, etc.

Figure 22:
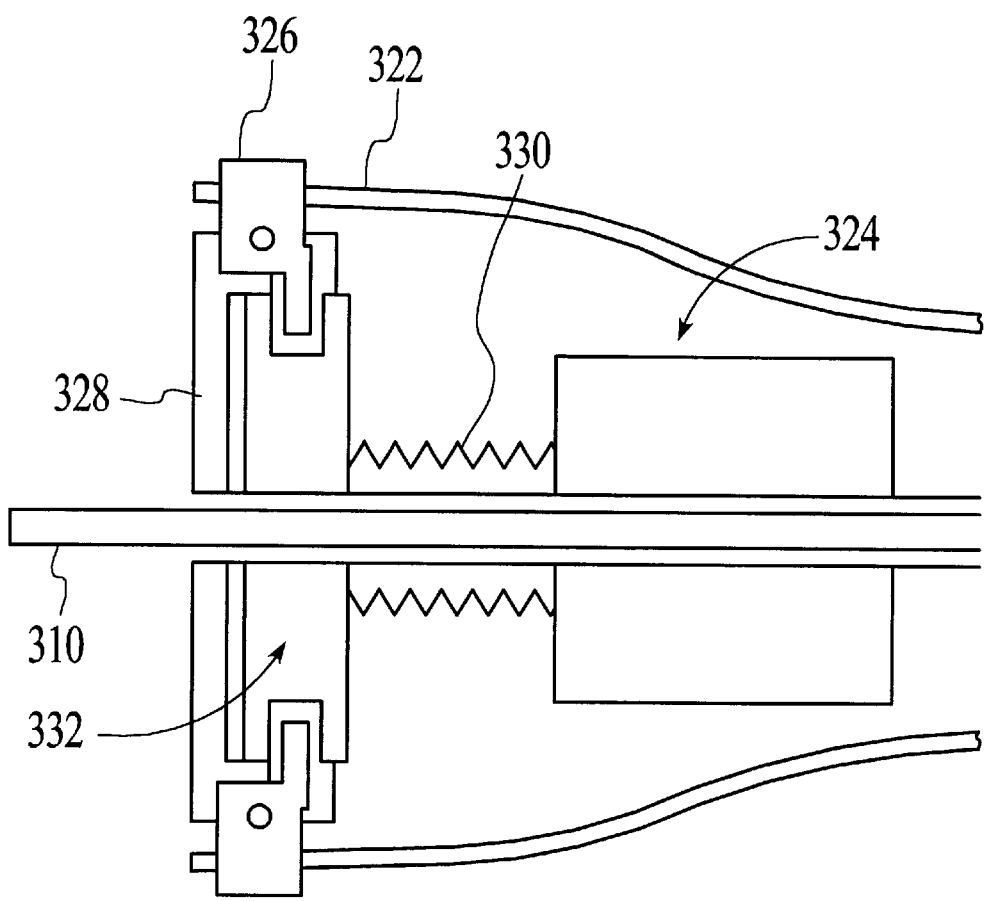

FIG. 22 illustrates an exemplary embodiment of a mechanical arrangement to adjust and measure the angle of the perimeter sensors. Each perimeter receiver/sensor 322 is mounted with pivot arm 326 on probe frame 328. Pivot arm 326 engages central ring 332 in a manner to form a cam mechanism. Central ring 332 includes a groove that holds a portion of pivot arm 326 to form the cam mechanism. Central ring 332 may be moved perpendicular with respect to probe frame 328 via linear actuator 324 and threaded spindle 330. The position of central ring 332 with respect to linear actuator 324 determines the angle of perimeter receivers/sensors 322 with respect to light source 310. Such angular position data vis-a-vis the position of linear actuator 324 may be calibrated in advance and stored in non-volatile memory, and later used to produce color/optical characteristic measurement data as previously described.

Figure 24:
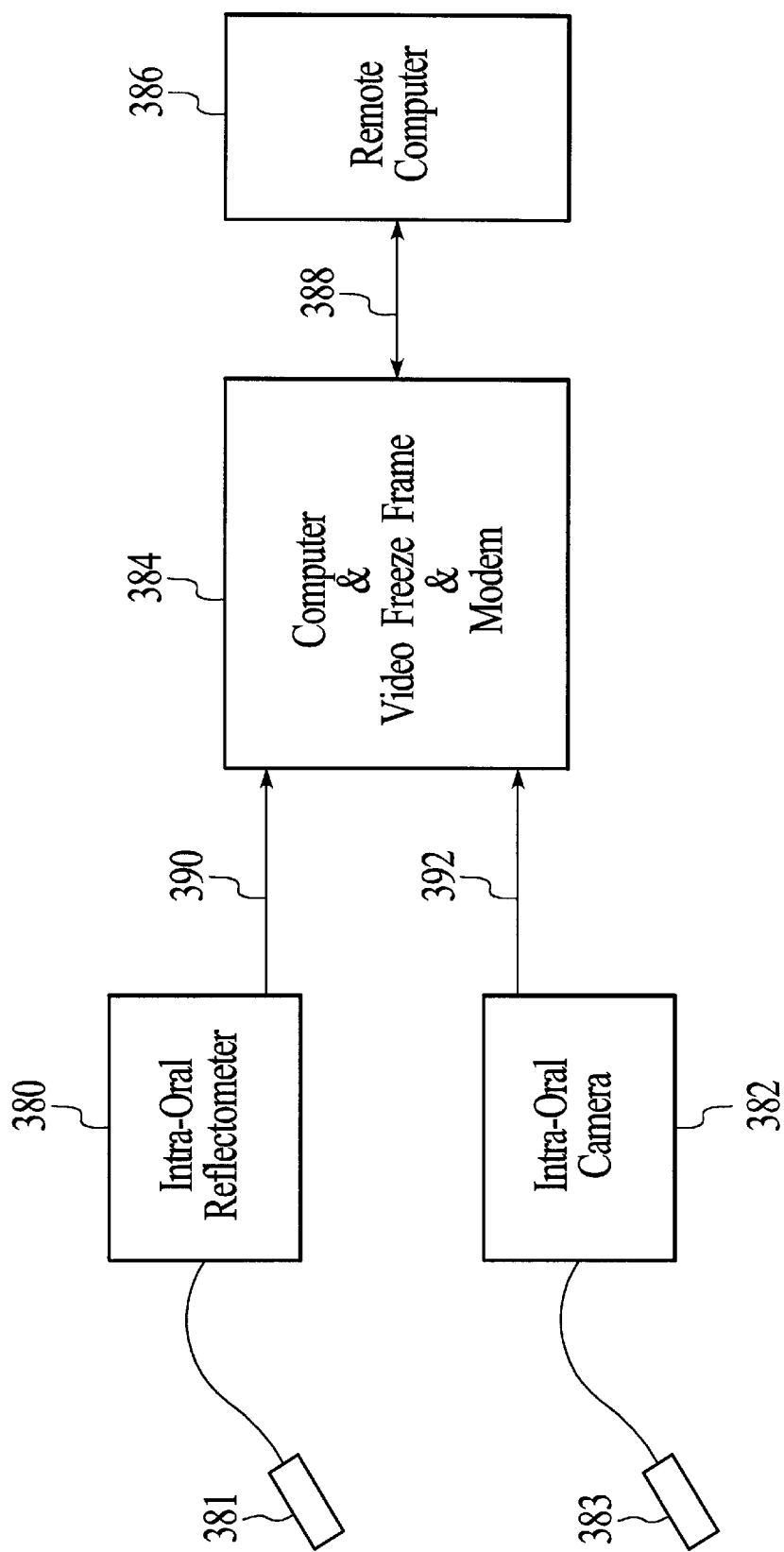
FIGS. 24, 25 and 26 illustrate further embodiments of the present invention utilizing intraoral reflectometers, intraoral cameras and/or color calibration charts in accordance with the present invention.

Referring now to FIG. 24, a further embodiment of the present invention will be explained.

Intraoral reflectometer 380, which may be constructed as described above, includes probe 381. Data output from reflectometer 380 is coupled to computer 384 over bus 390 (which may be a standard serial or parallel bus, etc.). Computer 384 includes a video freeze frame capability and preferably a modem. Intraoral camera 382 includes handpiece 383 and couples video data to computer 384 over bus 392. Computer 384 is coupled to remote computer 386 over telecommunication channel 388, which may be a standard telephone line, ISDN line, a LAN or WAN connection; etc. With such an embodiment, video measurements may be taken of one or more teeth by intraoral camera 382, along with optical measurements taken by intraoral reflectometer 380. Computer 384 may store still picture images taken from the output of intraoral camera 382.

Teeth are known to have variations in color from tooth to tooth, and teeth are known to have variations in color over the area of one tooth. Intraoral cameras are known to be useful for showing the details of teeth. Intraoral cameras, however, in general have poor color reproducibility. This is due to variations in the camera sensing elements (from camera to camera and over time etc.), in computer monitors, printers, etc. As a result of such variations, it presently is not possible to accurately quantify the color of a tooth with an intraoral camera. With the present embodiment, measuring and quantifying the color or other optical properties of teeth may be simplified through the use of an intraoral reflectometer in accordance with the present invention, along with an intraoral camera.

Figure 25:
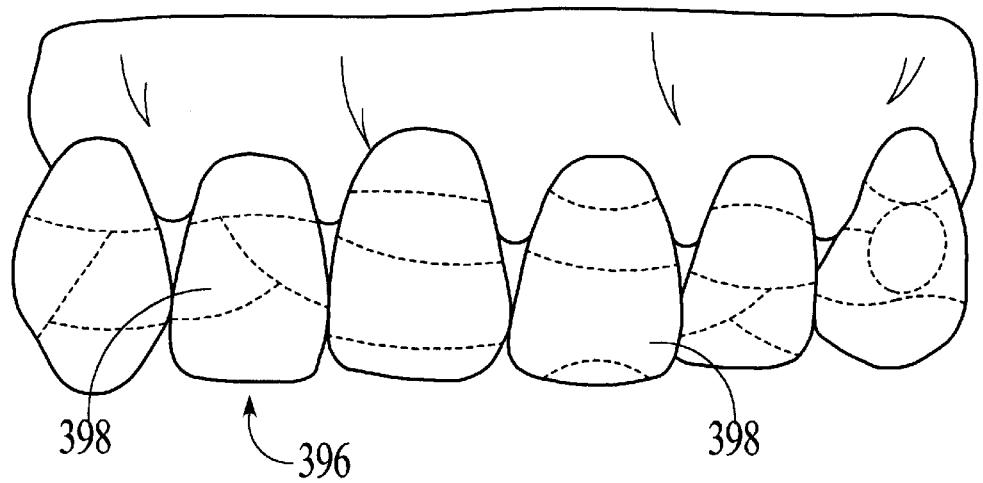

In accordance with this embodiment, the dentist may capture a still picture of a tooth and its adjacent teeth using the freeze frame feature of computer 384. Computer 384, under appropriate software and operator control, may then "postureize" the image of the tooth and its adjacent teeth, such as by limiting the number of gray levels of the luminance signal, which can result in a color image that shows contours of adjacent color boundaries. As illustrated in FIG. 25, such a postureization process may result in teeth 396 being divided into regions 398, which follow color contours of teeth 396. As illustrated, in general the boundaries will be irregular in shape and follow the various color variations found on particular teeth.

With teeth postureized as illustrated in FIG. 25, computer 384 may then highlight (such as with a colored border, shading, highlight or the like) a particular color region on a tooth to be measured, and then the dentist may then measure the highlighted region with intraoral reflectometer 380. The output of intraoral reflectometer 380 is input to computer 384 over bus 390, and computer 384 may store in memory or on a hard disk or other storage medium the color/optical data associated with the highlighted region. Computer 384 may then highlight another region and continue the process until color/optical data associated with all desired highlighted regions have been stored in computer 384. Such color/optical data may then be stored in a suitable data base, along with the video image and postureized video image of the particular teeth, etc.

Computer 384 may then assess if the measured value of a particular color region is consistent with color measurements for adjacent color regions. If, for example, a color/optical measurement for one region indicates a darker region as compared to an adjacent region, but the postureized image indicates that the reverse should be true, then computer 384 may notify the dentist (such as with an audio tone) that one or more regions should be re-measured with intraoral reflectometer 380. Computer 384 may make such relative color determinations (even though the color values stored in computer 384 from the freeze frame process are not true color values) because the variations from region to region should follow the same pattern as the color/optical measurements taken by intraoral reflectometer 380. Thus, if one region is darker than its neighbors, then computer 384 will expect that the color measurement data from intraoral reflectometer 380 for the one region also will be darker relative to color measurement data for the neighboring regions, etc.

As with the optical characteristics measurement data and captured images discussed previously, the postureized image of the teeth, along with the color/optical measurement data for the various regions of the teeth, may be conveniently stored, maintained and accessed as part of the patient dental records. Such stored data may be utilized advantageously in creating dental prosthesis that more correctly match the colors/regions of adjacent teeth. Additionally, in certain embodiments, such data images are used in conjunction with smile analysis software to further said in the prosthesis preparation.

In a further refinement to the foregoing embodiment, computer 384 preferably has included therein, or coupled thereto, a modem. With such a modem capability (which may be hardware or software), computer 384 may couple data to remote computer 386 over telecommunication channel 388. For example, remote computer 386 may be located at a dental laboratory remotely located. Video images captured using intraoral camera 382 and color/optical data collected using intraoral reflectometer may be transmitted to a dental technician (for example) at the remote location, who may use such images and data to construct dental prosthesis. Additionally, computer 384 and remote computer 386 may be equipped with an internal or external video teleconference capability, thereby enabling a dentist and a dental technician or ceramist, etc., to have a live video or audio teleconference while viewing such images and/or data.

For example, a live teleconference could take place, whereby the dental technician or ceramist views video images captured using intraoral camera 383, and after viewing images of the patient's teeth and facial features and complexion, etc., instruct the dentist as to which areas of the patient's teeth are recommended for measurement using intraoral reflectometer 380. Such interaction between the dentist and dental technician or ceramist may occur with or without postureization as previously described. Such interaction may be especially desirable at, for example, a try-in phase of a dental prosthesis, when minor changes or subtle characterizations may be needed in order to modify the prosthesis for optimum esthetic results.

Figure 26:
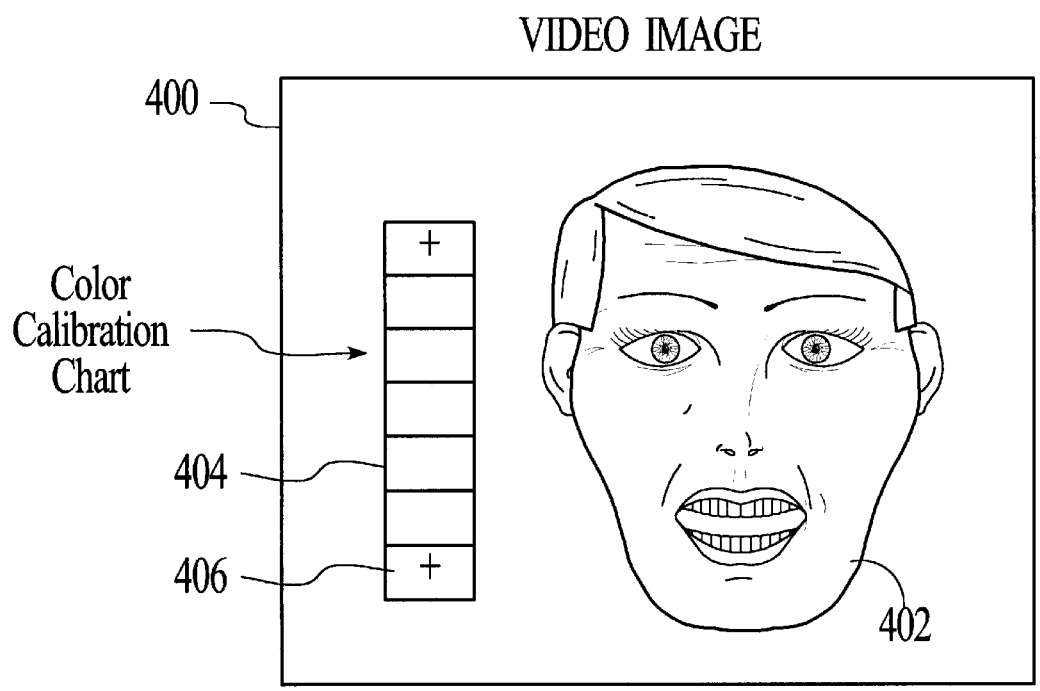

A still further refinement may be understood with reference to FIG. 26. As illustrated in FIG. 26, color calibration chart 404 could be utilized in combination with various elements of the previously described embodiments, including intraoral camera 382. Color calibration chart 404 may provide a chart of known color values, which may be employed, for example, in the video image to further enhance correct skin tones of patient 402 in the displayed video image. As the patient's gingival tissue, complexion and facial features, etc., may influence the final esthetic results of a dental prosthesis, such a color calibration chart may be desirably utilized to provide better esthetic results.

As an additional example, such a color calibration chart may be utilized by computer 384 and/or 386 to "calibrate" the color data within a captured image to true or known color values. For example, color calibration chart 404 may include one or more orientation markings 406, which may enable computers 384 and/or 386 to find and position color calibration chart 404 within a video frame. Thereafter, computers 384 and/or 386 may then compare "known" color data values from color calibration chart (data indicative of the colors within color calibration chart 404 and their position relative to orientation mark or markings 406 are stored within computers 384 and/or 386, such as in a lookup table, etc.) with the colors captured within the video image at positions corresponding to the various colors of color calibration chart 404. Based on such comparisons, computers 384 and/or 386 may color adjust the video image in order to bring about a closer correspondence between the colors of the video image and known or true colors from color calibration chart 404.

In certain embodiments, such color adjusted video data may be used in the prosthesis preparation process, such as to color adjust the video image (whether or not postureized) in conjunction with color/optical data collected using intraoral reflectometer 380 (for example, as described above or using data from intraoral reflectometer 380 to f lirther color adjust portions of the video image), or to add subtle characterizations or modifications to a dental prosthesis, or to even prepare a dental prosthesis, etc. While not believed to be as accurate, etc. as color/optical data collected using intraoral reflectometer 380, such color adjusted video data may be adequate in certain applications, environments, situations, etc., and such color adjusted video data may be utilized in a similar manner to color data taken by a device such as intraoral reflectometer 380, including, for example, prosthesis preparation, patient data collection and storage, materials preparation, such as described elsewhere herein.

It should be further noted that color calibration chart 404 may be specifically adapted (size, form and constituent materials, etc.) to be positioned inside of the patient's mouth to be placed near the tooth or teeth being examined, so as to be subject to the same or nearly the same ambient lighting and environmental conditions, etc., as is the tooth or teeth being examined. It also should further be noted that the utilization of color calibration chart 404 to color correct video image data with a computer as provided herein also may be adapted to be used in other fields, such as medical, industrial, etc., although its novel and advantageous use in the field of dentistry as described herein is of particular note and emphasis herein.

Figure 27:
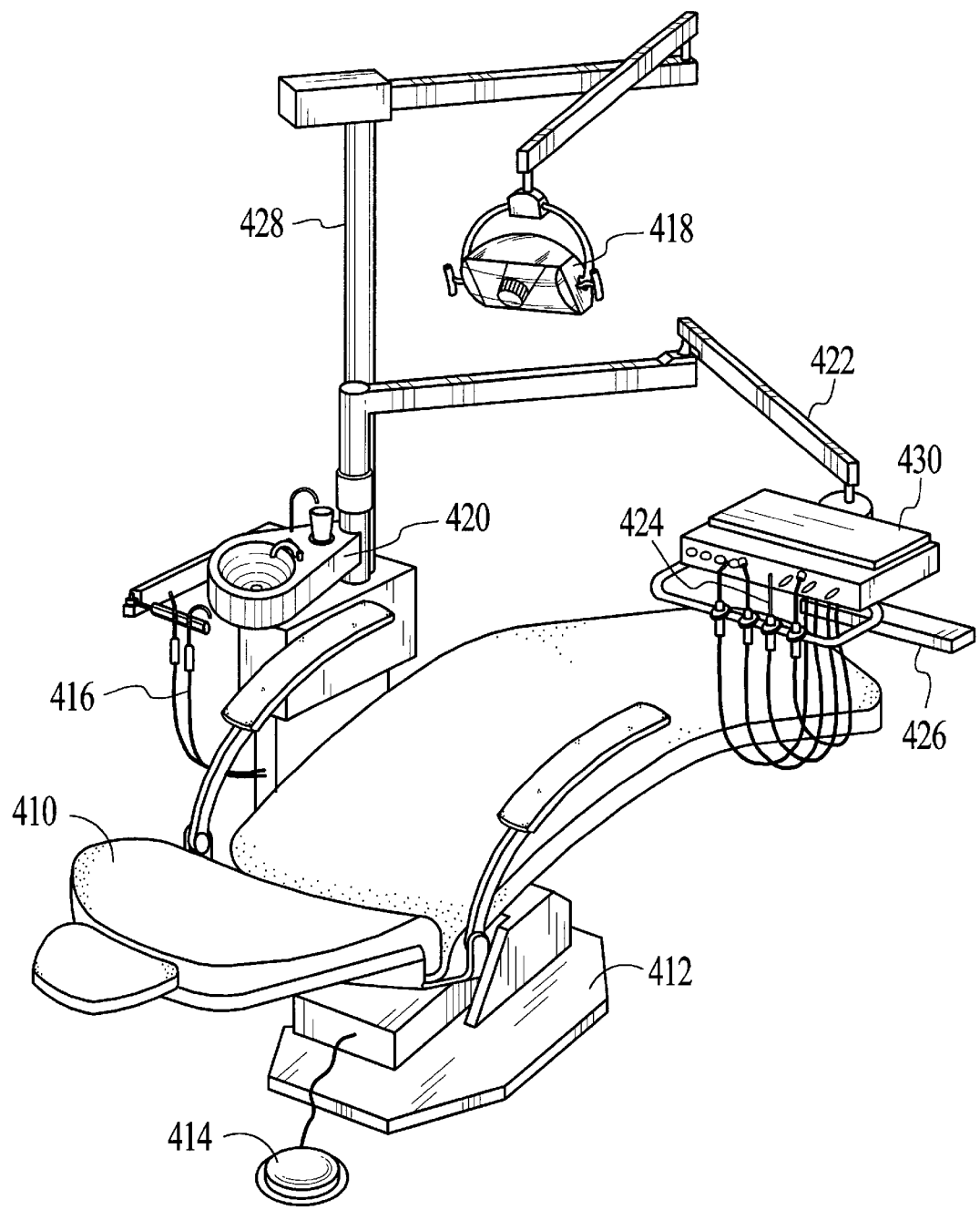
FIG. 27 illustrates an embodiment of the present invention in which an interoral camera and/or other instruments in accordance with the present invention may be adapted for use with a dental chair.

FIG. 27 illustrates a further embodiment of the present invention, in which an intraoral reflectometer in accordance with the present invention may be adapted to be mounted on, or removably affixed to, a dental chair. An exemplary dental chair arrangement in accordance with the present invention includes dental chair 410 is mounted on base 412, and may include typical accompaniments for such chairs, such as foot control 414, hose(s) 416 (for suction or water, etc.), cuspidor and water supply 420 and light 418. A preferably movable arm 422 extends out from support 428 in order to provide a conveniently locatable support 430 on which various dental instruments 424 are mounted or affixed in a removable manner. Bracket table 426 also may be included, on which a dentist may position other instruments or materials. In accordance with this embodiment, however, instruments 424 include an intraoral reflectometer in accordance with the present invention, which is conveniently positioned and removably mounted/affixed on support 430, so that color/optical measurements, data collection and storage and prosthesis preparation may be conveniently carried out by the dentist. As opposed to large and bulky prior art instruments, the present invention enables an intraoral reflectometer for collecting color/optical data, in some embodiments combined or utilized with an intraoral camera as described elsewhere herein, which may be readily adapted to be positioned in a convenient location on a dental chair. Such a dental chair also may be readily adapted to hold other instruments, such as intraoral cameras, combined intraoral camera/reflectors, drills, lights, etc.

With the foregoing as background, various additional preferred embodiments utilizing variable aperture receivers in order to measure, for example, the degree of gloss of the surface will now be described with references to FIGS. 28A to 30B. Various of the electronics and spectrophotometer/reflectometer implements described above will be applicable to such preferred embodiments.

Figure 28A:
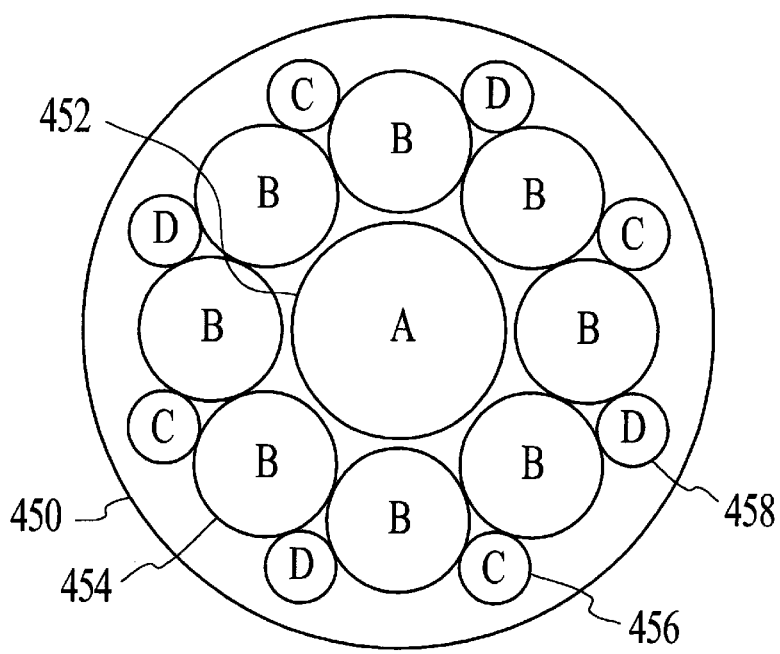
FIGS. 28A and 28B illustrate cross sections of probes that may be used in accordance with preferred embodiments of the present invention.

Referring to FIG. 28A, a probe utilizing variable aperture receivers will now be described. In FIG. 28A, source A452 represents a source fiber optic of a small numerical aperture NA, 0.25 for example; receivers B454 represent receiver fiber optics of a wider numerical aperture, 0.5 for example; receivers C456 represent receiver fiber optics of the same numerical aperture as source A but is shown with a smaller core diameter; and receivers D458 represent receiver fiber optics of a wider numerical aperture, 0.5 for example.

One or more of receiver(s) B54 (in certain embodiments one receiver B may be utilized, while in other embodiments a plurality of receivers B are utilized, which may be circularly arranged around source A, such as 6 or 8 such receivers B) pass to a spectrometer (see, e.g., FIGS. 1, 3, 11, 12, configured as appropriate for such preferred embodiments). Receiver(s) B 454 are used to measure the spectrum of the reflected light. Receivers C456 and D458 pass to broad band (wavelength) optical receivers and are used to correct the measurement made by receiver(s) B. Receivers C456 and D458 are used to correct for and to detect whether or not the probe is perpendicular to the surface and to measure/assess the degree of specular versus diffuse reflection (the coefficient of specular reflection, etc.) and to measure the translucency of the material/object.

Figure 28B:
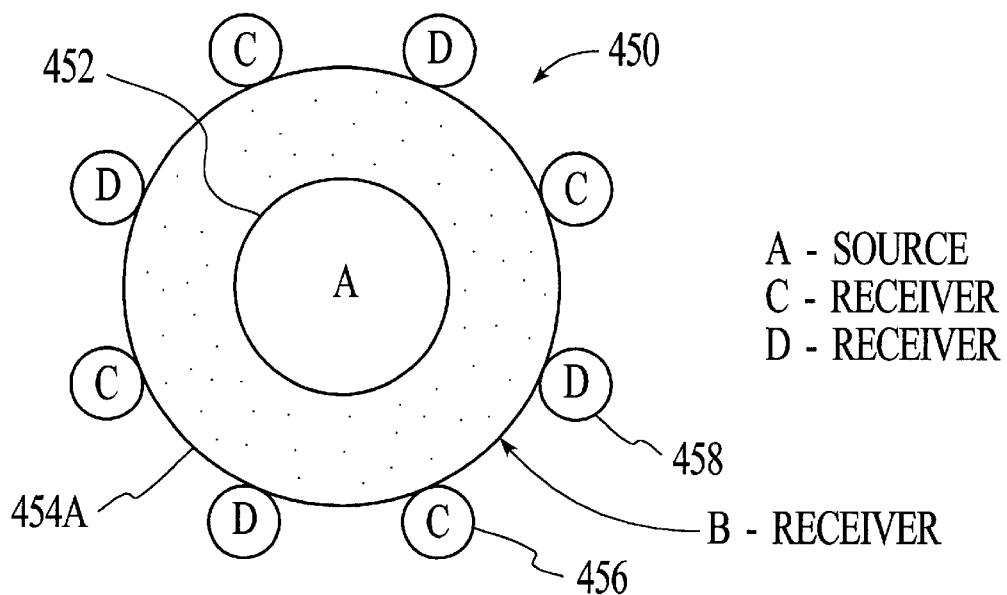

FIG. 28B illustrates a refinement of the embodiment of FIG. 28A, in which receivers B 454 are replaced by a cylindrical arrangement of closely packed, fine optical fibers 454 A, which generally surround light source 452 as illustrated. The fibers forming the cylindrical arrangement for receivers B 454, are divided into smaller groups of fibers and are presented, for example, to light sensors 8 shown in FIG. 1. The number of groups of fibers is determined by the number of light sensors. Alternately, the entire bundle of receiver fibers B 454 is presented to a spectrometer such as a diffraction grating spectrometer of conventional design. As previously described, receivers C456 and D458 may be arranged on the periphery thereof. In certain embodiments, receivers C and D may also consist of bundles of closely packed, fine optical fibers. In other embodiments they consist of single fiber optics.

The assessment of translucency in accordance with embodiments of the present invention have already been described. It should be noted, however, that in accordance with the preferred embodiment both the light reflected from the surface of the material/object (i.e., the peaking intensity) and its associated spectrum and the spectrum of the light when it is in contact with the surface of the material/object may be measured/assessed. The two spectrums typically will differ in amplitude (the intensity or luminance typically will be greater above the surface than in contact with the surface) and the spectrums for certain materials may differ in chrominance (i.e., the structure of the spectrum) as well.

When a probe in accordance with such embodiments measures the peaking intensity, it in general is measuring both the light reflected from the surface and light that penetrates the surface, gets bulk scattered within the material and re-emerges from the material (e.g., the result of translucency). When the probe is in contact with the surface (e.g., less than the critical height), no light reflecting from the surface can be detected by the receiver fiber optics, and thus any light detected by the receivers is a result of the translucency of the material and its spectrum is the result of scattering within the bulk of the material. The "reflected spectrum" and the "bulk spectrum" in general may be different for different materials, and assessments of such reflected and bulk spectrum provide additional parameters for measuring, assessing and/or characterizing materials, surfaces, objects, teeth, etc., and provide new mechanisms to distinguish translucent and other types of materials.

In accordance with preferred embodiments of the present invention, an assessment or measurement of the degree of gloss (or specular reflection) may be made. For understanding thereof, reference is made to FIGS. 29 to 30B.

Figure 29:
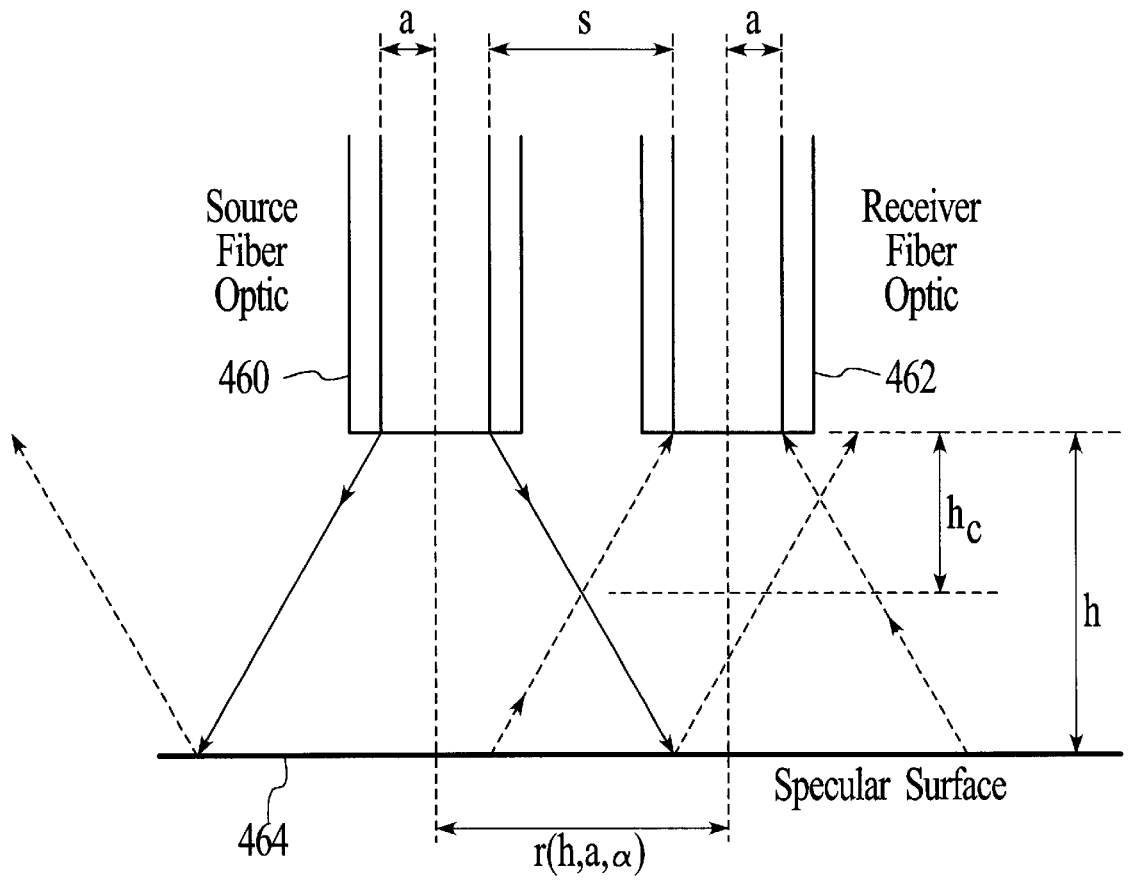
FIGS. 29 and 30A and 30B illustrate certain geometric and other properties of fiber optics for purposes of understanding certain preferred embodiments.

Referring to FIG. 29, consider two fiber optics, source fiber optic 460 and receiver fiber optic 462, arranged perpendicular to a specular surface as illustrated. The light reflecting from a purely specular surface will be reflected in the form of a cone. As long as the numerical aperture of the receiver fiber optic is greater than or equal to the numerical aperture of the source fiber optic, all the light reflected from the surface that strikes the receiver fiber optic will be within the receiver fiber optic's acceptance cone and will be detected. In general, it does not matter what the numerical aperture of the receiver fiber optic is, so long as it is greater than or equal to the numerical aperture of the source fiber optic. When the fiber optic pair is far from the surface, receiver fiber optic 462 is fully illuminated. Eventually, as the pair approaches surface 464, receiver fiber optic 462 is only partially illuminated. Eventually, at heights less than or equal to the critical height $h_c$ receiver fiber optic 462 will not be illuminated. In general, such as for purely specular surfaces, it should be noted that the critical height is a function of the numerical aperture of source fiber optic 460, and is not a function of the numerical aperture of the receiver.

Figure 30A:
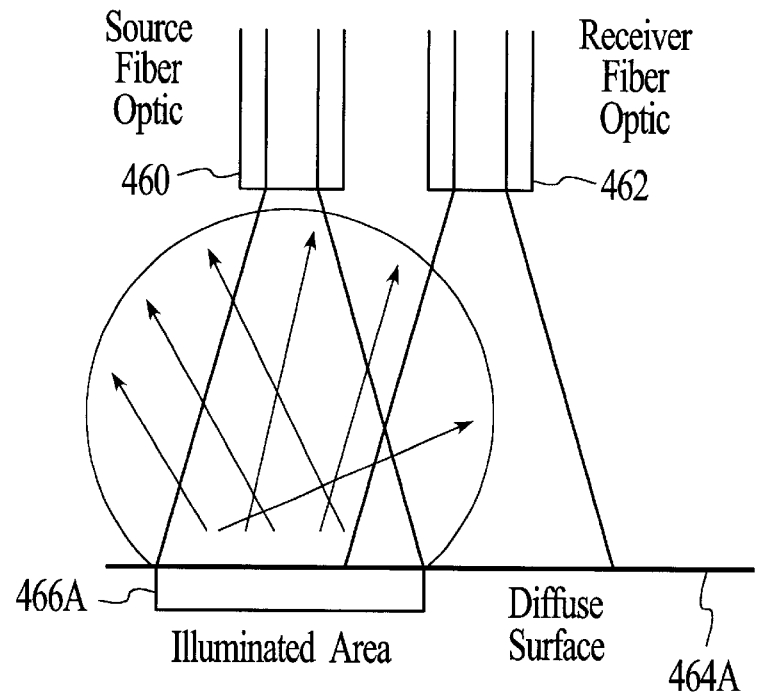
Figure 30B:
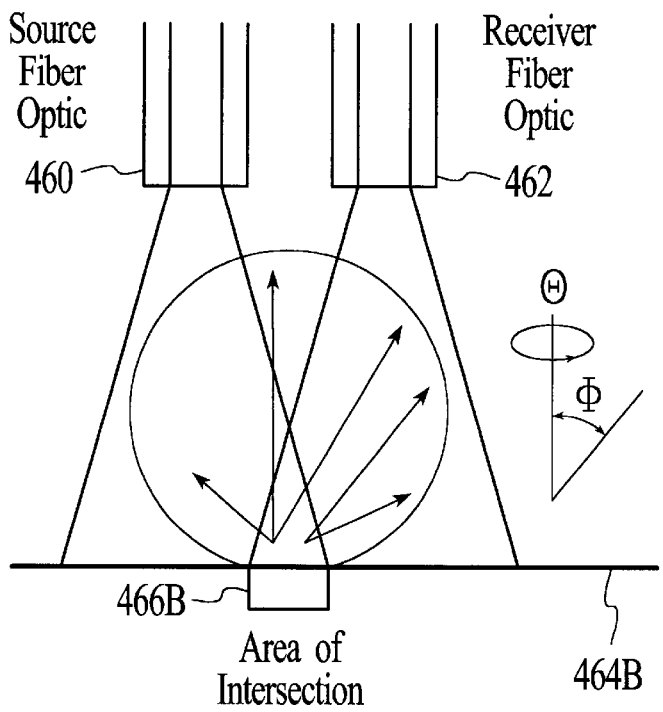

Referring now to FIGS. 30A and 30B, consider two fiber optics (source 460 and receiver 462) perpendicular to diffuse surface 464 A as illustrated in FIG. 30A (FIG. 30B depicts mixed specular/diffuse surface 464 B and area of intersection 466B). Source fiber optic 460 illuminates circular area 466A on surface 464A, and the light is reflected from surface 464A. The light, however, will be reflected at all angles, unlike a specular surface where the light will only be reflected in the form of a cone. Receiver fiber optic 462 in general is always illuminated at all heights, although it can only propagate and detect light that strikes its surface at an angle less than or equal to its acceptance angle. Thus, when the fiber optic pair is less than the critical height, receiver fiber optic 462 detects no light. As the height increases above the critical height, receiver fiber optic 462 starts to detect light that originates from the area of intersection of the source and receiver cones as illustrated. Although light may be incident upon receiver fiber optic 462 from other areas of the illuminated circle, it is not detected because it is greater than the acceptance angle of the receiver fiber.

As the numerical aperture of receiver fiber optic 462 increases, the intensity detected by receiver fiber optic 462 will increase for diffuse surfaces, unlike a specular surface where the received intensity is not a function of receiver fiber optic numerical aperture. Thus, for a probe constructed with a plurality of receiver fiber optics with different numerical apertures, as in preferred embodiments of the present invention, if the surface is a highly glossy surface, both receivers (see, e.g., receivers 456 and 458 of FIG. 28A, will measure the same light intensity. As the surface becomes increasingly diffuse, however receiver D458 will have a greater intensity than receiver C456. The ratio of the two intensities from receivers C/D is a measure of, or correlates to, the degree of specular reflection of the material, and may be directly or indirectly used to quantify the "glossiness" of the surface. Additionally, it should be noted that generally receiver C456 (preferably having the same numerical aperture as source fiber optic A452) measures principally the specular reflected component. Receiver D 458, on the other hand, generally measures both diffuse and specular components. As will be appreciated by those skilled in the art, such probes and methods utilizing receivers of different/varying numerical apertures may be advantageously utilized, with or without additional optical characteristic determinations as described elsewhere herein, to further quantify materials such as teeth or other objects.

Figure 31A:
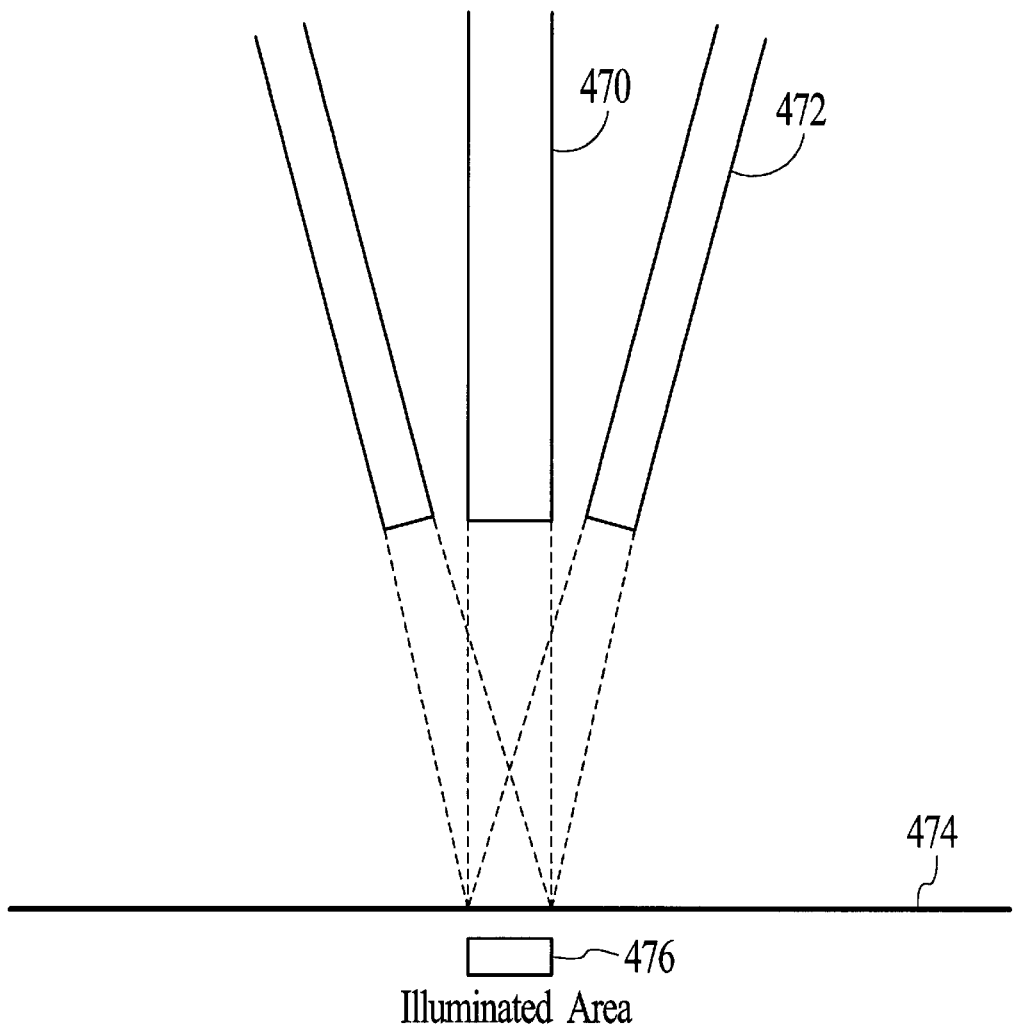
FIGS. 31A and 31B illustrate probes for measuring "specular-excluded" type spectrums in accordance with the present invention.

Referring now to FIG. 31A, additional preferred embodiments will be described. The embodiment of FIG. 31A utilizes very narrow numerical aperture, non-parallel fiber optic receivers 472 and very narrow numerical aperture source fiber optic 470 or utilizes other optical elements to create collimated or nearly collimated source and receiver elements. Central source fiber optic 470 is a narrow numerical aperture fiber optic and receiver fiber optics 472 as illustrated (preferably more than two such receivers are utilized in such embodiments) are also narrow fiber optics. Other receiver fiber optics may be wide numerical aperture fiber optics (e.g., receivers such as receivers 458 of FIG. 28A). As illustrated, receiver fiber optics 472 of such embodiments are at an angle with respect to source fiber optic 470, with the numerical aperture of the receiver fiber optics selected such that, when the received intensity peaks as the probe is lowered to the surface, the receiver fiber optics' acceptance cones intersect with the entire circular area illuminated by the source fiber optic, or at least with a substantial portion of the area illuminated by the source. Thus, the receivers generally are measuring the same central spot illuminated by the source fiber optic.

Figure 31B:
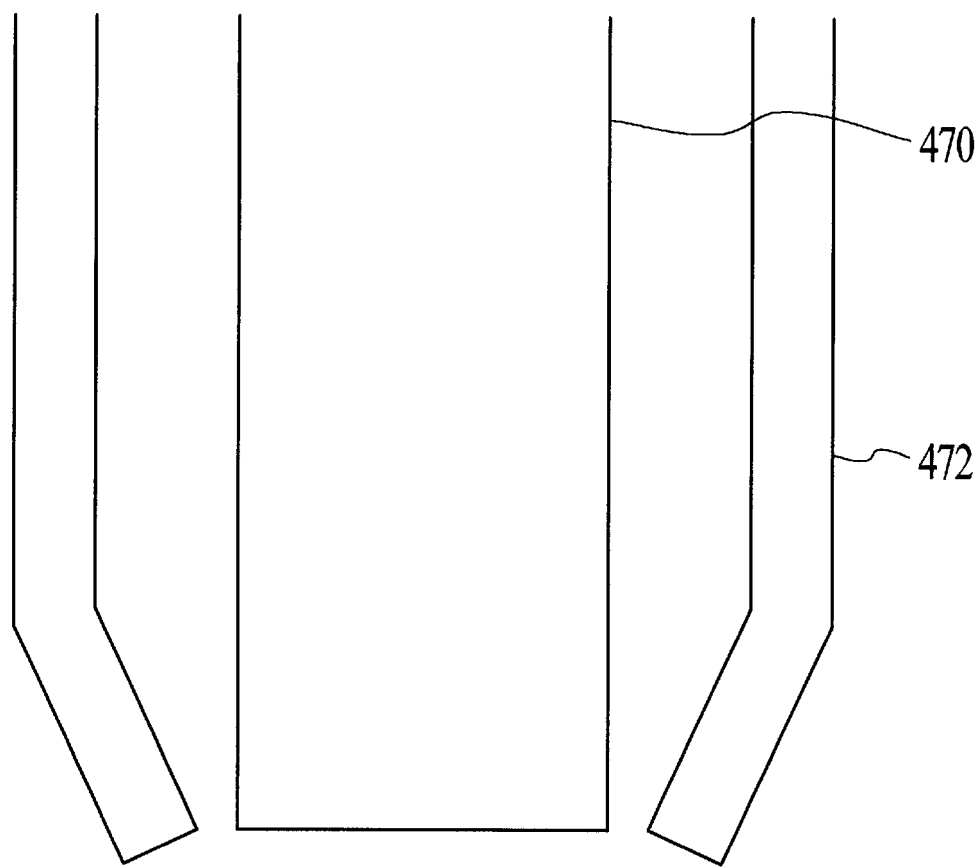

A particular aspect of such embodiments is that a specular excluded probe/measurement technique may be provided. In general, the spectrally reflected light is not incident upon the receiver fiber optics, and thus the probe is only sensitive to diffuse light. Such embodiments may be useful for coupling reflected light to a multi-band spectrometer (such as described previously) or to more wide band sensors. Additionally, such embodiments may be useful as a part of a probe/measurement technique utilizing both specular included and specular excluded sensors. An illustrative arrangement utilizing such an arrangement is shown in FIG. 31B. In FIG. 31B, element 470 may consist of a source fiber optic, or alternatively may consist of all or part of the elements shown in cross-section in FIG. 28A or 28B. Still alternatively, non-parallel receiver fiber optics 472 may be parallel along their length but have a machined, polished, or other finished or other bent surface on the end thereof in order to exclude all, or a substantial or significant portion, of the specularly reflected light. In other embodiments, receiver fiber optics 472 may contain optical elements which exclude specularly reflected light. An additional aspect of embodiments of the present invention is that they may be more fully integrated with an intraoral camera.

Figure 32:
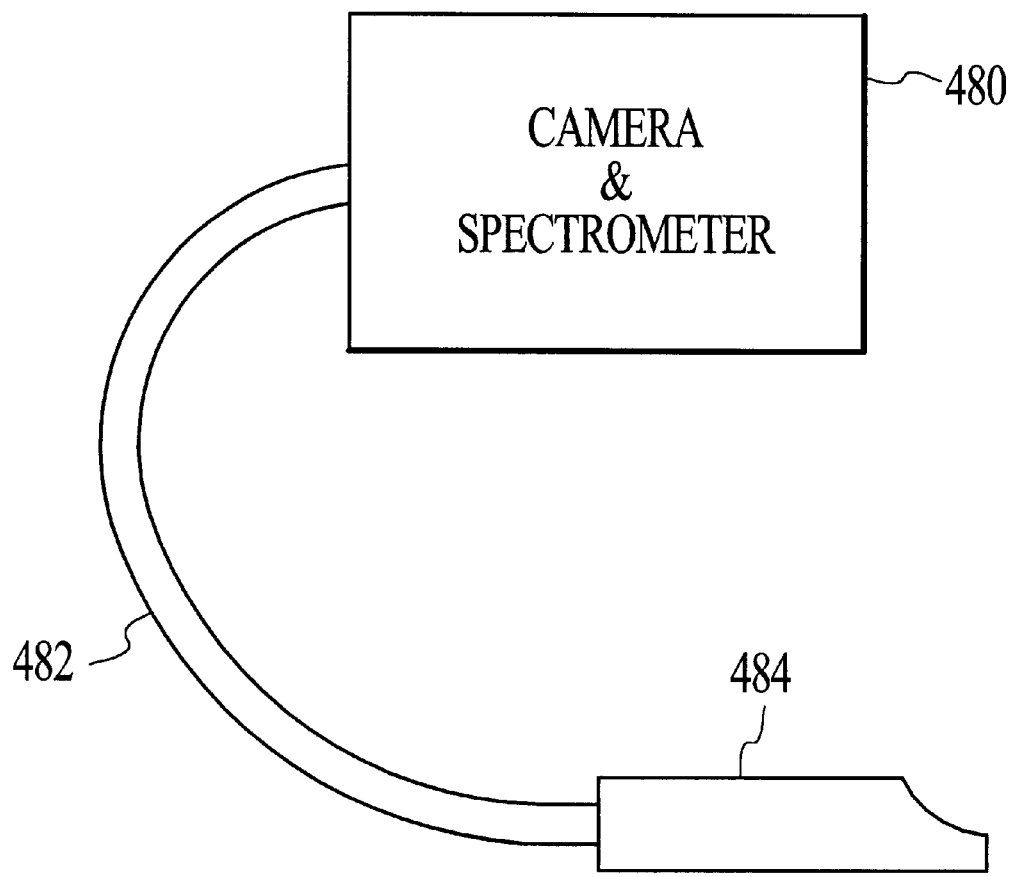
FIGS. 32, 33 and 34 illustrate embodiments in which intra oral cameras and reflectometer type instruments in accordance with the present invention are integrated.
Figure 33:
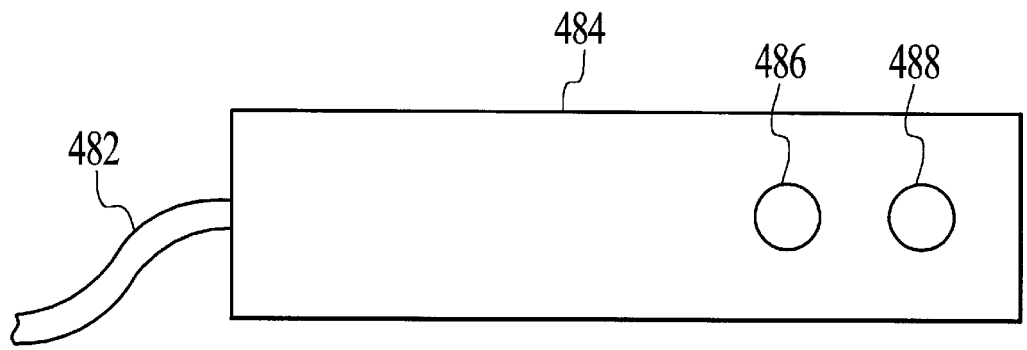
Figure 34:
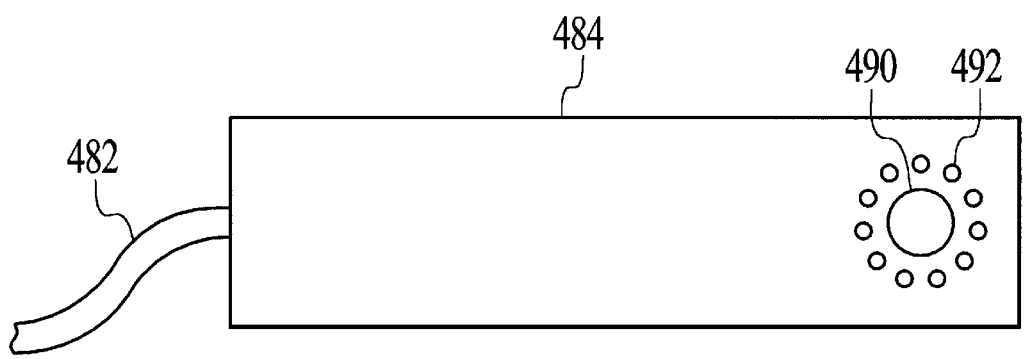

Referring now to FIGS. 32 to 34, various of such embodiments will be described for illustrative purposes. In such embodiments, optical characteristic measurement implements such as previously described may be more closely integrated with an intraoral camera, including common chassis 480, common cord or cable 482, and common probe 484. In one such alternative preferred embodiment, camera optics 486 are positioned adjacent to spectrometer optics 488 near the end of probe 484, such as illustrated in FIG. 33. Spectrometer optics 488 may incorporate, for example, elements of color and other optical characteristics measuring embodiments described elsewhere herein, such as shown in FIGS. 1–3, 9–10B, 11–12, 20–21, 28A, 28B and 31A and 31B. In another embodiment, camera optics and lamp/light source 490 is positioned near the end of probe 484, around which are positioned a plurality of light receivers 492. Camera optics and lamplight source 490 provide illumination and optics for the camera sensing element and a light source for making color/optical characteristics in accordance with techniques described elsewhere herein. It should be noted that light receivers 492 are shown as a single ring for illustrative purposes, although in other embodiments light receivers such as described elsewhere herein (such as in the above-listed embodiments including multiple rings/groups, etc.) may be utilized in an analogous manner. Principles of such camera optics generally are known in the borescope or endoscopes fields.

With respect to such embodiments, one instrument may be utilized for both intraoral camera uses and for quantifying the optical properties of teeth. The intraoral camera may be utilized for showing patients the general state of the tooth, teeth or other dental health, or for measuring certain properties of teeth or dental structure such as size and esthetics or for color postureization as previously described. The optical characteristic measuring implement may then measure the optical properties of the teeth such as previously described herein. In certain embodiments, such as illustrated in FIGS. 33 and 34, a protective shield is placed over the camera for intraoral use in a conventional manner, and the protective shield is removed and a specialized tip is inserted into spectrometer optics 488 or over camera optics and lamp/light source 490 and light receivers 492 (such tips may be as discussed in connection with FIGS. 23A–23C, with a suitable securing mechanism) for infection control, thereby facilitating measuring and quantifying the optical properties. In other embodiments a common protective shield (preferably thin and tightly fitted, and optically transparent, such as are known for intraoral cameras) that covers both the camera portion and spectrometer portion are utilized.

Based on the foregoing embodiments, with which translucency and gloss may be measured or assessed, further aspects of the present invention will be described. As previously discussed, when light strikes an object, it may be reflected from the surface, absorbed by the bulk of the material, or it may penetrate into the material and either be emitted from the surface or pass entirely through the material (i.e., the result of translucency). Light reflected from the surface may be either reflected specularly (i.e., the angle of reflection equals the angle of incidence), or it may be reflected diffusely (i.e., light may be reflected at any angle). When light is reflected from a specular surface, the reflected light tends to be concentrated. When it is reflected from a diffuse surface, the light tends to be distributed over an entire solid hemisphere (assuming the surface is planar) (see, e.g., FIGS. 29–30B). Accordingly, if the receivers of such embodiments measure only diffusely reflected light, the light spectrum (integrated spectrum or gray scale) will be less than an instrument that measures both the specular and diffusely reflected light. Instruments that measure both the specular and diffuse components may be referred to as "specular included" instruments, while those that measure only the diffuse component may be referred to as "specular excluded."

An instrument that can distinguish and quantify the degree of gloss or the ratio of specular to diffusely reflected light, such as with embodiments previously described, may be utilized in accordance with the present invention to correct and/or normalize a measured color spectrum to that of a standardized surface of the same color, such as a purely diffuse or Lambertian surface. As will be apparent to one of skill in the art, this may be done, for example, by utilizing the gloss measurement to reduce the value or luminance of the color spectrum (the overall intensity of the spectrum) to that of the perfectly diffuse material.

A material that is translucent, on the other hand, tends to lower the intensity of the color spectrum of light reflected from the surface of the material. Thus, when measuring the color of a translucent material, the measured spectrum may appear darker than a similar colored material that is opaque. With translucency measurements made as previously described, such translucency measurements may be used to adjust the measured color spectrum to that of a similar colored material that is opaque. As will be understood, in accordance with the present invention the measured color spectrum may be adjusted, corrected or normalized based on such gloss and/or translucency data, with the resulting data utilized, for example, for prosthesis preparation or other industrial utilization as described elsewhere herein.

Additional aspects of the present invention relating to the output of optical properties to a dental laboratory for prosthesis preparation will now be described. There are many methods for quantifying color, including CIELab notation, Munsell notation, shade tab values, etc. Typically, the color of a tooth is reported by a dentist to the lab in the form of a shade tab value. The nomenclature of the shade tab or its value is an arbitrary number assigned to a particular standardized shade guide. Dentists typically obtain the shade tabs from shade tab suppliers. The labs utilize the shade tabs values in porcelain recipes to obtain the final color of the dental prosthesis.

Unfortunately, however, there are variances in the color of shade tabs, and there are variances in the color of batches of dental prosthesis ceramics or other materials. Thus, there are variances in the ceramics/material recipes to obtain a final color of a tooth resulting in a prosthesis that does not match the neighboring teeth.

In accordance with the present invention, such problems may be addressed as follows. A dental lab may receive a new batch of ceramic materials and produce a test batch of materials covering desired color, translucency and/or gloss range(s). The test materials may then be measured, with values assigned to the test materials. The values and associated color, translucency and gloss and other optical properties may then be saved and stored, including into the dental instruments that the lab services (such as by modem download). Thereafter, when a dentist measures the optical properties of a patient's tooth, the output values for the optical properties may be reported to the lab in a formula that is directly related, or more desirably correlated, to the materials that the lab will utilize in order to prepare the prosthesis. Additionally, such functionality may enable the use of "virtual shade guides" or other data for customizing or configuring the instrument for the particular application.

Figure 35:
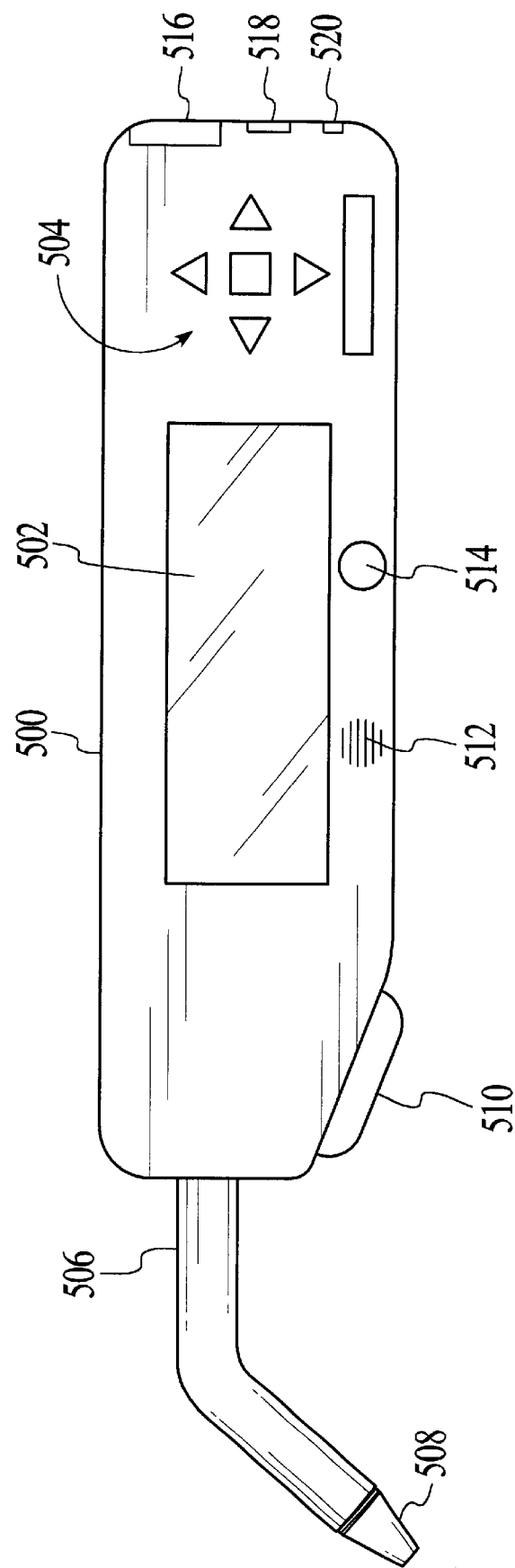
FIGS. 35 and 36 illustrate certain handheld embodiments of the present invention.
Figure 36:
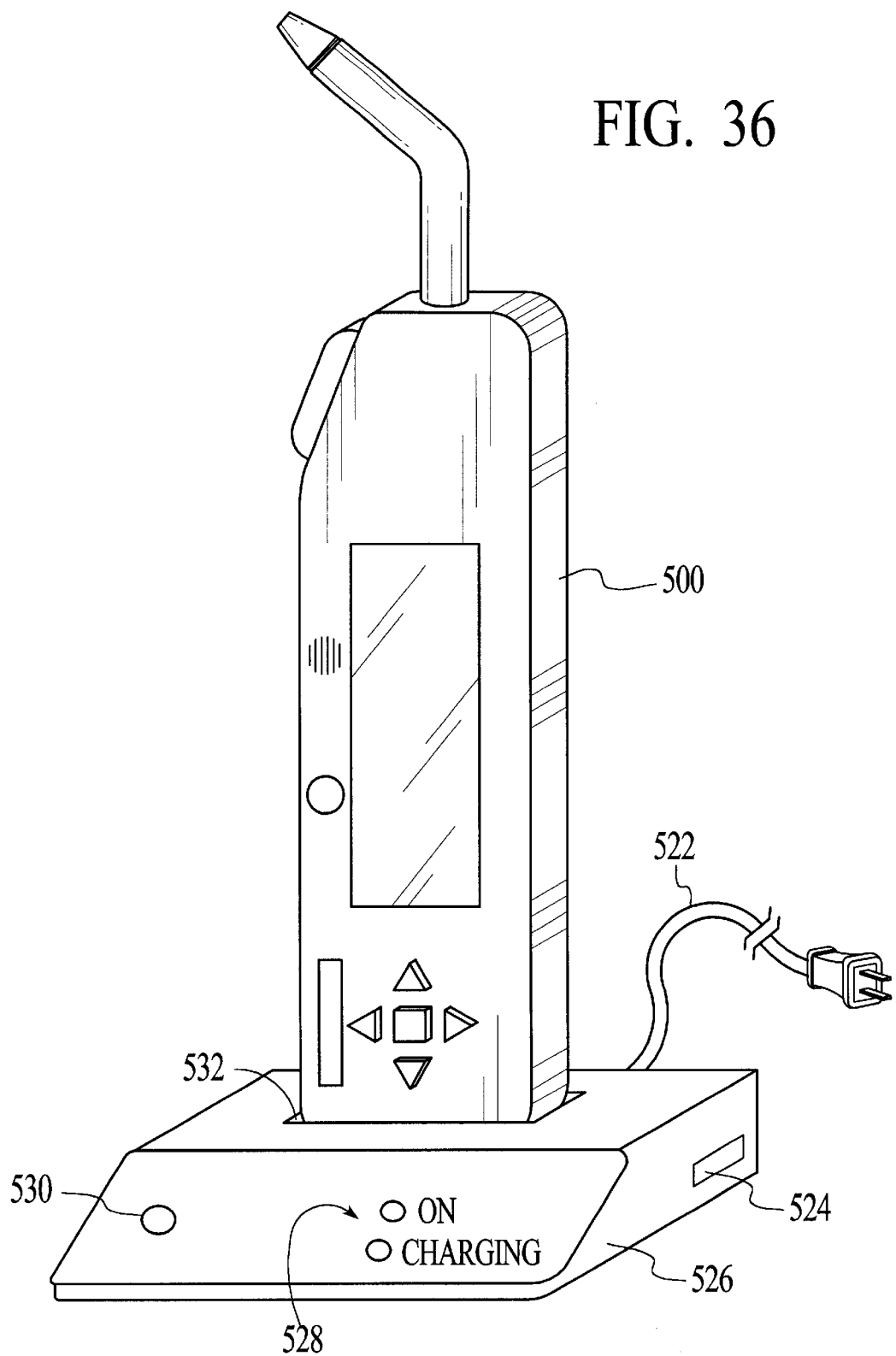

Still other aspects of the present invention will be described with reference to FIGS. 35 and 36, which illustrate a cordless embodiment of the present invention. Cordless unit 500 includes a housing on which is mounted display 502 for display of color/optical property data or status or other information. Keypad 504 is provided to input various commands or information. Unit 500 also may be provided with control switch 510 for initiating measurements or the like, along with speaker 512 for audio feedback (such as previously described), wireless infrared serial transceiver for wireless data transmission such as to an intelligent charging stand (as hereinafter described) and/or to a host computer or the like, battery compartment 516, serial port socket 518 (for conventional serial communications to an intelligent charging stand and/or host computer, and/or battery recharging port 520. Unit 500 includes probe 506, which in preferred embodiments may include removable tip 508 (such as previously described). Of course, unit 500 may contain elements of the various embodiments as previously described herein.

Charging stand 526 preferably includes socket/holder 532 for holding unit 500 while it is being recharged, and preferably includes a socket to connect to wired serial port 518, wireless IR serial transceiver 530, wired serial port 524 (such as an RS232 port) for connection to a host computer (such as previously described), power cable 522 for providing external power to the system, and lamps 528 showing the charging state of the battery and/or other status information or the like.

The system battery may be charged in charging stand 526 in a conventional manner. A charging indicator (such as lamps 528) may be used to provide an indication of the state of the internal battery. Unit 500 may be removed from the stand, and an optical measurement may be made by the dentist. If the dentist chooses, the optical measurement may be read from display 502, and a prescription may be handwritten or otherwise prepared by the dentist. Alternately, the color/optical characteristics data may be transmitted by wireless IR transceiver 514 (or other cordless system such as RF) to a wireless transceiver, such as transceiver 530 of charging stand 526. The prescription may then be electronically created based upon the color/optical characteristics data. The electronic prescription may be sent from serial port 524 to a computer or modem or other communications channel to the dental laboratory.

Figure 37A:
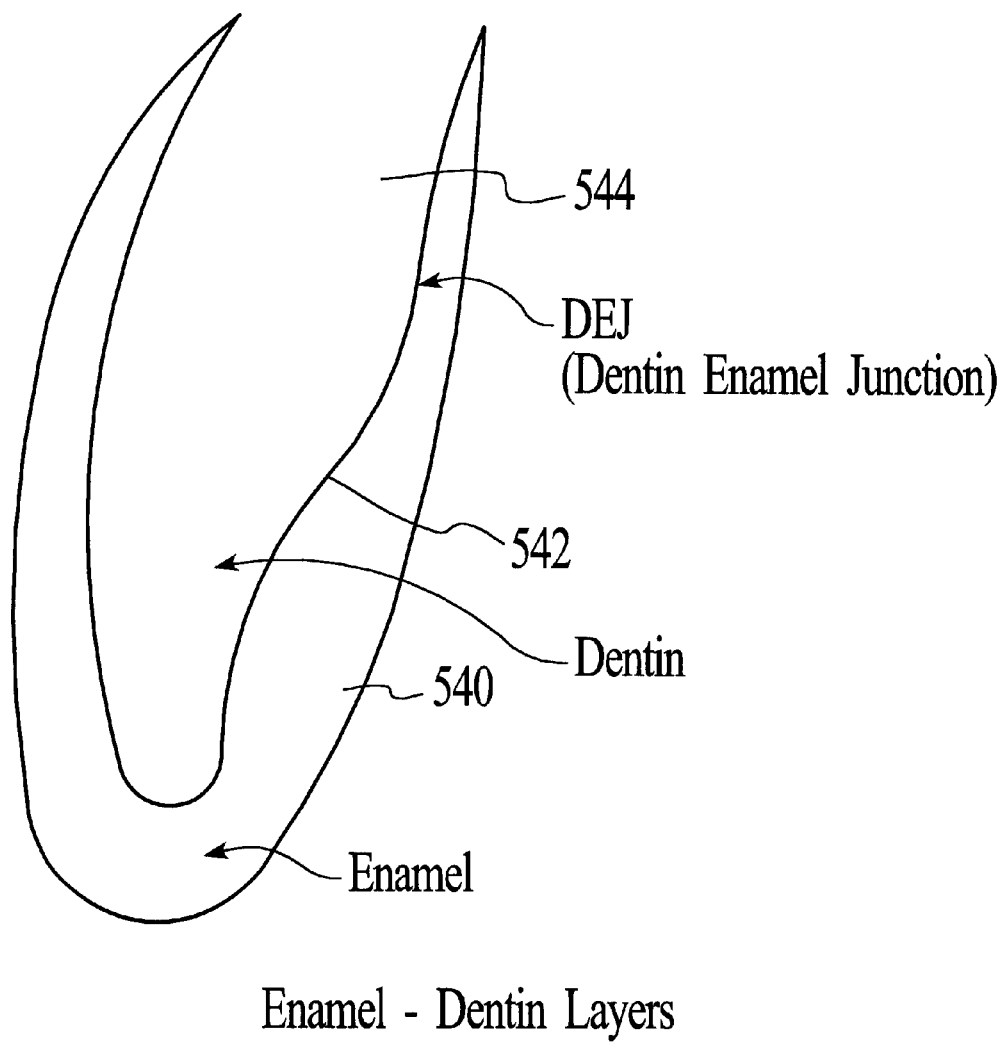
FIGS. 37A and 37B illustrate a tooth dental object in cross section, illustrating how embodiments of the present invention may be used to assess subsurface characteristics of various types of objects.
Figure 37B:
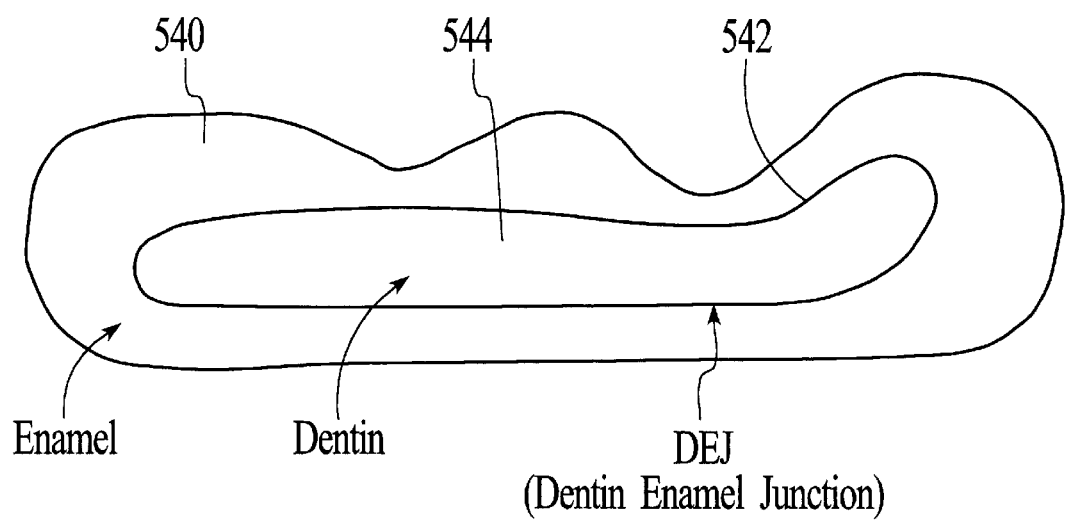

With reference to FIGS. 37A and 37B, additional aspects of the present invention will be discussed.

As is known, human teeth consist of an inner, generally opaque, dentin layer, and an outer, generally translucent, enamel layer. As previously discussed, light that is incident on a tooth generally can be affected by the tooth in three ways. First, the light can be reflected from the outer surface of the tooth, either diffusely or specularly. Second, the light can be internally scattered and absorbed by the tooth structures. Third, the light can be internally scattered and transmitted through the tooth structures and re-emerge from the surface of the tooth. Traditionally, it was difficult, if not impossible, to distinguish light reflected from the surface of the tooth, whether specularly or diffusely, from light that has penetrated the tooth, been scattered internally and re-emitted from the tooth. In accordance with the present invention, however, a differentiation may be made between light that is reflected from the surface of the tooth and light that is internally scattered and re-emitted from the tooth :

As previously described, a critical height h , occurs when a pair of fiber optics serve to illuminate a surface or object and receive light reflected from the surface or object. When the probe's distance from the tooth's surface is greater than the critical height $h_c$ the receiver fiber optic is receiving light that is both reflected from the tooth's surface and light that is internally scattered and re-emitted by the tooth. When the distance of the probe is less than the critical height $h_c$, light that is reflected from the surface of the tooth no longer can be received by the received fiber optic. In general, the only light that can be accepted by the receiver fiber optic is light that has penetrated enamel layer 540 and is re-emitted by the tooth (in cases where the object is a tooth).

Most of the internal light reflection and absorption within a tooth occurs at enamel-dentin interface or junction (DEJ) 542, which in general separates enamel layer 540 from dentin 544. In accordance with the present invention, an apparatus and method may be provided for quantifying optical properties of such sub-surface structures, such as the color of DEJ 542, with or without comparison with data previously taken in order to facilitate the assessment or prediction of such structures.

Critical height $h_c$ of the fiber optic probe such as previously described is a function of the fiber's numerical aperture and the separation between the fibers. Thus, the critical height $h_c$ of the probe can be optimized based on the particular application.. In addition, a probe may be constructed with multiple rings of receive fiber optics and/or with multiple numerical aperture receiving fiber optics, thereby facilitating assessment, etc., of enamel thickness, surface gloss, tooth morphology etc.

It is widely known that the thickness of the enamel layer of a tooth varies from the incisal edge to the cervical portion of the tooth crown, and from the middle of the tooth to the mesial and distal edges of the tooth (see FIGS. 37A and 37B, etc.). By utilizing multiple rings of receiver fiber optics, a measurement of the approximate thickness of the enamel layer may be made based on a comparison of the peak intensity above the tooth surface and a measurement in contact with the tooth surface. A probe with multiple critical heights will give different intensity levels when in contact with the tooth surface, thereby producing data that may be indicative of the degree of internal scattering and enamel thickness or tooth morphology at the point of contact, etc.

Accordingly, in accordance with the present invention, the color or other optical characteristics of a sub-surface structure, such as DEJ 542 of a tooth, may be assessed or quantified in a manner that is in general independent of the optical characteristics of the surface of the tooth, and do so non-invasively, and do so in a manner that may also assess the thickness of the outer layer, such as enamel layer 540.

Additionally, and to emphasize the wide utility and variability of various of the inventive concepts and techniques disclosed herein, it should be apparent to those skilled in the art in view of the disclosures herein that the apparatus and methodology may be utilized to measure the optical properties of objects/teeth using other optical focusing and gathering elements, in addition to the fiber optics employed in preferred embodiments herein. For example, lenses or mirrors or other optical elements may also be utilized to construct both the light source element and the light receiver element. A flashlight or other commonly available light source, as particular examples, may be utilized as the light source element, and a common telescope with a photoreceiver may be utilized as the receiver element in a large scale embodiment of the invention. Such refinements utilizing teachings provided herein are expressly within the scope of the present invention.

As will be apparent to those skilled in the art, certain refinements may be made in accordance with the present invention. For example, a central light source fiber optic is utilized in certain preferred embodiments, but other light source arrangements (such as a plurality of light source fibers, etc.). In addition, lookup tables are utilized for various aspects of the present invention, but polynomial type calculations could similarly be employed. Thus, although various preferred embodiments of the present invention have been disclosed for illustrative purposes, those skilled in the art will appreciate that various modifications, additions and/or substitutions are possible without departing from the scope and spirit of the present invention as disclosed in the claims. In addition, while various embodiments utilize light principally in the visible light spectrum, the present invention is not necessarily limited to all or part of such visible light spectrum, and may include radiant energy not within such visible light spectrum.

With reference to FIG. 5A, the intensity measured by a single receiver fiber is shown as a function of time as a source fiber optic and a receiver fiber optic pair are moved into contact with an object and are moved away from the object. FIG. 5A illustrates the intensity as a function of time, however as will be apparent to one skilled in the art, the intensity detected by the receiver fiber can also be measured and plotted as a function of height. A given fiber optic pair of source and receiver fiber optics, perpendicular to a surface (or at least at a fixed angle relative to a surface) will exhibit a certain intensity vs. height relationship. That relationship generally is consistent for certain materials of consistent gloss, color and translucency. The mathematical intensity vs. height relationship for certain source and receiver fiber optic pairs can be calculated or measured and stored as a look up table value or as a polynomial or other mathematical relationship. What is important to note is that there is an intensity peak that is a function of the gloss, translucency and color of the object being measured. For similar materials, the intensity value at a given height varies dependent upon color, although the shape of the intensity vs. height curve is largely independent of color. Thus, as will be apparent to one skilled in the art, the present invention may also serve as a proximity sensor, determining height from the intensity measurements. The instrument is calibrated by moving it towards the object until the peaking intensity is detected. While the instrument moves towards the object, the light intensities are rapidly measured and saved in memory such as RAM shown in FIG. 1. From the value of the measured peaking intensity (utilized to normalize the intensity vs. height relationship of the fiber pair) the proximity sensor can be calibrated. Thereafter, the present invention may be utilized to measure the height of the fiber optic pair from the surface of the object without contacting the object.

The present invention may find application in a wide range of industrial activities. Certain applications of the present invention include, but are not limited to, measuring the optical properties of teeth and utilizing the measurements as part of a patient data base and utilizing the measurements for dental prosthesis preparation.

Another application of the present invention is its use in dermatology in quantifying the optical properties including color of skin and other tissues and saving the measurements as part of a patient data base record and utilizing the measurements made over a period of time for diagnostic purposes.

Yet another application of the present invention is in the food preparation industry where the color and other optical properties of certain foods that are affected by the preparation process are measured and monitored with the disclosed invention and are utilized to determine whether or not the food meets certain acceptance criteria and where the measurements may be also utilized as part of a control and feed back process whereby the food is further processed until it is either accepted or rejected. Similarly, in automated food processing, such as for vegetables or fruit, measurements may be taken and an assessment or prediction of the condition of the vegetable or fruit made, such as ripeness.

Yet another application of the present invention is to measure the color and optical properties of objects newly painted as part of a control process. For example, paint may be applied to the object, with the object then measured to determine if a suitable amount or type of paint has been applied, perhaps with the process repeated until a measurement corresponding to a desired surface condition is obtained, etc.

Yet another application of the present invention is to measure the optical properties of newly painted objects over a period of time to discern if the paint has cured or dried. Similarly, such an object may be measured to determine if additional gloss coatings, surface texture factors or fluorescence factors, etc., should be added to achieve a more optimum or desired object.

Yet another application of the present invention is in an industrial or other control system, where items are color coded or have color or gloss or translucency or combinations of optical properties that identify the objects and where the optical properties are measured utilizing the disclosed invention and are sorted according to their optical properties. In general, the present invention may be utilized to measure the optical properties of objects in an industrial process flow, and then compare such measurements with previously stored data in order to sort, categorize, or control the direction of movement of the object in the industrial process.

Yet another application of the present invention is to place color coded or gloss coated or translucent tags or stickers on objects that serve as inventory control or routing control or other types of identification of objects in industrial processes.

Yet another application of the present invention is part of the printing process to measure and control the color or other optical properties of inks or dies imprinted on materials. In such embodiments, implements as described herein may be integrated into the printer or printing equipment, or used as a separate implement.

Yet another application of the present invention is part of the photographic process to measure, monitor and control the optical properties of the photographic process. In such embodiments, implements as described herein may be integrated into the camera or other photographic instrument, or used as a separate implement.

Yet another application of the present invention is to measure the distance to the surface of objects without being placed into contact with the object.

The present invention may be used in an industrial process in which coatings or material are added to or removed from an object. The object may be measured, and coatings or materials added or removed, with the object re-measured and the process repeated until a desired object or other acceptance criteria are satisfied. In such processes, comparisons with previously stored data may be used to assess whether the desired object is obtained or the acceptance criteria satisfied, etc.

In yet another application, the present invention is utilized in the restoration of paintings or other painted objects, such as art works, automobiles or other objects for which all or part may need to be painted, with the applied paint matching certain existing paint or other criteria. The present invention may be used to characterize whether paint to be applied will match the existing paint, etc. In such processes, comparisons with previously stored data may be used to assess whether the desired paint match will be obtained, etc.

In general, the present invention may find application in any industrial process in which an object or material may be measured for surface and/or subsurface optical characteristics, with the condition or status of such object or material assessed or predicted based on such measurements, possibly including comparisons with previously stored data as previously described, etc. Additionally, and to emphasize the wide utility and variability of various of the inventive concepts and techniques disclosed herein, it should be apparent to those skilled in the art in view of the disclosures herein that the apparatus and methodology may be utilized to measure the optical properties of objects using other optical focusing and gathering elements, in addition to the fiber optics employed in preferred embodiments herein. For example, lenses or mirrors or other optical elements may also be utilized to construct both the light source element and the light receiver element. A flashlight or other commonly available light source, as particular examples, may be utilized as the light source element, and a common telescope with a photoreceiver may be utilized as the receiver element in a large scale embodiment of the invention. Such refinements utilizing teachings provided herein are expressly within the scope of the present invention.

In addition to the foregoing embodiments, features, applications and uses, other embodiments and refinements in accordance with the present invention will now be described. As with prior descriptions, descriptions to follow are without being bound by any particular theory, with the description provided for illustrative purposes. As before, although certain of the description to follow makes reference to objects or materials, within the scope of the various embodiments of the present invention are dental objects such as teeth. Also as before, teeth or any other particular objects referenced herein are exemplary uses, and various embodiments and aspects of the present invention may be used in other fields of endeavor.

A variety of devices may be used to measure and quantify the intensity of light, including, for example, photodiodes, charge coupled devices, silicon photo detectors, photomultiplier tubes and the like. In certain applications it is desirable to measure light intensity over a broad band of light frequencies such as over the entire visible band. In other applications it is desirable to measure light intensities over narrow bands such as in spectroscopy applications. In yet other applications it is desirable to measure high light intensities such as in photographic light meters. In still other applications it is desirable to measure low light intensities such as in abridged spectrometers. Typically when measuring low light intensities, long sampling periods of the order of one second or longer are required.

In accordance with other aspects of the present invention, a method and apparatus are disclosed that may be used to measure multiple light inputs rapidly. Such an embodiment preferably utilizes a photodiode array, such as the TSL 230 manufactured by Texas Instruments, Inc., and a gate array manufactured by Altera Corporation or Xilinx, Inc. In certain applications, such an embodiment may be utilized to measure broad band visible and infra-red light. In other applications, such an embodiment may be utilized as an abridged spectrometer in which each photodiode array has a notch filter, such as an interference filter, positioned above the light sensor.

The TSL 230 consists of 100 silicon photodiodes arranged in a square by array. The 100 photodiodes serve as an input to an integrator that produces an output signal of a frequency proportional to the intensity of light incident upon the array. The TSL 230 has scale and sensitivity inputs allowing the sensitivity and scale to each be varied by a factor of 100, for a net range of $10^4$. The output frequency can vary from a maximum of approximately 300 k Hz (sensor is saturated) to sub Hz ranges. Thus, the sensor can detect light inputs ranging over seven orders of magnitude by varying the sensitivity and/or scale of the sensor and can detect light ranges of over five orders of magnitude at a given setting.

In spectroscopy applications for such embodiments, each sensor is mounted with an optical filter such as an interference filter. As is known in the art, interference filters have high out-of-band rejection and high in-band transmission, and may be constructed with very narrow band pass properties. As an example, interference filters may be constructed with band pass ranges of nanometers or less. In accordance with certain aspects of the present invention, an abridged-type spectrometer may be constructed with TSL 230 (or similar) sensors and interference filters that is suitable for reflectivity or transmission spectrographic applications such as measuring the color of objects. In color determination applications it is not necessary to detect "line" spectra, but it often is desirable to have high gray scale resolution, e.g., to be able to resolve the light intensity to 1 part in 1000 or greater.

Instruments and methods for measuring the optical properties of materials and objects have been previously described. Such an instrument may consist of a probe and an abridged spectrometer. The probe may be moved into contact or near contact with the surface of the material or object (by movement of the probe or material/object, etc.), and the spectrum of the light received by the probe was analyzed as the probe was moved towards the surface. Since the probe was not stationary, preferably numerous measurements are taken in succession, with the spectra dynamically taken and/or analyzed as the probe relatively moves in proximity with the object.

One difficulty that results from narrowing the band width of notch or interference filters is that such narrowing reduces the light intensity incident upon each sensor. Thus, to measure low light levels, long sampling times typically are required. In the case of the TSL 230 sensor, as the light level decreases, the output frequency of the device decreases. Thus, if it is desired to make 200 samples per second with an abridged spectrometer constructed with notch filters and TSL 230s, one needs enough light to cause the TSL 230 output to oscillate at a rate of at least 200 Hz. Since the maximum range of the sensor is approximately 300 k Hz, the maximum dynamic range of the sensor is reduced to (300 k Hz)/(200 Hz) or roughly $1.5 \times 10^3$. If the light inputs are low, then the dynamic range is reduced still further.

Figure 38:
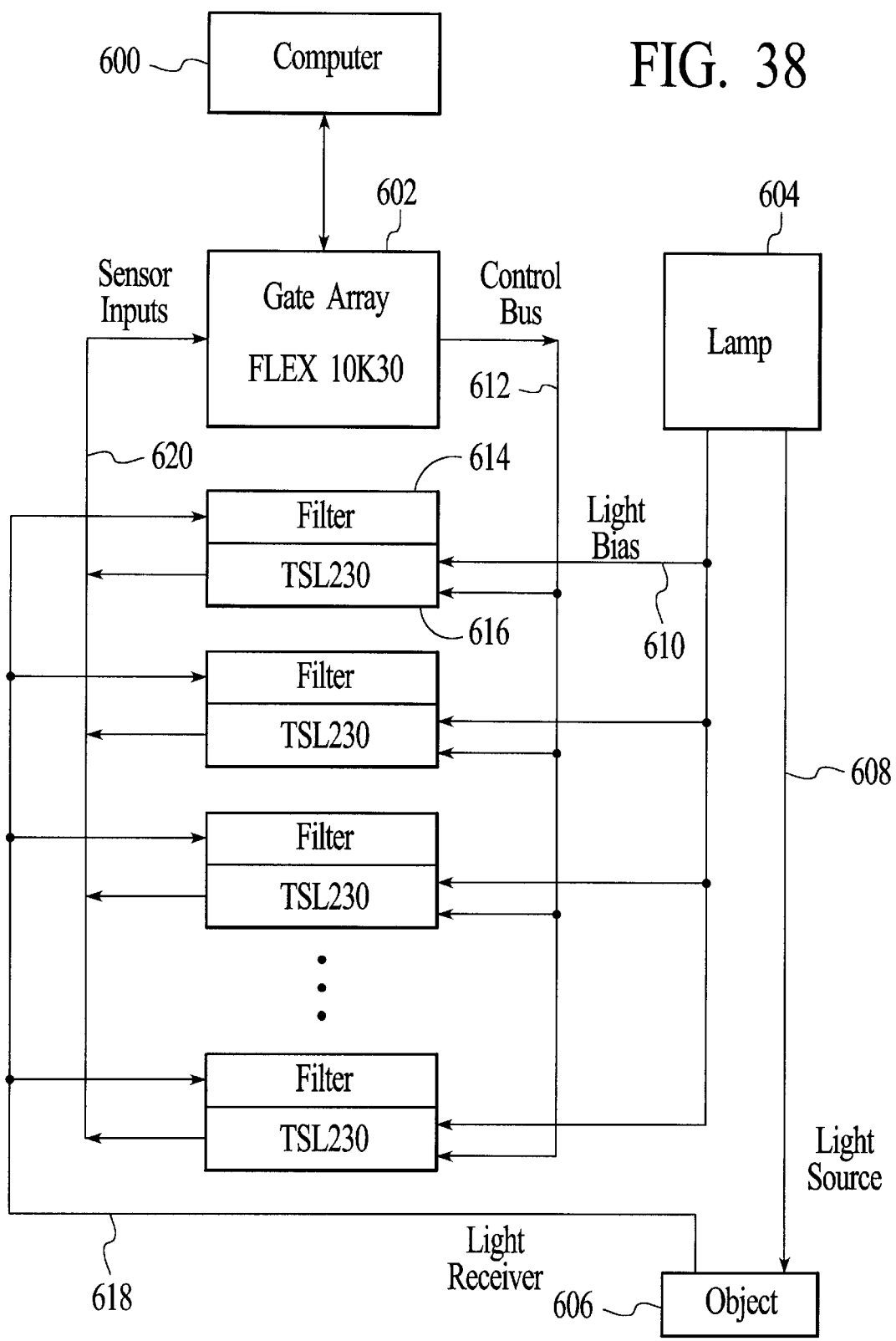

FIG. 38 illustrates an abridged visible light range spectrometer in accordance with another embodiment of the present invention. This embodiment utilizes TSL230 sensors 616, a light source or lamp 604, preferably a hot mirror that reflects IR light with wavelengths above 700 nanometers (not expressly shown in FIG. 38), fiber optic cable assembly consisting of one or more sources (illustrated by light path 608) providing light to object 606, and one or more receivers (illustrated by light path 618) receiving light from object 606, gate array 602 such as an Altera FLEX 10K30™ (believed to be a trademark of Altera Corporation), which is coupled to computer 600 and receives signal inputs from sensors 616 over bus 620. In one preferred embodiment up to fifteen or more TSL 230 sensors are utilized. Each TSL 230 sensor 616 has an interference filter 614 positioned above the sensor, with each filter preferably having a nominal bandwidth of nanometers (or other bandwidth suitable for the particular application). Sensors 616 also preferably receive a small and controlled amount of light (light path 610) directly from light source 604, preferably after IR filtering. The light source input to sensors 616 serves to bias sensors 616 to produce an output of at least 200 Hz when no light is input to sensors 616 from filters 614. Thus, sensors 616 will always produce an output signal frequency greater than or equal to the sampling frequency of the system. When input light intensities are small, the frequency change is small, and when the light input is large, the frequency change will be large. The scale and sensitivity of sensors 616 are set (by gate array 602 over control bus 612, which may be under control of computer 600) to detect the entire range of light input values. In most cases, particularly in object color determination, the maximum amount of light input into any one of sensors 616 is determined by light source 604 and filters 614 and can be appropriately controlled.

Gate array 602 serves to measure the output frequency and period of each of sensors 616 independently. This may be done by detecting whenever an output changes and both counting the number of changes per sampling period and storing the value of a high speed counter in a first register the first time an output changes, and storing the value in a second register for each subsequent change. The second register will thus hold the final value of the timer. Both high to low and low to high transitions preferably are detected. The output frequency (f) of each sensor is thus:

$$1) \; f = \frac{(N-1)}{(P_h - P_l)}$$

where:

N=Number of transitions in sample period;

$P_l$=Initial timer count; and $P_h$=Final timer count.

The internal high speed timer is reset at the start of each sampling period ensuring that the condition $P_h > P_l$ is always true.

The precision of a system in accordance with such an embodiment may be determined by the system timer clock frequency. If P, is the desired precision and Sr is the sampling rate, then the frequency of the timer clock is:

$$2) \; f = P_r \cdot S_r$$

For example, for a sampling rate of 200 and a precision of $2^{16}$, the timer clock frequency is $200 \times 2^{16}$ 6 or 13 MHz.

If the input light intensities are high, N will be a large number. If the input light intensities are low, N will be small (but always greater than 2, with proper light biasing). In either case, however, $P_h - P_l$ will be a large number and will always be on the order of ½ the precision of the system. Thus, in accordance with such embodiments, the theoretical precision to which the light intensities can be measured may be the same for all sensors, independent of light input intensity. If one sensor has an output range of 200 to 205 Hz (very low light input), the intensities of light received by this sensor may be measured to about the same precision as a sensor with 10,000 times more light input (range of 200 to 50,200 Hz). This aspect of such embodiments is very unlike certain conventional light sensors, such as those utilizing ADCs, analog multiplexers and sample and hold amplifiers, where the precision of the system is limited to the number of bits of the ADC available over the input range. To provide for the wide input range in a system with an ADC, a variable gain sample and hold amplifier typically is required. It is also difficult for an ADC to sample to 16 bits accurately.

With such embodiments of the present invention, the absolute accuracy generally is limited by the stability of the lamp and electrical noise, both of which may be reduced and in general are minimal because of the simplicity of the design and the few components required on a circuit card. A gate array, which may be field programmable or the like, typically may readily accommodate 20 or more TSL230 sensors and also provide for an interface to a computer, microprocessor or microcontroller utilizing the light data. It also should be noted that, instead of a gate array, such embodiments may be implemented with high speed RISC processors or by DSPs or other processing elements.

It should be noted that the use of light biasing, and other aspects thereof, also are described elsewhere herein.

In addition to the foregoing embodiments, features, applications and uses, still other embodiments and refinements in accordance with the present invention will now be described.

Certain objects and materials such as gems and teeth exhibit reflected light spectrums that are a function of incident light angle and reflected light angle. Such objects and materials are sometimes referred to as opalescent materials. In accordance with other embodiments of the present invention, instruments and methodologies may be provided for specifically measuring and/or quantifying the opalescent characteristics of objects and materials, in addition to characteristics such as color, gloss, translucency and surface texture, it being understood that previously described embodiments also may be used to capture spectral and other data (such as a plurality of spectrums), which can be compared and/or processed to quantify such opalescent materials.

Figure 39:
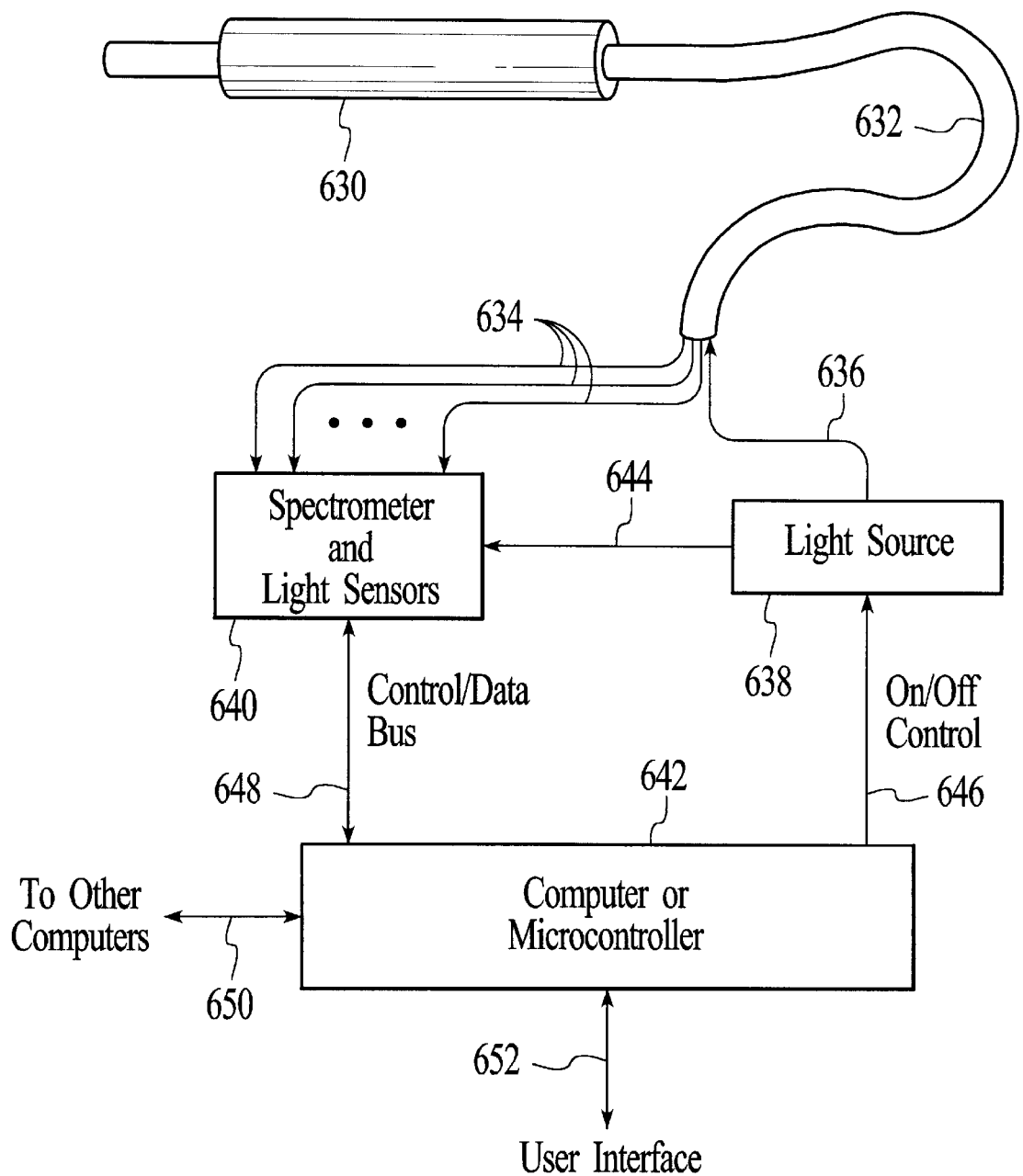

Such a further embodiment of the present invention is illustrated in FIG. 39. In accordance with this embodiment, light source 638 provides light coupled through a light path (preferably light source fiber 636) to probe 630 through optical cable 632. Light received by the probe (i.e., returned from the object or material being evaluated) is coupled to spectrometer/light sensors 640 through a suitable light path (preferably one or more light receiver fibers from optical cable 632). Computer 642 is coupled to spectrometer/light sensors 640 by way of control/data bus 648. Computer 642 also is coupled to light source 638 by way of control line(s) 646, which preferably control the on/off condition of light source 638, and optionally may provide other control information, analog or digital signal levels, etc., to light source 638 as may be desired to optimally control the particular light chosen for light source 638, and its particular characteristics, and for the particular application. Light from light source 638 optionally may be coupled to spectrometer/light sensors 640 by light path 644, such as for purposes of providing light bias (if required or desired for the particular spectrometer chosen), or for monitoring the characteristics of light source 638 (such as drift, temperature effects and the like).

Computer 642 may be a conventional computer such as a PC or microcontroller or other processing device, and preferably is coupled to a user interface (e.g., display, control switches, keyboard, etc.), which is generically illustrated in FIG. 39 by interface 652. Optionally, computer 642 is coupled to other computing devices, such as may be used for data processing, manipulation, storage or further display, through interface 650. Computer 642 preferably includes the typical components such as (but not limited to) a CPU, random access or other memory, non-volatile memory/storage for storing program code, and may include interfaces for the user such as display, audio generators, keyboard or keypad or touch screen or mouse or other user input device (which may be through interface 652), and optionally interfaces to other computers such as parallel or serial interfaces (which may be through interface 650). Computer 642 interfaces to spectrometer/light sensors 640 for control of the spectrometer and overall system and to receive light intensity and light spectrum data from spectrometer/light sensors 640. In a preferred embodiment, control/data bus 648 for interfacing to spectrometer/light sensors 640 is a standard pin bi-directional parallel port. In certain embodiments, computer 642 may be separate, standalone and/or detachable from spectrometer/light sensors 640 and may be a conventional laptop, notebook or other portable or handheld-type personal computer. In other embodiments, computer 642 may be an integral part of the system contained in one or more enclosure(s), and may be an embedded personal computer or other type of integrated computer. Purposes of computer 642 preferably include controlling light source 638 and spectrometer/light sensors 640, receiving light intensity and spectral or other data output from spectrometer/light sensors 640, analyzing received or other data and determining the optical properties of the object or material, and displaying or outputting data to a user or other computing device or data gathering system.

Figure 40:
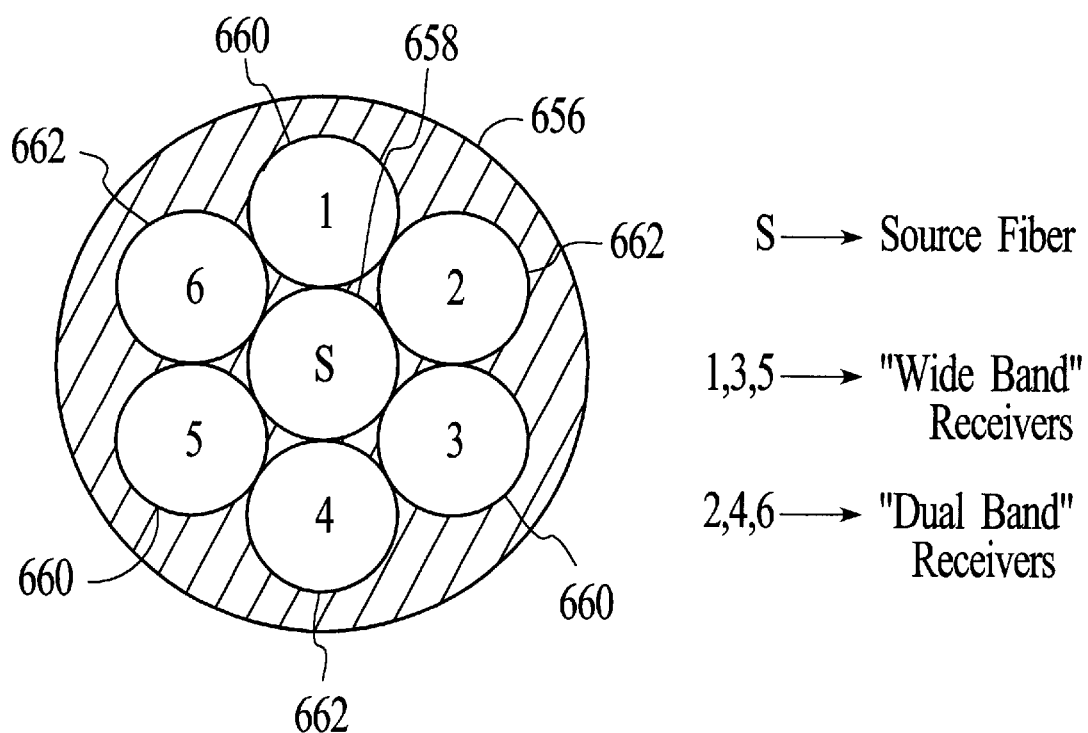

In a preferred embodiment, the output end of probe 630 may be constructed as illustrated in FIG. 40. Numerous other probe configurations, including probe configurations as described elsewhere herein, may be used in such embodiments. In accordance with such preferred embodiments, optical characteristics determination systems/methods may be obtained that provide for a broader range of measurement parameters, and, in certain applications, may be easier to construct. Probe cross section 656 includes central fiber optic 658, which is preferably surrounded by six perimeter fiber optics 660 and 662. Central fiber optic 658 is supplied by light from the light source (such as light source 638). Six perimeter fiber optics 660 and 662 are light receivers and pass to spectrometer/light sensors 640. In one preferred embodiment, all seven fiber optics have the same numerical aperture (NA); however, as disclosed below, the numerical aperture of the light source and consequently the source fiber optic preferably can be varied. Also, in certain embodiments the received cone of light from certain of the receiver fiber optics is also controlled and varied to effectively vary the NA of certain receivers.

As illustrated in FIG. 40, central fiber optic 658 (S) serves as the light source. Fiber optics 660 labeled 1,3,5 preferably are "wide band" fibers and pass to light sensors (preferably within spectrometer/light sensors 640) that measure light intensity over an entire spectral range. The other three light receivers 662 labeled 2,4,6 preferably are "dual" receivers and pass to both a spectrometer and to "wide band" light sensors (also preferably within spectrometer/light sensors 640). As previously described, the probe in conjunction with a spectrometer, computer, light source and "wide band" light receivers can be used to measure the color and translucency and surface properties of teeth and other materials. Also as previously described, the probe with a combination of NA "wide band" receiver fiber optics can additionally be utilized to measure the gloss or the degree of specular versus diffuse light received from a surface.

Figure 41A:
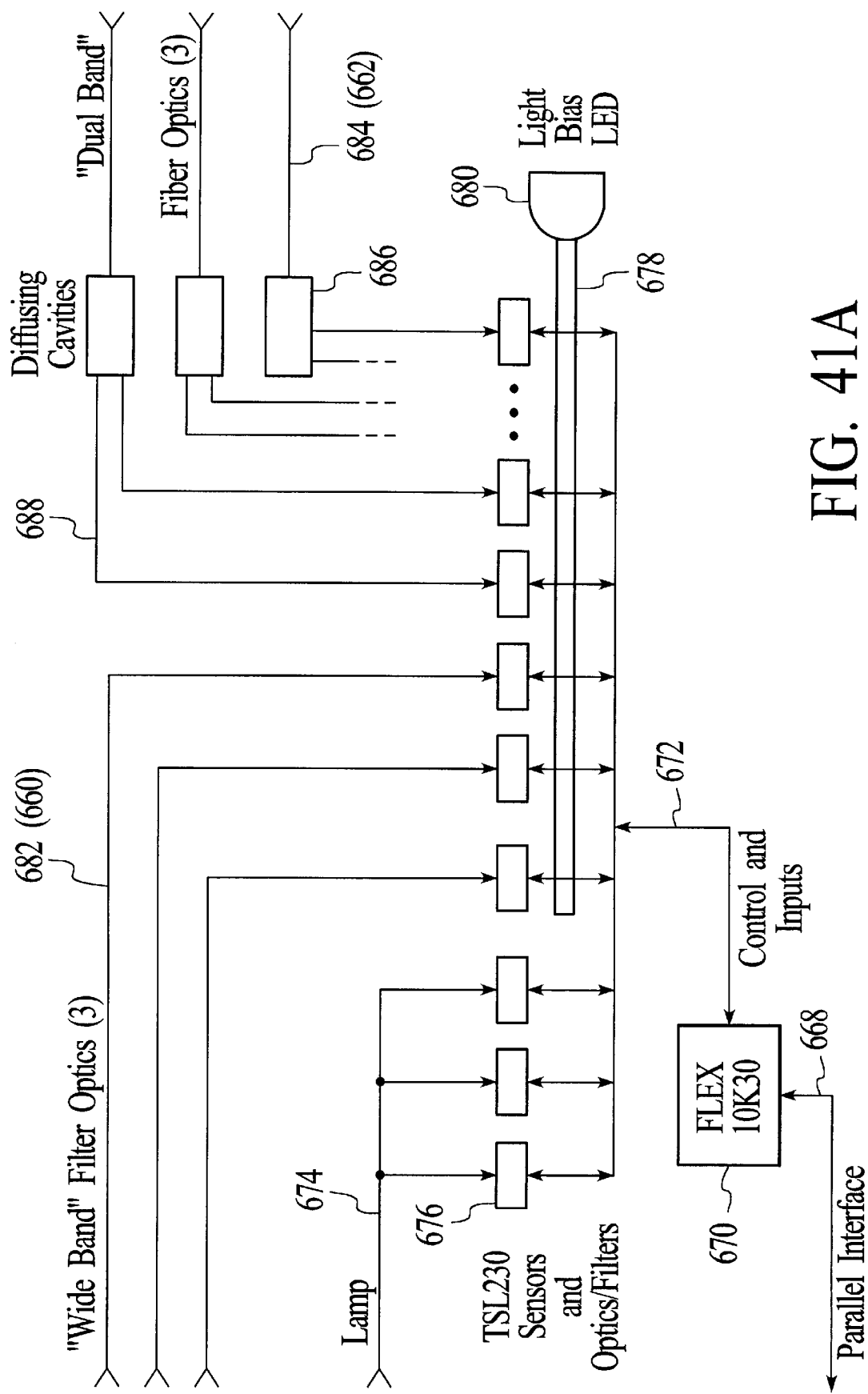
Figure 42:
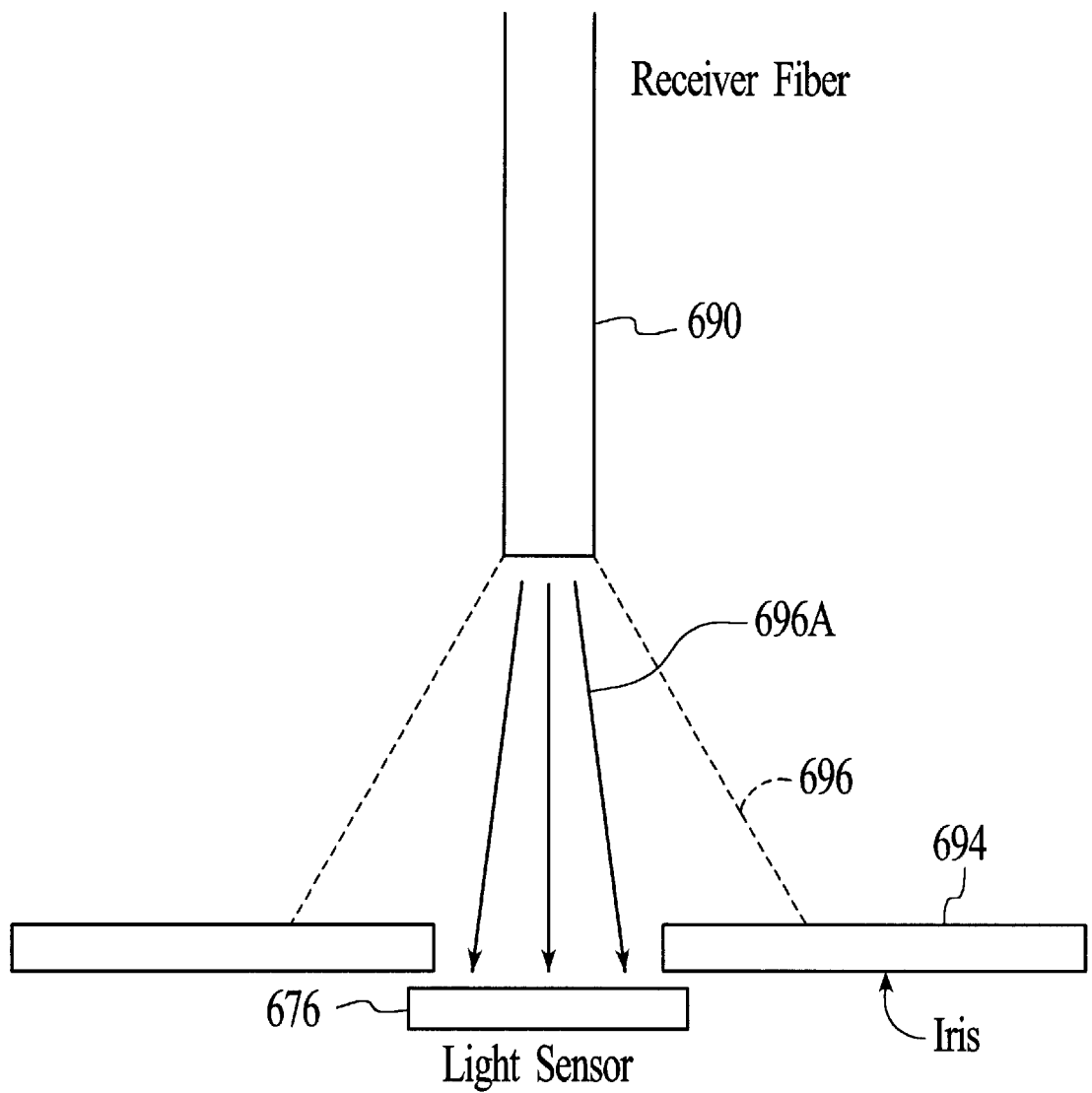

FIG. 41A is a diagram of a preferred embodiment of spectrometer/light sensors 640. In this embodiment, certain optical fibers from the probe are coupled to wide band light sensors (such sensors, which may include TSL230 sensors and optics and/or filters as described elsewhere herein are illustrated as sensors 676 in FIG. 41A), while other of the optical fibers are coupled to both a spectrometer, in order to spectrally measure the light received by the probe, and to wide band light sensors. Fibers 660 (1,3,5) preferably are coupled to three wide band light sensors (light path 682 of FIG. 41A). Preferably, the light receiving/sensing elements are Texas Instruments TSL 230 s, although they may also be photo diodes, CCDs or other light sensors. Fibers 660 (1,3,5) preferably are masked by iris 694 to reduce the size of the cone of light produced by the fiber as illustrated in FIG. 42. Mask or iris 694 serves to limit the NA of the receiver by allowing only light rays with a maximum angle of a to be received by the receiver light sensor.
If:
h=height of end of fiber to iris
r=radius of opening of the iris
a=radius of the fiber 1) then: $\operatorname{Tan}^{-1}\left(\frac{r+a}{h}\right)$ Hence, the effective NA of the receiver fiber optic can be reduced and controlled with iris 694. By utilizing a variable iris or an iris that is controlled with a servo such as those utilized in conventional cameras, the NA of the receiver fiber optic can be controlled by the system and can be varied to best match the object or material being measured. Referring again to FIG. 42, exemplary receiver fiber 690 provides light to exemplary light sensor 676 through iris 694. Light rays such as light rays 696A of a certain limited angle pass through iris 694, while other light rays within the acceptance angle of fiber 690 (the outer limit of the acceptance angle is illustrated by dashed line 696 in FIG. 42) but not within the limited angular range allowed by iris 694 are blocked, thereby enabling iris 694 to effectively emulate having a reduced or variable NA light receiver.

Referring again to FIG. 41A, light source 638 may be coupled to certain of sensors 676 through light path 674. Light bias, such as previously described, may be provided from the light source, or alternatively, from separately provided LED 680, which may couple light to certain of sensors 676 for providing controllable light bias to sensors 676 through light conduit 678. Control of LED 680 for providing controllable light bias to certain of sensors 676, etc., is described elsewhere herein. Light from fibers 662 preferably are coupled (through light path 684 in FIG. 41A) to one or more diffusing cavities 686 (described in more detail elsewhere herein), outputs of which are coupled to certain of sensors 676 through light paths/conduits 688 as illustrated. Control of sensors 676, and data output from sensors 676, preferably is achieved by way of gate array 670, which may be coupled to a computing device by way of interface 668 (the use of gate array or similar processing element and the use of such a computer device are described elsewhere herein).

Figure 43A:
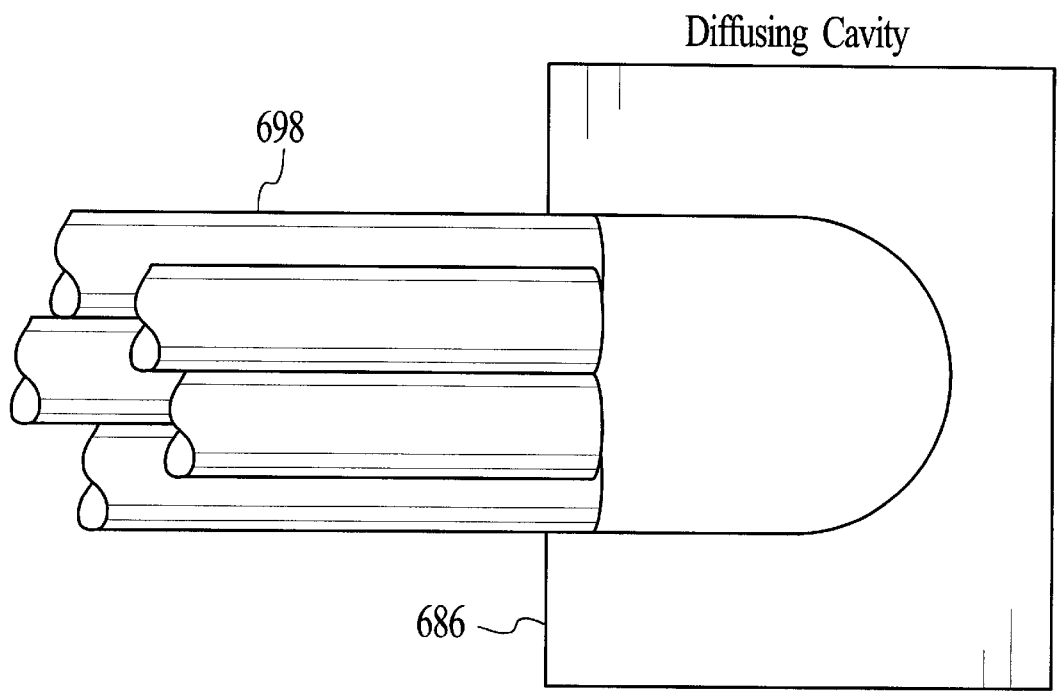
Figure 43B:
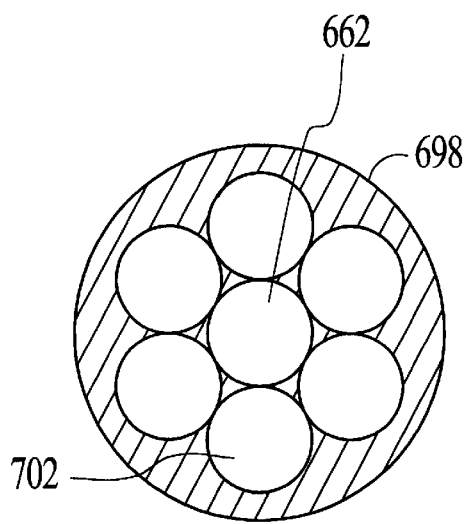
Figure 43C:
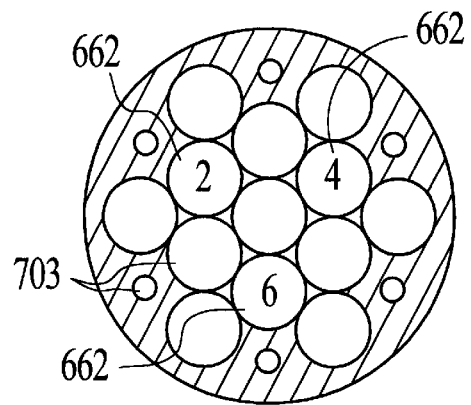

The use of diffusing cavities 686 in such embodiments will now be further described. As illustrated, certain of the light receivers 662 (2,4,6) may be coupled to one or more diffusing cavities 686 through light path 684, which may serve to split the light receivers into, for example, six (or more or fewer) fiber optics with a diffusing cavity as illustrated in FIGS. 43A, 43B, and 43C. One of light receivers 662 is the central fiber in diffusing cavity 686 and is surrounded by six fiber optics 702 as part of fiber optic bundle 698. Diffusing cavity 686 serves to remove any radial or angular light distribution patterns that may be present in receiver fiber optic 662, and also serves to more evenly illuminate the six surrounding fiber optics. Thus, light receivers 662 (2,4,6) illustrated in FIG. 40 may each be split into six (or a different number) fibers resulting in eighteen receivers. Three of the eighteen fibers, one per diffusing cavity, preferably pass to wide band sensors which may have iris 694 (see FIG. 42). The other fifteen fibers preferably pass to a spectrometer system (such as part of spectrometer/ light sensors 640, which may consist of a plurality of sensors 676, such as previously described). For the visible band, fifteen fiber optics and interference notch filters preferably are used to provide a spectral resolution of:

2) $\dfrac{700\,\text{nm} - 400\,\text{nm}}{15} = 20\,\text{nm.}$

A greater or lesser number of fibers and filters may be utilized in accordance with such embodiments in order to increase or decrease the spectral resolution of the system/ spectrometer.

Figure 41B:
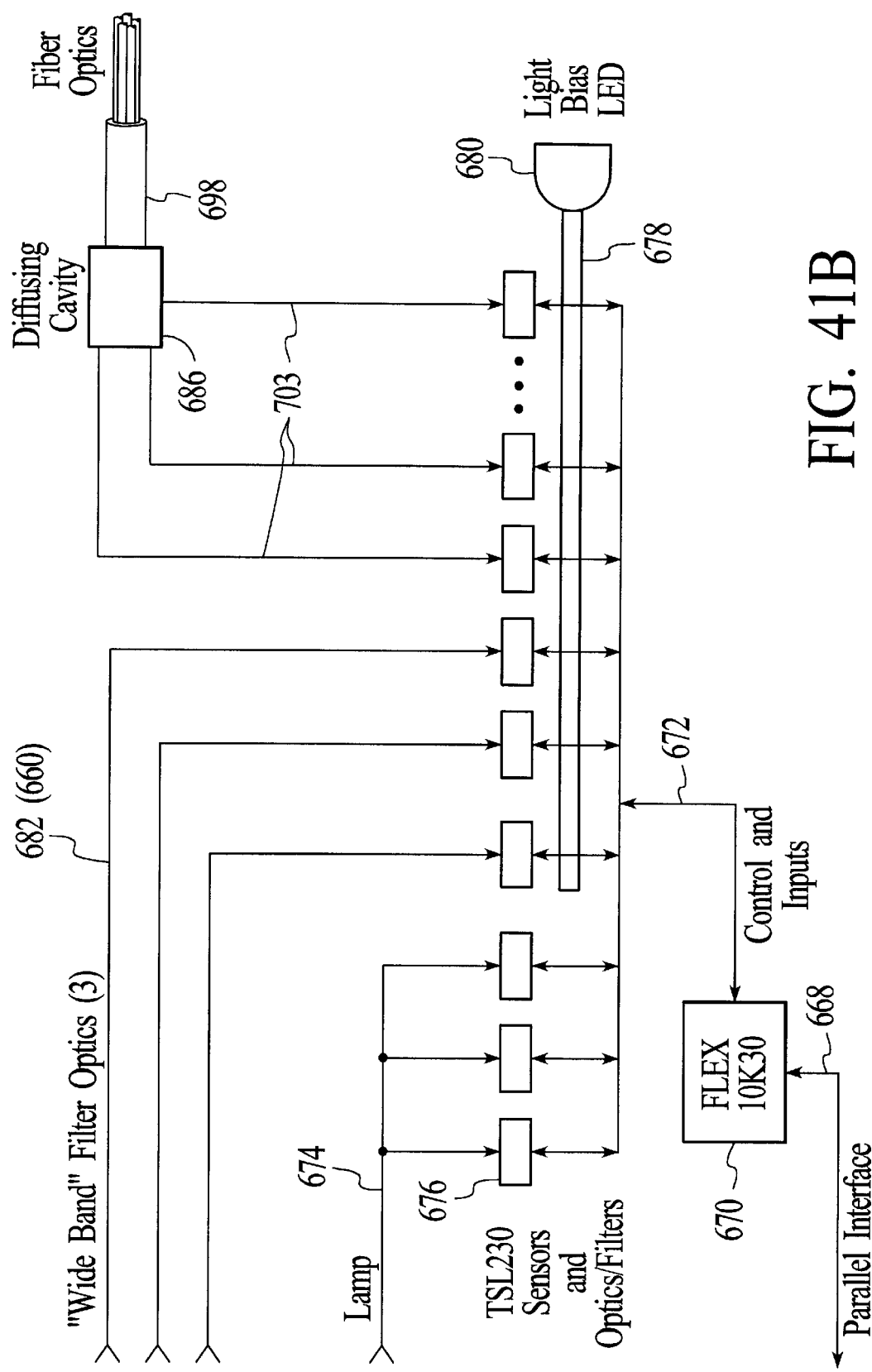

In FIGS. 41B and 43C, an alternate embodiment of the present invention utilizing a different arrangement of diffusing cavity 686 will now be described. In such embodiments, three "dual band" receivers 662 are all positioned in common fiber optic bundle 698 and one diffusing cavity 686 is utilized. Fiber optic bundle 698 preferably contains three receiver fibers 662 and fifteen additional fibers 703 for the spectrometer system, although greater or fewer fibers may be utilized in other arrangements depending on the number of color sensors in the system. In certain embodiments, fifteen fiber optics 703 in the bundle may be of different diameters to increase the efficiency of diffusing cavity 686 and the cross sectional packing arrangement of the optical fibers in fiber optic bundle 698. As an example of such preferred fiber bundle arrangements in accordance with such embodiments, larger diameter fibers may be utilized for the color filters in the blue range of the visible spectrum, where the light intensity from a tungsten-halogen lamp source 638 is significantly less than in the red region of the visible spectrum.

As described elsewhere herein, a spectrometer system may be constructed of Texas Instruments TSL230 light sensors, interference filters, light biasing elements and a gate array such an Altera FLEX10K in order to control the light sensors, interface to a computer via a parallel or other interface and to measure the frequency and period of the light sensors simultaneously at a high rate in order to accurately and rapidly measure light spectrums and light intensities. Although such spectrometer systems are used in preferred embodiments, other spectrometers such as those utilizing, for example, CCDs with diffraction gratings are utilized in other embodiments.

Figure 44:
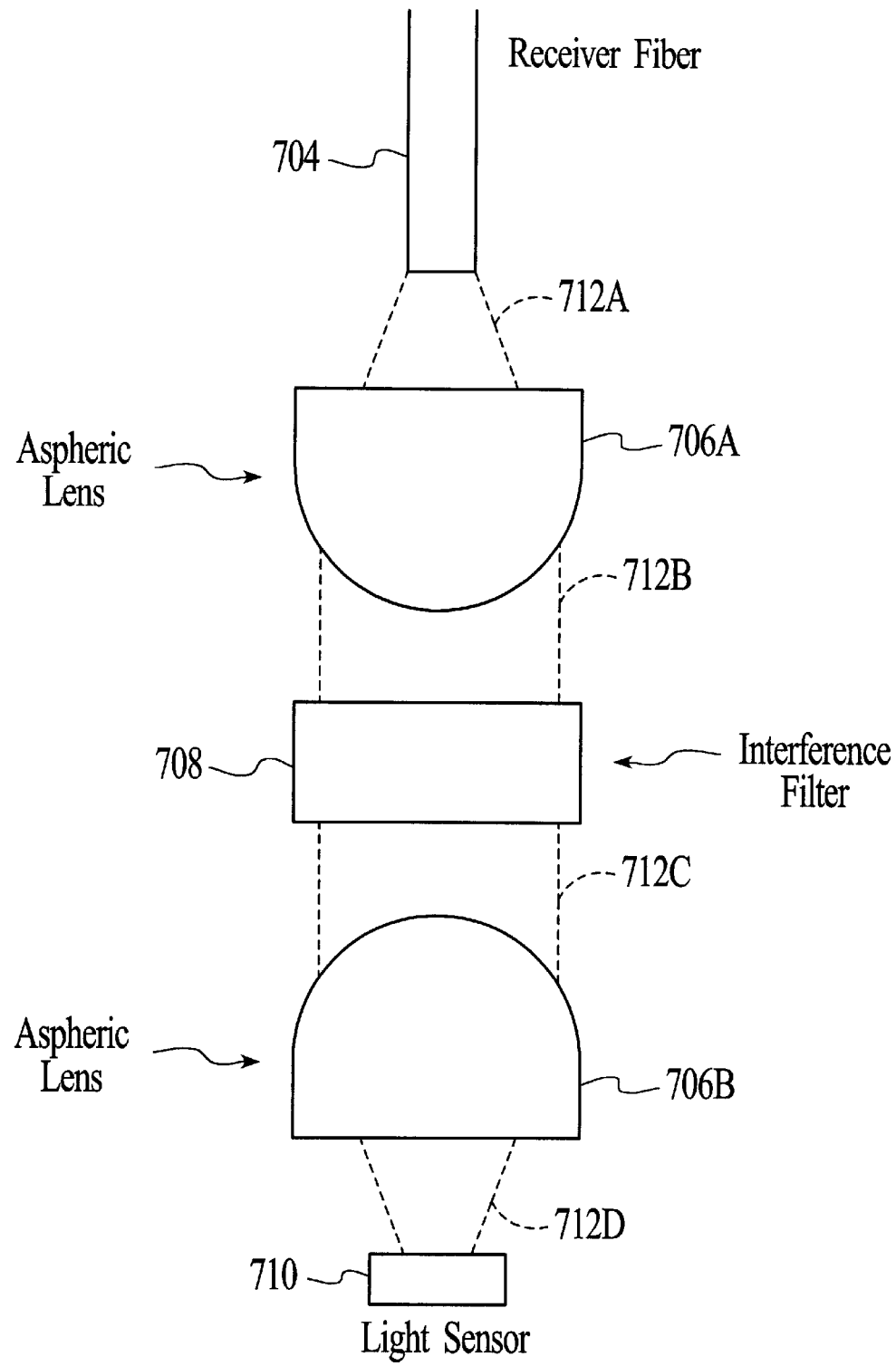

FIG. 44 illustrates a further refinement of aspects of a spectrometer-type system in accordance with the present invention. A fiber optic, such as one of the fifteen fibers from three diffusing cavities as described earlier, preferably pass to light sensor 710 (which may be a TSL230 light sensor, as previously described) through interference filter 708. Interference filters such as interference filter 708 serve as notch filters passing light over a narrow bandwidth and rejecting light that is out of band. The bandwidth of the light transmitted through the filter, however, is dependent upon the angle of incidence of the light on the filter, and in general is broadened as the angle of incidence increases. Since fiber optics produce a cone of light, it has been determined that it is desirable to collimate the cone to reduce such bandwidth spreading. As illustrated in FIG. 44, the cone of light produced by exemplary fiber optic 704 (illustrated by lines 712A) preferably is collimated with first aspheric lens (or fresnel lens) 706A (illustrated by lines 712B) prior to entering interference filter 708. Light emitted from filter 708

(illustrated by lines 712C) is "gathered" by second aspheric lens (or fresnel lens) 706B to concentrate (illustrated by lines 712D) as much light as possible on light sensor 710. In accordance with such embodiments, filters, particularly interference-type filters, may more optimally be utilized in a manner to reduce such bandwidth spreading or other undesirable effects.

Referring again to FIG. 41A (the discussion also is generally applicable to FIG. 41B), light biasing as previously described will be discussed in greater detail. As previously described, in order to rapidly sample TSL230-type sensors, the sensors may require light biasing. Without light biasing, depending upon the light intensity presented to the particular sensors, a TSL230 sensor may not produce an output change pair of transitions (e.g., high to low and low to high transitions, or low to high and high to low transitions) during the sampling period, hence a light intensity measurement may not be possible for that sensor. In preferred embodiments, the sensing system detects both high to low and low to high transitions and requires at minimum two transitions to make a measurement. In other words, such system measures half periods. For example, assume that as the light intensity on a particular TSL230 decreases such that its output frequency decreases from 201 Hz to 199 Hz. At 201 Hz, the output of the TSL230 transitions with a period of 1/201 sec or every 4.975 ms. At 199 Hz, the output transition period is 1/199 sec or 5.025 ms. If the sampling rate is 200 samples per second, then the sampling period is 5.00 ms. Thus, if the TSL230 transitions every 4.975 ms, the sensing system will always detect either two or three transitions and will always be able to make an intensity measurement. At 199 Hz, however, the detection circuitry will detect either one or two transitions. As a result, during certain sampling intervals, measurements are possible, while during other intervals measurements are not possible, thereby resulting in measurement discontinuities even though the light intensity has not changed.

It is desirable to measure light over a broad range of intensity values at high rates including very low light intensities. By utilizing light biasing of the TSL230 sensors as illustrated in FIG. 41A, the minimal output frequency of the TSL230s can be controlled. The minimal light value preferably is measured as part of a normalization or calibration procedure as follows:

1. The light bias is turned on and allowed to stabilize.
2. The probe is placed into a black enclosure. A "black level" intensity measurement $I_b$ is made and recorded for each sensor, preferably in a simultaneous manner.
3. The light source is turned on and allowed to stabilize. A "white level" intensity measurement $I_W$, is made and recorded for each sensor, again preferably in a simultaneous manner, on a "white" standard such as barium sulfide or on "Spectralon," believed to be a trademarked product of Labsphere, Inc. The actual intensities measured by all sensors will vary from the standard values $I_S$. Typically in color measurements the standard value $I_S$ is nominally "100%."
4. Subsequent light measurements may be normalized by subtracting the "black level" intensity and by adjusting the gain from the white level measurement resulting in a normalized intensity $I_N$ for each sensor as follows:

$$3)\ I_N = \frac{I_s}{I_w - I_b}(I - I_b)$$

where I=Intensity measurement and $I_N$ is the normalized or calibrated intensity measurement. It should be noted that in such preferred embodiments the normalization is made for each light sensor, and independent "black level" and "white level" intensities are saved for each sensor.

In certain situations, a long time may be required for the light source and for the light bias source to stabilize. In other situations, the light source and bias source may drift. In preferred embodiments, the light source is a 18 W, 3300 K halogen stabilized tungsten filament lamp manufactured by Welch Allyn, Inc. The light bias preferably is provided by a high intensity LED and a fiber optic light guide or conduit (see LED 680 and light conduit 678 of FIG. 41A) that passes to each biased sensor of sensors 676. The intensity of LED 680 preferably is controlled and varied with high frequency pulse width modulation, or by analog constant current controllers. By controlling the intensity of bias LED 680, the bias light level can be varied to best match the sensor sampling rate.

Preferably, one sensor, such as a TSL 230 sensor, is provided to measure the intensity of LED 680 and to correct for intensity variations of the LED light biasing system. Since LED 680 is monochromatic, one sensor typically is sufficient to track and correct for bias LED intensity drift. The LED bias intensity preferably is measured and recorded when the "black level" measurement is made. For each subsequent light intensity measurement, the black level for each sensor is corrected for LED drift as follows:

$$4)\ I_b(Corrected) = I_b \frac{I(BiasSensor)}{I_b(BiasSensor)}$$

where: I(BiasSensor) is the intensity measured by the bias sensor, $I_b$(BiasSensor) is the "black level" intensity measured by the bias sensor, $I_b$ is the "black level" intensity measured by a light sensor (other than the bias sensor) and $I_b$(Corrected) is the adjusted bias used in equation 4) above.

Light source drift preferably is measured by a plurality of light sensors. Since the light source is polychromatic light, its spectrum may also drift. It is understood that tungsten filament lamps produce spectrums that are very nearly approximated by the spectrums of black body radiators and can be represented by the Planck law for black body radiators.

$$5)\ I(\lambda) = \left(\frac{2 \cdot \pi \cdot h \cdot c}{\lambda^3}\right)\left(\frac{1}{e^{\frac{hc}{k \cdot T \cdot \lambda}} - 1}\right)$$

The only variable affecting the intensity of a black body radiator at any wavelength within the visible band is the temperature (T) of the source. Thus, a single narrow band light sensor may be utilized to detect temperature variations of such a source. Additional factors, however, may affect the spectral output of the lamp, such as depositing of the filament on the lamp envelope or adjusting the spectrum of the lamp as described below. In the preferred embodiment, for more accurate spectral corrections and intensity variations of the lamp, additional narrow band filters are utilized. In certain of such preferred embodiments, three band pass filters and sensors are utilized to measure the spectral shift and intensity of the lamp in a continuous manner, and such filters and sensors preferably are further utilized to correct for lamp spectral and intensity drift.

Figure 45:
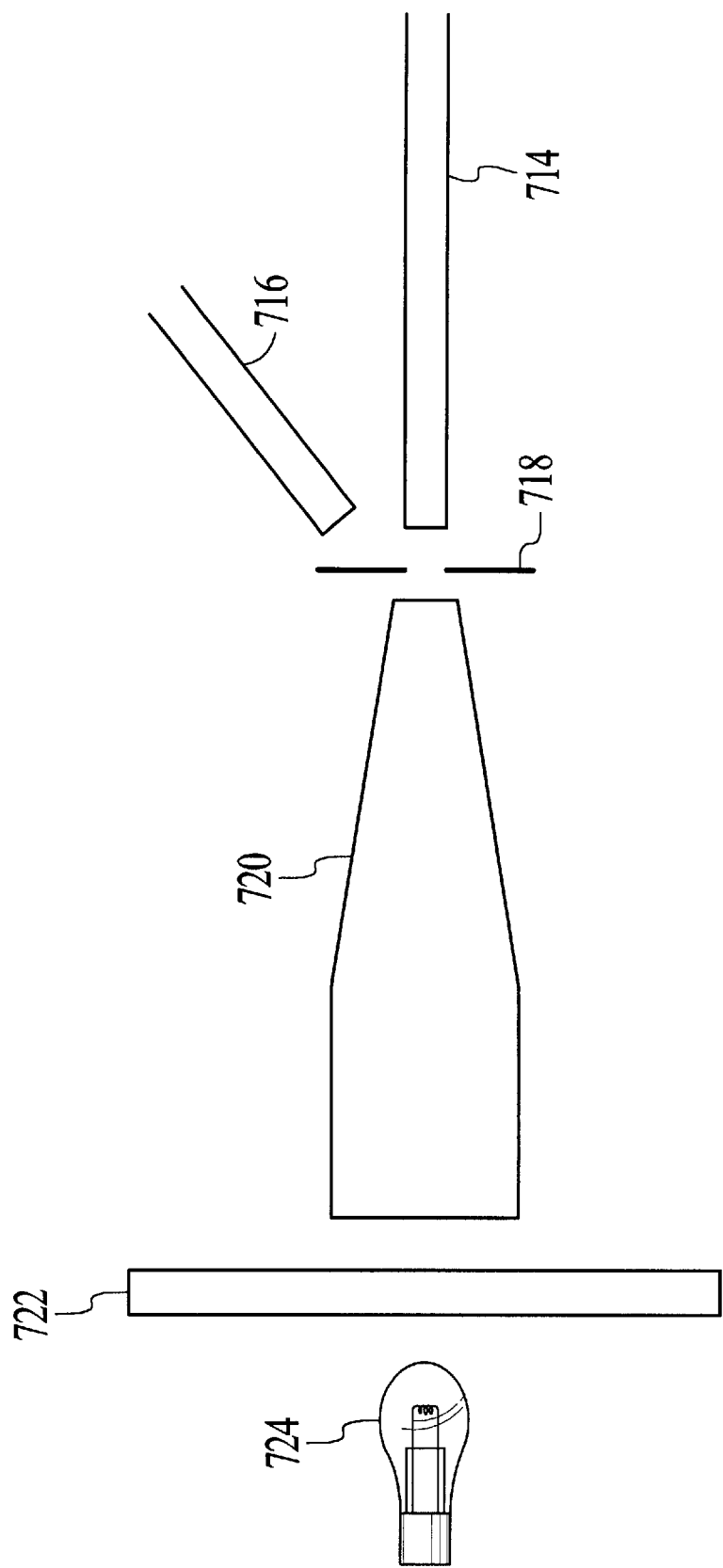

FIG. 45 illustrates a preferred embodiment of a light source used in preferred embodiments of the present invention. Such a light source preferably consists of halogen tungsten filament lamp 724, with a lens molded into the envelope of the lamp that produces a concentrated light pattern on an axis parallel to the body of lamp 724. The use of such a lens in lamp 724 is to concentrate the light output and to reduce the shadowing of the lamp filament that may result from lamps with reflectors. Hot mirror 722, which preferably is a "0° hot mirror," reduces the intensity of IR light input into the system. In certain embodiments, the hot mirror may also contain color correction properties, for example, reducing light intensity for longer (red) wavelengths more than for shorter (blue) wavelengths. Light output from lamp 724 passes through hot mirror 722 preferably to tapered glass rod 720. The end of glass rod 720 nearest lamp 724 preferably has a diameter nominally the diameter of the envelope of lamp 724. The other end of glass rod 720 preferably is nominally 4 mm, or up to four times or more the diameter of source fiber optic 714.

Glass rod 720 serves a number of purposes. First, glass rod 720 serves as a heat shield for fiber optic 714 by allowing fiber optic 714 to be displaced from lamp 724, with fiber optic 714 being thermally insulated from lamp 724 by the existence of glass rod 720. Second, glass rod 720 serves to concentrate the light over a smaller area near fiber optic 714 and to broaden the angular distribution of light emerging from the narrow end to provide a distributed light pattern that can uniformly "fill" the NA of source fiber optic 714. Without tapered glass rod 720, the angular distribution pattern of light emerging from lamp 724 may not entirely or evenly fill the acceptance cone of source fiber optic 714. To ensure that source fiber optic 714 is desirably filled with light without an implement such as glass rod 720 would require source fiber optic 714 to be very close to lamp 724, thereby creating a risk that source fiber optic 714 will overheat and possibly melt.

Between source fiber optic 714 and glass rod 720 preferably is iris 718. Iris 718 preferably is utilized to limit the angular range of light rays entering source fiber optic 714. When iris 718 is fully open, the entire acceptance cone of source fiber optic 714 may be filled. As iris 718 is closed, the cone of light incident upon source fiber optic 714 is reduced, and hence the angular distribution of light incident upon fiber optic 714 is reduced. As iris 718 is reduced further, it is possible to produce a nearly collimated beam of light incident upon fiber optic 714.

It is understood that a property of fiber optics whose ends are highly polished perpendicular to the axis of the fiber optic is that the angle of light incident on one end of the fiber optic is preserved as it exits the other end of the fiber optic. As is known to those skilled in the art, numerous technologies exist for polishing fiber optic cables. Thus, with a highly polished fiber optic, by varying the diameter of iris 718, the cone of light entering source fiber optic 714 can be controlled, and thus the cone of light emerging from source fiber optic 714 can be controlled.

Figure 46A:
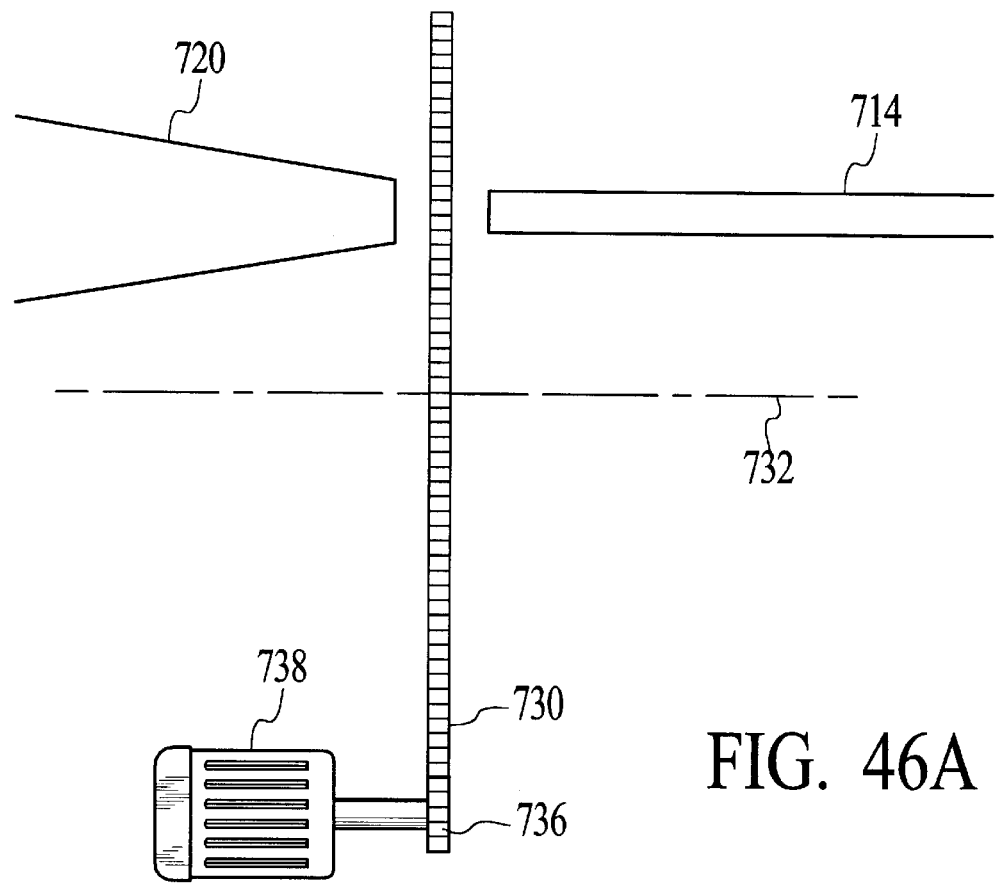
Figure 46B:
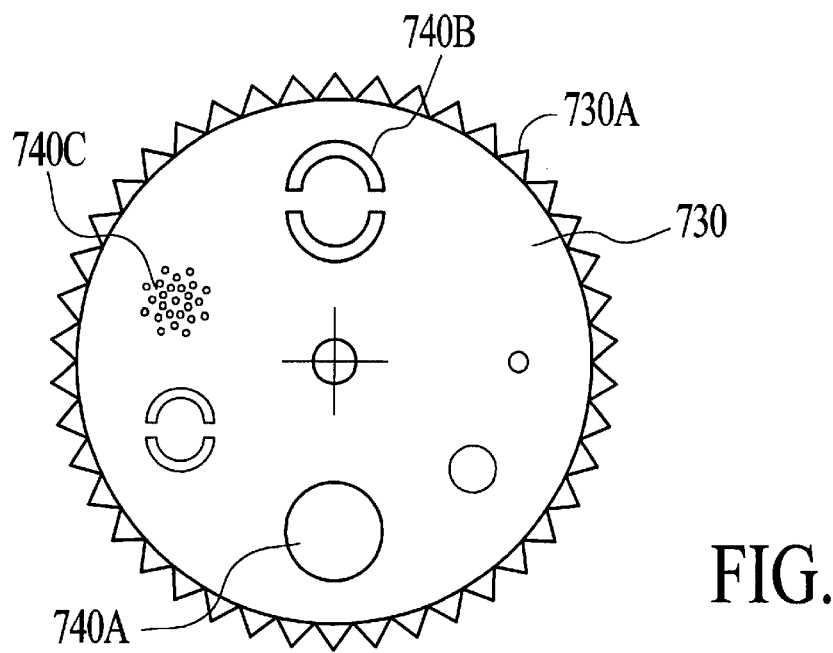

In an alternate embodiment, iris 718 is replaced by disk 730, which preferably includes a pattern of holes positioned near its perimeter as illustrated in FIGS. 46A and 46B. Preferably, disk 730 is driven with stepping motor 738 through gear 736 and gear teeth 730A so that disk 730 may be rapidly moved to a desired position and held it in a stable position in order to make a light measurement. Stepping motor 738 is controlled by a computer (such as described elsewhere herein; see, e.g., FIGS. 38 and 39), which controls disk 730 to rotate about axis 732 and stop in a desired and controllable position. Thus, such a computer in effect can vary , the NA of the light source synchronously to each measurement. The procedure preferably progresses as follows.

1. Rotate the disk to the desired aperture.
2. Pause to allow the disk to stabilize.
3. Measure one light sample.
4. Rotate the disk to the next desired aperture and repeat the process as required.

As illustrated FIG. 46B, the pattern of holes on disk 730 may be round or any other desired shape. Such apertures also may constitute a pattern of microscopic holes distributed to affect the light pattern of light or spectrum of light entering the source fiber. Additionally, the disk may contain filters or diffraction gratings or the like to affect the spectrum of the light entering the source fiber. Such holes or apertures also may consist of rings that produce cones of light where the light rays entering the fiber are distributed over a narrow or other desiredrange of angles. With the disk embodiment of FIGS. 46A and 46B, it is possible to control the light pattern of source fiber optic 714 effectively over a wide range of angles.

Referring again to FIG. 45, light conduit 716 passes light such as through light path 674 to sensors 676 (see, e.g., FIGS. 41A and 41B) for measuring the spectral properties of the lamp as described earlier. If the iris or aperture disk controlling the distribution of light entering source fiber optic 714 modifies the spectral properties of the light source, then the resulting spectrum can be adjusted as described earlier.

When a pair of fiber optics is utilized as described herein where one fiber serves as a light source and another fiber serves as a light receiver, the intensity of light received by the receiver fiber varies with the height of the pair above the surface of the object or material and also with the angle of the pair relative to the surface of the object or material. As described earlier, in certain preferred embodiments the angle of the probe relative to the surface may be detected by utilizing three or more fiber optic receivers having the same receiver NA. After normalization of the system, if the intensities of the three receiver fibers (such as fibers 660 (1,3,5) in FIG. 40) are the same, then this is an indication that the probe is perpendicular to the surface. If the intensities vary between the three sensors, then this is an indication that the probe is not perpendicular to the surface. As a general statement, this phenomenon occurs at all heights. In general, the intensity variation of the three fibers is dependent upon the geometry of the three fibers in the probe and is independent of the color of the material. Thus, as the probe is tilted towards fiber 1, for example, the intensities measured by sensors 3 and will be nominally equal, but the intensity measured by fiber 1 will vary from fibers 3 and 5. As a result, the system can detect an angular shift towards fiber 1. In preferred embodiments, by comparing the intensity values of fiber 1 to fibers 3 and 5, a measurement of the angle can be made and the intensity of fibers 1, 3 and can be corrected by a correction or gain factor to "adjust" its light measurement to compensate for the angular shift of the probe. It is thus possible with the probe arrangement illustrated in FIG. 40 to detect and measure angular changes.

Angular changes also will affect the intensities measured by the other fibers 662 (2,4,6). In a similar manner, the difference between the "wide band" sensors in fibers 662 (2,4,6) can also be utilized to further quantify the angle of the probe and can be utilized to adjust the light intensity measurements. It should be noted, however, that the intensity shift due to angle of the probe affects the fibers differently. If sensors 662 (2,4,6) are utilized in the spectrometer illustrated in FIG. 41A, the intensity adjustment must be made independently for each fiber and for the set of six fibers emerging from diffusing cavity 686 illustrated in FIG.

43A. However, if one diffusing cavity 686 is utilized as illustrated in FIG. 41B, the angle correction applies to all sensors supplied by light paths 703 equally. With such an embodiment as illustrated in FIG. 41B, angle determination and/or correction may be made in a manner more desirable for some applications.

As the probe approaches the surface of an object or material (the probe may be moved towards the material or the material may be moved towards the probe), the source fiber illuminates the object/material. Some light may reflect from the surface of the object/material, and some light may penetrate the object/material (if it is translucent or has a translucent layer on its surface) and re-emerge from the material and may strike the receiver fiber optic. As described elsewhere herein, the intensity measured by the receiver exhibits a peaking phenomenon where the light intensity varies to a maximum value, and then falls until the probe is in contact with the object/material where it exhibits a minimum. If the object/material is opaque, then the light intensity at the minimum is essentially zero. If the object/material is highly translucent, then the intensity may be near the peaking intensity.

Based on such phenomena, in accordance with other aspects of the present invention, it is possible to quantify the height of the probe and to adjust for height variations of the probe near the peaking height by measuring the peaking height intensity of the "wide band" sensors and comparing the intensity value at other heights and adjusting the gain of all sensors by the ratio of the measured intensity to the peaking intensity. If $I_p$ is the peak intensity of a wide band receiver, and $I_m$ is the intensity measured when the probe is in contact with the material, and 1 is the intensity measured at a height less than the peaking height then the ratio:

$$6)\ G = \frac{I_p - I_m}{1 - I_m}$$

the gain adjustment factor. If the gain adjustment factor is applied to the spectrometer sensors, then the spectrum may be measured independent of height for a wide range of heights within the peaking height.

Figure 47A:
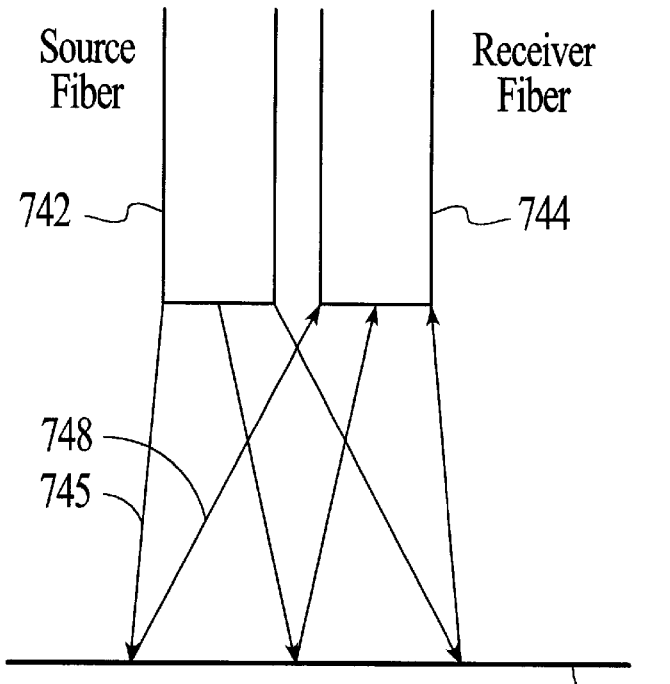
Figure 47B:
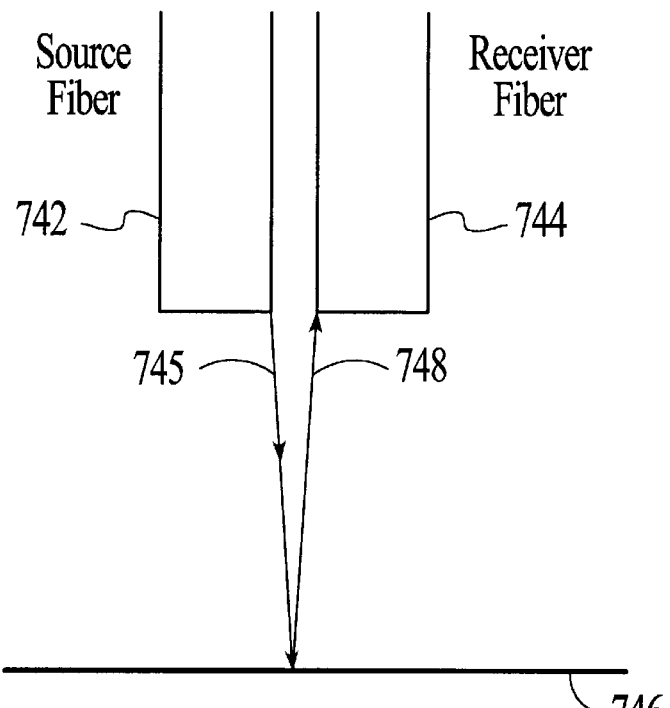

Reference should now be made to FIGS. 47A and 47B. As a fiber optic pair (e.g., source fiber optic 742 and receiver fiber optic 744) approach a material or object 746, material or object 746 is illuminated by source fiber optic 742 (see, e.g., lines 745 of FIG. 47A). The light emitted from source fiber optic 742 may be controlled as described elsewhere herein. Thus, source fiber optic 742 can be controlled so as to illuminate material or object 746 with nearly collimated light (small incident angles), or source fiber optic 742 can be controlled to illuminate material or object 746 with wide incident angles, or with a pattern of angles or with different spectral properties. If source fiber optic 742 is illuminated with an aperture disk with a slit pattern as illustrated in FIG. 46B, then source fiber optic 742 may be used to illuminate material or object 746 with a narrow singular range of angles.

Consider source fiber optic 742 and receiver fiber optic 744 with the same NA as illustrated in FIGS. 47A and 47B. The angular distribution of light provided by source fiber optic 742 is dependent upon the source fiber only (and the angle of the probe) and is independent of the height of the fiber from the material. If the probe is held substantially perpendicular to material or object 746, the angular distribution of light is independent of height. The area illuminated by source fiber 742, however, is height dependent and increases with increasing height. Receiver fiber optic 744 can only receive light that is within its acceptance angle, thus it can only detect light reflected from the surface that is reflected from the area of overlap of the two cones illustrated in FIGS. 47A and 47B.

FIG. 47A illustrates the fiber pair at the peaking height, while FIG. 47B illustrates the fiber pair at the critical height. At the critical height, the only light reflecting from the surface that can be received by receiver fiber 744 is the source ray 745 and the reflected ray 748 with angle of incidence equal to angle of reflection, or it can only detect "spectrally" reflected light. When the probe is at the peaking height, however, the reflected light rays that can be received by the receiver fiber vary over both a wider angle of incidence range and wider angle of reflection range. Thus, at the peaking height, the receiver is detecting a broad range of incident angle light rays and reflected angle light rays. By adjusting the spectrum for height shifts as described above and by detecting the angle of the probe relative to the surface of the material or object, the reflected or returned spectrum can be measured over a wide incident angular range and reflected angular range.

In general, for opaque surfaces, diffuse or specular, the height adjusted spectrum will appear constant as the probe approaches the material or object. In general, for opalescent materials or objects, i.e., materials with a translucent surface in which light rays may penetrate the material and be re-emitted, the height adjusted spectrum will shift as the probe approaches the material or object. In general, for translucent materials such as teeth or gem stones, the spectrum will further shift when the probe is less than the critical height and in contact or near contact with the material or object.

As a further refinement to certain aspect of the present invention, the iris illustrated in FIG. 45 or the aperture disk illustrated in FIGS. 46A and 46B may be utilized. In one such embodiment, the NA of source fiber optic 714 is held constant as the probe approaches the material or object, and light intensity and spectrum measurements are made and saved in a data queue as described earlier. When the probe is in contact with the material or object, the NA of source fiber optic 714 is changed (either from narrow to wide or from wide to narrow, depending upon the state of the first set of measurements), and spectral measurements are made as a function of source NA. The probe is then moved away from the material and light intensity and spectral measurements are made as the distance from the probe increases and as the probe passes through the peaking height. The spectral shift that occurs as a result of the variance of the source NA and height preferably is used to quantify the opalescence of the material or object.

In an alternate embodiment, the aperture disk illustrated in FIGS. 46A and 46B is rotated by stepping motor 738 synchronously to measuring the light and spectral data as the probe is moved into proximity to the material or object or into contact with the material or object. In another alternate embodiment, the probe is positioned at a fixed height from the material or in contact with the material or object and the NA of the source fiber is varied as light intensity and spectral data are measured. In yet another alternate embodiment, both the source and receiver fiber NAs are varied as described earlier, and the resulting spectra are utilized to quantify the optical properties of the material.

An alternative embodiment of the present invention for quantifying the degree of gloss of a material will now be described with reference to FIGS. 48A and 48B. FIGS. 48A and 48B illustrate source (74) and receiver (744) fiber pair positioned above a highly specular surface such as a mirror (FIG. 48A) and above a diffuse surface (FIG. 48B). The cone of light from source fiber optic 742 is illustrated by circle 742 A, and the acceptance cone of receiver fiber optic 744 is illustrated by circle 744 A, with the overlap illustrated by area 750. On a specular surface, the only light that will be received by receiver fiber optic 744 are the light rays whose angle of reflection equal the angle of incidence, thus the only light rays striking the surface of receiver 744 are the light rays striking the small circular area the size of the diameter of the fiber optics as illustrated by circle 752 in FIG. 48A. As long as receiver fiber optic 744 has an NA greater than source fiber optic 742, all light incident upon receiver fiber optic 744 will be accepted. Thus, the angular distribution of received light rays in receiver fiber optic 744 is limited to a very narrow range and is dependent upon the height of the fiber optic pair from the surface.

Consider FIG. 48B, which illustrates a fiber optic pair positioned above a diffuse surface. Any light ray incident upon the area of overlap of the two cones can be received by receiver fiber optic 744 (provided of course that it is incident upon the receiver fiber). Thus, for diffuse surfaces, the angular distribution of light rays received by receiver fiber optic 744 is also height dependent, but is greater than the angular distribution for a specular surface. In accordance with such embodiments of the present invention, such angular distribution variation may be used to quantify optical properties such as gloss for a particular material or object.

Figure 49:
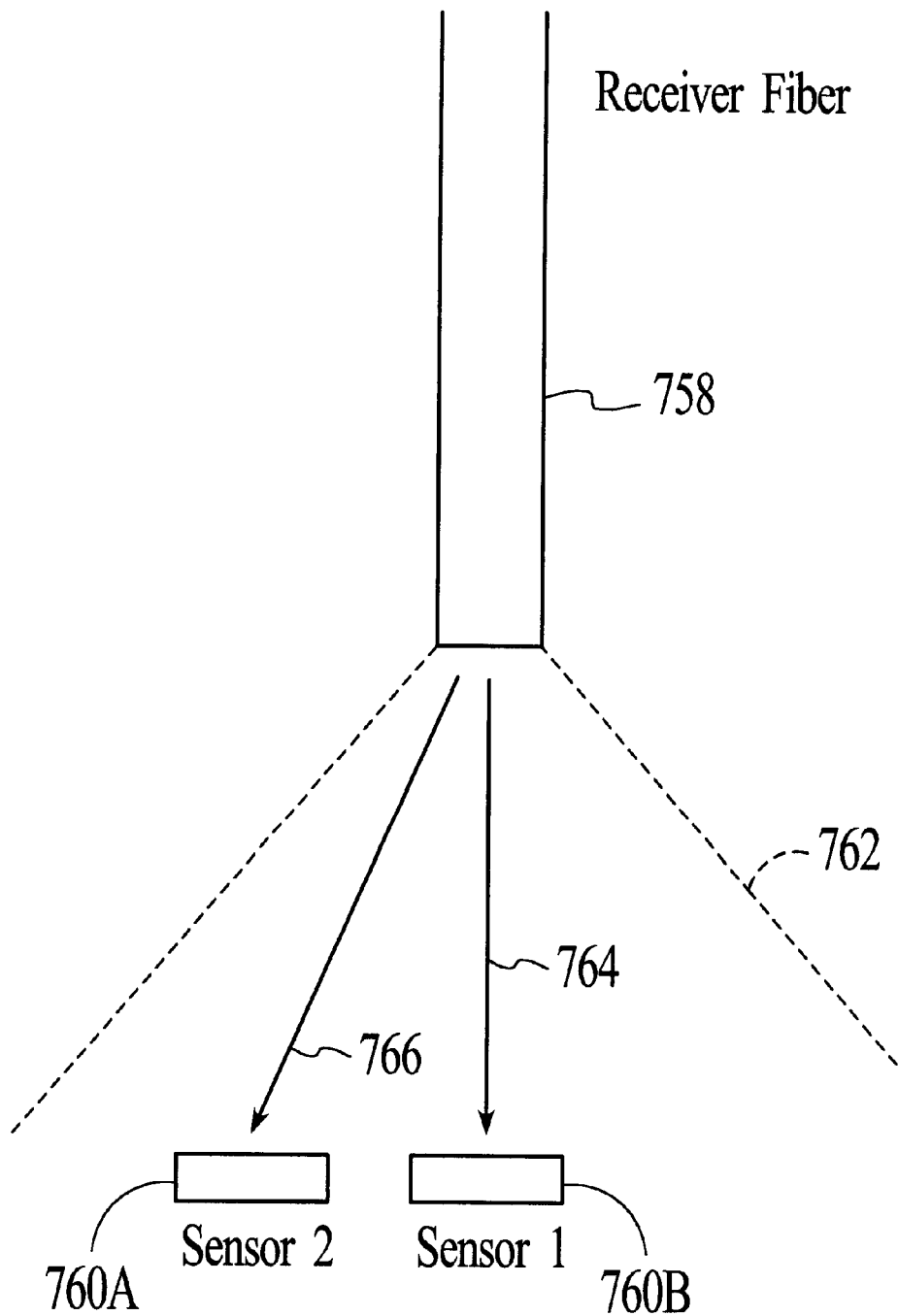

A detector in accordance with other embodiments of the present invention is illustrated in FIG. 49, where single receiver fiber 758 is positioned above a radial distribution of sensors (illustrated by sensors 760A and 760B). Two or more sensors may be utilized, in one or two dimensions, although only two sensors are illustrated in FIG. 49 for discussion purposes. In the illustrated embodiment, one sensor (sensor 760B) is positioned corresponding to the center of fiber 758 and measures angles near zero, and the other sensor (sensor 760A) is positioned at approximately ½ the acceptance angle of receiver fiber 758. In alternate embodiments, the sensors may be arranged or configured in a linear array such as a CCD, or a two dimensional sensor such as a video camera CCD or MOS sensor. In accordance with aspects of the present invention, by analyzing the intensity patterns of the sensors, the degree of gloss of the material may be measured and quantified.

Figure 50A:
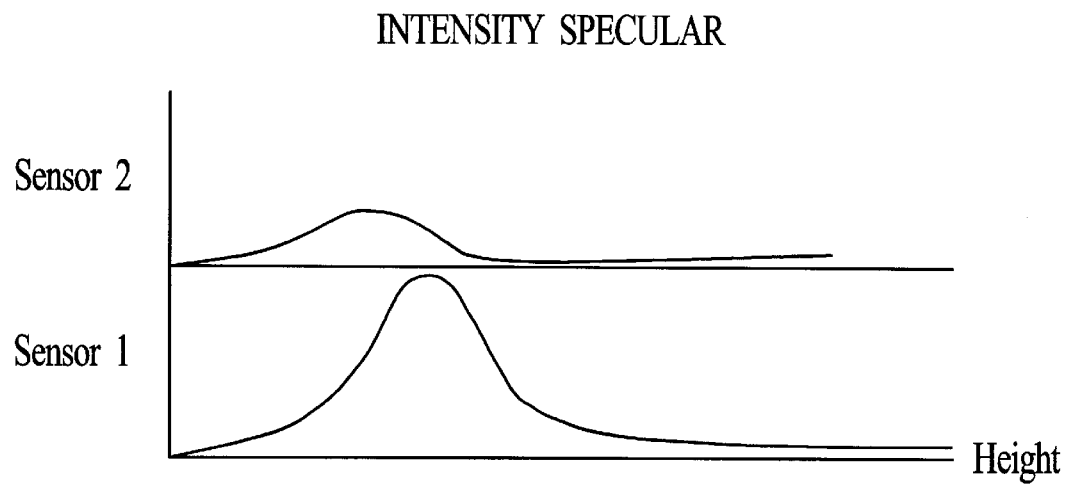
Figure 50B:
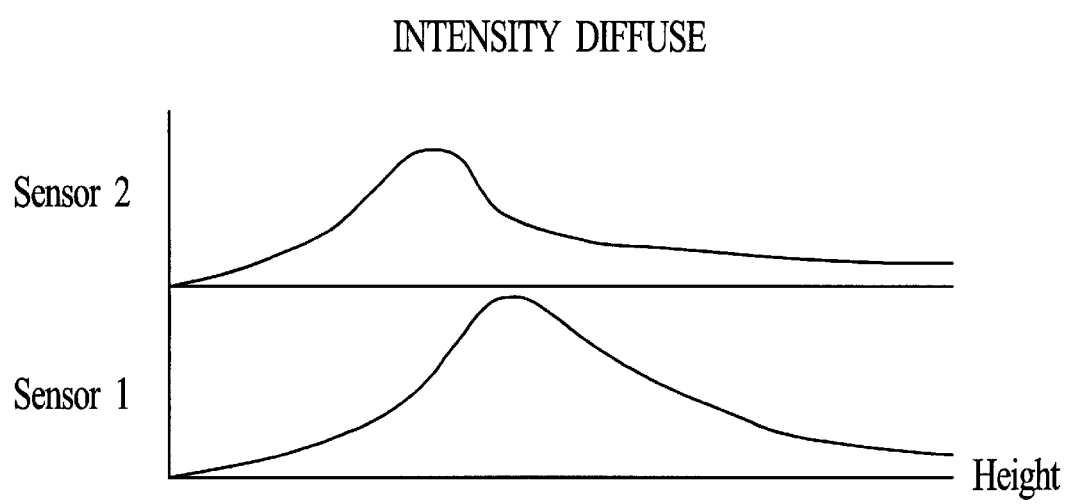

As the probe is moved towards the material or object, the angular distribution of light received by receiver fiber 758 changes dependent upon the surface of the material or object as illustrated in FIGS. 50A and 50B. FIG. 50A illustrates the intensity pattern for the two sensors for a specular surface, and FIG. 50B shows the intensity pattern for a diffuse surface. Specular materials in general will tend to exhibit a peaking pattern where the peaking intensity of sensor 1 is much larger than the peaking intensity of sensor 2. For diffuse materials the peaking intensity of sensor 2 (wide angles) is closer to the peaking intensity of sensor 1. By quantifying the variation in peaking intensity the degree of gloss of the material can be additionally quantified. In addition, in alternative embodiments, the relative values of the sensors at a time when one or the other sensors is peaking are captured and further used to quantify the optical properties of the material or object.

Various particular preferred embodiments of the present invention will now be described that relate to detecting and preventing counterfeiting and the like.

Numerous negotiable instruments exist that are created utilizing printing processes or the like. Such negotiable instruments include currency, bonds, stocks, securities, travelers checks, checks, credit cards, passports, and other types of business, legal and/or governmental documents or certificates, etc. In many cases the printing process is highly refined utilizing microprint or other forms of printing that are difficult to reproduce, thereby rendering the instrument, document, or negotiable item difficult to reproduce or to create. Additionally, the item may contain a paper or other backing material difficult to reproduce. In other cases, the item may contain holographs or other fields making it further difficult to reproduce. In yet other applications, the item may contain inks that have radioactive isotopes, or magnetic qualities, or other properties that are difficult to detect or to reproduce. In yet other applications the item may have strips of materials or certain pigments imbedded internally that are identifiable but difficult to reproduce. In general, numerous methods and methodologies exist or have been proposed that render certain documents or negotiable instruments difficult to reproduce. Such processes however, tend to be inherently difficult to implement, and, indeed, the difficulty in creating the process is the counterfeiting preventive measure.

With optical characteristics determinations made in accordance with the present invention, improved methods of detecting and preventing counterfeiting may be obtained. In accordance with the present invention, layers of pigment or other materials in the printing or similar process may be utilized that render items difficult to reproduce, but relatively easy to create and/or detect.

As previously described, various optical properties of an object may be measured, assessed or predicted in accordance with the present invention. Such optical properties include surface reflection, translucency of surface layers, gloss of the surface and the spectral properties of semi-translucent layers on the surface and of the spectral properties of layers below the surface. Such apparatus and methodologies can be utilized to render printing or similar processes difficult to reproduce.

Figure 51A:
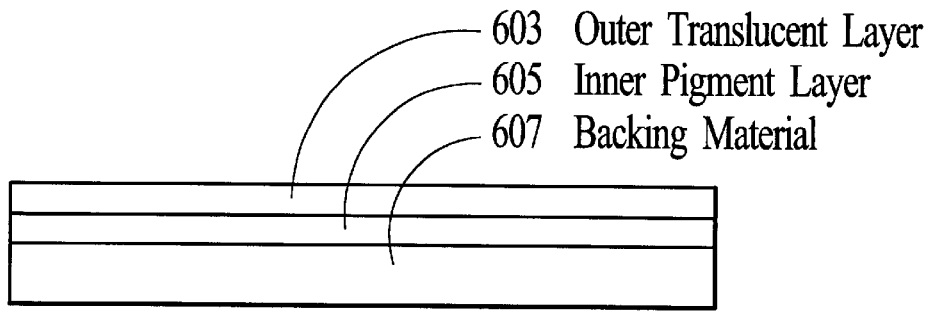
Figure 51B:
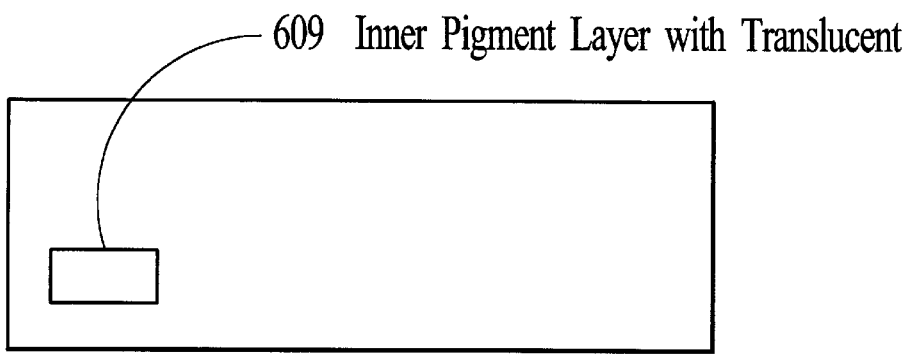
Figure 51C:
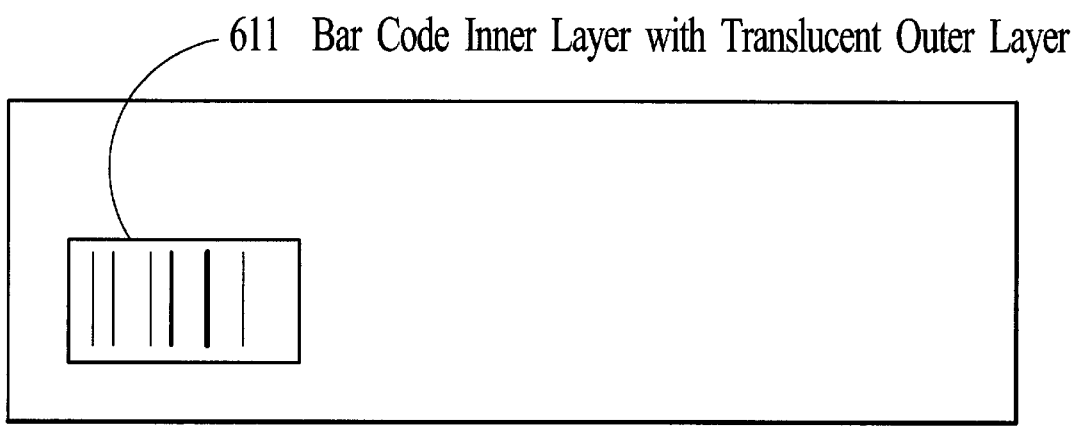

FIGS. 51A to C illustrates instrument 601 (which may be any of the items previously discussed or other items needing counterfeit protection, etc.) that includes a number of layers of pigment or other material. Outer layer or layers (603) generally are semi-transparent or translucent or semi-translucent. Inner layer or layers 605 may be opaque or semi-translucent. The layers are deposited by successively printing pigments (or painting or other deposition or application, etc.) on substrate 607, which may be any suitable backing material, such as paper or plastic or other materials, etc.

If light is reflected from the surface of instrument 601 it in general will exhibit certain optical properties which can be measured by conventional spectrographic or colorimetry techniques. The spectrum of the reflected light will be principally influenced by the surface properties of outer layer(s) 603 and to a lesser degree by inner layer(s) 605 and/or substrate 607, depending upon the degree of translucency of the various layers, etc. If the material is illuminated from the rear, in general the spectral properties of the material will be influenced by all layers of the material, and in general can be quite different from the spectral properties of light reflected from the face of the object.

Preferred embodiments herein provide an instrument and methodology that can distinguish surface reflection properties of an item/material from bulk spectral properties of the item/material, which can be advantageously utilized for preventing/detecting counterfeiting. In such preferred embodiments, an instrument or item document includes substrate 607 printed (or otherwise formed) with inner layer(s) 605 consisting of a relatively long term (depending upon the particular application) stable dye or other pigment or material, and also includes outer layer(s) 603, that preferably consist of a semi-translucent layer printed or otherwise deposited or from inner layer(s) 605. It should be noted that such layer formation may be part of the overall process that forms the instrument or other item, or it may be separate processes that form layers 603 and 605 in a particular location or locations 609 on instrument 601. In certain embodiments, layers 603 and 605 are formed from a fixed or predetermined position from a location marker also included on instrument 601. Such location marker may facilitate the measuring of optical properties of such layers, as will be described, and may provide a further barrier in that the location of the position where optical properties are to be assessed may not be known to an unauthorized person or device, etc.

Following the printing or other formation processes of layers 603 and 605 (and drying or curing, etc.), the optical properties of instrument 601 are quantified including, for example, the surface spectral properties and the spectral properties of the inner layer. Such optical properties may be measured at a single or multiple locations. Such spectral or other optical properties may be recorded and saved such as in a computer data base for future reference. To determine if the document or material is genuine, the spectral properties of instrument 601, and in particular layers 603 and 605, are measured and compared to the previously recorded measurements. Based on such comparisons, which may include a number of acceptance criteria (such as delta E values or other such thresholds or ranges), an assessment or prediction may be made of whether instrument 601 is genuine or counterfeit.

In another such embodiment, inner layer(s) 605 may be printed/formed with different layers of pigments that are changed from batch to batch or periodically, from time to time. The particular pigment for particular instruments may be recorded and stored and may be identified to the particular instruments with a serial number or other form of identification. The pigments of inner and outer layers 603 and 605 may be adjusted in order to insure that the instrument appears to have the same color when visually inspected or when measured with traditional spectrographic or colorimetry techniques. Thus, an entire series of instruments, materials or documents or currency can be printed/formed which visually appear the same, yet have internal or subsurface properties that can be quantified utilizing the apparatus and methodology disclosed elsewhere to uniquely distinguish the documents.

In another such embodiment, inner layer(s) 605 are printed/formed with pattern 611 (see FIG. 51C) such as a pattern utilized in a bar code. The pigments of the inner and outer layers are chosen to render the inner bar codes difficult if not impossible to discern visually by utilizing conventional spectrographic or colorimetry techniques.

In yet another embodiment, inner layer(s) 605 are printed/formed with pattern 611 such as a bar code where the bar code utilizes not only differences in the widths of the lines of the bars as a method of storing data in the pattern, but also where the bars themselves are of different pigments. In such applications, data for the bar code can be encoded in the bars themselves and in the color of the bars. If the material is layered as disclosed above, the bar data is difficult if not impossible to discern, rendering it difficult if not impossible to reproduce. With such embodiments, individuals or institutions may create an "identifier stamp" or the like that uniquely identifies objects, with the stamp consisting of a color bar code or other spectrally identifying feature or aspect. This could be combined, for example, with a visible bar or other code, and with other information or bar code (or message), etc., that is discernible only with an instrument such as provided herein. In such embodiments, a subsurface bar code or spectral identification may be provided, with or without a visible code, message or data.

In yet another embodiment, inner layer(s) 605 are printed/formed with geometric two dimensional patterns that can be discerned as described herein by scanning the instrument, document or material, such as on two or more axis. In yet another embodiment, inner layer(s) 605 are printed/formed in multiple layers. Certain configurations of the measuring apparatus may be constructed to principally measure specific layers or thickness of layers or spectral properties of layers. Thus, one measurement may produce one set of optical properties, while another measurement produces yet another set of optical properties, and so on rendering the instrument, document or material even more difficult to reproduce.

Such embodiments may be applicable to a wide class of objects. Although the foregoing discussion has focused on documents or negotiable instruments of paper or plastic such as currency or checks etc., it is equally applicable as an identification to works of art or objects or precious items or any material or object than can accept imprinting or other material preparation. Indeed, the quality of the printing of the original object need not be highly controlled either in color or in print quality. Since the imprint placed on the object is recorded both spectrally and spatially after the imprinting process (either as linear or multi-axis measurements) and recorded, it renders the identification mark difficult to reproduce.

Additionally, and particularly with respect to objects such as paintings, sculptures, and the like, it may be possible to determine optical properties as described herein in one or more locations, based on the constituent layers of the object (i.e., without forming special layers 603, 605, etc.). In general, it may be possible to optically characterize such objects, with optical characteristic data stored for later comparisons to determine if the object is genuine or counterfeit. Still additionally, it may be possible to use specially formed inner layers that include codes or other subsurface spectral characteristics that may be measured in accordance with the present invention, but which would not be discernible visually or by utilizing conventional spectrographic or colorimetry techniques. In such embodiments, the outer visible characteristics may completely mask the subsurface code or spectral identifier, which may remain hidden except when assessed as provided herein in order to detect for genuineness, etc.

As will be apparent to those skilled in the art, certain refinements may be made in accordance with the present invention. For example, a central light source fiber optic is utilized in certain preferred embodiments, but other light source arrangements (such as a plurality of light source fibers, etc.). In addition, lookup tables are utilized for various aspects of the present invention, but polynomial type calculations could similarly be employed. Thus, although various preferred embodiments of the present invention have been disclosed for illustrative purposes, those skilled in the art will appreciate that various modifications, additions and/or substitutions are possible without departing from the scope and spirit of the present invention as disclosed in the claims. In addition, while various embodiments utilize light principally in the visible light spectrum, the present invention is not necessarily limited to all or part of such visible light spectrum, and may include radiant energy not within such visible light spectrum.

As described above, in accordance with the present invention various methods, methodologies, implements and embodiments may be employed for measuring the optical properties of teeth and other materials. While much of the description herein describes exemplary embodiments employing a probe with a central element serving as a light source, as will apparent to those skilled in the art principles, techniques and implements in accordance with the present invention may be employed in other probe configurations. The following description discusses additional exemplary embodiments, methods and systems for distinguishing the optical properties of teeth and other materials and objects based on such previous principles, techniques and implements and enhancements thereof.

Previously described exemplary embodiments preferably have utilized probes and methods with one or more source elements, preferably fiber optics, and one or more receiver elements, also preferably fiber optics, in order to adjust spectral or other optical characteristics data for height and angular changes resulting, for example, from not holding the probe perpendicular to a surface or to irregularities in a surface. In accordance with other aspects and exemplary embodiments of the present invention, a central receiver element, also preferably a fiber optic, will now be described in more detail.

Figure 52:
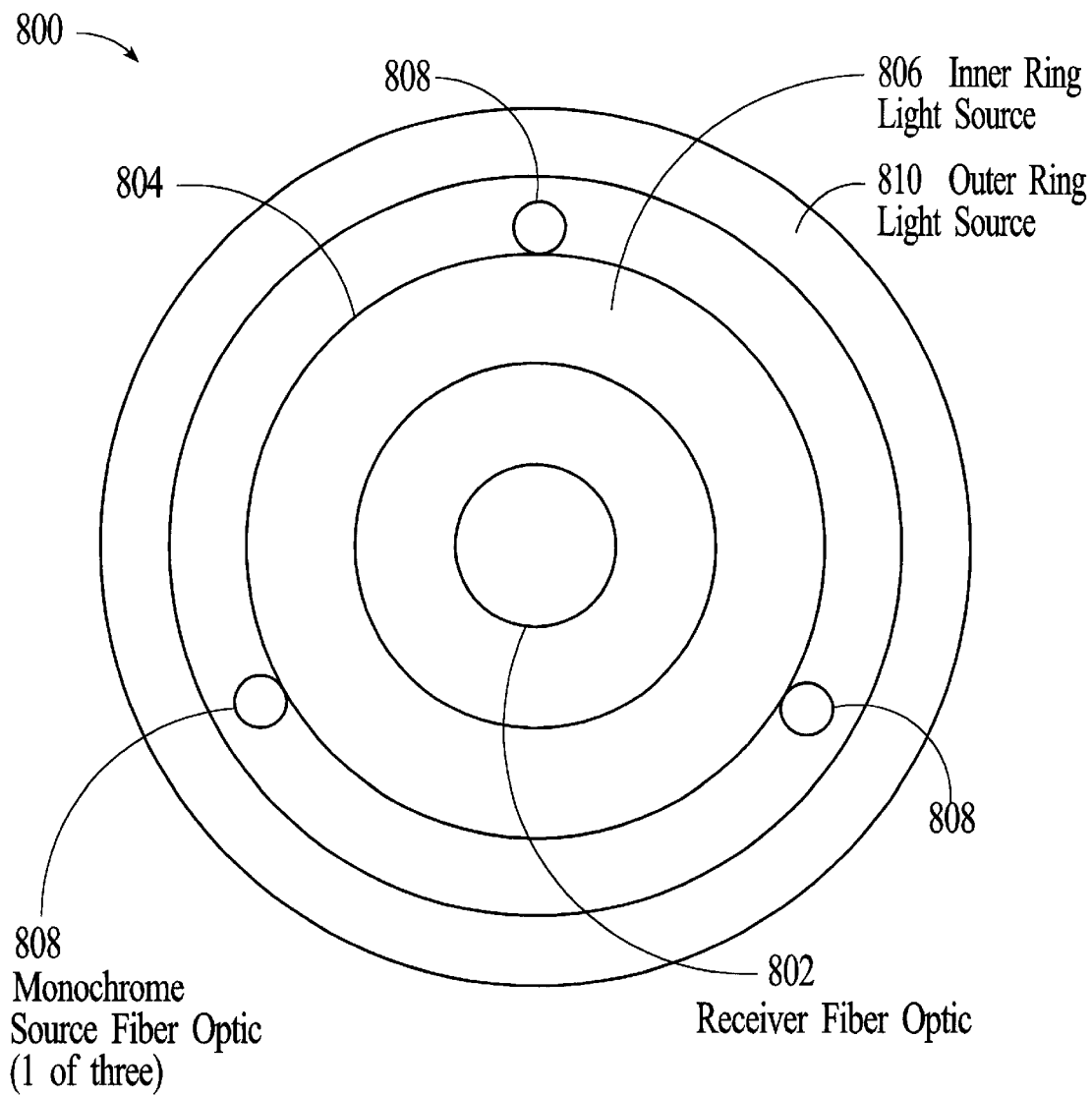
FIGS. 52 to 58 illustrate yet other embodiments (systems, sources, receivers, methods, etc.), aspects and features within the scope of the present invention, including implements having a central receiver element and detecting and quantifying flex of a cable.
Figure 53:
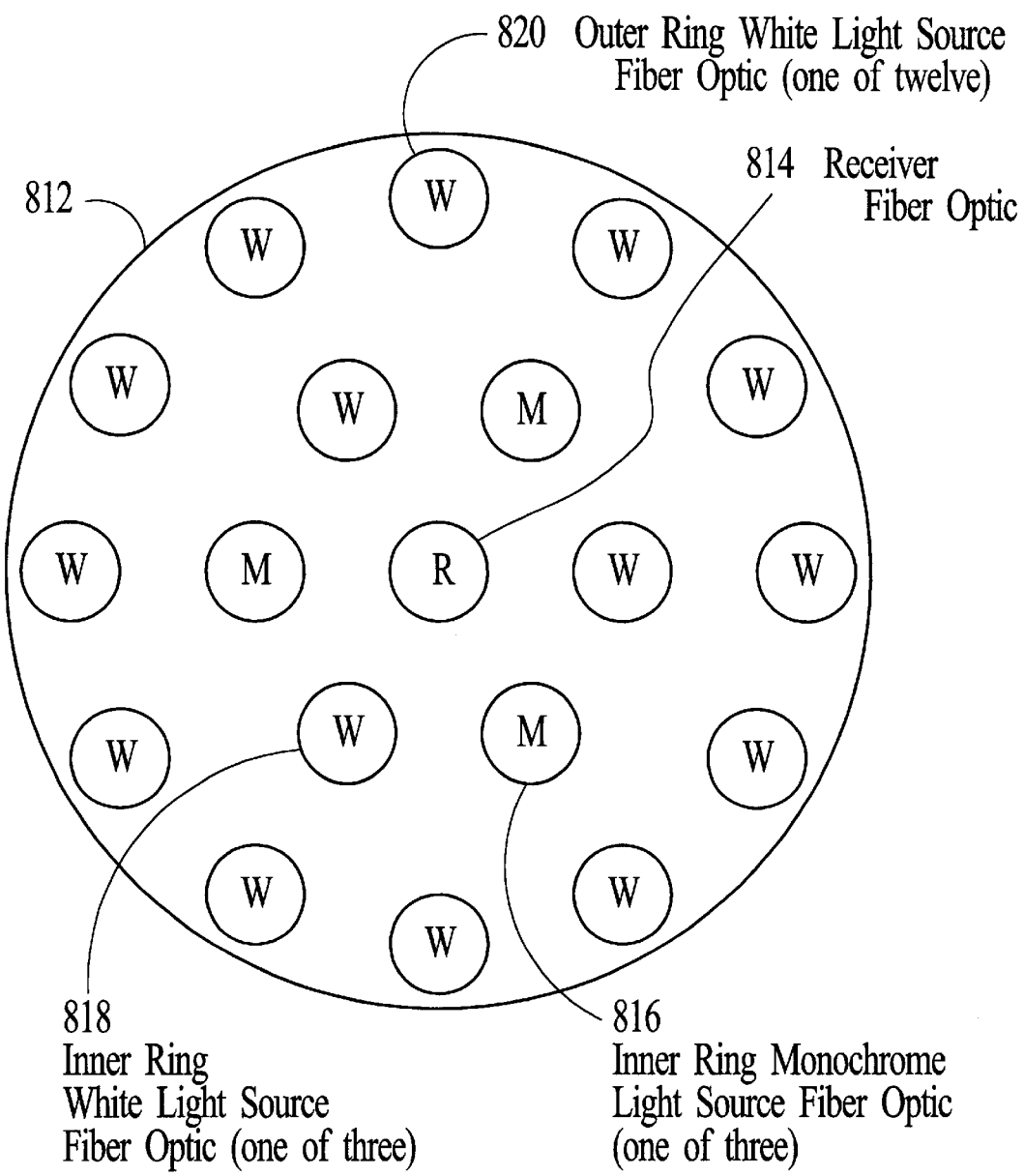

Referring now to FIG. 52, an embodiment of the present invention utilizing probe 800 (illustrated in cross section) including central receiver 802 (preferably a fiber optic) surrounded by two rings 806 and 810 of light sources (also preferably fiber optics). Rings 806 and/or 810 in preferred embodiments are constructed of strands and/or a ring of fiber optics. In alternate embodiments rings 806 and 810 are constructed of cylindrical light guides. FIG. 53 illustrates an embodiment of the present invention utilizing probe 812 (illustrated in cross section) including central receiver 814 (also preferably a fiber optic) surrounded by two rings of sources (preferably fiber optics) where the inner ring includes a plurality of sources or fiber optics 816 and 818, preferably six evenly spaced apart, and the outer ring includes a plurality sources or fiber optics 820, preferably twelve evenly spaced apart. As will be described in greater detail later, the use of two rings of light sources in such embodiments may be in used in accordance with the present invention to provide a method for measuring the opalescence or other optical characteristics of materials or objects.

Consider a probe (such as probe 802 and/or 812) approaching a material or object. As the probe approaches the surface of the material or object, the intensity of light reflected from the material or object and received by a receiver will increase as the height from the object decreases. Eventually, at a peaking height the intensity will peak, and as the probe is lowered to the critical height the intensity will fall to a minimum. This phenomenon has been described in detail previously herein. In general, as will be appreciated by those skilled in the art, this phenomenon does not depend on whether the central element is the light source and the inner and outer rings are light receivers, or if the central element is the receiver and the inner and outer to rings are sources. In both cases, the intensity received by a single or plurality of receiver fibers varies with height. Similarly, the intensity received by a single or plurality of receiver fibers varies as the angle of the probe changes from being normal to the surface. Additionally, if the surface has irregularities, the intensity also will vary.

Among the advantages of utilizing a plurality of receiver fibers is that certain of the receiver fibers can be utilized to measure angle and height, as previously described. An advantage of utilizing a single receiver is that the instrument requires only one light receiver/spectrometer detector. In accordance with other aspects of the present invention, however, methods and implements to quantify and/or correct for height and angle with a single receiver may also be provided.

Referring again to FIG. 52, in addition to the two rings of light sources, three monochrome sources 808 (preferably fiber optics) preferably are positioned in a ring between the two rings of light sources. FIG. 53 illustrates three monochrome light sources 816 positioned within the first ring. The number of monochrome sources and their precise locations are not limited to what is illustrated, and other arrangements are utilized in other embodiments for specific applications. It has been determined, however, that three monochrome sources may be advantageously utilized in many applications.

In accordance with such embodiments, monochrome sources 808 and 816 are supplied with monochromatic or nearly monochromatic light that preferably is out of the band of interest. For color determination, the optical band of interest is typically 400 to 700 nanometers. Most spectrometers, however, such as those described elsewhere herein and/or CCD spectrometers such as those manufactured by Ocean Optics, are sensitive well into the infra-red light band. Thus, many spectrometers are capable of detecting light from 700 nanometers to 800 nanometers or even longer wavelengths.

In preferred embodiments utilizing this aspect of the present invention, the three monochromatic light source fibers are each supplied with monochromatic light of different wavelengths. One preferred way to provide such monochromatic light is by utilizing three infra-red LEDs of different wavelengths, for example, or by filtering a white light source with interference notch filters with different center wavelengths.

In one such preferred embodiment, a broad band white light source supplies light to all light source fibers/light guides. Light supplied to the three monochromatic light sources is filtered with narrow band pass notch filters with center wavelengths greater than 700 nanometers. For example, one center wavelength may be 750 nanometers, while another center wavelength may be 775 nanometers, and a third center wavelength may be 800 nanometers. It should be noted that the exact filter wavelengths are not important; it is only important that such wavelengths be sufficiently different so that they do not overlap and may be separately detected, as described herein. The other two rings of light sources include, for example, a broad-band visible range filter that passes light from 400 to 700 nanometers and rejects light in the range of the three monochrome filters. What is important is the broad-band light sources preferably do not emit light in the frequency range of the monochromatic light sources, or at least do not emit light in such frequency range to a degree that would interfere with the detection of the monochromatic light as described herein.

Figure 54:
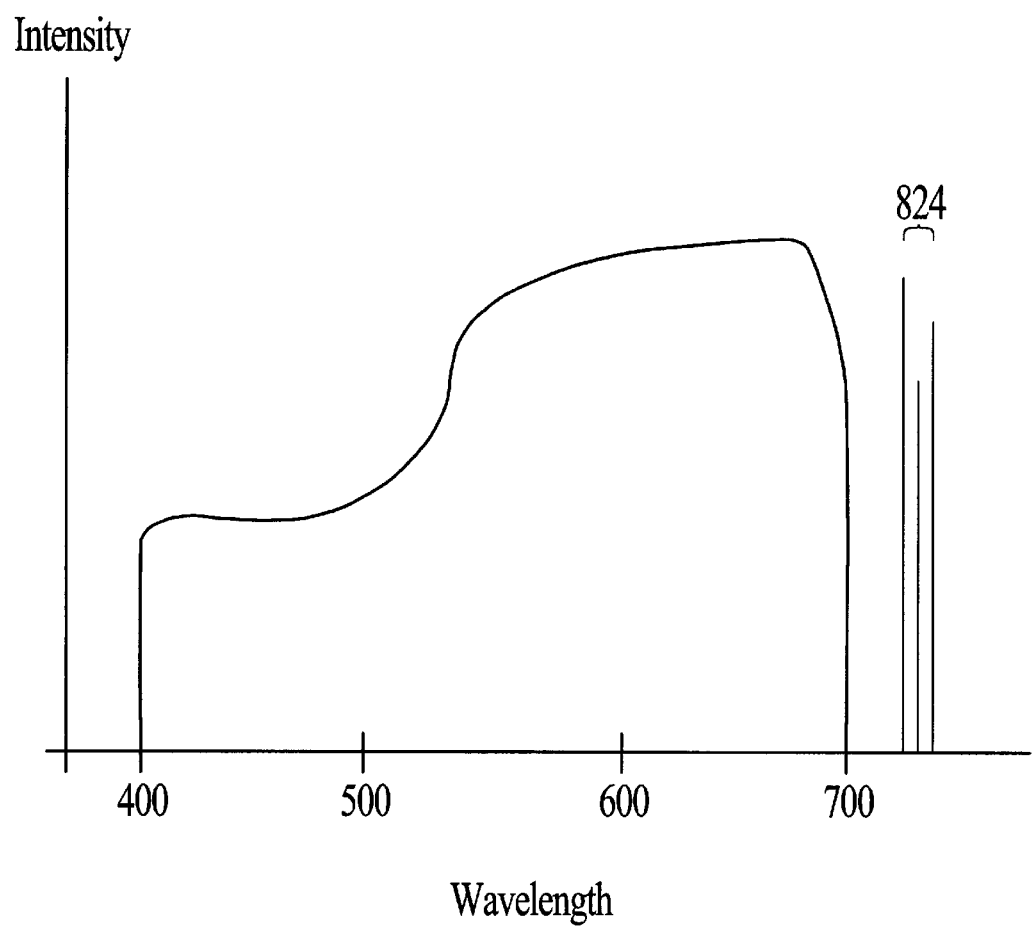

As such a probe in accordance with the present invention approaches a material or object, receiver fiber 802 or 814 will receive visible light and infra-red light as illustrated in FIG. 54. The visible light preferably is spectrally analyzed to determine the optical properties of the material or object, preferably as described elsewhere herein. The analyzed spectrum also will include light intensities at the three monochrome source center wavelengths as illustrated in FIG. 54 (illustrated as frequency band 824). The three intensities are independent of each other and can be utilized to determine height and angle in a manner similar to that for the perimeter receivers as previously described.

Such a probe in accordance with the present invention preferably is normalized to a standard material. If the probe is perpendicular to a material, the three out of band intensities should be equal. If the probe is not perpendicular to the material they will differ such as is illustrated in FIG. 54. The difference in the intensities is a function of the angle of the probe with respect to the surface of the material or object and may be used to measure and quantify the angular change and to adjust the intensity of the visible region of the spectrum if desired, as described elsewhere herein. The intensity of the three out of band intensities of the monochromatic sources also may be utilized to determine or quantify the height of the probe as described elsewhere herein. The three intensities will demonstrate a peaking phenomena as described earlier. It also should be noted that the visible band also will demonstrate a peaking phenomena and is utilized in certain applications/embodiments to determine/quantify height as well.

In one alternate embodiment, the three monochrome sources are not filtered and are supplied light with the same spectral properties as the inner and outer rings (the three sources in such embodiments may not be monochrome, but may be broad-band). With such an alternate embodiment, the light sources may be alternately turned on and off in a manner synchronous with the measurement of spectral data. As an exemplary operation of such an alternative, as the probe approaches a material or object, the inner ring source may be turned on and a measurement is made. The inner ring may then be turned off and the outer ring turned on and a measurement is made. Both inner and outer rings may then be turned off and the three monochrome (or broadband) sources are each in turn turned on and off as a measurement is made. The plurality of spectrums or measurements are utilized to determine the optical properties of the material and to measure and/or adjust for height and angular changes in accordance with previously described principles.

As will be understood from the previous discussion, the use of at least inner and outer rings of light sources is to provide a method to determine optical characteristics such as the opalescence or translucency of the material or object. Such inner/outer rings may be utilized in conjunction with the three monochrome or other light sources utilized to determine angle and height as described earlier. As will be understood from previous description, when the inner ring of light sources is on it provides light to the material that is geometrically within a certain angular range. When the outer ring is on it provides light that is geometrically at larger angles. If the material is opalescent, for example, a spectral shift will occur between the two measurements, thereby allowing such optical characteristics to be quantified.

Certain spectrometer systems can collect data at high data rates such as certain spectrometers manufactured by Ocean Optics, Inc., which can have an integration time of 1 millisecond. In typical data gathering applications, the spectrometer is run at a high rate and the data is signal averaged over many samples to reduce noise. Such signal averaging techniques are well known to those skilled in the art. In an alternate embodiment of the present invention, the three monochrome sources each have the same out of band wavelength. The inner and outer ring sources provide light filtered or otherwise generated to include only the visible band. The light provided to the inner and outer rings is gated on and off as discussed above or one or the other rings is left on (but still a plurality of spectral measurements preferably are taken). The three monochrome sources, however, are turned on and off rapidly, synchronous with the spectral measurements being taken at, for example, a rate of 1000 Hz. The visible band of the spectrum preferably are signal averaged to reduce noise and the out of band sensors preferably are utilized for angle and height determinations.

Figure 55:
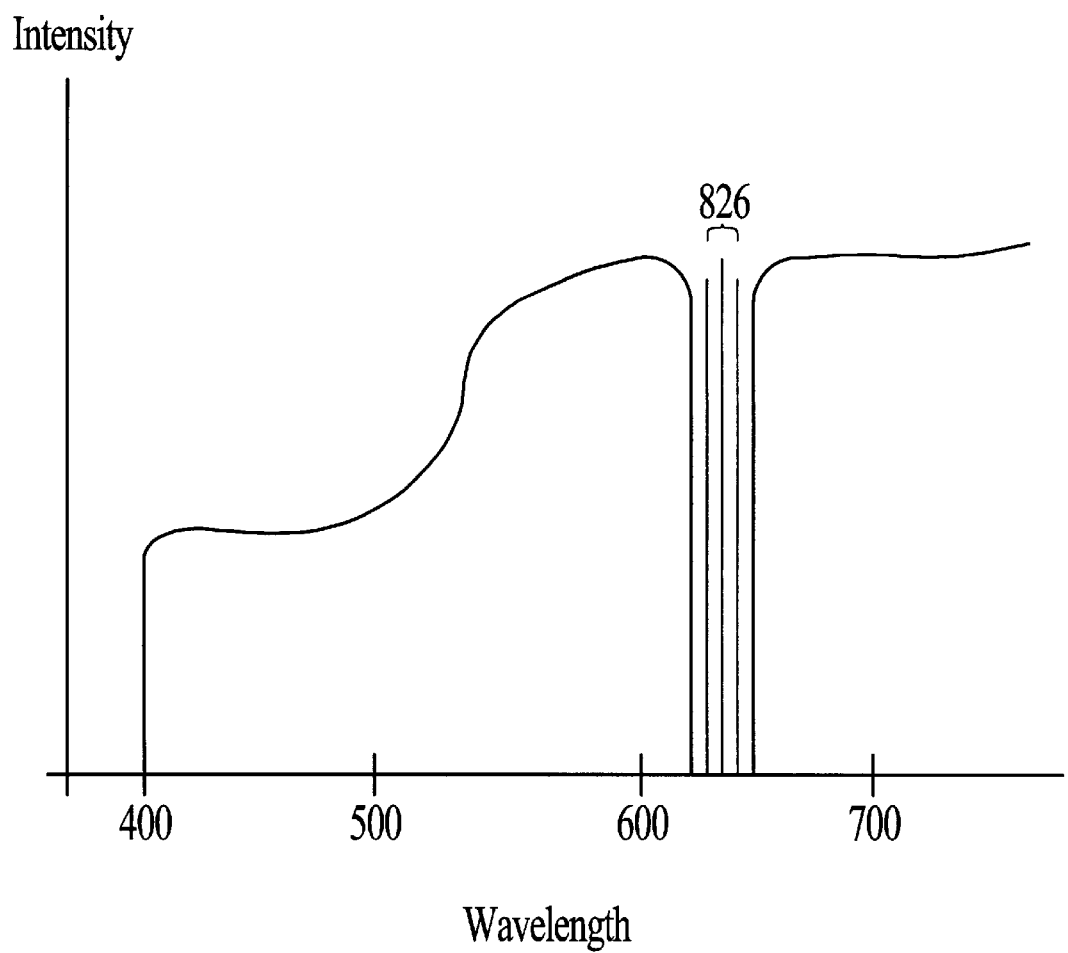

In another alternate embodiment of the invention, the monochrome light sources and sensors are in band. The light provided to the inner and outer ring sources are notched to exclude a small portion of light at the wavelengths of the monochrome receivers, such as is illustrated in FIG. 55 (see frequency band 826). With such embodiments, the monochrome receivers/sensors may be of different wavelengths as described earlier or may be of the same wavelength and pulsed on and off as described earlier.

It should be noted that such aspects of the present invention may be applied to embodiments with one or more light sources and/or with one or more light receivers. The positions of the sources and sensors illustrated in the figures is for illustration and discussion purposes only. Such aspects of the present invention may be applied to any positioning of the source and receivers consistent with the principles described herein. Although the present invention was disclosed for light, such techniques may be applied to other measurement techniques as well, such as acoustical imaging systems. With such embodiments, height and/or angle determination, quantification and/or correction may be applied to a variety of probe configurations, including a probe with a central element, and including probes in which the central element is a source or a receiver, etc.

Yet other aspects of the present invention will now be described.

As previously described, certain embodiments of the present invention may be implemented through the use of a flexible cable assembly consisting of one or more fiber optics. As previously described, fiber optics conduct light that is within a certain angular range or acceptance range of the fiber optic. The range of angles is quantified by designating a Numerical Aperture (NA) for a fiber optic, as described elsewhere herein. It has been determined that the amplitude of light propagating within a fiber optic, and the spectral properties of the light propagating within a fiber optic, changes as the fiber optic is bent over small radii. The degree of amplitude change, spectral shift and angular shift in general depends upon the geometric properties of the fiber and the degree of flexing of the fiber. The above spectral, angular and amplitude shifting can affect spectroscopy measurements and optical properties measurements in systems that utilize fiber optic cables.

One solution to such problems is to provide a cable that is held rigid or fixed to avoid flexing, such as the "hand held" embodiments of the present invention described elsewhere herein, where flexing of the fiber optics is inhibited or prevented. Another solution is to provide a semi-rigid cable that can not be flexed over small radii. In some applications such as dentistry, however, a semi-rigid cable may be undesirable or impractical. Thus, in accordance with other aspects of the present invention, techniques are provided to measure or quantify the spectral, intensity and/or angular shift in such a cable and to utilize such a measurement to desirably affect the overall optical properties measurement.

Figure 56:
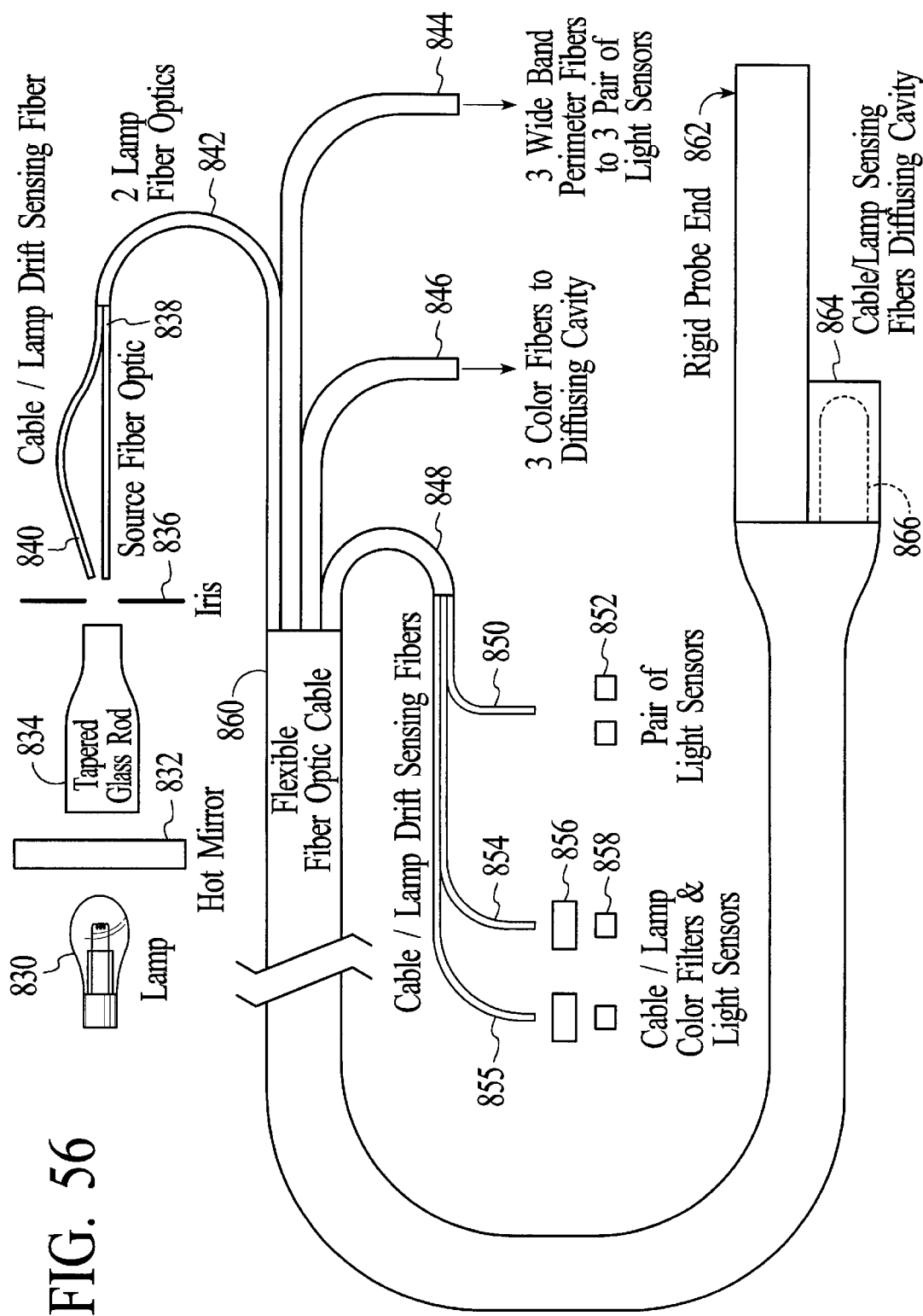

FIG. 56 illustrates an embodiment of the present invention utilizing such techniques. Such an embodiment preferably includes a spectrometer, light sensors, a CPU or computer, a fiber optic cable and a probe, such as in one or more embodiments described elsewhere herein. Cable 860 is such a preferred embodiment and contains one or more source fiber optics (see source fiber optic 838) that provide light from the light source (a preferred arrangement is illustrated as lamp 830, hot mirror 832, glass rod 834 and iris 836, such as previously described) to the material or object being measured and one or more receiver fiber optics that receive light reflected or returned from the material or object and serve to provide light to the spectrometer and/or light sensors. Various embodiments of such a spectrometer and/or light sensors have been described elsewhere herein. In addition, details of exemplary cable constructions and methods also have been described elsewhere herein.

A cable in accordance with such preferred embodiments includes one or more additional fibers. Included is at least one additional source fiber, hereinafter referred to as the secondary source fiber or cable/lamp drift source fiber (see fiber 840), and one or more additional receiver fiber(s), hereinafter referred to as secondary receiver fibers or cable/lamp drift sensor fibers (see fibers 848, 850, 854 and 855). Such secondary source fiber and secondary receiver fibers pass down the length of cable 860 parallel to the other fibers (see fibers 838, 846 and 844) in the cable, and the secondary fibers are joined at probe end 862 in portion 864 that includes diffusing cavity 866, preferably a small diffusing cavity such as previously describe herein. Diffusing cavity 866 serves to cause light provided by secondary source fiber 840 to be presented to secondary receiver fibers 848. Secondary receiver fibers 848 provide a light path from diffusing cavity 866 to one or more secondary light sensors (see, e.g., sensors 852 and 858). Fibers 844 and/or 846 preferably pass to optical sensors for purposes of taking spectral or perimeter measurements, as described elsewhere herein.

Preferably, one of the secondary light sensors is a spectrometer for measuring the spectrum of the light source (or some portion of the spectrum of the light source) after it passes over the length of the cable and back through the cable (see, e.g., filters 856 and sensors 858, implementing one type of spectrometer, such as previously described elsewhere herein). Another of the light sensors preferably is a "wide band" sensor pair which consists of two or more sensors 852 that are positioned to measure the radial distribution of light in a secondary receiver fiber optic. The details of such a spectrometer for measuring the spectrum of the light source and for adjusting the spectral or other optical characteristics data of such a system in accordance with embodiments of the present invention have been described elsewhere herein. The details of such a "wide band" sensor that measures the angular distribution of light within a fiber optic have also been described elsewhere herein.

In accordance with such embodiments, the spectrum of the secondary receiver fibers is measured and saved as part of a normalization process (e.g., with the cable in an unflexed or known flexed condition, etc.; e.g., a first degree of flex). The intensity and angular distribution pattern of the secondary receiver fiber(s) similarly are measured and saved as part of the normalization process. As the system is utilized following the normalization process, the spectrum and angular distribution of the lamp and secondary receiver fibers are monitored while other system measurements (e.g., spectral measurements as described previously) are being taken. In general, if the secondary spectrum and angular distribution do not change, the cable has not been flexed. If, however, there is a change in such parameters, either the lamp spectral properties (including angular distribution such as caused by heating of lamp elements or apertures or infrared filters, etc.) has changed, or the cable has been flexed (e.g., to a second degree of flex, different from the first degree of flex) or otherwise changed to a degree to produce a detectable change. Such changes may thus be measured and monitored.

By providing additional sensors to monitor the lamp source directly such as described herein, it can be determined if the cable is being flexed or if the lamp and/or lamp hardware are changing. In certain applications it may not be necessary to determine which is changing (e.g., either cable flexing or lamp drift), but to simply monitor the overall system drift/changes and adjust the measurements to compensate for drift or to reject the measurements if the system has drifted out of calibration. Such use of normalization data and monitoring of the lamp and cable, etc., is used in preferred embodiments to compensate, and accept or reject, spectral or other optical characteristics data taken in accordance with the present invention.

It should be noted that such embodiments may be used, for example, as a strain gauge or as an instrument to measure if the curvature in a system is changing (see Apparatus and Method for Detecting Curvature filed on even date herewith by the inventors hereof, which is hereby incorporated by reference). In addition, such embodiments may be applied to one or more secondary source fibers and one or more secondary receiver fibers. Such embodiments also may utilize a plurality of secondary source and receiver fibers and a plurality of diffusing cavities distributed along the length of a cable assembly to quantify not only whether or not a cable is being flexed (and to measure and quantify the degree of flexing), but at what point or approximately what point in the cable the flex is occurring.

The secondary source fiber optic also may be provided by the primary source fiber optic utilizing mirrors or the like, or by notching the source fiber and providing a small amount of light to the secondary receiver fibers. What is important in such embodiments is that a portion of the light from the primary source fiber be controllably provided to the secondary receiver fiber(s). Additionally, in a system with a plurality of secondary receiver fibers, one secondary (or primary) source fiber may be utilized to provide sufficient light to all secondary receiver fibers in order for flex determination/quantification purposes in accordance with the present invention. The secondary source fiber may alternately have a light source different from the primary source fiber, and separate correction factors may be accordingly determined for the lamp and for the cable flexing.

It also should be noted that the diffusing cavity optionally may be replaced by a single fiber that serves both as a secondary source and secondary receiver fiber by looping the fiber optic back in the probe (or creating an equivalent of a fiber or optic loop). In accordance with such optional embodiments, two strands of fibers run the length of the cable and serve as a secondary source fiber and a secondary receiver fiber.

In an alternate embodiment, no additional fibers are added to the probe but a mirror such as a hot mirror is mounted or positioned near the end of the probe permitting light of certain frequencies, preferably frequencies that are out of the visible band, to be reflected/returned from one or more primary source fibers to one or more primary receiver fibers. The out of band light frequencies preferably are detected by sensors with notch filters that reject in band light frequencies as discussed earlier herein and that are primarily sensitive to flexing of the cable.

Again, what is important is that a secondary receiver fiber (or equivalent return optical path) couple light to optical sensors so that spectral or other changes due to cable flexing and/or lamp drift or the like may be determined and/or quantified, with such flex and/or lamp drift-type data available for correction or further quantification of optical characteristics data in accordance with the present invention.

Still other aspects of the present invention will now be described.

Figure 57:
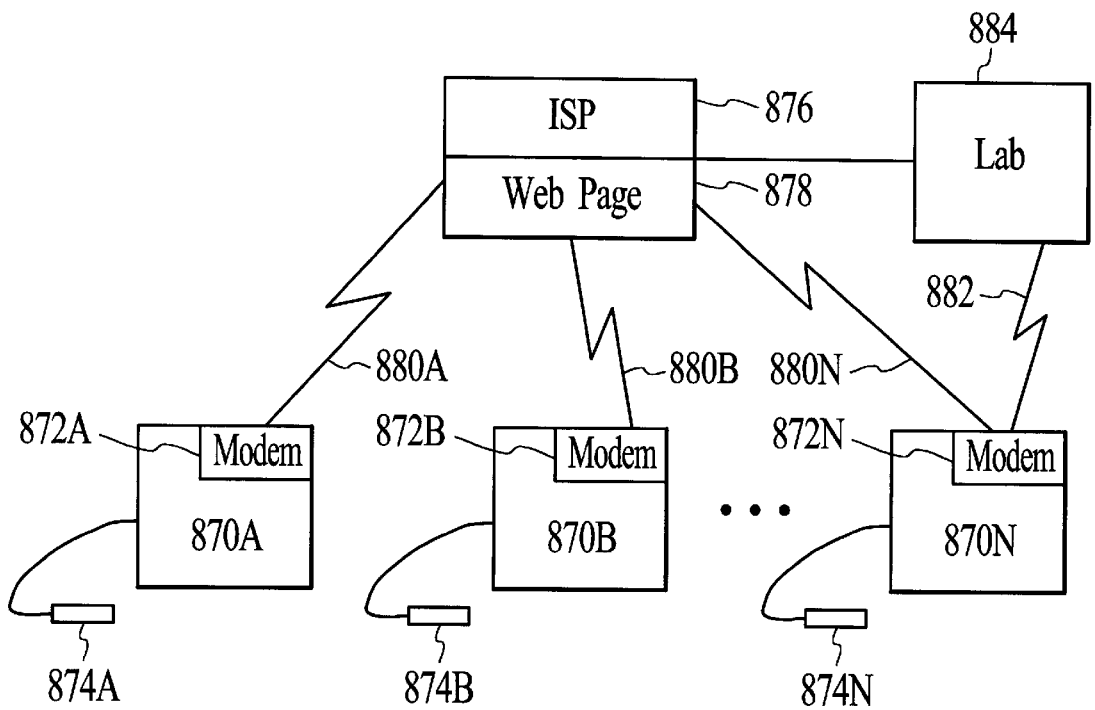

FIG. 57 illustrates one or more systems 870A, 870B . . . 870N having probes 874A, 874B . . . 874N, preferably constructed and operated in accordance with previously described embodiments, each of which is adapted to include a modem (illustrated as modems 872A, 872B . . . 872N). The modems may be a part of, or coupled to, the CPU, computer or other processing unit included as part of systems 870A, 870B . . . 870N (the use of CPUs, computers or other processing units as part of such systems is described elsewhere herein).

In accordance with such embodiments, under user initiated or other software control (such as a periodic call-in determined by software timing/real time clock algorithm, boot-up algorithm, etc.), one or more of systems 870A, 870B . . . 870N is coupled effectively to lab 884. Illustrated in FIG. 57 is an illustrated embodiment in which systems 870A, 870B . . . 870N are coupled via modem connection to web page 878, which for illustrative purposes is maintained on internet service provider (ISP) node 876. Lab 884 may include node 876, or lab 884 may be coupled to node 876 through a dedicated, dial-in or other connection. What is important is that systems 870A, 870B . . . 870N are able to coupled to a central electronic point that is a part of, or accessible by, lab 884. Lab 884 in this embodiment serves as a location for purposes of monitoring, controlling, servicing, etc., one or more of systems 870A, 870B . . . 870 N, as will described. In a typical application, lab 884 may be a part of, or working in conjunction with, the entity that manufactures, maintain, services or operates systems 870A, 870B . . . 870 N, etc., or uses such systems as part of an industrial process, examples of which are described elsewhere herein.

It should also be noted that the use of a web page and internet connection is illustrative only. As illustrated by connection 882, the connection between lab 884 and one or more of systems 870A, 870B . . . 870N may be made directly between the system(s) and lab 884, such as by modem or other electronic connection, either direct or over some wide area or other network.

In accordance with such embodiments, systems 870A, 870B . . . 870N may be electronically coupled to lab 884, which preferably is remotely located from one or more of the various systems. In one embodiment, lab 884 is able to convey operational commands to one or more of the systems. In one aspect of the present invention, one or more of systems 870A, 870B . . . 870N receive commands initiating a diagnostic or test mode, in response to which the system executes a diagnostic routine that generates diagnostic data (indicative of the operational status, failure mode or other diagnostic type data), which may be coupled to lab 884 by the electronic connection. In other aspects, during normal operation, one or more of the systems periodically capture and store operational data, such as lamp characteristics, calibration or normalization data or the like. The periodic storing of such operational data may be software initiated and/or controlled based on time (e.g., number of lamp or system operating hours), measurements, boot-up or initialization or other triggering event. Upon periodic or other connection to lab 884, such operational data may be transferred to lab 884 for evaluation, analysis, statistical processing and/or storage. In one such embodiment, lab 884 stores a history of such operational data for statistical or diagnostic purposes, such as for initiating a service call for the system, advising or predicting a need for a future service call (such as lamp, filter or other component replacement or repair). As an exemplary application, lab 884 monitors such operational data for key components (such as a light source) over time, and using stored data, look-up table or algorithm predicts remaining life of the component. Thereafter, lab 884 may send data or commands to one or more of systems 870A, 870B . . . 870N in order to have a suitable diagnostic, service call, informational or other message displayed on the system and/or a computer coupled to the system. In still other refinements of such embodiments, lab 884 may also generate an internet or other electronic message to a person or entity providing a status report or other data with respect to the particular system being monitored, diagnosed, controlled, etc.

In accordance with such embodiments, lab 884 may also use such an electronic connection to download software upgrades or other modifications to one or more of systems 870A, 870B . . . 870N. As exemplary uses, such software upgrades may consist of bug fixes or new releases of application, operating system, shade guide data or other software. In accordance with other aspects of the present invention, normalization or other data files (such as normalization, calibration or other files determined by the particular application, or files containing parameters controlling or used in a signal processing or filtering algorithm or the like) may be utilized by the system to make measurements or control decisions (for example, in one of the industrial applications described earlier), with such data files being upgradable or reconfigurable by under software control, which may be done remotely with a remote electronic connection as described earlier.

As a particular example, one or more of the systems may output shade guide values, such as for a dental application. In the event that new or updated shade guides are released, new or updated shade guide values may be electronically transferred to the one or more systems, thereby reducing downtime of the instrument, physical service calls or the like. Similar, in certain industrial applications, files indicative of or corresponding to particular materials or objects being optically characterized may be electronically downloading to one or more such systems (e.g., files that assist such a system in characterizing, identifying or sorting materials or objects that are being processed in a industrial, manufacturing or inventorying process, etc.). In applications in which constituent materials of a material or object are being predicted (either the material or object being optically characterized or a second material or object to be produced based on the material being optically characterized), files indicative of or corresponding to such constituent materials may be electronically downloading (also including recipe formulas and the like).

In accordance with another such aspect of the present invention, two or more systems may be coupled to lab 884, either in a simultaneous (parallel) or sequential (serial) manner in order to have either the same or different data files, software or other information to the two or more systems, such as for facilitating operation of the two or more systems that is synchronized in some manner (such as downloading calibration, normalization or other data files that enable or facilitate a more synchronized or corresponding operation between or among the two or more units).

It should also be noted that systems in accordance with the present invention may internally store operational data or other information such as for key components (e.g., light source) and predicting failure or a need for replacement or servicing of the component, with an appropriate message or alarm provided to a user. Monitoring the operating characteristics or duration of operation, etc. for key components may thus be implemented without being coupled to a remote lab.

Figure 58:
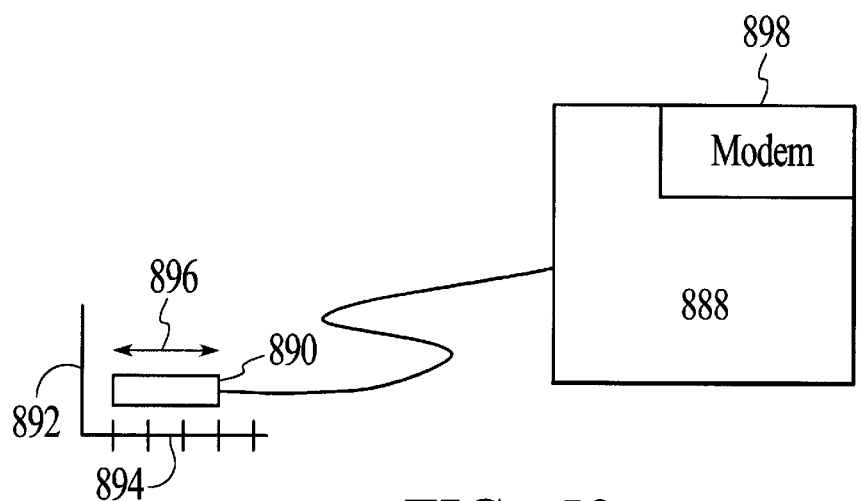

Aspects of the present invention relating to calibration of systems in accordance with the present invention will now be described with reference to FIG. 58.

In certain applications, it may be desirable to calibrate system 888, which may optionally include modem 898 or other communication device, by directing probe 890 towards color or other standard 892. Measurements taken as probe 890 is directed towards, or in proximity to, standard 892 may then be captured and stored and used to normalize, calibrate or otherwise adjust spectral measurements taken by the system. In accordance with certain preferred embodiments, such a calibration step is performed prior to measuring each object or material, or series of objects or material.

It also is contemplated by the present invention that as probe 890 is in the process of being moved relative to standard 892 sensors 894 detect the position of probe 890 with respect to standard 892 or a common physical reference point. Using sensors 894, a series of calibration or normalization measurements may be taken at determined positions relative to standard 892, with such positional information available for normalization or other adjustment of spectral or other measurements taken by the instrument.

Arrow 896 denotes that the motion of probe 890 with respect to standard 892 is a relative motion, and either the probe or the standard may be moved with respect to the other. In certain embodiments, probe 890 is retained in a fixed position, and standard 892 is moved towards probe 890 in a controlled manner, while sensors 894 similarly detect and provide information indicative of the relative position of the probe with respect to the standard. Standard 892 may be controllably moved by a servo motor or the like in order to provide the desired, controlled relative movement between the probe and the standard. If system 888 includes modem 898 or the like, a remote lab or operator may initiate, control, monitor and/or receive data from the calibration or normalization process in a manner similar to that described in connection with FIG. 57.

In conjunction with various of the foregoing embodiments, a variety of optic fibers may be utilized, with smaller fibers being used to assess optical characteristics of smaller spots on the object or material under evaluation. In accordance with such aspects of the present invention and with various of the embodiments described herein, fibers of about 300 microns in diameter, and up to or less than about 1 millimeter in diameter, and from about 1 to 1.5 millimeters have been utilized, although fibers of other diameters also are utilized in other embodiments and applications of the present invention. With such fibers, the optical properties of the object or materials under evaluation may be determined with a spot size of about 300 microns, or alternatively about 1 millimeter, or about 1.5 millimeters, or from about 0.3 to 1 millimeters, or from about 1 to 1.5 millimeters. In accordance with such embodiments, optical properties of such a spot size, including spectral, translucence, opalescence, gloss, surface texture, fluorescence, Rayleigh scattering, etc., may be quantified or determined, including by determining a plurality of spectrums as the probe is directed towards or in contact or near contact with the object or material and possible changes in such spectrums, all with an instrument that is simply directed towards a single surface of the object or material under evaluation.

It also should be noted that, in accordance with various principles of the various embodiments of the present invention described herein, refinements may be made within the scope of the present invention. Variations of source/receiver combinations may be utilized in accordance with certain embodiments of the present invention, and various optical properties may be determined in accordance with the various spectra obtained with the present invention, which may include spectra taken at one or more distances from the object or material (and including spectrally reflected light), and spectra taken at or near the surface (e.g., within the critical height, and substantially or wholly excluding spectrally reflected light). In certain embodiments, measurements may be taken in a manner to produce what is sometimes considered a goniometric measurement or assessment of the object or material under evaluation. In other embodiments, features may sometimes be used with or without certain features. For example, certain applications of aspects of the present invention may utilize perimeter fibers for height/angle determination or correction, while other applications may not. Such refinements, alternatives and specific examples are within the scope of the various embodiments of the present invention.

Various other features, embodiments, alternatives, etc., in accordance with the present invention will now be described.

As previously described, various devices, systems, methods, and methodologies for measuring the optical properties of teeth and other materials may be obtained in accordance with the present invention. Various embodiments herein utilize a spectrometer and other optical sensors. Particular preferred embodiments previously described preferably utilize light-to-frequency converters such as the TSL 230 sensor manufactured by Texas Instruments. Such embodiments include many unique and/or advantageous properties. As will be understood based on the disclosures herein, one such property is that the precision of the measurements for each spectral band may be independent of light intensity within the band. As a result, for example, the more blue bands, which typically have the lowest light intensity, may be measured with the same precision as the more red bands, which typically have the highest light intensity (please see the prior description of embodiments utilizing the TSL-type sensors).

Alternative embodiments may utilize linear or matrix charge coupled device (CCD) technology or other linear and/or matrix optical sensors as a spectrometer system (exemplary alternative embodiments are described elsewhere herein). It has been determined, however, that utilizing CCD or other linear or matrix sensors may present certain problems and disadvantages. One such difficulty is that the light sensitivity of light in the more blue bands is considerably less than the light sensitivity or intensity of light in the more red bands. The reduced sensitivity is due to the nature of the sensing elements and also due to the spectral properties of the light source and the spectral properties of the light conduction elements. It is not unusual in spectrometer systems, particularly in reflectance-type systems, for the blue system sensitivity to be several orders of magnitude less than the red sensitivity. Thus, if the spectrometer system is constructed with a linear or matrix array where the light receivers intensity is output serially to an analog to digital converter (ADC), then the range of the ADC and the precision of the ADC must be large enough to accommodate the high red light sensitivity (or else the system will saturate rendering the measurement invalid) and it must also be precise enough to permit the low sensitivity elements to have sufficient gain to make quality measurements. For example, if the red intensity and sensitivity is 128 times the blue intensity and sensitivity, then in general the blue readings will automatically have a precision that is 128 ($2^7$) times less than that for red. If, for example, a 16 bit ADC is utilized and providing $2^{16}$ levels of gray, then the maximum level of gray for blue is 128 times less or ($2^{(16-7)}$) or only $2^9$ levels of gray. In general, if a 10 bit ADC is utilized, blue will only have eight levels of gray, etc.

One approach in certain spectrometer systems, particularly those utilized for reflectance measurements, has been to optically normalize in order to flatten the spectral response. This may be done, for example, by reducing the intensity of the red light input to the spectrometer with filters or mirrors or the like, such as interference filters, to reduce the intensity of red light on the sensors and force the red intensity to be within the range of the blue sensors. The disadvantage of such systems is that it causes the noise level of the red sensors to be increased to the noise level of the blue sensors since the signal from the red sensors is reduced, requiring an increase in overall system gain, hence the system noise is forced to the level of the lowest sensitivity input.

Figure 59:
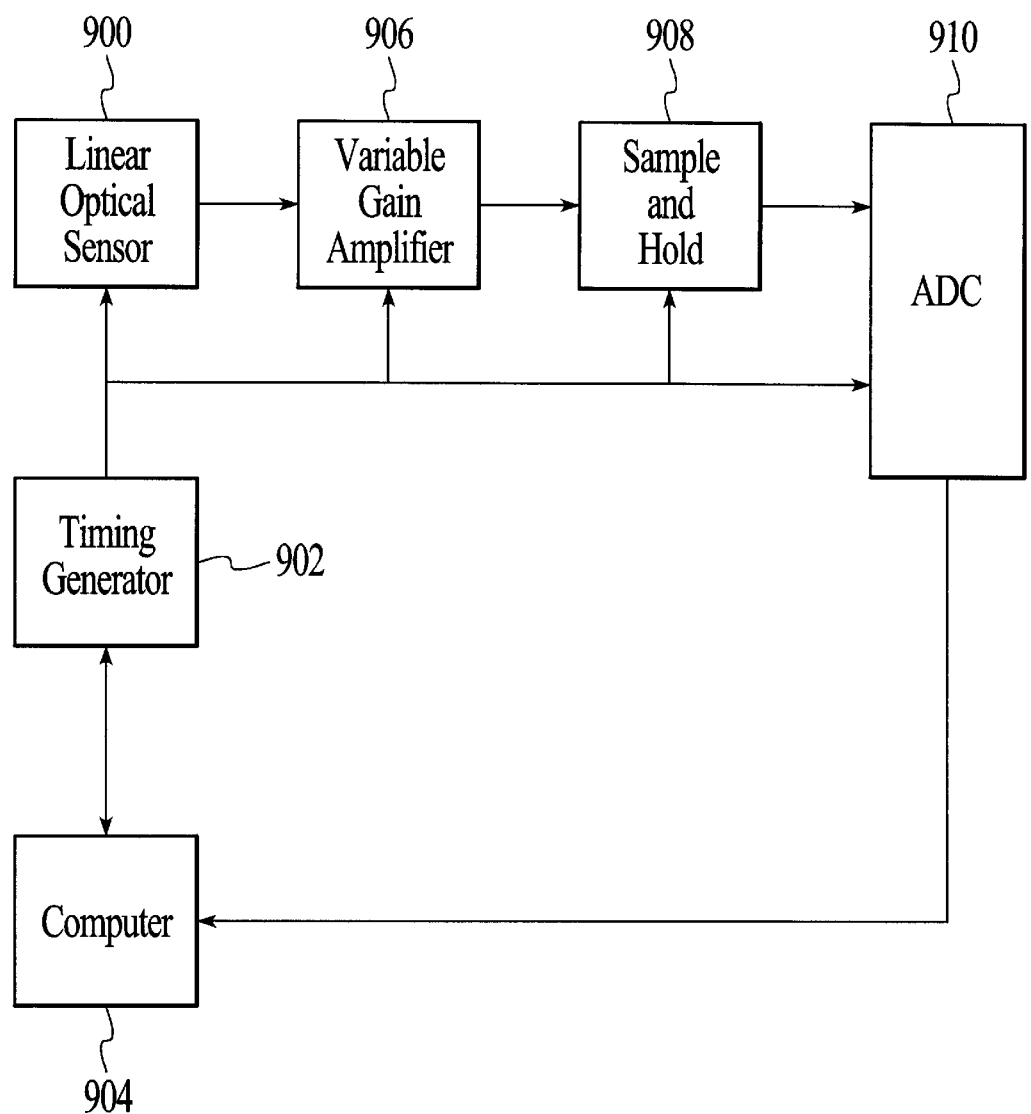
FIG. 59 illustrates an embodiment of the present invention employing a linear optical sensor.

In accordance with other alternative embodiments of the present invention, improved spectrometer-type systems may be produced. FIG. 59 is a block diagram of one such alternative embodiment. As illustrated, linear (or array) optical sensor 900, which preferably includes an optical manifold that receives and directs light of a given wavelength to appropriate sensing elements provided in linear optical sensor 900. Optical manifolds that direct light of a given wavelength are known in the art and may be constructed, for example, of diffraction gratings or optical filters (such as the optical manifolds and implements of the type described elsewhere herein). The output of linear optical sensor 900 passes through variable gain amplifier 906, to sample and hold amplifier 908 and to analog-to-digital converter (ADC) 910. Such variable gain amplifiers, sample and hold amplifiers and ADCs are known in the art and are sometimes available as a single unit. It is desired that the ADC have the desired precision and that the overall system provide for the speed required for the particular application.

In the illustrated embodiment, system timing is controlled by timing generator 902, coupled to computer 904 (which also preferably receives data from ADC 910). Timing generator 902 optimally controls linear optical sensor 900 (or CCD or other linear sensor, etc.) to integrate a measurement and to output it to variable gain amplifier 906 and sample and hold amplifier 908 and ADC 910. Timing generator 902 also preferably controls the analog output of linear optical sensor 900 to serially step from one sensor to the next in a controlled and desired manner.

In accordance with such embodiments, variable gain amplifier 906 is also controlled by timing generator 902 and/or computer 904, and preferably the gain of variable gain amplifier 906 is varied step by step and, preferably, uniquely for each sensor in the liner optical sensor 900. Thus, in accordance with such embodiments, the gain corresponding to a given first (e.g., red) element may be different than the gain for a given second (e.g., blue or green) element under control of timing generator 902 and/or computer 904. In accordance with such embodiments, the full (or substantially all of the) range of ADC 910 thus becomes available for each sensor, and timing generator 902 and/or computer 904 can normalize or cause the overall system sensitivity to be flat over the entire spectral range.

In certain embodiments, timing generator 902 is controlled by a computer or microprocessor or is a microprocessor such as a RISC processor such as a Hitachi SH 2 or SH 3 processor. In such embodiments the gain of variable gain amplifier 906 is variable dynamically by the processor as spectral measurements are being made. It also should be noted that such embodiments preferably utilize a linear-type array sensor, although such embodiments also may utilize matrix-type sensor elements or individual elements as well. What is important is that the sensing elements be provided with suitable gain for the light intensity presented to the particular sensing elements, etc.

Yet other alternative embodiments in accordance with the present invention will now be described.

As described previously, embodiments in accordance with the present invention typically utilize a spectrometer and/or other optical sensors. The measurements preferably were made while the probe was in motion with respect to the material being measured - either the probe was moving, the material was moving, or both. In accordance with such embodiments, it is desired that both rapid and precise measurements be made over the entire spectral range.

Making rapid spectral measurements with precision typically has been difficult or impossible to do because a spectrometer that can make rapid measurements typically consists of a plurality of light sensors, each measuring a small spectral region or band simultaneously in a parallel fashion, as opposed to an apparatus consisting of one optical sensor that measures spectral bands in sequence or serially one after the other. In general, an instrument that measures spectral bands in a parallel fashion can produce N times as many measurements per unit time as an instrument making serial measurements, assuming that the spectral receivers in both instruments are equivalent. In either case, whether the apparatus has many simultaneous sensors or one sensor making multiple measurements, in general the more rapid the apparatus operates, the shorter the integration time per spectral band, and hence the lower the precision of the spectral measurement.

In accordance with other alternative embodiments of the present invention, the precision and/or sampling rate of such spectrometers may be increased.

As described elsewhere herein, in accordance with preferred embodiments the spectral properties of materials may be measured as a probe moves into contact with or into proximity with an object. When the probe is far from the object, the total light energy received is small, and as it is moved towards the object the optical energy increases and eventually peaks and decreases as the probe is moved still further towards the material. In alternative probe designs, the light energy may not peak but may rise to a maximum as the prove is moved into contact or near contact with the material. In either case, peaking or not, as the probe moves relative to the material the total spectral energy received will vary.

Certain materials exhibit properties such as opalescence or pearlesence wherein the spectral reflectance curve is a function of angle of incidence and angle of reflection. Other materials (perhaps most materials) have consistent spectral reflectance curves that are not functions of angle (at least for angles within a limited range of angles). What does vary, however, for virtually all materials is the value or gain of the spectrum as a probe moves relative to an object. When the probe is far away the value will be low, and as it nears the object the value will increase. In many cases the value or gain will vary by orders of magnitude while the spectral shape or chroma will vary relatively little.

In accordance with alternative embodiments, it has been determined to be advantageous to measure the value of a spectrum for a probe moving relative to a material at a high rate (or at a first rate high enough to "freeze" the value at a precise location or range of locations), while it is only be necessary to measure the chroma at a second, lesser, rate and hence with higher precision.

Figure 60:
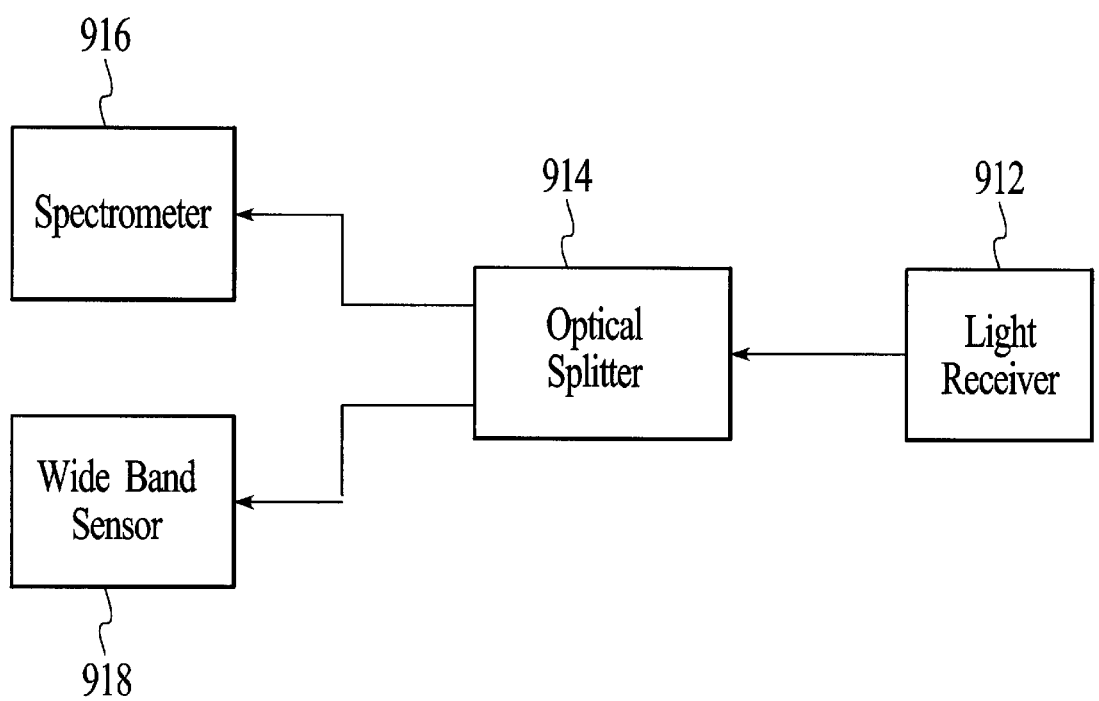
FIG. 60 illustrates an embodiment of the present invention in which light is split and provided to a spectrometer and wideband sensor(s)

FIG. 60 illustrates a preferred exemplary implementation of such an embodiment of the present invention. Such an embodiment preferably includes a reflectance-type probe having at least one light source and at least one light receiver element (examples of such probes and light sources/receivers are described elsewhere herein; FIG. 60 illustrates for discussion purposes only light receiver 912). Light receiver 912 couples received light to optical splitter 914, which couples received light to spectrometer 916 and also to wide band (value) sensor 918. In accordance with such embodiments, spectrometer 916 (which may be of a design/type described elsewhere herein) preferably measures the spectral properties of the received light as a function of optical wavelength over a band range such as the visible band (400 nm to 700 nm). Wide band sensor 918 preferably measures the light energy over a wide band, and preferably over the same total band as spectrometer 916.

Without being bound by theory, if V is the measurement of value/wide band sensor 918, and R(X) is the reflectance response of the material as a function of wavelength, then for static measurements or measurements where V and R(X) are made at the same rate:

$$V = \int_{band} R(\lambda) d\lambda = \sum_{bands} R(\lambda)$$

Value/wide band sensor 918 in general will always have an intensity much higher than the intensity of any of the individual spectral sensors of spectrometer 916 since it measures the light intensity over a broad band of wavelengths. Hence if the chroma of the spectrum varies slowly (such as as a function of angle), it is possible to measure the spectrum at a rate much less than the rate of the Value sensor, thus improving the precision of the spectral sensors. Preferably, however the value of the spectral sensors is adjusted to account for the variation in value due to the movement of the probe/material, or the reflectance spectrum should be adjusted by a gain factor G where:

$$G = \frac{V}{\sum_{bands} R(\lambda)}$$

and hence the adjusted reflectance spectrum with improved precision is:

$$R_1(\lambda) = G \cdot R(\lambda)$$

As will be appreciated, in accordance with such alternative embodiments sensors and means are provided to measure value at a first, preferably faster rate, and chroma at a second, preferably slower rate, in such a manner to make more precise and overall rapid measurements.

Still other alternative embodiments of the present invention will now be described.

As previously described, various devices, systems, methods, and methodologies for measuring the optical properties of teeth and other materials may be obtained in accordance with the present invention. In preferred embodiments, an instrument with a spectrometer and with "wide band" optical sensors is utilized. In general, the spectrometer measures optical intensities over narrow optical bandwidths, while the wide band sensors measured optical intensities over wide band width, typically over the entire visible spectrum.

Figure 61:
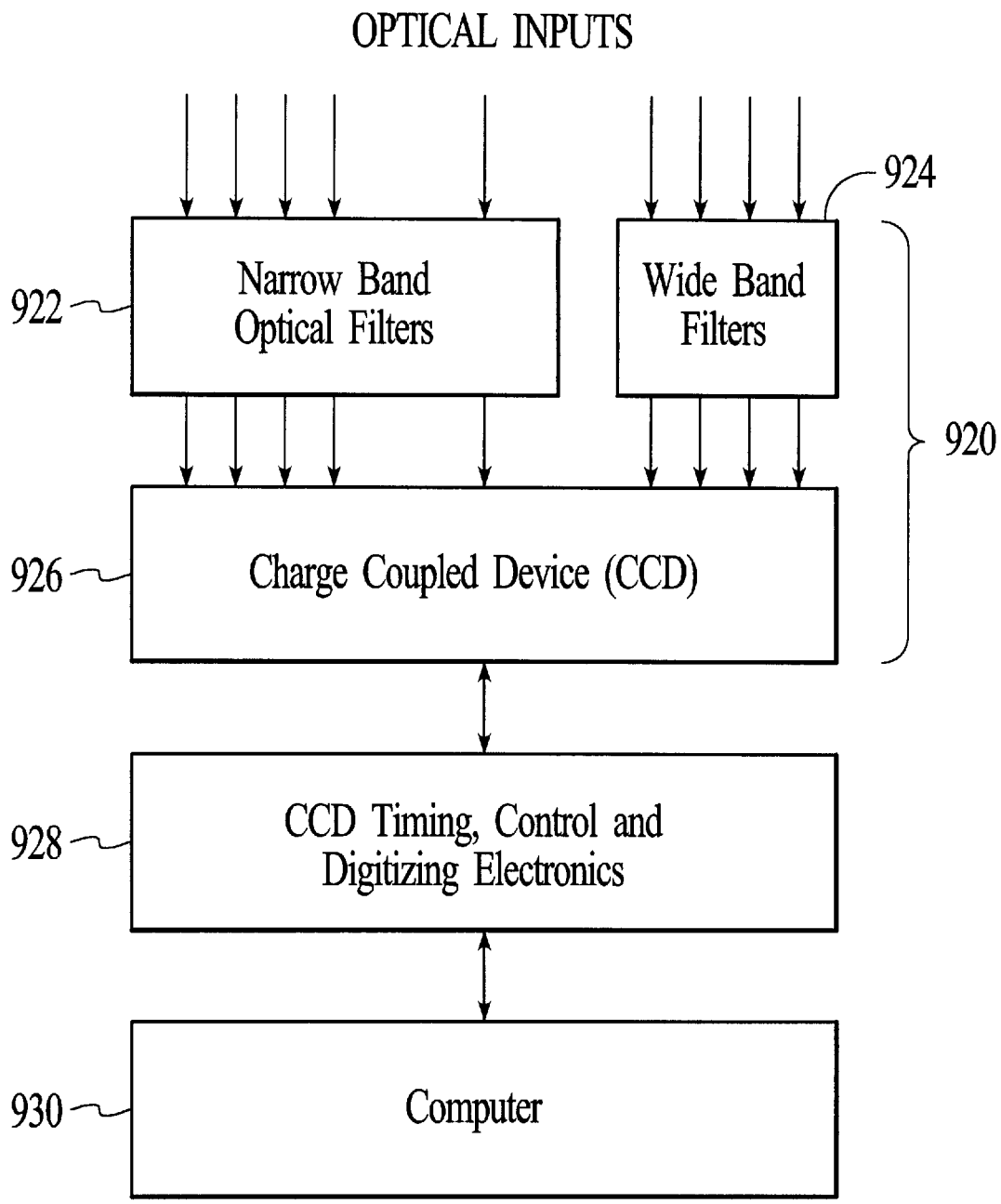
FIGS. 61 and 62 illustrate embodiments employing a CCD sensing element.

An alternative embodiment in accordance with the present invention will now be described. As illustrated in FIG. 61, optical sensor 920 consisting of a spectrometer (narrow band sensors) and wide band optical sensors are provided. Optical sensor 920 preferably consists of CCD (charge coupled device) 926 (or similar optical sensing device) for measuring light intensities, and CCD timing, control and digitizing electronics 928 for converting the analog output of CCD 926 into digital form (such as may be input into a computer or microprocessor or other data recording or analyzing device as described elsewhere herein). CCDs and the electronics for controlling and digitizing their output are known in the art.

In accordance with the illustrated embodiment, the optical elements of CCD 926 preferably are covered by optical filters 922 and 924, which preferably consists of one or more filter plates. Such a filter plate preferably is constructed of interference filters which pass light of a predetermined frequency and reflect light that is out of band. Interference filters are known in the art. In the preferred implementation of such embodiments, a portion (922) of the interference filters pass light with a narrow band width, while another portion (924) of the filters pass light with wide bandwidth. Thus, certain of the sensors in CCD 926 may serve to detect narrow band width light, while other of the sensors may serve to detect wide band width light. Thus, the output of CICD 926 preferably may include both the elements of a spectrometer and also the elements of a plurality of wide band sensors (which may be advantageously utilized as described elsewhere herein).

Figure 62:
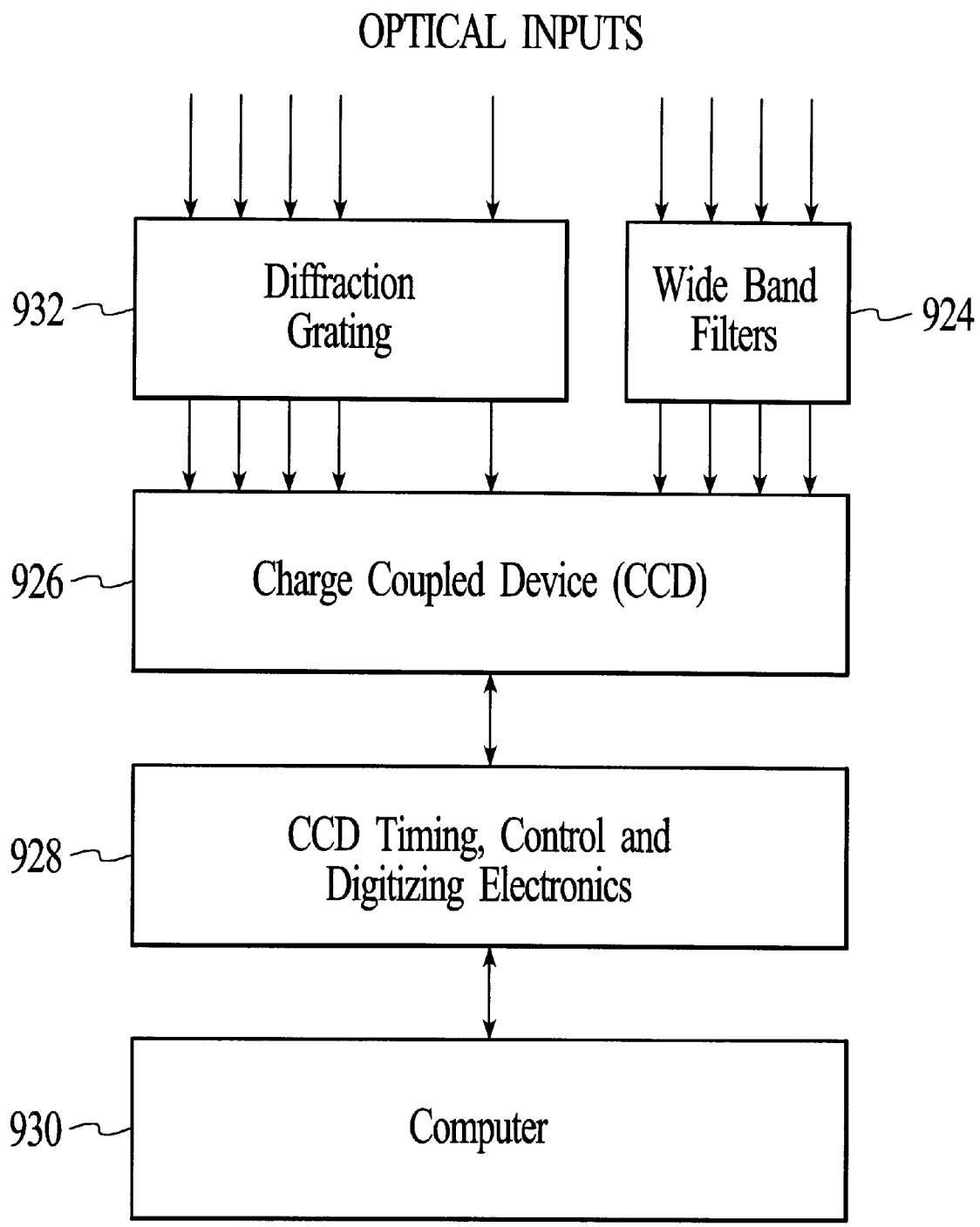

In an alternate such embodiment of the invention, CCD 926 may be coupled to diffraction grating 932 as illustrated in FIG. 62. Diffraction gratings such as diffraction grating 932 are known in the art and have been utilized extensively with CCD-type sensors. In an embodiments such as illustrated in FIG. 62, however, diffraction grating 932 covers (or provides diffracted light to) only a portion of CCD 926, allowing the remainder of the sensing elements of CCD 926 to be available for a plurality of wide band sensors (e.g., to receive from wide band filters 924).

Yet other embodiments of the present invention will now be described. A variety of types of systems and methods for measuring the color and other optical properties of teeth and other materials have previously been described. In certain of the previously described embodiments, spectrometers were disclosed consisting of filters that separated light into narrow wavelength bands and preferred light to frequency converter optical sensors that measured the intensity of each separated optical band (other types of optical sensors are utilized in certain other embodiments). In yet other embodiments as will be described, however, an optical filter/sensing arrangement is utilized that consists of a combination of a diffraction grating and optical filters that separate light into narrow wavelength bands, resulting in a spectrometer that may have small size and high efficiency.

Figure 63:
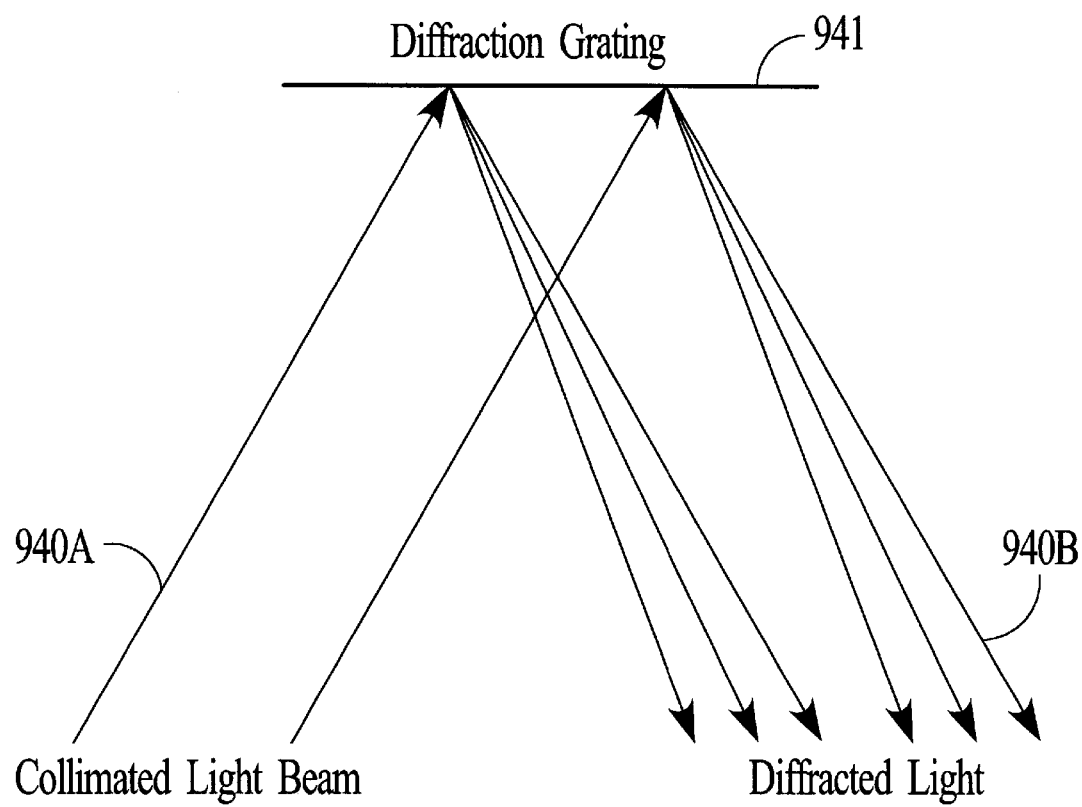
FIGS. 63 to 65 illustrate principles of diffraction gratings for purposes of understanding an alternative preferred embodiment.

Diffraction gratings are well known in the art. Generally speaking, diffraction gratings consist of a material with finely ruled or chemically etched lines that both reflect light and also separate it into its spectral components by utilizing the diffraction properties of light. When light passes next to a sharp edge the path of the light ray is altered from a straight line and is bent in a direction towards the edge. The degree of curvature of the light ray is dependent upon the wavelength or color of the light ray. Thus, diffraction can be utilized to separate light into its spectral components. A similar effect occurs when light reflects from a diffraction grating. Light beams 940A may be separated into beams 940B based on the incident light's spectral components by diffraction grating 941 as illustrated in FIG. 63. To focus the light, the diffraction grating typically is curved as illustrated by diffraction grating 942 in FIG. 64, or alternatively the light from the diffraction grating must otherwise be focused by a mirror or other optical element. It is believed to be more common to utilize a curved diffraction grating in spectrometer applications.

Figure 64:
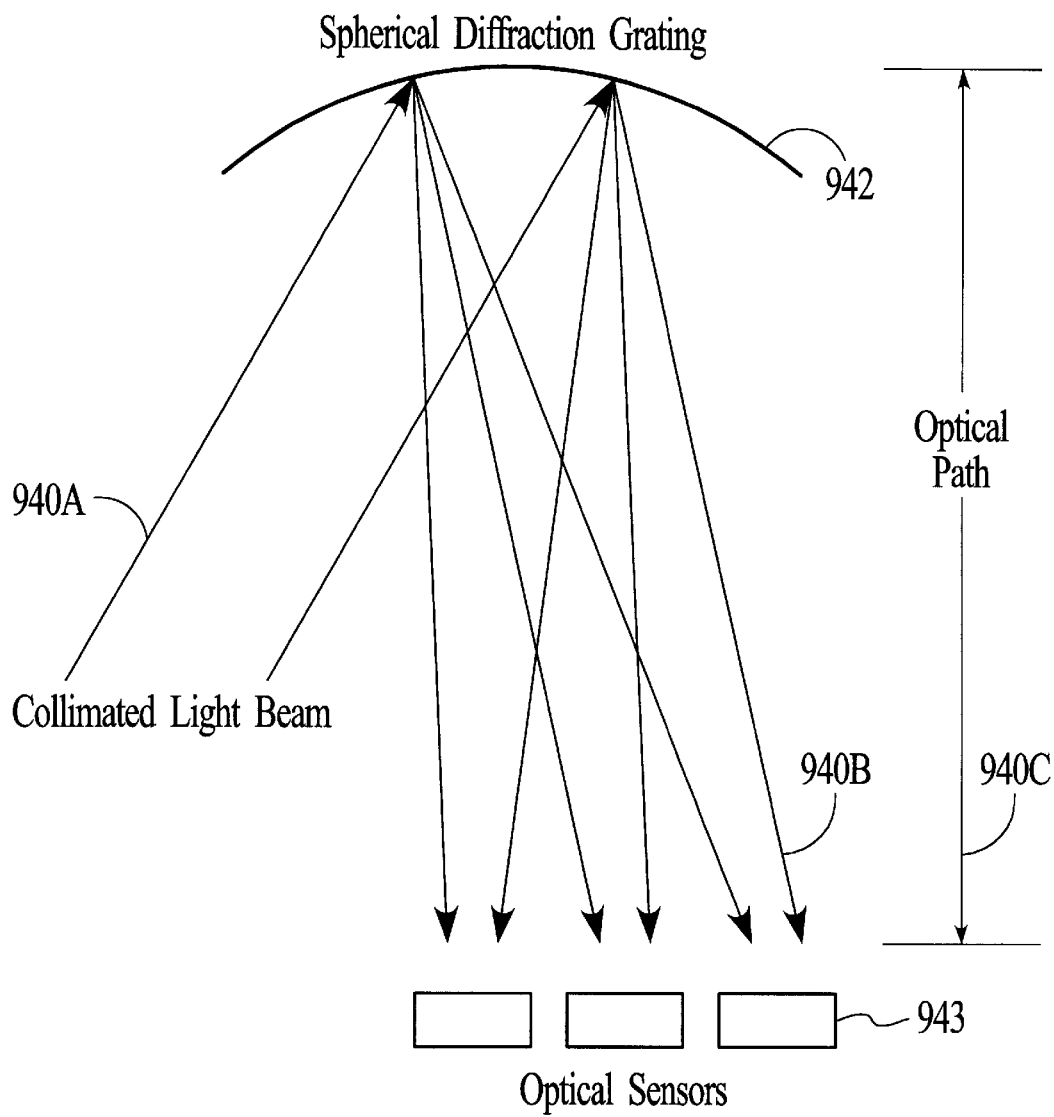
Figure 65:
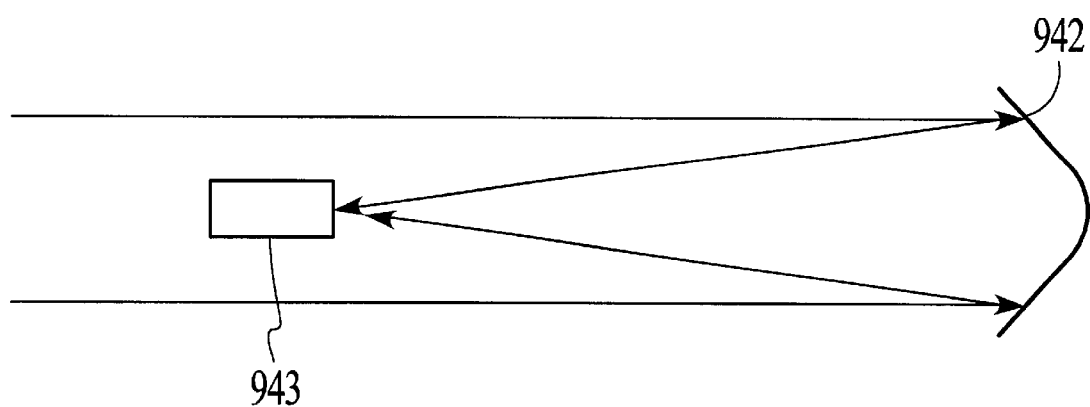

An advantage of diffraction gratings in spectrometer applications is that light entering the spectrometer system can be separated with high efficiency if the diffraction grating is a spherical reflector as illustrated in FIGS. 64 and 65 (generally, a top view and a side view, respectively). Virtually all the light entering the optical entrance port may be separated and presented to optical sensors 943. If the light presented to the collimating element has a radial or axial distribution pattern (as described elsewhere herein) the light is still separated and presented to the sensors within its spectral band. Generally, it does not matter where a light ray exits the collimating element (whether it is central or at the sides); it is still focused by the curvature of the diffraction grating mirror and presented to the optical sensors. Thus, a light ray at one edge of the collimated beam of light in FIGS. 64 and 65 generally will be separated and presented to optical sensors 943 the same as a light ray that is at the opposite edge of the collimated beam of light.

A difficulty occurs with diffraction gratings as is apparent in FIGS. 64 and 65. In order to obtain narrow spectral resolution, the optical sensors must be far from the diffraction grating, as the resolution generally is a function of the optical path length 940 C. This generally means that a spectrometer based on such a diffraction grating has certain physical size requirements. In accordance with certain embodiments of the present invention, however, what is desired is a spectrometer system with small size, and a spectrometer system that separates light into its spectral components with high efficiency (such as to implement a small, embeddable or handheld spectrometer, spectrophotometer, etc).

In an alternative preferred embodiment of the invention, the spectrometer consists of an optical manifold and optical sensors. The optical sensors may be CCD sensors, photo diode sensors, phototransistor sensors, or any other optical sensor (such as described elsewhere herein, including light to frequency converters). The sensors may be discrete elements or may be part of a linear, rectilinear or other sensor array.

Figure 66:
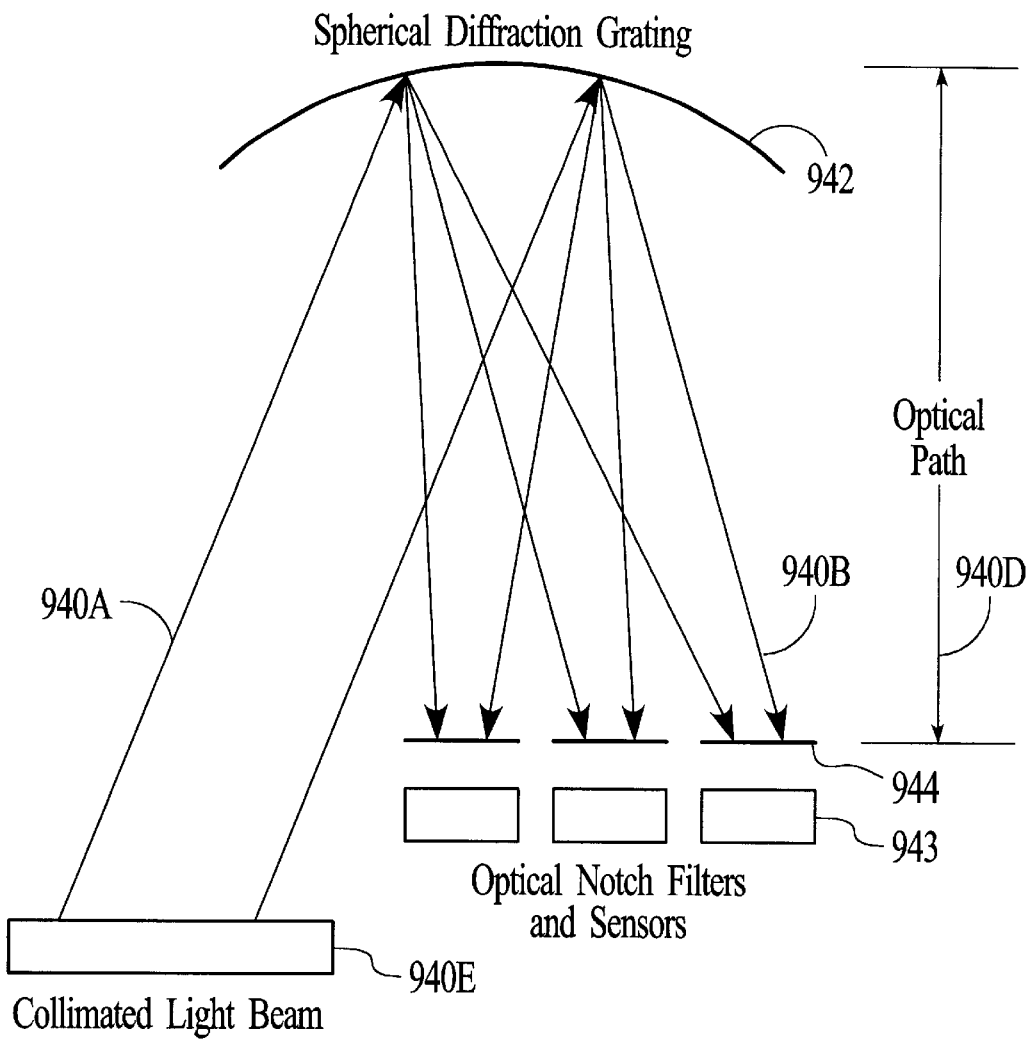
FIG. 66 illustrates an alternative preferred embodiment employing a two stage spectral separation, preferably utilizing a diffraction element and filters.

An exemplary optical manifold/spectrometer utilized in such embodiments is illustrated in FIG. 66. The optical manifold/spectrometer assembly consists of collimating element 940E, as required, to produce collimated light beams 940 A, diffraction grating 942, which is of a curved or preferably spherical shape, and optical filters 944. In a particular preferred embodiment, diffraction grating 942 is a spherical diffraction grating and optical filters 944 are interference filters. In other embodiments, filters are absorption filters constructed of organic or inorganic absorption pigments, or other filters, including those described elsewhere herein. In either case, the filters serve to pass light within a narrow wavelength bandwidth or "optical notch" and either absorb or reflect light (or both) that is out of the optical band pass width.

Collimating element 940 E serves to collimate the input light. In a preferred embodiment, collimating element 940 Et is an aspherical or other lens or lens assembly. Collimated beam of light 940 A strikes (preferably) spherical diffraction grating 942, which serves to separate the light into its spectral components. The light 940 B reflected from diffraction grating 942 then passes through (preferably) interference filters 944 before being presented to optical sensors 943.

The construction of interference filters 944 preferably consists of depositing layers of material with differing dielectric constants on an optical substrate, which in one preferred implementation may be part of an optical manifold including the spherical diffraction grating. A light ray striking an interference filter is either transmitted through the filter if it is within the optical transmission band, reflected if it is out of the optical transmission band or it is absorbed within the filter. The optical transmission properties and reflection properties are determined by the number and nature of the layers of the filters and by additional optical blocking elements (usually absorption elements) to prevent secondary transmission in the filter for light that has much higher or lower wavelengths. The blocking elements contribute to the thickness of the filter. The number and nature of the layers determine the transmission properties. Such interference filters may be deposited alternatively onto sensors 943, such as described in co- pending application Ser. No. , filed on Dec. 23, 1999 by the inventors hereof, which is hereby incorporated by reference.

Such an optical manifold/spectrometer assembly as illustrated in FIG. 66 has two optical spectral separation elements. The first spectral separation element is the diffraction grating, and the second one is the interference filters. In such embodiments, the two spectral separation elements are utilized in combination to separate the light into its spectral components coarsely in a first stage and then into narrower components in a second stage. The interference filters preferably are placed relatively closely to the diffraction grating and receive light that has relatively broad optical bandwidth. Generally, and without being bound by theory in connection with the discussion of such embodiments, the optical bandwidth of light presented to each filter varies from filter to filter and favors shorter wavelengths at one side of the optical manifold and favors longer wavelengths at the other side of the manifold.

The diffraction grating diffracts light in a first stage. The diffracted light is then presented to the interference filters. Because of their position relative to the diffraction grating and because each filter receives light over a narrow optical band, the number of layers of material required to produce each filter preferably is reduced from the number that would otherwise be required if the filters received light over a broad optical band such as light received from the sun or other light sources.

The distance of the filters and sensors from the diffraction grating is significantly reduced since each filter/sensor pair may receive light with a broader bandwidth than would otherwise be possible without the interference filters. This results, desirably, in a reduced optical path length 940D as illustrated in FIG. 66, thereby enabling spectrometers of reduced size, while retaining sufficient efficiency and resolution for many applications. As will be appreciated, such an optical manifold/spectrometer assembly may be used in combination with broadband or other sensors such as for purposes of detecting height, angle, gloss, translucency, texture, etc., and may be used to measure a wide variety of objects and materials such as described elsewhere herein. Such an optical manifold/spectrometer assembly thus will be understood to be used in combination with such other sensors, features and implements as described elsewhere herein.

It also should be understood that such alternative embodiments may utilize a refractive element (e.g., prism type element) instead of a diffractive element, such that a diffractive or refractive element produces a first stage of spectral separation, while interference or other filters provides a second stage of spectral separation, such as described previously. It also will be understood that, in accordance with such embodiments, characteristics of a material or object may be determined, such as spectral characteristics or whether the material or object contains a predetermined material, or a determination may be made if the object or material is genuine. Also in accordance with such embodiments, light may be provided to the material or object by a probe, wherein light received from the material or object may be provided to second optical sensors, wherein the second optical sensors provide data indicative of a height or angle of the probe with respect to the material or object, provide data indicative of an optical value measurement of the material or object, or provide data indicative of translucence, gloss, opalescence, texture or other optical characteristics of the material or object, and the material or object may be a gaseous material, a non-gaseous material, skin, non-skin body tissue, paint, fabric, a photograph, a dental object, a printed object, hair, make up or other material or object.

It should be understood that, in accordance with the various alternative embodiments described herein, various spectrometer-type devices, and uses and methods based on such devices, may be obtained. The various refinements and alternative and additional features also described may be combined to provide additional advantageous combinations and the like in accordance with the present invention.

Reference is made to the following copending applications, all by the inventors hereof, which are hereby incorporated by reference: U.S. Application Ser. No. , filed on Dec. 23, 1999; U.S. application Ser. No. 09/198,591, filed on Nov. 23, 1998; U.S. application Ser. No. 09/091,208, filed on Jun. 8, 1998, which is based on International Application No. PCT/US 97/00126, filed on Jan. 2, 1997, which is a continuation in part of U.S. patent application Ser. No. 08/581,851, now U.S. Pat. No. 5,745,229, issued Apr. 28, 1998, for Apparatus and Method for Measuring Optical Characteristics of an Object; U.S. application Ser. No. 09/091,170, filed on Jun. 8, 1998, which is based on International Application No. PCT/US 97/00129, filed on Jan. 2, 1997, which is a continuation in part of U.S. Application Ser. No. 08/582,054, now U.S. Pat. No. 5,759,030 issued Jun. 2, 1998, for Apparatus and Method for Measuring Optical Characteristics of Teeth; PCT Application No. PCT/US 98/13764, filed on Jun. 30, 1998, which is a continuation in part of U.S. application Ser. No. 08/886,223, filed on Jul. 1, 1997, for Apparatus and Method for Measuring Optical Characteristics of an Object; PCT Application No. PCT/US 98/13765, filed on Jun. 30, 1998, which is a continuation in part of U.S. application Ser. No. 08/886,564, filed on Jun. 30, 1998, for Apparatus and Method for Measuring Optical Characteristics of Teeth; U.S. application Ser. No. 08/886,566, filed on Jul. 1, 1997, for Method and Apparatus for Detecting and Preventing Counterfeiting; and U.S. application Ser. No. 09/113,033, filed Jul. 9, 1998, for Method and Apparatus for Measuring Optical Properties of an Object.

Additionally, it should be noted that the implements and methodologies may be applied to a wide variety of objects and materials, illustrative examples of which are described elsewhere herein and/or in the co-pending applications referenced above. Still additionally, embodiments and aspects of the present invention may be applied to characterizing gems or precious stones, minerals or other objects such as diamonds, pearls, rubies, sapphires, emeralds, opals, amethyst, corals, and other precious materials. Such gems may be characterized by optical properties (as described elsewhere herein) relating to the surface and/or subsurface characteristics of the object or material. As illustrative examples, such gems may be characterized as part of a buy, sell or other transaction involving the gem, or as part of a valuation assessment for such a transaction or for insurance purposes or the like, and such gems may be measured on subsequent occasions to indicate whether gem has surface contamination or has changed in some respect or if the gem is the same as a previously measured gem, etc. Measuring a gem or other object or material in accordance with the present invention may be used to provide a unique "fingerprint" or set of characteristics or identification for the gem, object or material, thereby enabling subsequent measurements to identify, or confirm the identity or non-identity of, a subsequently measured gem, object or material.

It also should be noted that the implements and methodologies described in the co-pending applications referenced above also may be applied to embodiments and features of the present invention as described herein. All such refinements, enhancements and further uses of the present invention are within the scope of the present invention.

What is claimed is:

1. A method comprising the steps of:
providing light to a diffraction grating;
receiving diffracted light from the diffraction grating with a plurality of optical sensors, wherein the light is incident upon and selectively transmitted through a plurality of filter elements prior to being received by the plurality of optical sensors, wherein the optical sensors comprise light to frequency converters;
wherein spectral characteristics of the light are determined.

2. The method of claim 1, wherein the optical sensors comprise an array of optical sensors.

3. The method of claim 1, wherein the optical sensors comprise a linear array of optical sensors.

4. The method of claim 1, wherein the filter elements comprise interference filters.

5. The method of claim 1, wherein the filter elements comprise a linear variable filter.

6. The method of claim 1, wherein the filter elements comprise a color gradient filter.

7. The method of claim 1, wherein the filter elements comprise interference filters deposited on an optical manifold, wherein the diffraction grating is part of the optical manifold, wherein light exits the optical manifold through the interference filters and is detected by the optical sensors.

8. The method of claim 1, wherein the diffraction grating is curved.

9. The method of claim 1, wherein the diffraction grating comprises a spherical diffraction grating.

10. The method of claim 1, wherein the light is collimated prior to being provided to the diffraction grating.

11. The method of claim 10, wherein the light is collimated by an aspheric lens or lens assembly.

12. The method of claim 1, further comprising the step of providing light to a material or object, wherein the light provided to the diffraction grating comprises light received from the material or object.

13. The method of claim 12, wherein characteristics of the material or object are determined.

14. The method of claim 13, wherein the characteristics comprise spectral characteristics.

15. The method of claim 13, wherein the characteristics comprise whether the material or object contains a predetermined material.

16. The method of claim 13, wherein a determination is made if the object or material is genuine.

17. The method of claim 12, wherein the light is provided to the material or object by a probe, wherein the method further comprises the step of providing light received from the material or object to second optical sensors, wherein the second optical sensors provide data indicative of a height or angle of the probe with respect to the material or object, provide data indicative of an optical value measurement of the material or object, or provide data indicative of translucence, gloss, opalescence, texture or other optical characteristics of the material or object.

18. The method of claim 12, wherein the material or object comprises a gaseous material, a non-gaseous material, skin, non-skin body tissue, paint, fabric, a photograph, a dental object, a printed object, hair, or makeup.

19. A method comprising the steps of:
providing light to a material or object;
providing light to a diffraction grating, wherein the light provided to the diffraction grating comprises light received from the material or object;
receiving diffracted light from the diffraction grating with a plurality of optical sensors, wherein the light is incident upon and selectively transmitted through a plurality of filter elements prior to being received by the plurality of optical sensors;
wherein spectral characteristics of the light are measured;
wherein the light is provided to the material or object by a probe, wherein the method further comprises the step of providing light received from the material or object to second optical sensors, wherein the second optical sensors provide data indicative of a height or angle of the probe with respect to the material or object, provide data indicative of an optical value measurement of the material or object, or provide data indicative of translucence, gloss, opalescence, texture or other optical characteristics of the material or object.

20. The method of claim 19, wherein the optical sensors comprise an array of optical sensors.

21. The method of claim 19, wherein the optical sensors comprise a linear array of optical sensors.

22. The method of claim 19, wherein the optical sensors comprise CCD sensors, photodiode sensors or phototransistor sensors.

23. The method of claim 19, wherein the optical sensors comprise light to frequency converters.

24. The method of claim 19, wherein the filter elements comprise interference filters.

25. The method of claim 19, wherein the filter elements comprise a linear variable filter.

26. The method of claim 19, wherein the filter elements comprise a color gradient filter.

27. The method of claim 19, wherein the filter elements comprise interference filters deposited on an optical manifold, wherein the diffraction grating is part of the optical manifold, wherein light exits the optical manifold through the interference filters and is detected by the optical sensors.

28. The method of claim 19, wherein the diffraction grating is curved.

29. The method of claim 19, wherein the diffraction grating comprises a spherical diffraction grating.

30. The method of claim 19, wherein the light is collimated prior to being provided to the diffraction grating.

31. The method of claim 30, wherein the light is collimated by an aspheric lens or lens assembly.

32. The method of claim 19, wherein the light is provided by one or more light sources.

33. The method of claim 32, wherein characteristics of the material or object are determined.

34. The method of claim 33, wherein the characteristics comprise spectral characteristics.

35. The method of claim 33, wherein the characteristics comprise whether the material or object contains a predetermined material.

36. The method of claim 33, wherein a determination is made if the object or material is genuine.

37. The method of claim 32, wherein the second optical sensors comprise light to frequency converters.

38. The method of claim 32, wherein the material or object comprises a gaseous material, a non-gaseous material, skin, non-skin body tissue, paint, fabric, a photograph, a dental object, a printed object, hair, or makeup.

39. A method comprising the steps of:
providing light to a diffraction grating;
receiving diffracted light from the diffraction grating with a plurality of optical sensors, wherein the optical sensors comprise light to frequency converters;
wherein spectral characteristics of the light are determined.

40. The method of claim 39, wherein the optical sensors comprise an array of optical sensors.

41. The method of claim 39, wherein the optical sensors comprise a linear array of optical sensors.

42. The method of claim 39, wherein the optical sensors comprise CCD sensors, photodiode sensors or phototransistor sensors.

43. The method of claim 39, wherein the optical sensors comprise an array of light to frequency converters.

44. The method of claim 39, wherein light is selectively coupled to the optical sensors through a plurality of filter elements, wherein the filter elements comprise interference filters.

45. The method of claim 39, wherein light is selectively coupled to the optical sensors through a plurality of filter elements, wherein the filter elements comprise a linear variable filter.

46. The method of claim 39, wherein light is selectively coupled to the optical sensors through a plurality of filter elements, wherein the filter elements comprise a color gradient filter.

47. The method of claim 39, wherein light is selectively coupled to the optical sensors through a plurality of filter elements, wherein the filter elements comprise interference filters deposited on an optical manifold, wherein the diffraction grating is part of the optical manifold, wherein light exits the optical manifold through the interference filters and is detected by the optical sensors.

48. The method of claim 39, wherein the diffraction grating is curved.

49. The method of claim 39, wherein the diffraction grating comprises a spherical diffraction grating.

50. The method of claim 39, wherein the light is collimated prior to being provided to the diffraction grating.

51. The method of claim 50, wherein the light is collimated by an aspheric lens or lens assembly.

52. The method of claim 39, further comprising the step of providing light to a material or object, wherein the light provided to the diffraction grating comprises light received from the material or object.

53. The method of claim 52, wherein characteristics of the material or object are determined.

54. The method of claim 53, wherein the characteristics comprise spectral characteristics.

55. The method of claim 53, wherein the characteristics comprise whether the material or object contains a predetermined material.

56. The method of claim 52, wherein a determination is made if the object or material is genuine.

57. The method of claim 52, wherein the light is provided to the material or object by a probe, wherein the method further comprises the step of providing light received from the material or object to second optical sensors, wherein the second optical sensors provide data indicative of a height or angle of the probe with respect to the material or object, provide data indicative of an optical value measurement of the material or object, or provide data indicative of translucence, gloss, opalescence, texture or other optical characteristics of the material or object.

58. The method of claim 52, wherein the material or object comprises a gaseous material, a non-gaseous material, skin, non-skin body tissue, paint, fabric, a photograph, a dental object, a printed object, hair, or makeup.

* * * * *